US010905837B2

(12) United States Patent
Ye et al.

(10) Patent No.: US 10,905,837 B2
(45) Date of Patent: Feb. 2, 2021

(54) RESPIRATORY THERAPY CYCLE CONTROL AND FEEDBACK

(71) Applicant: HILL-ROM SERVICES PTE. LTD., Singapore (SG)

(72) Inventors: Chau Chong Ye, Singapore (SG); Vinay Joshi, Singapore (SG); Suresha Venkataraya, Singapore (SG); Nookarajesh Varma Sangadi, Singapore (SG); Joel Preetham Fernandes, Singapore (SG); Jack Barney Sing, Batesville, IN (US); Eugene Hong Kheng Kung, Singapore (SG); Wei Teik Daniel Tan, Singapore (SG); Cong Jiang, Singapore (SG); Siew Ying Koh, Singapore (SG); Graham Keith Lacy, London (GB); Sergio Malorni, Windsor (GB); Alexander Cristian Hautenne Hanson, Altrincham (GB)

(73) Assignee: HILL-ROM SERVICES PTE. LTD., Singapore (SG)

(*) Notice: Subject to any disclaimer, the term of this patent is extended or adjusted under 35 U.S.C. 154(b) by 0 days.

(21) Appl. No.: 16/381,289

(22) Filed: Apr. 11, 2019

(65) Prior Publication Data

US 2019/0232001 A1    Aug. 1, 2019

Related U.S. Application Data

(63) Continuation of application No. 15/563,201, filed as application No. PCT/SG2016/050166 on Apr. 1, 2016.

(Continued)

(30) Foreign Application Priority Data

Apr. 2, 2015   (MY) .................... MYPI2015000844

(51) Int. Cl.
  *A61M 16/00*   (2006.01)
  *A61M 16/08*   (2006.01)
  (Continued)

(52) U.S. Cl.
  CPC .... *A61M 16/0006* (2014.02); *A61M 16/0009* (2014.02); *A61M 16/0069* (2014.02);
  (Continued)

(58) Field of Classification Search
  CPC ........ A61M 16/00; A61M 16/06–0694; A61M 16/20–209; A61M 16/0003–0012;
  (Continued)

(56) References Cited

U.S. PATENT DOCUMENTS

| 146,730 A | 1/1874 | Vickees |
| 236,719 A | 1/1881 | Bexton |

(Continued)

FOREIGN PATENT DOCUMENTS

| AU | 2011253797 A1 | 1/2012 |
| EP | 0625659 B1 | 6/1998 |

(Continued)

OTHER PUBLICATIONS

PCT Search Report and Written Opinion for PCT/SG2016/050166, completed Jun. 23, 2016.

(Continued)

*Primary Examiner* — Samchuan C Yao
*Assistant Examiner* — Ned T Heffner
(74) *Attorney, Agent, or Firm* — Barnes & Thornburg LLP

(57) ABSTRACT

A respiratory device includes a blower having an inlet and an outlet, a patient interface, and a valve including a valve member that is rotatable through a first angular displacement in a first direction from a first position to a second position. The outlet of the blower is coupled to the patient interface (Continued)

so that positive pressure is provided to a patient's airway via the patient interface when the valve member is in the first position. The inlet of the blower is coupled to the patient interface so that negative pressure is provided to the patient's airway via the patient interface when the valve member is in the second position. The valve member is rotatably oscillated back and forth when the valve member is in the first position and when the valve member is in the second position so that oscillations in the positive pressure and negative pressure, respectively, are provided to the patient's airway.

24 Claims, 46 Drawing Sheets

Related U.S. Application Data

(60) Provisional application No. 62/170,335, filed on Jun. 3, 2015.

(51) Int. Cl.
 *A61M 16/10* (2006.01)
 *A61M 16/20* (2006.01)
 *A61M 16/06* (2006.01)

(52) U.S. Cl.
 CPC ...... *A61M 16/024* (2017.08); *A61M 16/0833* (2014.02); *A61M 16/107* (2014.02); *A61M 16/201* (2014.02); *A61M 16/06* (2013.01); *A61M 16/0683* (2013.01); *A61M 2016/003* (2013.01); *A61M 2016/0027* (2013.01); *A61M 2016/1025* (2013.01); *A61M 2205/078* (2013.01); *A61M 2205/15* (2013.01); *A61M 2205/3368* (2013.01); *A61M 2205/3553* (2013.01); *A61M 2205/3561* (2013.01); *A61M 2205/3592* (2013.01); *A61M 2205/502* (2013.01); *A61M 2205/505* (2013.01); *A61M 2205/8206* (2013.01)

(58) Field of Classification Search
 CPC ........ A61M 16/0069; A61M 16/00833; A61M 16/107; A61M 16/024; A61M 2016/0015–0042; A62B 7/00; A62B 7/04; A62B 7/14; A62B 18/00; A62B 18/10
 See application file for complete search history.

(56) References Cited

U.S. PATENT DOCUMENTS

| | | |
|---|---|---|
| 307,795 A | 11/1884 | Peery |
| 370,255 A | 9/1887 | Hart |
| 374,831 A | 12/1887 | Habbington |
| 393,869 A | 12/1888 | Warren |
| 402,755 A | 5/1889 | Lyon |
| 402,779 A | 5/1889 | Steinhoff |
| 439,093 A | 10/1890 | Barian |
| 440,713 A | 11/1890 | Krohne |
| 460,458 A | 9/1891 | Bates |
| 471,389 A | 3/1892 | Lacey |
| 478,744 A | 7/1892 | Evans |
| 487,744 A | 12/1892 | Jacob |
| 513,189 A | 1/1894 | Knode |
| 540,464 A | 6/1895 | Stockmann |
| 593,190 A | 11/1897 | Berniiardt |
| 724,675 A | 4/1903 | Decker |
| 733,027 A | 7/1903 | Goldan |
| 793,103 A | 6/1905 | Scholtz |
| 803,066 A | 10/1905 | Orewiler |
| 806,065 A | 11/1905 | Childs |
| 812,706 A | 2/1906 | Warbasse |
| 853,439 A | 5/1907 | Clark |
| 859,156 A | 7/1907 | Warnken |
| 1,096,690 A | 5/1914 | Derbyshire |
| 1,105,127 A | 7/1914 | Draeger |
| 1,109,318 A | 9/1914 | Browne et al. |
| 1,150,238 A | 8/1915 | Winbray |
| 1,162,416 A | 11/1915 | Teter |
| 1,176,886 A | 3/1916 | Ermold |
| 1,214,941 A | 2/1917 | Morris et al. |
| 1,249,293 A | 12/1917 | Norwood |
| 1,263,079 A | 4/1918 | Leon |
| 1,270,565 A | 6/1918 | Teter |
| 1,272,274 A | 7/1918 | Kinealy |
| 1,276,245 A | 8/1918 | Millard et al. |
| 1,288,856 A | 12/1918 | Farr |
| 2,521,657 A | 9/1950 | Severy |
| 2,523,844 A | 9/1950 | Rohrman |
| 2,681,041 A | 6/1954 | Zodtner et al. |
| 2,768,643 A | 10/1956 | Acomb |
| 2,869,188 A | 1/1959 | Cameto |
| 2,918,917 A | 12/1959 | Emerson |
| 2,945,503 A | 7/1960 | Atkinson |
| 3,083,707 A | 4/1963 | Seeler |
| 3,182,659 A | 5/1965 | Blount |
| 3,291,122 A | 12/1966 | Engstrom et al. |
| 3,301,255 A | 1/1967 | Thompson |
| 3,392,916 A | 7/1968 | Engstrom et al. |
| 3,473,530 A | 10/1969 | Urbanowicz |
| 3,490,697 A | 1/1970 | Best, Jr. |
| 3,537,448 A | 11/1970 | Liston |
| 3,561,444 A | 2/1971 | Eoucher |
| 3,746,000 A | 7/1973 | Edwards |
| 3,774,602 A | 11/1973 | Edwards |
| 3,807,396 A | 4/1974 | Fischel |
| 3,861,386 A | 1/1975 | Harris et al. |
| 3,974,828 A | 8/1976 | Bird |
| 3,984,133 A | 10/1976 | Bird |
| 4,020,834 A | 5/1977 | Bird |
| 4,037,994 A | 7/1977 | Bird |
| 4,039,139 A | 8/1977 | Bird |
| 4,044,763 A | 8/1977 | Bird |
| 4,054,134 A | 10/1977 | Kritzer |
| 4,060,078 A | 11/1977 | Bird |
| 4,062,358 A | 12/1977 | Kritzer |
| 4,080,103 A | 3/1978 | Bird |
| 4,121,579 A | 10/1978 | Bird |
| 4,127,123 A | 11/1978 | Bird |
| 4,148,312 A | 4/1979 | Bird |
| 4,148,313 A | 4/1979 | Bird et al. |
| 4,150,071 A | 4/1979 | Pecina |
| 4,164,219 A | 8/1979 | Bird |
| 4,182,599 A | 1/1980 | Brown et al. |
| 4,197,843 A | 4/1980 | Bird |
| 4,226,233 A | 10/1980 | Kritzer |
| 4,245,633 A | 1/1981 | Erceg |
| 4,436,090 A | 3/1984 | Darling |
| 4,558,710 A | 12/1985 | Eichler |
| 4,592,349 A | 6/1986 | Bird |
| 4,601,465 A | 7/1986 | Roy |
| 4,635,857 A | 1/1987 | Hughes |
| 4,637,432 A | 1/1987 | Medvick et al. |
| 4,677,975 A | 7/1987 | Edgar et al. |
| 4,719,910 A | 1/1988 | Jensen |
| 4,742,823 A | 5/1988 | Bird |
| 4,770,164 A | 9/1988 | Lach et al. |
| 4,805,612 A | 2/1989 | Jensen |
| 4,805,613 A | 2/1989 | Bird |
| 4,819,629 A | 4/1989 | Jonson |
| 4,821,709 A | 4/1989 | Jensen |
| 4,838,257 A | 6/1989 | Hatch |
| 4,838,260 A | 6/1989 | Bird |
| 4,867,151 A | 9/1989 | Bird |
| 4,913,401 A | 4/1990 | Handke |
| 4,922,901 A | 5/1990 | Brooks et al. |
| 4,930,501 A | 6/1990 | Bird |
| 4,951,659 A | 8/1990 | Weiler et al. |
| 4,964,404 A | 10/1990 | Stone |
| 4,973,047 A | 11/1990 | Norell |
| 4,981,295 A | 1/1991 | Belman et al. |

(56) References Cited

U.S. PATENT DOCUMENTS

| | | |
|---|---|---|
| 4,982,735 A | 1/1991 | Yagata et al. |
| 4,986,269 A | 1/1991 | Hakkinen |
| 5,007,420 A | 4/1991 | Bird |
| 5,009,635 A | 4/1991 | Scarberry |
| 5,014,748 A | 5/1991 | Nogami et al. |
| 5,018,517 A | 5/1991 | Liardet |
| 5,027,809 A | 7/1991 | Robinson |
| 5,061,405 A | 10/1991 | Stanek et al. |
| 5,067,707 A | 11/1991 | Kohnke |
| 5,069,449 A | 12/1991 | Wardwell |
| 5,072,729 A | 12/1991 | Devries |
| 5,080,093 A | 1/1992 | Raabe et al. |
| 5,092,326 A | 3/1992 | Winn et al. |
| 5,107,830 A | 4/1992 | Younes |
| 5,116,088 A | 5/1992 | Bird |
| 5,127,400 A | 7/1992 | Devries et al. |
| 5,129,390 A | 7/1992 | Chopin et al. |
| 5,131,816 A | 7/1992 | Brown et al. |
| 5,134,993 A | 8/1992 | van der Linden et al. |
| 5,148,802 A | 9/1992 | Sanders et al. |
| 5,150,291 A | 9/1992 | Cummings et al. |
| 5,152,456 A | 10/1992 | Ross et al. |
| 5,154,167 A | 10/1992 | Hepburn |
| 5,165,398 A | 11/1992 | Bird |
| 5,186,166 A | 2/1993 | Riggs et al. |
| 5,193,529 A | 3/1993 | Labaere |
| 5,239,995 A | 8/1993 | Estes et al. |
| 5,253,651 A | 10/1993 | Stockwell et al. |
| D340,975 S | 11/1993 | Sladek |
| 5,261,394 A | 11/1993 | Mulligan et al. |
| 5,262,451 A | 11/1993 | Winters et al. |
| 5,277,175 A | 1/1994 | Riggs et al. |
| 5,280,784 A | 1/1994 | Koehler |
| 5,301,663 A | 4/1994 | Small, Jr. |
| 5,303,699 A | 4/1994 | Bonassa et al. |
| 5,313,937 A | 5/1994 | Zdrojkowski |
| 5,314,454 A | 5/1994 | Jaeger et al. |
| 5,320,107 A | 6/1994 | O'Brien |
| 5,322,057 A | 6/1994 | Raabe et al. |
| 5,343,878 A | 9/1994 | Scarberry et al. |
| 5,353,788 A | 10/1994 | Miles |
| 5,355,872 A | 10/1994 | Riggs et al. |
| 5,363,842 A | 11/1994 | Mishelevich et al. |
| 5,367,604 A | 11/1994 | Murray |
| 5,373,851 A | 12/1994 | Reinhold et al. |
| 5,390,665 A | 2/1995 | Leach |
| 5,390,666 A | 2/1995 | Kimm et al. |
| 5,392,768 A | 2/1995 | Johansson et al. |
| 5,394,866 A | 3/1995 | Ritson et al. |
| 5,394,882 A | 3/1995 | Mawhinney |
| 5,397,337 A | 3/1995 | Jaeger et al. |
| 5,398,676 A | 3/1995 | Press et al. |
| 5,400,777 A | 3/1995 | Olsson et al. |
| 5,404,871 A | 4/1995 | Goodman et al. |
| 5,413,110 A | 5/1995 | Cummings et al. |
| 5,419,315 A | 5/1995 | Rubsamen |
| 5,423,313 A | 6/1995 | Olsson et al. |
| 5,433,193 A | 7/1995 | Sanders et al. |
| 5,435,282 A | 7/1995 | Haber et al. |
| 5,438,981 A | 8/1995 | Starr et al. |
| 5,439,430 A | 8/1995 | Rubens et al. |
| 5,439,452 A | 8/1995 | McCarty |
| 5,441,046 A | 8/1995 | Starr et al. |
| 5,443,062 A | 8/1995 | Hayes |
| D362,061 S | 9/1995 | McGinnis et al. |
| D362,500 S | 9/1995 | Cook et al. |
| 5,450,336 A | 9/1995 | Rubsamen et al. |
| 5,451,190 A | 9/1995 | Liardet |
| 5,458,137 A | 10/1995 | Axe et al. |
| 5,474,062 A | 12/1995 | Devires et al. |
| 5,479,920 A | 1/1996 | Piper et al. |
| 5,480,588 A | 1/1996 | Tomasiak et al. |
| 5,483,955 A | 1/1996 | Morris |
| 5,485,827 A | 1/1996 | Zapol et al. |
| 5,487,378 A | 1/1996 | Robertson et al. |
| 5,490,502 A | 2/1996 | Rapoport et al. |
| 5,492,113 A | 2/1996 | Estes et al. |
| 5,492,116 A | 2/1996 | Scarberry et al. |
| 5,494,028 A | 2/1996 | Devries et al. |
| 5,497,944 A | 3/1996 | Weston et al. |
| 5,501,214 A | 3/1996 | Sabo |
| 5,507,282 A | 4/1996 | Younes |
| 5,509,404 A | 4/1996 | Lloyd et al. |
| 5,517,986 A | 5/1996 | Starr et al. |
| 5,522,378 A | 6/1996 | Ritson et al. |
| 5,522,385 A | 6/1996 | Lloyd et al. |
| RE35,295 E | 7/1996 | Estes et al. |
| 5,535,738 A | 7/1996 | Estes et al. |
| 5,535,739 A | 7/1996 | Rapoport et al. |
| 5,537,997 A | 7/1996 | Mechlenburg et al. |
| 5,540,219 A | 7/1996 | Mechlenburg et al. |
| 5,540,221 A | 7/1996 | Kaigler et al. |
| 5,540,223 A | 7/1996 | Starr et al. |
| 5,542,410 A | 8/1996 | Goodman et al. |
| 5,542,415 A | 8/1996 | Brody |
| 5,542,416 A | 8/1996 | Chalvignac |
| 5,546,933 A | 8/1996 | Rapoport et al. |
| 5,546,934 A | 8/1996 | Kaigler et al. |
| 5,547,440 A | 8/1996 | Rubens et al. |
| 5,549,106 A | 8/1996 | Gruenke et al. |
| 5,551,418 A | 9/1996 | Estes et al. |
| 5,551,419 A | 9/1996 | Froehlich et al. |
| 5,555,880 A | 9/1996 | Winter et al. |
| 5,558,085 A | 9/1996 | Rubsamen et al. |
| 5,558,086 A | 9/1996 | Smith et al. |
| 5,558,371 A | 9/1996 | Lordo |
| RE35,339 E | 10/1996 | Rapoport |
| 5,560,353 A | 10/1996 | Willemot et al. |
| 5,560,371 A | 10/1996 | Carvalho da Silva |
| 5,569,122 A | 10/1996 | Cegla |
| 5,570,682 A | 11/1996 | Johnson |
| 5,570,683 A | 11/1996 | Zapol |
| 5,570,689 A | 11/1996 | Starr et al. |
| 5,572,993 A | 11/1996 | Kurome et al. |
| 5,573,713 A | 11/1996 | Tomasiak et al. |
| 5,575,283 A | 11/1996 | Sjoestrand |
| D377,089 S | 12/1996 | Starr et al. |
| 5,579,757 A | 12/1996 | McMahon et al. |
| 5,582,163 A | 12/1996 | Bonassa |
| 5,586,550 A | 12/1996 | Ivri et al. |
| 5,592,938 A | 1/1997 | Scarberry et al. |
| 5,598,837 A | 2/1997 | Sirianne et al. |
| 5,598,838 A | 2/1997 | Servidio et al. |
| 5,598,839 A | 2/1997 | Niles et al. |
| 5,613,489 A | 3/1997 | Miller et al. |
| 5,617,846 A | 4/1997 | Graetz et al. |
| 5,617,847 A | 4/1997 | Howe |
| 5,622,162 A | 4/1997 | Johansson et al. |
| 5,626,131 A | 5/1997 | Chua et al. |
| 5,632,269 A | 5/1997 | Zdrojkowski |
| 5,632,298 A | 5/1997 | Artinian |
| 5,637,103 A | 6/1997 | Kerwin et al. |
| 5,645,053 A | 7/1997 | Remmers et al. |
| 5,647,351 A | 7/1997 | Weismann et al. |
| 5,647,355 A | 7/1997 | Starr et al. |
| 5,647,357 A | 7/1997 | Barnett et al. |
| 5,655,516 A | 8/1997 | Goodman et al. |
| 5,655,522 A | 8/1997 | Mechlenburg et al. |
| 5,655,527 A | 8/1997 | Scarberry et al. |
| 5,658,221 A | 8/1997 | Hougen |
| 5,660,166 A | 8/1997 | Lloyd et al. |
| 5,662,101 A | 9/1997 | Ogden et al. |
| 5,664,562 A | 9/1997 | Bourdon |
| 5,666,945 A | 9/1997 | Davenport |
| 5,673,687 A | 10/1997 | Dobson et al. |
| 5,682,878 A | 11/1997 | Ogden |
| 5,685,296 A | 11/1997 | Zdrojkowski et al. |
| 5,694,923 A | 12/1997 | Hete et al. |
| 5,694,929 A * | 12/1997 | Christopher ...... A61M 16/0488 128/205.25 |
| 5,697,364 A | 12/1997 | Chua et al. |
| 5,701,883 A | 12/1997 | Hete et al. |
| 5,704,346 A | 1/1998 | Inoue |
| 5,706,830 A | 1/1998 | Parker |

(56) References Cited

U.S. PATENT DOCUMENTS

| | | |
|---|---|---|
| 5,709,202 A | 1/1998 | Lloyd et al. |
| 5,713,349 A | 2/1998 | Keaney |
| 5,724,965 A | 3/1998 | Handke et al. |
| 5,740,796 A | 4/1998 | Skog |
| 5,743,252 A | 4/1998 | Rubsamen et al. |
| 5,746,359 A | 5/1998 | Stanek et al. |
| 5,752,509 A | 5/1998 | Lachmann et al. |
| 5,758,637 A | 6/1998 | Ivri et al. |
| 5,759,451 A | 6/1998 | Tomasiak et al. |
| 5,771,884 A | 6/1998 | Yarnall et al. |
| 5,785,049 A | 7/1998 | Smith et al. |
| 5,791,339 A | 8/1998 | Winter |
| 5,794,615 A | 8/1998 | Estes |
| 5,797,393 A | 8/1998 | Kohl |
| 5,799,282 A | 8/1998 | Rakshit et al. |
| 5,799,652 A | 9/1998 | Kotliar |
| 5,803,065 A | 9/1998 | Zdrojkowski et al. |
| 5,813,397 A | 9/1998 | Goodman et al. |
| 5,813,400 A | 9/1998 | Buhlmann et al. |
| 5,816,246 A | 10/1998 | Mirza |
| 5,819,726 A | 10/1998 | Rubsamen et al. |
| 5,827,703 A | 10/1998 | Debs et al. |
| 5,829,429 A | 11/1998 | Hughes |
| 5,829,723 A | 11/1998 | Brunner et al. |
| 5,839,429 A | 11/1998 | Marnfeldt et al. |
| 5,839,434 A | 11/1998 | Enterline |
| 5,840,026 A | 11/1998 | Uber, III et al. |
| 5,862,802 A | 1/1999 | Bird |
| 5,873,359 A | 2/1999 | Zapol et al. |
| 5,875,777 A | 3/1999 | Eriksson |
| 5,878,743 A | 3/1999 | Zdrojkowski et al. |
| 5,878,744 A | 3/1999 | Pfeiffer |
| 5,881,722 A | 3/1999 | Devries et al. |
| 5,881,724 A | 3/1999 | Graetz et al. |
| 5,884,624 A | 3/1999 | Barnett et al. |
| 5,890,998 A | 4/1999 | Hougen |
| 5,893,515 A | 4/1999 | Hahn et al. |
| 5,894,841 A | 4/1999 | Voges |
| 5,899,832 A | 5/1999 | Hougen |
| 5,899,998 A | 5/1999 | McGauley et al. |
| 5,901,704 A | 5/1999 | Estes et al. |
| 5,904,141 A | 5/1999 | Estes et al. |
| 5,906,198 A | 5/1999 | Flickinger |
| 5,910,071 A | 6/1999 | Hougen |
| 5,913,830 A | 6/1999 | Miles |
| 5,915,381 A | 6/1999 | Nord |
| 5,921,238 A | 7/1999 | Bourdon |
| 5,927,274 A | 7/1999 | Servidio et al. |
| 5,931,159 A | 8/1999 | Suzuki et al. |
| 5,931,160 A | 8/1999 | Gilmore et al. |
| 5,931,163 A | 8/1999 | Stegmann et al. |
| 5,934,272 A | 8/1999 | Lloyd et al. |
| 5,937,851 A | 8/1999 | Serowski et al. |
| 5,937,853 A | 8/1999 | Stroem |
| 5,937,854 A | 8/1999 | Stenzler |
| 5,937,855 A | 8/1999 | Zdrojkowski et al. |
| 5,937,857 A | 8/1999 | Caterini et al. |
| 5,938,117 A | 8/1999 | Ivri |
| 5,947,115 A | 9/1999 | Lordo et al. |
| 5,950,619 A | 9/1999 | Van Der Linden et al. |
| 5,957,124 A | 9/1999 | Lloyd et al. |
| 5,960,792 A | 10/1999 | Lloyd et al. |
| 5,964,223 A | 10/1999 | Baran |
| 5,970,974 A | 10/1999 | Van Der Linden et al. |
| 5,970,975 A | 10/1999 | Estes et al. |
| 5,979,440 A | 11/1999 | Honkonen et al. |
| 5,984,873 A | 11/1999 | Crumb et al. |
| 5,996,731 A | 12/1999 | Czabala et al. |
| 5,997,617 A | 12/1999 | Czabala et al. |
| 5,999,834 A | 12/1999 | Wang et al. |
| 6,003,511 A | 12/1999 | Fukunaga et al. |
| 6,006,748 A | 12/1999 | Hollis |
| 6,009,869 A | 1/2000 | Corbeil |
| 6,009,871 A | 1/2000 | Kiske et al. |
| 6,010,460 A | 1/2000 | McNaughton |
| 6,017,315 A | 1/2000 | Starr et al. |
| 6,024,090 A | 2/2000 | Gonda et al. |
| 6,026,312 A | 2/2000 | Shemwell et al. |
| 6,029,660 A | 2/2000 | Calluaud et al. |
| 6,029,664 A | 2/2000 | Zdrojkowski et al. |
| 6,032,667 A | 3/2000 | Heinonen |
| 6,038,913 A | 3/2000 | Gustafsson et al. |
| 6,044,841 A | 4/2000 | Verdun et al. |
| 6,058,932 A | 5/2000 | Hughes |
| 6,073,630 A | 6/2000 | Adahan |
| 6,076,519 A | 6/2000 | Johnson |
| 6,076,520 A | 6/2000 | Cooper |
| 6,079,412 A | 6/2000 | Meier et al. |
| 6,082,357 A | 7/2000 | Bates et al. |
| 6,083,141 A | 7/2000 | Hougen |
| 6,085,740 A | 7/2000 | Ivri et al. |
| 6,085,746 A | 7/2000 | Fox |
| 6,085,747 A | 7/2000 | Axe et al. |
| 6,089,105 A | 7/2000 | Ricciardelli |
| D429,330 S | 8/2000 | Hoenig |
| 6,095,140 A | 8/2000 | Poon et al. |
| 6,095,974 A | 8/2000 | Shemwell et al. |
| 6,098,620 A | 8/2000 | Lloyd et al. |
| 6,102,038 A | 8/2000 | Devries |
| 6,102,042 A | 8/2000 | Hete et al. |
| 6,105,571 A | 8/2000 | Coffee |
| 6,105,575 A | 8/2000 | Estes et al. |
| D431,077 S | 9/2000 | McGinnis et al. |
| 6,116,233 A | 9/2000 | Denyer et al. |
| 6,119,684 A | 9/2000 | Nohl et al. |
| 6,119,694 A | 9/2000 | Correa et al. |
| 6,123,074 A | 9/2000 | Hete et al. |
| 6,135,106 A | 10/2000 | Dirks et al. |
| 6,161,580 A | 12/2000 | Johannesson |
| 6,165,105 A | 12/2000 | Boutellier et al. |
| 6,176,235 B1 | 1/2001 | Benarrouch et al. |
| 6,176,474 B1 | 1/2001 | Stanek et al. |
| 6,182,326 B1 | 2/2001 | Rhea et al. |
| 6,182,655 B1 | 2/2001 | Keller et al. |
| 6,182,657 B1 | 2/2001 | Brydon et al. |
| 6,183,423 B1 | 2/2001 | Gaumond et al. |
| 6,186,142 B1 | 2/2001 | Schmidt et al. |
| 6,190,441 B1 | 2/2001 | Czabala et al. |
| 6,192,876 B1 | 2/2001 | Denyer et al. |
| 6,196,218 B1 | 3/2001 | Voges |
| 6,196,222 B1 | 3/2001 | Heinonen et al. |
| 6,201,223 B1 | 3/2001 | Nitta |
| 6,202,988 B1 | 3/2001 | Abe et al. |
| 6,205,999 B1 | 3/2001 | Ivri et al. |
| D440,651 S | 4/2001 | Foran et al. |
| D441,070 S | 4/2001 | Niles et al. |
| 6,209,540 B1 | 4/2001 | Sugiura et al. |
| 6,210,345 B1 | 4/2001 | Van Brunt |
| 6,212,435 B1 | 4/2001 | Lattner et al. |
| 6,212,904 B1 | 4/2001 | Arkharov et al. |
| 6,213,119 B1 | 4/2001 | Brydon et al. |
| D441,860 S | 5/2001 | Kopacko et al. |
| 6,225,901 B1 | 5/2001 | Kail, IV |
| 6,227,196 B1 | 5/2001 | Jaffe et al. |
| 6,227,197 B1 | 5/2001 | Fitzgerald |
| 6,230,704 B1 | 5/2001 | Durkin et al. |
| 6,234,167 B1 | 5/2001 | Cox et al. |
| 6,240,919 B1 | 6/2001 | MacDonald et al. |
| 6,250,253 B1 | 6/2001 | Margulis |
| 6,253,764 B1 | 7/2001 | Calluaud |
| 6,253,765 B1 | 7/2001 | Hgnelid et al. |
| 6,253,766 B1 | 7/2001 | Niles et al. |
| 6,253,767 B1 | 7/2001 | Mantz |
| 6,257,234 B1 | 7/2001 | Sun |
| 6,259,938 B1 | 7/2001 | Zarychta et al. |
| 6,269,811 B1 | 8/2001 | Duff et al. |
| 6,269,813 B1 | 8/2001 | Fitzgerald et al. |
| 6,273,087 B1 | 8/2001 | Boussignac et al. |
| D448,473 S | 9/2001 | Barnett et al. |
| 6,283,119 B1 | 9/2001 | Bourdon |
| 6,283,122 B1 | 9/2001 | Adahan |
| 6,289,890 B1 | 9/2001 | Bliss et al. |
| 6,290,991 B1 | 9/2001 | Roser et al. |
| 6,305,372 B1 | 10/2001 | Servidio |

(56) References Cited

U.S. PATENT DOCUMENTS

| | | |
|---|---|---|
| 6,305,374 B1 | 10/2001 | Zdrojkowski et al. |
| D450,381 S | 11/2001 | Weinstein et al. |
| 6,314,324 B1 | 11/2001 | Lattner et al. |
| 6,332,462 B1 | 12/2001 | Krohn |
| 6,332,463 B1 | 12/2001 | Farrugia et al. |
| 6,334,073 B1 | 12/2001 | Levine |
| 6,336,454 B1 | 1/2002 | Farrell et al. |
| 6,336,455 B1 | 1/2002 | Howlett |
| 6,340,025 B1 | 1/2002 | Van Brunt |
| 6,342,040 B1 | 1/2002 | Starr et al. |
| 6,345,319 B2 | 2/2002 | Lin et al. |
| 6,345,619 B1 | 2/2002 | Finn |
| 6,346,139 B1 | 2/2002 | Czabala |
| 6,348,082 B1 | 2/2002 | Murdoch et al. |
| 6,355,002 B1 | 3/2002 | Faram et al. |
| 6,360,741 B2 | 3/2002 | Truschel |
| 6,360,745 B1 * | 3/2002 | Wallace ............ A61M 16/0051 128/204.21 |
| 6,363,932 B1 | 4/2002 | Forchione et al. |
| 6,363,933 B1 | 4/2002 | Berthon-Jones |
| 6,367,474 B1 | 4/2002 | Berthon-Jones et al. |
| 6,378,520 B1 | 4/2002 | Davenport |
| 6,379,311 B1 | 4/2002 | Gaumond et al. |
| D457,622 S | 5/2002 | Kopacko et al. |
| 6,382,205 B1 | 5/2002 | Weinstein et al. |
| 6,382,931 B1 | 5/2002 | Czabala et al. |
| 6,390,088 B1 | 5/2002 | Nhl et al. |
| 6,390,091 B1 | 5/2002 | Banner et al. |
| 6,394,084 B1 | 5/2002 | Nitta |
| 6,395,065 B1 | 5/2002 | Murdoch et al. |
| D458,365 S | 6/2002 | Kopacko et al. |
| D458,993 S | 6/2002 | Kopacko et al. |
| 6,397,845 B1 | 6/2002 | Burton |
| 6,397,847 B1 | 6/2002 | Scarberry et al. |
| 6,401,713 B1 | 6/2002 | Hill et al. |
| 6,402,046 B1 | 6/2002 | Lser |
| 6,405,725 B1 | 6/2002 | Christopher |
| 6,405,934 B1 | 6/2002 | Hess et al. |
| 6,411,843 B1 | 6/2002 | Zarychta |
| 6,412,481 B1 | 7/2002 | Bienvenu et al. |
| 6,412,488 B1 | 7/2002 | Barnett et al. |
| 6,413,226 B1 | 7/2002 | Starr et al. |
| 6,415,791 B1 | 7/2002 | Van Brunt |
| 6,418,924 B1 | 7/2002 | Poley et al. |
| 6,418,928 B1 | 7/2002 | Bordewick et al. |
| 6,421,650 B1 | 7/2002 | Goetz et al. |
| 6,425,393 B1 | 7/2002 | Lurie et al. |
| 6,425,861 B1 | 7/2002 | Haberland et al. |
| 6,427,681 B1 | 8/2002 | Gonda et al. |
| 6,427,682 B1 | 8/2002 | Klimowicz et al. |
| 6,427,688 B1 | 8/2002 | Ligotke et al. |
| 6,427,689 B1 | 8/2002 | Estes et al. |
| 6,427,690 B1 | 8/2002 | McCombs et al. |
| 6,427,691 B1 | 8/2002 | Jinotti |
| 6,427,692 B1 | 8/2002 | Hglund |
| 6,427,694 B1 | 8/2002 | Hecker et al. |
| 6,431,170 B1 | 8/2002 | Truitt et al. |
| 6,431,171 B1 | 8/2002 | Burton |
| 6,439,228 B1 | 8/2002 | Hete et al. |
| 6,439,229 B1 | 8/2002 | Du et al. |
| 6,443,146 B1 | 9/2002 | Voges |
| 6,450,163 B1 | 9/2002 | Blacker et al. |
| 6,454,680 B1 | 9/2002 | Taimela |
| 6,454,997 B1 | 9/2002 | Divino et al. |
| D464,133 S | 10/2002 | Barnett et al. |
| D464,428 S | 10/2002 | Barnett et al. |
| D464,728 S | 10/2002 | Paul et al. |
| 6,463,930 B2 | 10/2002 | Biondi et al. |
| 6,467,476 B1 | 10/2002 | Ivri et al. |
| 6,467,477 B1 | 10/2002 | Frank et al. |
| 6,467,483 B1 | 10/2002 | Kopacko et al. |
| 6,478,857 B2 | 11/2002 | Czabala |
| 6,484,719 B1 | 11/2002 | Berthon-Jones |
| 6,485,690 B1 | 11/2002 | Pfost et al. |
| 6,488,641 B2 | 12/2002 | Hansen |
| 6,494,207 B1 | 12/2002 | Kwok |
| 6,494,899 B1 | 12/2002 | Griffin et al. |
| 6,497,755 B2 | 12/2002 | Murdoch et al. |
| 6,500,095 B1 | 12/2002 | Hougen |
| 6,502,572 B1 | 1/2003 | Berthon-Jones et al. |
| 6,510,846 B1 | 1/2003 | O'Rourke |
| 6,514,177 B1 | 2/2003 | Brugger et al. |
| 6,516,799 B1 | 2/2003 | Greenwood et al. |
| 6,516,801 B2 | 2/2003 | Boussignac |
| 6,516,802 B2 | 2/2003 | Hansen et al. |
| 6,520,180 B1 | 2/2003 | Sahmkow et al. |
| 6,526,970 B2 | 3/2003 | DeVries et al. |
| 6,526,974 B1 | 3/2003 | Brydon et al. |
| 6,526,976 B1 | 3/2003 | Baran |
| 6,530,372 B1 | 3/2003 | Madaus et al. |
| 6,532,956 B2 | 3/2003 | Hill |
| 6,532,957 B2 | 3/2003 | Berthon-Jones |
| 6,532,960 B1 | 3/2003 | Yurko |
| 6,533,739 B1 | 3/2003 | Palmer et al. |
| 6,536,432 B2 | 3/2003 | Truschel |
| 6,536,433 B1 | 3/2003 | Cewers |
| 6,539,938 B2 | 4/2003 | Weinstein et al. |
| 6,539,940 B2 | 4/2003 | Zdrojkowski et al. |
| 6,540,153 B1 | 4/2003 | Ivri |
| 6,540,154 B1 | 4/2003 | Ivri et al. |
| 6,543,449 B1 | 4/2003 | Woodring et al. |
| 6,544,192 B2 | 4/2003 | Starr et al. |
| 6,546,927 B2 | 4/2003 | Litherland et al. |
| 6,550,472 B2 | 4/2003 | Litherland et al. |
| 6,550,476 B1 | 4/2003 | Ryder |
| 6,550,478 B2 | 4/2003 | Remmers et al. |
| 6,550,694 B1 | 4/2003 | Foster et al. |
| 6,550,748 B2 | 4/2003 | Stanek et al. |
| 6,551,542 B1 | 4/2003 | Patel et al. |
| 6,553,893 B2 | 4/2003 | Murdoch |
| 6,553,988 B1 | 4/2003 | Holroyd |
| 6,553,990 B2 | 4/2003 | Hoffmann |
| 6,553,991 B1 | 4/2003 | Isaza |
| 6,553,992 B1 | 4/2003 | Berthon-Jones et al. |
| 6,554,746 B1 | 4/2003 | McConnell et al. |
| 6,557,549 B2 | 5/2003 | Schmidt et al. |
| 6,557,551 B2 | 5/2003 | Nitta |
| 6,557,552 B1 | 5/2003 | Cox et al. |
| 6,561,190 B1 | 5/2003 | Kwok |
| 6,564,797 B1 | 5/2003 | Mechlenburg et al. |
| 6,568,387 B2 | 5/2003 | Davenport et al. |
| D475,453 S | 6/2003 | Paul et al. |
| 6,571,790 B1 | 6/2003 | Weinstein |
| 6,571,792 B1 | 6/2003 | Hendrickson et al. |
| 6,571,793 B1 | 6/2003 | Nilsson |
| 6,571,795 B2 | 6/2003 | Bourdon |
| 6,571,796 B2 | 6/2003 | Banner et al. |
| 6,571,798 B1 | 6/2003 | Thornton |
| 6,575,162 B1 | 6/2003 | Rand |
| 6,575,163 B1 | 6/2003 | Berthon-Jones |
| 6,575,164 B1 | 6/2003 | Jaffe et al. |
| 6,575,165 B1 | 6/2003 | Cook et al. |
| 6,575,166 B2 | 6/2003 | Boussignac |
| 6,578,571 B1 | 6/2003 | Watt |
| 6,579,231 B1 | 6/2003 | Phipps |
| 6,581,595 B1 | 6/2003 | Murdock et al. |
| 6,581,596 B1 | 6/2003 | Truitt et al. |
| 6,581,598 B1 | 6/2003 | Foran et al. |
| 6,581,600 B2 | 6/2003 | Bird |
| 6,582,728 B1 | 6/2003 | Platz et al. |
| 6,584,976 B2 | 7/2003 | Japuntich et al. |
| 6,584,977 B1 | 7/2003 | Serowski |
| 6,588,422 B1 | 7/2003 | Berthon-Jones et al. |
| 6,588,427 B1 | 7/2003 | Carlsen et al. |
| 6,595,203 B1 | 7/2003 | Bird |
| 6,595,204 B2 | 7/2003 | Genova et al. |
| 6,595,205 B1 | 7/2003 | Andersson et al. |
| 6,595,208 B1 | 7/2003 | Coffee et al. |
| 6,595,212 B1 | 7/2003 | Arnott |
| 6,595,213 B2 | 7/2003 | Bennarsten |
| 6,595,215 B2 | 7/2003 | Wood |
| 6,598,602 B1 | 7/2003 | Sjholm |
| 6,598,603 B1 | 7/2003 | Andersson et al. |
| 6,599,252 B2 | 7/2003 | Starr |

(56) References Cited

U.S. PATENT DOCUMENTS

| | | |
|---|---|---|
| 6,601,581 B1 | 8/2003 | Babaev |
| 6,601,582 B2 | 8/2003 | Rand et al. |
| 6,601,583 B2 | 8/2003 | Pessala et al. |
| 6,609,517 B1 | 8/2003 | Estes et al. |
| 6,615,814 B1 | 9/2003 | Rice et al. |
| 6,615,830 B1 | 9/2003 | Serowski et al. |
| 6,615,831 B1 | 9/2003 | Tuitt et al. |
| 6,618,627 B2 | 9/2003 | Lattner et al. |
| 6,622,724 B1 | 9/2003 | Truitt et al. |
| 6,626,175 B2 | 9/2003 | Jafari et al. |
| 6,629,527 B1 | 10/2003 | Estes et al. |
| 6,629,646 B1 | 10/2003 | Ivri |
| 6,631,716 B1 | 10/2003 | Robinson et al. |
| 6,631,721 B1 | 10/2003 | Salter et al. |
| 6,637,430 B1 | 10/2003 | Voges et al. |
| 6,637,432 B2 | 10/2003 | Wakefield et al. |
| 6,637,433 B2 | 10/2003 | Schöb |
| 6,637,434 B2 | 10/2003 | Noble |
| 6,640,804 B2 | 11/2003 | Ivri et al. |
| 6,640,806 B2 | 11/2003 | Yurko |
| 6,640,807 B2 | 11/2003 | Bennarsten |
| 6,644,304 B2 | 11/2003 | Grychowski et al. |
| 6,644,305 B2 | 11/2003 | MacRae et al. |
| 6,644,310 B1 | 11/2003 | Delache et al. |
| 6,644,311 B1 | 11/2003 | Truitt et al. |
| 6,644,312 B2 | 11/2003 | Berthon-Jones et al. |
| 6,644,976 B2 | 11/2003 | Kullok et al. |
| 6,651,650 B1 | 11/2003 | Yamamoto et al. |
| 6,651,654 B2 | 11/2003 | Rogacki |
| 6,651,663 B2 | 11/2003 | Barnett et al. |
| 6,656,129 B2 | 12/2003 | Niles et al. |
| 6,662,032 B1 | 12/2003 | Gavish et al. |
| 6,663,574 B2 | 12/2003 | Faram et al. |
| 6,666,209 B2 | 12/2003 | Bennett et al. |
| 6,666,226 B2 | 12/2003 | Gill et al. |
| 6,668,827 B2 | 12/2003 | Schuler et al. |
| 6,668,828 B1 | 12/2003 | Figley et al. |
| 6,671,532 B1 | 12/2003 | Fudge et al. |
| 6,672,300 B1 | 1/2004 | Grant |
| 6,679,258 B1 | 1/2004 | Ström |
| 6,679,483 B2 | 1/2004 | Stanek et al. |
| 6,691,579 B2 | 2/2004 | Orr et al. |
| 6,694,969 B1 | 2/2004 | Heinonen et al. |
| 6,694,978 B1 | 2/2004 | Bennarsten |
| 6,699,203 B2 | 3/2004 | Starr et al. |
| 6,702,720 B2 | 3/2004 | Dardik |
| 6,702,769 B1 | 3/2004 | Fowler-Hawkins |
| 6,702,998 B2 | 3/2004 | Conner |
| 6,708,688 B1 | 3/2004 | Rubin et al. |
| 6,708,690 B1 | 3/2004 | Hete et al. |
| 6,708,691 B1 | 3/2004 | Hayek |
| D489,129 S | 4/2004 | King et al. |
| 6,718,969 B1 | 4/2004 | Rubin et al. |
| 6,722,362 B2 | 4/2004 | Hete et al. |
| 6,723,115 B1 | 4/2004 | Daly |
| 6,726,598 B1 | 4/2004 | Jarvis et al. |
| D490,519 S | 5/2004 | Pelerossi et al. |
| 6,729,333 B2 | 5/2004 | Barnett et al. |
| 6,737,042 B2 | 5/2004 | Rabinowitz et al. |
| 6,737,043 B2 | 5/2004 | Rabinowitz et al. |
| 6,748,275 B2 | 6/2004 | Lattner et al. |
| 6,752,151 B2 | 6/2004 | Hill |
| D493,523 S | 7/2004 | Barnett et al. |
| 6,761,165 B2 | 7/2004 | Strickland |
| 6,766,800 B2 | 7/2004 | Chu et al. |
| 6,770,022 B2 | 8/2004 | Mechlenburg et al. |
| 6,776,159 B2 | 8/2004 | Pelerossi et al. |
| 6,776,978 B2 | 8/2004 | Rabinowitz et al. |
| 6,780,400 B2 | 8/2004 | Rabinowitz et al. |
| 6,782,886 B2 | 8/2004 | Narayan et al. |
| 6,791,086 B2 | 9/2004 | Russell |
| 6,792,942 B1 | 9/2004 | Ho et al. |
| 6,798,345 B2 | 9/2004 | Satoh |
| 6,805,118 B2 | 10/2004 | Brooker et al. |
| 6,805,120 B1 | 10/2004 | Jeffrey et al. |
| 6,814,074 B1 | 11/2004 | Nadjafizadeh et al. |
| 6,814,076 B2 | 11/2004 | Shusterman et al. |
| 6,817,361 B2 | 11/2004 | Berthon-Jones et al. |
| 6,820,613 B2 | 11/2004 | Wenkebach et al. |
| 6,823,866 B2 | 11/2004 | Jafari et al. |
| 6,837,260 B1 | 1/2005 | Kuehn |
| RE38,700 E | 2/2005 | Briggs, III |
| D502,261 S | 2/2005 | Kopacko et al. |
| 6,848,443 B2 | 2/2005 | Schmidt et al. |
| 6,851,425 B2 | 2/2005 | Jaffre et al. |
| 6,854,462 B2 | 2/2005 | Berthon-Jones et al. |
| 6,860,265 B1 | 3/2005 | Emerson |
| 6,863,068 B2 | 3/2005 | Jamison et al. |
| 6,866,040 B1 | 3/2005 | Bourdon |
| 6,877,510 B2 | 4/2005 | Nitta |
| 6,877,511 B2 | 4/2005 | DeVries et al. |
| 6,877,513 B2 | 4/2005 | Scarberry et al. |
| 6,880,556 B2 | 4/2005 | Uchiyama et al. |
| 6,882,873 B2 | 4/2005 | Samuels et al. |
| 6,888,101 B2 | 5/2005 | Davis |
| 6,889,312 B1 | 5/2005 | McGrath et al. |
| 6,889,691 B2 | 5/2005 | Eklund et al. |
| 6,895,965 B2 | 5/2005 | Scarberry et al. |
| 6,899,100 B2 | 5/2005 | Wickham et al. |
| 6,904,906 B2 | 6/2005 | Salter et al. |
| 6,907,881 B2 | 6/2005 | Suki et al. |
| 6,908,438 B2 | 6/2005 | Orr et al. |
| 6,910,479 B1 | 6/2005 | Van Brunt |
| 6,910,483 B2 | 6/2005 | Daly et al. |
| 6,910,484 B1 | 6/2005 | Skog |
| 6,915,705 B1 | 7/2005 | Truitt et al. |
| 6,915,803 B2 | 7/2005 | Berthon-Jones et al. |
| 6,920,875 B1 | 7/2005 | Hill et al. |
| 6,920,877 B2 | 7/2005 | Remmers et al. |
| 6,920,878 B2 | 7/2005 | Sinderby et al. |
| 6,932,084 B2 | 8/2005 | Estes et al. |
| 6,935,338 B1 | 8/2005 | Triunfo, Jr. |
| 6,938,619 B1 | 9/2005 | Hickle |
| 6,941,162 B2 | 9/2005 | Fudge et al. |
| 6,948,497 B2 | 9/2005 | Zdrojkowski et al. |
| 6,951,546 B2 | 10/2005 | Palmer et al. |
| 6,952,605 B1 | 10/2005 | Scarberry |
| 6,955,651 B2 | 10/2005 | Kck et al. |
| 6,959,710 B2 | 11/2005 | Barnett et al. |
| 6,968,741 B2 | 11/2005 | Orr et al. |
| 6,968,840 B2 | 11/2005 | Smith et al. |
| 6,976,488 B2 | 12/2005 | Halperin |
| 6,976,491 B2 | 12/2005 | D'Agosto |
| 6,984,214 B2 | 1/2006 | Fowler-Hawkins |
| 6,988,498 B2 | 1/2006 | Berthon-Jones et al. |
| 6,988,994 B2 | 1/2006 | Rapoport et al. |
| 6,990,975 B1 | 1/2006 | Jones et al. |
| 6,997,183 B2 | 2/2006 | Koch et al. |
| 7,000,610 B2 | 2/2006 | Bennarsten et al. |
| 7,000,611 B2 | 2/2006 | Klemperer |
| 7,000,612 B2 | 2/2006 | Jafari et al. |
| 7,004,168 B2 | 2/2006 | Mace et al. |
| 7,007,692 B2 | 3/2006 | Aylsworth et al. |
| 7,007,693 B2 | 3/2006 | Fuhrman et al. |
| 7,011,087 B1 | 3/2006 | Sullivan |
| 7,011,091 B2 | 3/2006 | Hill et al. |
| 7,013,892 B2 | 3/2006 | Estes et al. |
| 7,025,731 B2 | 4/2006 | Orr et al. |
| 7,036,500 B2 | 5/2006 | Niles et al. |
| 7,040,318 B2 | 5/2006 | Dscher et al. |
| 7,044,129 B1 | 5/2006 | Truschel et al. |
| 7,059,324 B2 | 6/2006 | Pelerossi et al. |
| 7,066,176 B2 | 6/2006 | Jaffe et al. |
| 7,067,114 B2 | 6/2006 | Rabinowitz et al. |
| 7,070,761 B2 | 7/2006 | Rabinowitz et al. |
| 7,070,764 B2 | 7/2006 | Rabinowitz et al. |
| 7,070,765 B2 | 7/2006 | Rabinowitz et al. |
| 7,073,500 B2 | 7/2006 | Kates |
| 7,074,196 B2 | 7/2006 | Kck et al. |
| 7,082,944 B2 | 8/2006 | Gossweiler |
| 7,096,866 B2 | 8/2006 | Be'eri et al. |
| 7,100,607 B2 | 9/2006 | Zdrojkowski et al. |
| 7,121,134 B2 | 10/2006 | Rich |
| 7,121,277 B2 | 10/2006 | Strm |

(56) References Cited

U.S. PATENT DOCUMENTS

| | | |
|---|---|---|
| 7,128,069 B2 | 10/2006 | Farrugia et al. |
| 7,134,434 B2 | 11/2006 | Truitt et al. |
| 7,137,389 B2 | 11/2006 | Berthon-Jones |
| 7,141,021 B2 | 11/2006 | Sullivan et al. |
| 7,151,456 B2 | 12/2006 | Godfrey |
| 7,156,095 B2 | 1/2007 | Melker et al. |
| 7,162,296 B2 | 1/2007 | Leonhardt et al. |
| 7,165,547 B2 | 1/2007 | Truitt et al. |
| 7,169,378 B2 | 1/2007 | Rabinowitz et al. |
| 7,182,082 B2 | 2/2007 | Hoffrichter |
| 7,188,621 B2 | 3/2007 | DeVries et al. |
| 7,191,776 B2 | 3/2007 | Niles et al. |
| 7,191,777 B2 | 3/2007 | Brand et al. |
| 7,191,780 B2 | 3/2007 | Faram |
| 7,191,782 B2 | 3/2007 | Madsen |
| 7,198,044 B2 | 4/2007 | Trueba |
| 7,204,245 B2 | 4/2007 | Johnson et al. |
| 7,207,331 B2 | 4/2007 | Mashak |
| 7,210,478 B2 | 5/2007 | Banner et al. |
| 7,210,480 B2 | 5/2007 | Lurie et al. |
| 7,213,400 B2 | 5/2007 | Dickerson et al. |
| 7,219,666 B2 | 5/2007 | Friberg et al. |
| 7,225,807 B2 | 6/2007 | Papania et al. |
| 7,225,809 B1 | 6/2007 | Bowen et al. |
| 7,231,919 B2 | 6/2007 | Giroux |
| 7,267,120 B2 | 9/2007 | Rustad et al. |
| 7,267,122 B2 | 9/2007 | Hill |
| 7,270,128 B2 | 9/2007 | Berthon-Jones et al. |
| 7,278,423 B2 | 10/2007 | Serowski et al. |
| 7,296,573 B2 | 11/2007 | Estes et al. |
| 7,297,125 B2 | 11/2007 | Palmer et al. |
| 7,302,949 B2 | 12/2007 | Pelerossi et al. |
| 7,302,950 B2 | 12/2007 | Berthon-Jones et al. |
| 7,318,327 B2 | 1/2008 | Dickerson et al. |
| 7,320,320 B2 | 1/2008 | Berthon-Jones |
| 7,320,321 B2 | 1/2008 | Pranger et al. |
| 7,321,802 B2 | 1/2008 | Wasner et al. |
| 7,322,937 B2 | 1/2008 | Blomberg et al. |
| D561,330 S | 2/2008 | Richards et al. |
| 7,328,698 B2 | 2/2008 | Scarberry et al. |
| 7,329,304 B2 | 2/2008 | Bliss et al. |
| 7,331,344 B2 | 2/2008 | Foster et al. |
| 7,335,164 B2 | 2/2008 | Mace et al. |
| 7,338,410 B2 | 3/2008 | Dardik |
| 7,341,059 B2 | 3/2008 | Moody et al. |
| 7,343,917 B2 | 3/2008 | Jones |
| D566,833 S | 4/2008 | Richards et al. |
| 7,353,824 B1 | 4/2008 | Forsyth et al. |
| 7,367,335 B2 | 5/2008 | Fuhrman et al. |
| 7,367,935 B2 | 5/2008 | Mechlenburg et al. |
| 7,367,954 B2 | 5/2008 | Starr et al. |
| 7,368,005 B2 | 5/2008 | Bliss et al. |
| RE40,402 E | 6/2008 | Leonhardt et al. |
| 7,402,193 B2 | 7/2008 | Bliss et al. |
| 7,406,966 B2 | 8/2008 | Wondka |
| 7,422,014 B1 | 9/2008 | Smith |
| 7,428,902 B2 | 9/2008 | Du et al. |
| 7,431,031 B2 | 10/2008 | Hete et al. |
| 7,445,607 B2 | 11/2008 | Plante |
| 7,448,375 B2 | 11/2008 | Gonda et al. |
| 7,448,381 B2 | 11/2008 | Sasaki et al. |
| 7,448,383 B2 | 11/2008 | Delache et al. |
| 7,451,760 B2 | 11/2008 | Denyer et al. |
| 7,459,008 B2 | 12/2008 | Aylsworth et al. |
| 7,469,158 B2 | 12/2008 | Cutler et al. |
| 7,469,162 B2 | 12/2008 | Lattner et al. |
| 7,472,702 B2 | 1/2009 | Beck et al. |
| 7,472,705 B2 | 1/2009 | Baran |
| 7,478,635 B2 | 1/2009 | Wixey et al. |
| 7,484,508 B2 | 2/2009 | Younes |
| 7,487,774 B2 | 2/2009 | Acker |
| 7,500,481 B2 | 3/2009 | Delache et al. |
| 7,520,279 B2 | 4/2009 | Berthon-Jones |
| 7,555,916 B2 | 7/2009 | Dickerson et al. |
| 7,562,657 B2 | 7/2009 | Blanch et al. |
| 7,565,906 B2 | 7/2009 | Arcilla et al. |
| 7,568,482 B2 | 8/2009 | Jaffre et al. |
| 7,574,368 B2 | 8/2009 | Pawlikowski et al. |
| 7,578,294 B2 | 8/2009 | Pierro et al. |
| 7,588,033 B2 | 9/2009 | Wondka |
| 7,618,383 B2 | 11/2009 | Palmer et al. |
| 7,624,735 B2 | 12/2009 | Ho et al. |
| 7,644,713 B2 | 1/2010 | Berthon-Jones |
| 7,661,426 B2 | 2/2010 | Lauk et al. |
| 7,665,464 B2 | 2/2010 | Kopacko et al. |
| 7,682,312 B2 | 3/2010 | Lurie |
| 7,686,012 B2 | 3/2010 | Orr et al. |
| 7,691,049 B2 | 4/2010 | Wood et al. |
| 7,699,054 B2 | 4/2010 | Pelerossi et al. |
| 7,703,457 B2 | 4/2010 | Barnett et al. |
| RE41,298 E | 5/2010 | Smith et al. |
| 7,708,015 B2 | 5/2010 | Seeger et al. |
| 7,708,016 B2 | 5/2010 | Zaiser et al. |
| 7,711,438 B2 | 5/2010 | Lattner et al. |
| 7,717,109 B2 | 5/2010 | Fukunaga et al. |
| 7,717,111 B2 | 5/2010 | Schneider et al. |
| 7,717,112 B2 | 5/2010 | Sun et al. |
| 7,717,113 B2 | 5/2010 | Andrieux |
| 7,721,729 B2 | 5/2010 | Von Hollen et al. |
| 7,721,734 B2 | 5/2010 | Rustad et al. |
| 7,721,735 B2 | 5/2010 | Hamilton et al. |
| 7,721,736 B2 | 5/2010 | Urias et al. |
| 7,726,309 B2 | 6/2010 | Ho et al. |
| 7,726,314 B1 | 6/2010 | Ming |
| 7,727,160 B2 | 6/2010 | Green et al. |
| 7,730,886 B2 | 6/2010 | Berthon-Jones |
| 7,735,490 B2 | 6/2010 | Rinaldi |
| 7,736,132 B2 | 6/2010 | Bliss et al. |
| 7,739,957 B2 | 6/2010 | Patterson et al. |
| 7,740,013 B2 | 6/2010 | Ishizaki et al. |
| 7,743,770 B2 | 6/2010 | Curti et al. |
| 7,748,381 B2 | 7/2010 | Croll et al. |
| 7,748,382 B2 | 7/2010 | Denyer et al. |
| 7,753,073 B2 | 7/2010 | Owczarczak |
| 7,753,991 B2 | 7/2010 | Kertzman |
| 7,757,690 B2 | 7/2010 | Stahmann et al. |
| 7,762,252 B2 | 7/2010 | Prete |
| 7,762,253 B2 | 7/2010 | Acker et al. |
| 7,762,254 B2 | 7/2010 | Ho |
| 7,762,255 B2 | 7/2010 | Mills |
| 7,762,289 B2 | 7/2010 | McCulloh et al. |
| 7,766,857 B2 | 8/2010 | Tham et al. |
| 7,770,577 B2 | 8/2010 | Conner |
| 7,770,578 B2 | 8/2010 | Estes et al. |
| 7,770,579 B2 | 8/2010 | O'Connor et al. |
| 7,770,580 B2 | 8/2010 | Krger et al. |
| 7,775,208 B2 | 8/2010 | Carepa et al. |
| 7,779,834 B2 | 8/2010 | Calluaud et al. |
| 7,779,841 B2 | 8/2010 | Dunsmore et al. |
| 7,784,462 B2 | 8/2010 | Vogt et al. |
| 7,784,463 B2 | 8/2010 | Cannon |
| 7,789,084 B2 | 9/2010 | Rittner et al. |
| 7,793,659 B2 | 9/2010 | Breen |
| 7,793,660 B2 | 9/2010 | Kimmel et al. |
| 7,794,522 B2 | 9/2010 | Bliss et al. |
| 7,798,143 B1 | 9/2010 | Kirby |
| 7,798,144 B2 | 9/2010 | Kwok et al. |
| 7,798,145 B2 | 9/2010 | Weismann et al. |
| 7,798,148 B2 | 9/2010 | Doshi et al. |
| 7,802,571 B2 | 9/2010 | Tehrani |
| 7,810,496 B2 | 10/2010 | Estes et al. |
| 7,810,497 B2 | 10/2010 | Pittman et al. |
| 7,814,901 B2 | 10/2010 | Lieberman et al. |
| 7,814,906 B2 | 10/2010 | Moretti |
| 7,814,907 B2 | 10/2010 | Bremner et al. |
| 7,819,118 B2 | 10/2010 | Lucas, Jr. et al. |
| 7,823,588 B2 | 11/2010 | Hansen |
| 7,827,038 B2 | 11/2010 | Richard et al. |
| 7,827,987 B2 | 11/2010 | Woodard et al. |
| 7,832,400 B2 | 11/2010 | Curti et al. |
| 7,832,403 B2 | 11/2010 | Halstrom et al. |
| 7,837,761 B2 | 11/2010 | Bliss et al. |
| 7,841,343 B2 | 11/2010 | Deane et al. |
| 7,841,347 B2 | 11/2010 | Sonnenschein et al. |

(56) References Cited

U.S. PATENT DOCUMENTS

| | | |
|---|---|---|
| 7,845,350 B1 | 12/2010 | Kayyali et al. |
| 7,849,852 B2 | 12/2010 | Bremner et al. |
| 7,849,854 B2 | 12/2010 | DeVries et al. |
| 7,849,855 B2 | 12/2010 | Woodard et al. |
| 7,849,857 B2 | 12/2010 | Gbel |
| 7,856,975 B2 | 12/2010 | Nobutani et al. |
| 7,856,979 B2 | 12/2010 | Doshi et al. |
| 7,856,981 B2 | 12/2010 | McAuley et al. |
| 7,861,714 B2 | 1/2011 | Smart |
| 7,861,716 B2 | 1/2011 | Borrello |
| 7,866,315 B2 | 1/2011 | Jagger et al. |
| 7,866,317 B2 | 1/2011 | Muellinger et al. |
| 7,866,318 B2 | 1/2011 | Bassin |
| 7,866,320 B2 | 1/2011 | Nichols |
| 7,870,857 B2 | 1/2011 | Dhuper et al. |
| 7,870,859 B2 | 1/2011 | Barnett et al. |
| 7,874,290 B2 | 1/2011 | Chalvignac |
| 7,874,293 B2 | 1/2011 | Gunaratnam et al. |
| 7,878,194 B2 | 2/2011 | Hamaguchi et al. |
| 7,878,198 B2 | 2/2011 | Farrell et al. |
| 7,878,201 B2 | 2/2011 | Mongeon |
| 7,882,834 B2 | 2/2011 | Gradon et al. |
| 7,882,835 B2 | 2/2011 | Eger et al. |
| 7,886,739 B2 | 2/2011 | Soliman et al. |
| 7,886,740 B2 | 2/2011 | Thomas et al. |
| 7,891,353 B2 | 2/2011 | Chalvignac |
| 7,891,354 B2 | 2/2011 | Farbarik |
| 7,900,626 B2 | 3/2011 | Daly |
| 7,900,627 B2 | 3/2011 | Aylsworth et al. |
| 7,905,231 B2 | 3/2011 | Chalvignac |
| 7,909,033 B2 | 3/2011 | Faram |
| 7,909,034 B2 | 3/2011 | Sinderby et al. |
| 7,913,497 B2 | 3/2011 | Dickerson |
| 7,913,689 B2 | 3/2011 | Henry et al. |
| 7,914,459 B2 | 3/2011 | Green et al. |
| 7,918,223 B2 | 4/2011 | Soliman et al. |
| 7,918,227 B1 | 4/2011 | Phythyon |
| 7,921,845 B2 | 4/2011 | Kim |
| 7,926,486 B2 | 4/2011 | Childers |
| 7,926,487 B2 | 4/2011 | Drew et al. |
| 7,928,852 B2 | 4/2011 | Durtschi et al. |
| 7,931,021 B2 | 4/2011 | Livingston et al. |
| 7,931,023 B2 | 4/2011 | Berthon-Jones et al. |
| 7,934,498 B1 | 5/2011 | Heidelberger |
| 7,934,499 B2 | 5/2011 | Berthon-Jones |
| 7,934,500 B2 | 5/2011 | Madaus et al. |
| 7,938,112 B2 | 5/2011 | Mayer et al. |
| 7,938,114 B2 | 5/2011 | Matthews et al. |
| 7,942,823 B2 | 5/2011 | Wright et al. |
| 7,946,291 B2 | 5/2011 | Fink et al. |
| 7,958,892 B2 | 6/2011 | Kwok et al. |
| 7,963,283 B2 | 6/2011 | Sinderby |
| 7,967,012 B2 | 6/2011 | Berthon-Jones |
| 7,967,576 B2 | 6/2011 | Abate et al. |
| 7,971,588 B2 | 7/2011 | Fink et al. |
| 7,975,691 B2 | 7/2011 | Cha et al. |
| 7,975,692 B2 | 7/2011 | Eifler et al. |
| 7,984,712 B2 | 7/2011 | Soliman et al. |
| 7,987,847 B2 | 8/2011 | Wickham et al. |
| 7,987,848 B2 | 8/2011 | Dammann |
| 7,987,849 B2 | 8/2011 | Heesch |
| 7,992,554 B2 | 8/2011 | Radomski et al. |
| 7,992,557 B2 | 8/2011 | Nadjafizadeh et al. |
| 7,997,267 B2 | 8/2011 | Ging et al. |
| 7,997,269 B2 | 8/2011 | Yudkovitch et al. |
| 7,997,271 B2 | 8/2011 | Hickle et al. |
| 7,997,272 B2 | 8/2011 | Isaza |
| 8,001,966 B1 | 8/2011 | Goldstein et al. |
| 8,001,968 B2 | 8/2011 | Doty et al. |
| 8,002,711 B2 | 8/2011 | Wood et al. |
| 8,006,691 B2 | 8/2011 | Kenyon et al. |
| 8,006,696 B2 | 8/2011 | Jensen |
| 8,011,362 B2 | 9/2011 | Adams |
| 8,011,368 B2 | 9/2011 | Crutchfield |
| 8,012,099 B2 | 9/2011 | Schermeier et al. |
| 8,015,971 B2 | 9/2011 | Kwok |
| 8,015,972 B2 | 9/2011 | Pirzada |
| 8,015,974 B2 | 9/2011 | Christopher et al. |
| 8,020,551 B2 | 9/2011 | Virr et al. |
| 8,020,552 B2 | 9/2011 | Dillon et al. |
| 8,020,556 B2 | 9/2011 | Hayek |
| 8,020,558 B2 | 9/2011 | Christopher et al. |
| 8,021,309 B2 | 9/2011 | Zilberg |
| 8,025,054 B2 | 9/2011 | Dunsmore et al. |
| 8,025,055 B1 | 9/2011 | Grady |
| 8,025,056 B2 | 9/2011 | Lewis |
| 8,028,692 B2 | 10/2011 | Ho |
| 8,028,693 B2 | 10/2011 | Trevor-Wilson et al. |
| 8,028,695 B2 | 10/2011 | Acker et al. |
| 8,028,697 B2 | 10/2011 | Grychowski et al. |
| 8,028,700 B2 | 10/2011 | Hannah et al. |
| 8,028,701 B2 | 10/2011 | Al-Ali et al. |
| 8,037,882 B2 | 10/2011 | Smith et al. |
| 8,038,576 B2 | 10/2011 | Farinelli et al. |
| 8,042,535 B2 | 10/2011 | Kenyon et al. |
| 8,042,546 B2 | 10/2011 | Gunaratnam et al. |
| 8,047,205 B2 | 11/2011 | von Blumenthal et al. |
| 8,048,043 B2 | 11/2011 | Herting et al. |
| 8,051,852 B2 | 11/2011 | Bassin |
| 8,052,626 B2 | 11/2011 | Huster et al. |
| 8,056,557 B2 | 11/2011 | Lieberman et al. |
| 8,056,559 B2 | 11/2011 | O'Connor et al. |
| 8,061,353 B2 | 11/2011 | Easley et al. |
| 8,061,355 B2 | 11/2011 | Jaffre et al. |
| 8,066,003 B2 | 11/2011 | Cong et al. |
| 8,069,852 B2 | 12/2011 | Burton et al. |
| 8,069,853 B2 | 12/2011 | Tilley |
| 8,069,854 B2 | 12/2011 | Colla et al. |
| 8,074,646 B2 | 12/2011 | Daly |
| 8,074,647 B2 | 12/2011 | Truitt et al. |
| 8,082,312 B2 | 12/2011 | Chan et al. |
| 8,091,549 B2 | 1/2012 | Montgomery et al. |
| 8,096,301 B2 | 1/2012 | Smith et al. |
| 8,100,123 B2 | 1/2012 | Belson |
| 8,100,124 B2 | 1/2012 | Becker et al. |
| 8,100,125 B2 | 1/2012 | Duquette et al. |
| 8,104,470 B2 | 1/2012 | Lee et al. |
| 8,104,471 B2 | 1/2012 | Schtzl |
| 8,109,268 B2 | 2/2012 | Rohde et al. |
| 8,113,197 B2 | 2/2012 | Smart et al. |
| 8,113,198 B2 | 2/2012 | Teetzel et al. |
| 8,118,023 B2 | 2/2012 | Short |
| 8,118,024 B2 | 2/2012 | DeVries et al. |
| 8,118,027 B2 | 2/2012 | Matula, Jr. et al. |
| 8,122,883 B2 | 2/2012 | Banner et al. |
| 8,122,884 B2 | 2/2012 | Daly et al. |
| 8,122,885 B2 | 2/2012 | Berthon-Jones et al. |
| 8,127,767 B2 | 3/2012 | Mutti et al. |
| 8,136,521 B2 | 3/2012 | Matthews et al. |
| 8,146,591 B2 | 4/2012 | Niklewski et al. |
| 8,146,592 B2 | 4/2012 | Voege et al. |
| 8,146,593 B2 | 4/2012 | Riecke |
| 8,151,790 B2 | 4/2012 | Lurie et al. |
| 8,151,792 B2 | 4/2012 | Ishizaki et al. |
| 8,151,794 B2 | 4/2012 | Meyer et al. |
| 8,151,795 B2 | 4/2012 | Fishman et al. |
| 8,156,937 B2 | 4/2012 | DeVries et al. |
| 8,161,966 B2 | 4/2012 | Foley et al. |
| 8,161,972 B2 | 4/2012 | Isaza |
| 8,166,971 B2 | 5/2012 | Jaffe et al. |
| 8,167,812 B2 | 5/2012 | Schller et al. |
| 8,171,932 B2 | 5/2012 | Rittner et al. |
| 8,176,915 B2 | 5/2012 | Jaffe et al. |
| 8,176,917 B2 | 5/2012 | Cannon |
| 8,181,646 B2 | 5/2012 | Dhuper et al. |
| 8,181,648 B2 | 5/2012 | Perine et al. |
| 8,181,649 B2 | 5/2012 | Brunner |
| 8,186,344 B2 | 5/2012 | Bonassa |
| 8,191,551 B2 | 6/2012 | Skovgard |
| 8,196,579 B2 | 6/2012 | Richards et al. |
| 8,196,580 B2 | 6/2012 | Gross |
| 8,196,584 B2 | 6/2012 | Maguire et al. |
| 8,201,558 B2 | 6/2012 | Ralfs |
| 8,205,615 B1 | 6/2012 | Ho |

(56) References Cited

U.S. PATENT DOCUMENTS

| | | |
|---|---|---|
| 8,210,169 B2 | 7/2012 | Ahlmn et al. |
| 8,210,174 B2 | 7/2012 | Farbarik |
| 8,210,176 B2 | 7/2012 | Metzger et al. |
| 8,215,301 B2 | 7/2012 | Richards et al. |
| 8,215,302 B2 | 7/2012 | Kassatly et al. |
| 8,220,457 B2 | 7/2012 | Berthon-Jones et al. |
| 8,225,783 B2 | 7/2012 | Schnaars et al. |
| 8,225,785 B2 | 7/2012 | Richards et al. |
| 8,225,786 B2 | 7/2012 | Daly et al. |
| 8,225,787 B2 | 7/2012 | Newman, Jr. |
| 8,225,788 B2 | 7/2012 | Manigel et al. |
| 8,225,789 B2 | 7/2012 | Berthon-Jones |
| 8,225,790 B2 | 7/2012 | Bowman et al. |
| 8,225,794 B2 | 7/2012 | Mikkaichi et al. |
| 8,225,796 B2 | 7/2012 | Davenport et al. |
| 8,230,852 B2 | 7/2012 | Zhang et al. |
| 8,230,855 B2 | 7/2012 | Raje et al. |
| 8,230,857 B2 | 7/2012 | Cewers |
| 8,230,858 B2 | 7/2012 | Karlsson |
| 8,230,859 B1 | 7/2012 | Voege et al. |
| 8,235,042 B2 | 8/2012 | Newman, Jr. |
| 8,235,043 B2 | 8/2012 | Halpern |
| 8,236,095 B1 | 8/2012 | Bassine |
| 8,240,307 B2 | 8/2012 | Albertelli |
| 8,240,684 B2 | 8/2012 | Ross et al. |
| 8,245,708 B2 | 8/2012 | Smaldone et al. |
| 8,245,710 B2 | 8/2012 | Makinson et al. |
| 8,251,061 B2 | 8/2012 | Lee et al. |
| 8,251,062 B2 | 8/2012 | Chalvignac |
| 8,251,066 B1 | 8/2012 | Ho et al. |
| 8,252,582 B2 | 8/2012 | Baumfalk et al. |
| 8,253,577 B2 | 8/2012 | Durtschi et al. |
| 8,256,417 B2 | 9/2012 | Sun |
| 8,256,420 B2 | 9/2012 | Prete |
| 8,261,741 B2 | 9/2012 | Nagorny et al. |
| 8,261,744 B2 | 9/2012 | Rittner et al. |
| 8,267,081 B2 | 9/2012 | Flanagan et al. |
| 8,267,083 B1 | 9/2012 | Goldstein et al. |
| 8,267,084 B2 | 9/2012 | Kwok |
| 8,267,085 B2 | 9/2012 | Jafari et al. |
| 8,267,648 B2 | 9/2012 | Kenyon et al. |
| 8,276,584 B2 | 10/2012 | Tatarek |
| 8,276,585 B2 | 10/2012 | Buckley et al. |
| 8,281,786 B2 | 10/2012 | Belson |
| 8,281,787 B2 | 10/2012 | Burton |
| 8,281,788 B2 | 10/2012 | Thompson et al. |
| 8,297,279 B2 | 10/2012 | DeVries et al. |
| 8,297,280 B2 | 10/2012 | Watanabe |
| 8,302,597 B2 | 11/2012 | Beely et al. |
| 8,302,598 B2 | 11/2012 | Haase et al. |
| 8,302,602 B2 | 11/2012 | Andrieux et al. |
| 8,302,603 B1 | 11/2012 | Weber |
| 8,302,604 B2 | 11/2012 | Rittner et al. |
| 8,307,828 B2 | 11/2012 | Zaiser et al. |
| 8,312,875 B2 | 11/2012 | Frater |
| 8,312,877 B2 | 11/2012 | Elaz et al. |
| 8,312,879 B2 | 11/2012 | Choncholas et al. |
| 8,316,847 B2 | 11/2012 | Hallett |
| 8,316,848 B2 | 11/2012 | Kwok et al. |
| 8,316,849 B2 | 11/2012 | Lomask et al. |
| 8,322,334 B2 | 12/2012 | Lee et al. |
| 8,322,339 B2 | 12/2012 | Gottlib et al. |
| 8,323,378 B2 | 12/2012 | Swami et al. |
| 8,326,545 B2 | 12/2012 | Yudkovitch et al. |
| 8,327,846 B2 | 12/2012 | Bowditch et al. |
| 8,327,848 B2 | 12/2012 | Ho et al. |
| 8,327,849 B2 | 12/2012 | Foley et al. |
| 8,333,194 B2 | 12/2012 | Lewis et al. |
| 8,333,200 B2 | 12/2012 | Tero |
| 8,336,545 B2 | 12/2012 | Fink et al. |
| 8,336,546 B2 | 12/2012 | Bowditch et al. |
| 8,336,547 B1 | 12/2012 | Ritchie et al. |
| 8,336,553 B2 | 12/2012 | Bhat et al. |
| 8,337,145 B2 | 12/2012 | Frater et al. |
| RE43,886 E | 1/2013 | Mijers |
| 8,342,182 B2 | 1/2013 | Nair et al. |
| 8,347,883 B2 | 1/2013 | Bird |
| 8,347,884 B2 | 1/2013 | Cheng et al. |
| 8,353,288 B2 | 1/2013 | Schermeier et al. |
| 8,353,289 B2 | 1/2013 | Farrugia et al. |
| 8,353,290 B2 | 1/2013 | Adams |
| 8,353,293 B1 | 1/2013 | Fuhrman |
| 8,355,753 B2 | 1/2013 | Bochenko et al. |
| 8,356,594 B2 | 1/2013 | Ujhazy et al. |
| 8,356,595 B2 | 1/2013 | Schaeffer, Jr. et al. |
| 8,356,596 B2 | 1/2013 | Brandt et al. |
| 8,356,603 B2 | 1/2013 | Thornton |
| 8,360,060 B2 | 1/2013 | Berthon-Jones |
| 8,360,061 B2 | 1/2013 | Brown et al. |
| 8,361,204 B1 | 1/2013 | Bassine |
| 8,365,727 B2 | 2/2013 | Dunsmore et al. |
| 8,365,728 B2 | 2/2013 | Hamilton et al. |
| 8,365,729 B2 | 2/2013 | Alder et al. |
| 8,365,730 B2 | 2/2013 | Baker, Jr. et al. |
| 8,365,731 B2 | 2/2013 | Ho et al. |
| 8,365,736 B2 | 2/2013 | Doshi et al. |
| 8,366,815 B2 | 2/2013 | Taylor et al. |
| 8,371,297 B2 | 2/2013 | Carey et al. |
| 8,371,299 B2 | 2/2013 | Denyer et al. |
| 8,371,300 B2 | 2/2013 | Rapoport |
| 8,371,303 B2 | 2/2013 | Schaner et al. |
| 8,375,944 B2 | 2/2013 | Kwok |
| 8,375,945 B2 | 2/2013 | Kepler et al. |
| 8,375,946 B2 | 2/2013 | Boussignac |
| 8,375,948 B2 | 2/2013 | Turiello |
| 8,375,952 B2 | 2/2013 | Miller et al. |
| 8,381,723 B2 | 2/2013 | DiBlasi et al. |
| 8,381,724 B2 | 2/2013 | Bowen et al. |
| 8,381,725 B2 | 2/2013 | Chalvignac |
| 8,381,726 B2 | 2/2013 | Turiello |
| 8,387,616 B2 | 3/2013 | Ging et al. |
| 8,393,320 B2 | 3/2013 | Kenyon |
| 8,393,323 B2 | 3/2013 | Andrieux et al. |
| 8,393,328 B2 | 3/2013 | Angel et al. |
| 8,397,716 B2 | 3/2013 | Calluaud et al. |
| 8,397,719 B2 | 3/2013 | Kepler et al. |
| 8,397,720 B2 | 3/2013 | Eger et al. |
| 8,397,721 B2 | 3/2013 | Montgomery et al. |
| 8,397,722 B2 | 3/2013 | Berthon-Jones et al. |
| 8,397,723 B2 | 3/2013 | Conrad et al. |
| 8,397,724 B2 | 3/2013 | Sher et al. |
| 8,397,727 B2 | 3/2013 | Ng et al. |
| 8,400,290 B2 | 3/2013 | Baker, Jr. |
| 8,402,965 B1 | 3/2013 | Scharfenberg et al. |
| 8,402,968 B2 | 3/2013 | Belson |
| 8,402,969 B2 | 3/2013 | Gabriel et al. |
| 8,402,970 B2 | 3/2013 | Levi et al. |
| 8,408,203 B2 | 4/2013 | Tham et al. |
| 8,408,204 B2 | 4/2013 | Lurie |
| 8,408,206 B2 | 4/2013 | Montgomery et al. |
| 8,408,208 B2 | 4/2013 | Bacon |
| 8,408,209 B2 | 4/2013 | Matsubara et al. |
| 8,413,653 B2 | 4/2013 | Turiello |
| 8,413,654 B2 | 4/2013 | Bateman |
| 8,418,691 B2 | 4/2013 | Jafari et al. |
| 8,418,692 B2 | 4/2013 | Sanchez |
| 8,418,693 B2 | 4/2013 | Kaestle et al. |
| 8,424,519 B2 | 4/2013 | Loescher et al. |
| 8,424,520 B2 | 4/2013 | Thiessen |
| 8,424,524 B2 | 4/2013 | Heinonen |
| 8,424,525 B2 | 4/2013 | Peacey et al. |
| 8,424,529 B2 | 4/2013 | Efrati et al. |
| 8,428,702 B2 | 4/2013 | Wood et al. |
| 8,430,096 B2 | 4/2013 | Chambers |
| 8,430,098 B1 | 4/2013 | Buddharaju |
| 8,434,479 B2 | 5/2013 | Jafari et al. |
| 8,434,481 B2 | 5/2013 | Ogilvie et al. |
| 8,434,482 B2 | 5/2013 | Borrello |
| 8,434,485 B2 | 5/2013 | Osier et al. |
| 8,434,493 B1 | 5/2013 | McGhie et al. |
| 8,439,031 B1 | 5/2013 | Rothermel et al. |
| 8,439,034 B2 | 5/2013 | Decker et al. |
| 8,439,035 B2 | 5/2013 | Dantanarayana et al. |
| 8,440,004 B2 | 5/2013 | Taylor et al. |

(56) References Cited

U.S. PATENT DOCUMENTS

| | | |
|---|---|---|
| 8,443,800 B2 | 5/2013 | Turiello |
| 8,443,802 B2 | 5/2013 | Schaeffer, Jr. et al. |
| 8,448,639 B2 | 5/2013 | Richards et al. |
| 8,448,640 B2 | 5/2013 | Bassin |
| 8,448,641 B2 | 5/2013 | Jafari et al. |
| 8,449,713 B2 | 5/2013 | Brain |
| 8,453,640 B2 | 6/2013 | Martin et al. |
| 8,453,642 B2 | 6/2013 | Kwok et al. |
| 8,453,643 B2 | 6/2013 | Sanchez et al. |
| 8,453,644 B2 | 6/2013 | Soliman et al. |
| 8,453,647 B2 | 6/2013 | Caspary |
| 8,454,938 B2 | 6/2013 | Green et al. |
| 8,459,260 B2 | 6/2013 | Bassin |
| 8,459,261 B2 | 6/2013 | Ricciardelli et al. |
| 8,459,262 B2 | 6/2013 | Ahlmn et al. |
| 8,460,203 B2 | 6/2013 | Ricciardelli |
| 8,464,706 B2 | 6/2013 | Crockford et al. |
| 8,466,644 B2 | 6/2013 | Shimizu et al. |
| 8,469,025 B2 | 6/2013 | Mayer et al. |
| 8,469,026 B2 | 6/2013 | Blomberg et al. |
| 8,469,027 B2 | 6/2013 | Choncholas |
| 8,469,028 B2 | 6/2013 | Sung |
| 8,469,029 B2 | 6/2013 | Brown et al. |
| 8,474,455 B2 | 7/2013 | Soliman et al. |
| 8,485,181 B2 | 7/2013 | Daly |
| 8,485,193 B2 | 7/2013 | Worley |
| 8,485,194 B2 | 7/2013 | Guerra et al. |
| 8,490,622 B2 | 7/2013 | Stenzler et al. |
| 8,490,623 B2 | 7/2013 | Berthon-Jones et al. |
| 8,490,624 B2 | 7/2013 | Ho et al. |
| 8,496,001 B2 | 7/2013 | Schermeier et al. |
| 8,499,759 B2 | 8/2013 | DiBlasi et al. |
| 8,499,760 B2 | 8/2013 | Daly et al. |
| 8,499,763 B2 | 8/2013 | Ledwith |
| 8,500,879 B2 | 8/2013 | Phuc et al. |
| 8,505,533 B2 | 8/2013 | Raphael et al. |
| 8,511,305 B2 | 8/2013 | Liu et al. |
| 8,511,306 B2 | 8/2013 | Sanchez et al. |
| 8,511,307 B2 | 8/2013 | Berthon-Jones et al. |
| 8,511,309 B2 | 8/2013 | Worley |
| 8,517,012 B2 | 8/2013 | Daly et al. |
| 8,517,013 B2 | 8/2013 | Ni et al. |
| 8,517,014 B2 | 8/2013 | Farrell et al. |
| 8,517,015 B2 | 8/2013 | Montgomery et al. |
| 8,517,016 B2 | 8/2013 | Caro et al. |
| 8,517,017 B2 | 8/2013 | Bowditch et al. |
| 8,517,020 B2 | 8/2013 | Rehberg |
| 8,522,779 B2 | 9/2013 | Lee et al. |
| 8,522,780 B2 | 9/2013 | DeVries et al. |
| 8,522,782 B2 | 9/2013 | Lewis et al. |
| 8,522,785 B2 | 9/2013 | Berthon-Jones et al. |
| 8,528,546 B2 | 9/2013 | Heesch et al. |
| 8,528,547 B2 | 9/2013 | Dunsmore et al. |
| 8,528,551 B2 | 9/2013 | Mulcahy et al. |
| 8,528,552 B2 | 9/2013 | von Blumenthal |
| 8,528,553 B2 | 9/2013 | Wysocki et al. |
| 8,528,554 B2 | 9/2013 | Jafari et al. |
| 8,528,555 B2 | 9/2013 | Conrad et al. |
| 8,528,556 B2 | 9/2013 | Berthon-Jones |
| 8,528,557 B2 | 9/2013 | Duquette et al. |
| 8,528,558 B2 | 9/2013 | Drew et al. |
| 8,528,559 B2 | 9/2013 | Crutchfield |
| 8,534,284 B2 | 9/2013 | Dunsmore et al. |
| 8,534,286 B2 | 9/2013 | Pierro et al. |
| 8,534,618 B2 | 9/2013 | Mays |
| 8,539,949 B2 | 9/2013 | Leone et al. |
| 8,539,951 B1 | 9/2013 | Meyer et al. |
| 8,539,952 B2 | 9/2013 | Carbone et al. |
| 8,544,465 B2 | 10/2013 | Smith et al. |
| 8,544,467 B2 | 10/2013 | Berthon-Jones et al. |
| 8,544,468 B2 | 10/2013 | Arnott |
| 8,550,077 B2 | 10/2013 | Chatburn et al. |
| 8,554,298 B2 | 10/2013 | Doyle et al. |
| 8,554,305 B2 | 10/2013 | Tailor et al. |
| 8,555,887 B2 | 10/2013 | Lisogurski |
| 8,556,633 B2 | 10/2013 | Aaberg |
| 8,561,611 B2 | 10/2013 | Shissler et al. |
| 8,561,612 B2 | 10/2013 | Heinonen |
| 8,561,613 B2 | 10/2013 | Brambilla et al. |
| 8,567,393 B2 | 10/2013 | Hickle et al. |
| 8,567,396 B2 | 10/2013 | Whitesel et al. |
| 8,567,398 B2 | 10/2013 | Truschel et al. |
| 8,567,399 B2 | 10/2013 | Wondka et al. |
| 8,567,400 B2 | 10/2013 | Mansour et al. |
| 8,567,401 B2 | 10/2013 | Brewer et al. |
| 8,567,402 B2 | 10/2013 | Gunaratnam et al. |
| 8,573,200 B2 | 11/2013 | Busch et al. |
| 8,573,206 B2 | 11/2013 | Bourdon |
| 8,573,207 B2 | 11/2013 | Gutierrez |
| 8,573,208 B2 | 11/2013 | Ho |
| 8,578,934 B2 | 11/2013 | Morton et al. |
| 8,584,675 B2 | 11/2013 | Gandini |
| 8,593,278 B2 | 11/2013 | Churbock et al. |
| 8,595,639 B2 | 11/2013 | Milne et al. |
| 8,602,027 B2 | 12/2013 | Berthon-Jones et al. |
| 8,602,028 B2 | 12/2013 | Cree |
| 8,603,006 B2 | 12/2013 | Mulqueeny et al. |
| 8,607,785 B2 | 12/2013 | Fine et al. |
| 8,607,788 B2 | 12/2013 | Milne et al. |
| 8,607,789 B2 | 12/2013 | Milne et al. |
| 8,607,790 B2 | 12/2013 | Milne et al. |
| 8,607,791 B2 | 12/2013 | Milne et al. |
| 8,607,792 B2 | 12/2013 | Montgomery et al. |
| 8,607,793 B2 | 12/2013 | Armitstead et al. |
| 8,607,794 B2 | 12/2013 | Varga et al. |
| 8,607,796 B2 | 12/2013 | Thornton |
| 8,608,827 B2 | 12/2013 | Haberland et al. |
| 8,616,203 B2 | 12/2013 | Jaffe et al. |
| 8,616,204 B2 | 12/2013 | Montgomery et al. |
| 8,616,206 B2 | 12/2013 | Richard et al. |
| 8,616,208 B2 | 12/2013 | Chen et al. |
| 8,622,057 B2 | 1/2014 | Ujhazy et al. |
| 8,627,819 B2 | 1/2014 | DeVries et al. |
| 8,627,820 B2 | 1/2014 | Matthiessen et al. |
| 8,631,789 B2 | 1/2014 | Virr et al. |
| 8,631,797 B2 | 1/2014 | Freitag et al. |
| 8,631,799 B2 | 1/2014 | Davenport et al. |
| 8,636,002 B2 | 1/2014 | McAuley et al. |
| 8,636,003 B2 | 1/2014 | Deutscher et al. |
| 8,638,200 B2 | 1/2014 | Milne et al. |
| 8,640,696 B2 | 2/2014 | Pujol et al. |
| 8,640,697 B2 | 2/2014 | Reed |
| 8,640,698 B2 | 2/2014 | Darkin et al. |
| 8,640,699 B2 | 2/2014 | Baker, Jr. |
| 8,640,700 B2 | 2/2014 | Baker, Jr. |
| 8,640,701 B2 | 2/2014 | Richey, II |
| 8,646,447 B2 | 2/2014 | Martin et al. |
| 8,651,105 B2 | 2/2014 | Christopher et al. |
| 8,656,909 B2 | 2/2014 | Godfrey et al. |
| 8,656,912 B2 | 2/2014 | Johannessen |
| 8,656,913 B2 | 2/2014 | Kroupa |
| 8,656,914 B2 | 2/2014 | Almagro Frutos et al. |
| 8,661,108 B2 | 2/2014 | Gamaley et al. |
| 8,667,962 B2 | 3/2014 | Kenyon et al. |
| 8,667,963 B2 | 3/2014 | Sherman et al. |
| 8,676,323 B2 | 3/2014 | Ignagni et al. |
| 8,677,994 B2 | 3/2014 | Schermeier et al. |
| 8,677,995 B2 | 3/2014 | Boyle et al. |
| 8,677,996 B2 | 3/2014 | Sanchez |
| 8,677,997 B2 | 3/2014 | O'Connor et al. |
| 8,677,999 B2 | 3/2014 | Allum et al. |
| 8,678,000 B2 | 3/2014 | Ottestad |
| 8,683,997 B2 | 4/2014 | DeVries et al. |
| 8,683,998 B2 | 4/2014 | Swanson |
| 8,684,000 B2 | 4/2014 | Berthon-Jones et al. |
| 8,684,001 B2 | 4/2014 | Sun |
| 8,684,002 B2 | 4/2014 | Huber et al. |
| 8,689,787 B2 | 4/2014 | Dellaca' et al. |
| 8,689,788 B2 | 4/2014 | Rabi |
| 8,689,790 B2 | 4/2014 | Cannon |
| 8,689,791 B2 | 4/2014 | Hayek |
| 8,695,593 B2 | 4/2014 | Tehrani |
| 8,695,596 B2 | 4/2014 | Ronen et al. |
| 8,695,597 B2 | 4/2014 | Glaw |

(56) References Cited

U.S. PATENT DOCUMENTS

| | | | |
|---|---|---|---|
| 8,695,598 B2 | 4/2014 | Rittner et al. |
| 8,695,599 B2 | 4/2014 | Friberg et al. |
| 8,701,657 B2 | 4/2014 | Fine et al. |
| 8,701,659 B2 | 4/2014 | Cosic |
| 8,701,664 B2 | 4/2014 | O'dea |
| 8,701,665 B2 | 4/2014 | Tehrani |
| 8,701,666 B2 | 4/2014 | Frick et al. |
| 8,701,708 B2 | 4/2014 | Bricard et al. |
| 8,702,379 B2 | 4/2014 | Frater et al. |
| 8,703,697 B2 | 4/2014 | Quintin |
| 8,707,952 B2 | 4/2014 | Jourdain et al. |
| 8,707,953 B2 | 4/2014 | Wickham |
| 8,707,954 B2 | 4/2014 | McCarthy |
| 8,714,152 B2 | 5/2014 | Truschel et al. |
| 8,714,153 B2 | 5/2014 | Scarberry et al. |
| 8,714,155 B2 | 5/2014 | Hsiao |
| 8,714,156 B2 | 5/2014 | Cooke et al. |
| 8,720,439 B1 | 5/2014 | Kolkowski et al. |
| 8,720,440 B2 | 5/2014 | Montgomery et al. |
| 8,720,441 B2 | 5/2014 | Sinderby |
| 8,720,442 B2 | 5/2014 | Perine et al. |
| 8,721,561 B2 | 5/2014 | Thomas et al. |
| 8,728,059 B2 | 5/2014 | Karst et al. |
| 8,733,348 B2 | 5/2014 | Korneff et al. |
| 8,733,350 B2 | 5/2014 | Smaldone et al. |
| 8,733,353 B2 | 5/2014 | Kramer et al. |
| 8,733,355 B2 | 5/2014 | Turiello |
| 8,739,780 B2 | 6/2014 | Tang et al. |
| 8,739,789 B2 | 6/2014 | Wickham |
| 8,739,793 B2 | 6/2014 | Ho |
| 8,746,246 B2 | 6/2014 | Lueckenhoff |
| 8,746,247 B2 | 6/2014 | Mechlenburg |
| 8,746,248 B2 | 6/2014 | Jafari et al. |
| 8,752,546 B2 | 6/2014 | Acker et al. |
| 8,752,549 B2 | 6/2014 | Doyle |
| 8,753,435 B2 | 6/2014 | Atlas et al. |
| 8,757,151 B2 | 6/2014 | Johnstone et al. |
| 8,757,153 B2 | 6/2014 | Milne et al. |
| 8,757,154 B2 | 6/2014 | Schuller |
| 8,757,155 B2 | 6/2014 | Bellefeuille |
| 8,757,158 B2 | 6/2014 | Klemperer |
| 8,770,194 B2 | 7/2014 | Cree |
| 8,770,984 B2 | 7/2014 | Cegla |
| 8,776,790 B2 | 7/2014 | Gentner et al. |
| 8,776,791 B2 | 7/2014 | Huang et al. |
| 8,776,792 B2 | 7/2014 | Milne |
| 8,777,923 B2 | 7/2014 | Katz et al. |
| 8,783,247 B2 | 7/2014 | Newman, Jr. |
| 8,783,251 B2 | 7/2014 | Koledin |
| 8,783,257 B2 | 7/2014 | McAuley et al. |
| 8,789,526 B2 | 7/2014 | Kwok et al. |
| 8,789,527 B2 | 7/2014 | Carter et al. |
| 8,794,233 B2 | 8/2014 | Ahearn et al. |
| 8,794,234 B2 | 8/2014 | Jafari et al. |
| 8,794,235 B2 | 8/2014 | Garde et al. |
| 8,794,236 B2 | 8/2014 | Phuah et al. |
| 8,794,237 B2 | 8/2014 | Wilkinson et al. |
| 8,800,552 B2 | 8/2014 | Burns |
| 8,800,553 B2 | 8/2014 | Schmid et al. |
| 8,800,556 B2 | 8/2014 | Richey, II et al. |
| 8,800,557 B2 | 8/2014 | Andreiux |
| 8,800,562 B2 | 8/2014 | Burchell et al. |
| 8,807,133 B2 | 8/2014 | Anderson |
| 8,807,139 B1 | 8/2014 | Kostrzewski |
| 8,813,745 B2 | 8/2014 | Ho et al. |
| 8,813,746 B2 | 8/2014 | Mansour |
| 8,813,751 B2 | 8/2014 | Filho |
| 8,820,325 B2 | 9/2014 | Breen |
| 8,821,133 B2 | 9/2014 | Rogers, Jr. |
| 8,826,906 B2 | 9/2014 | Bassin |
| 8,833,367 B2 | 9/2014 | Kwok |
| 8,833,368 B2 | 9/2014 | Rapoport |
| 8,833,372 B2 | 9/2014 | Han et al. |
| 8,839,786 B2 | 9/2014 | Heidmann et al. |
| 8,844,521 B2 | 9/2014 | McCarthy |
| 8,844,524 B2 | 9/2014 | Kwok |
| 8,844,527 B2 | 9/2014 | Martin et al. |
| 8,844,531 B2 | 9/2014 | Witt et al. |
| 8,851,072 B2 | 10/2014 | Boyden et al. |
| 8,857,430 B2 | 10/2014 | Berthon-Jones |
| 8,857,432 B2 | 10/2014 | Fenton |
| 8,869,795 B2 | 10/2014 | Bassin |
| 8,875,706 B2 | 11/2014 | Meyer et al. |
| 8,875,707 B2 | 11/2014 | Aylsworth et al. |
| 8,881,723 B2 | 11/2014 | Frater |
| 8,881,724 B2 | 11/2014 | Choncholas et al. |
| 8,881,725 B2 | 11/2014 | Sinderby et al. |
| 8,881,726 B2 | 11/2014 | Wyatt |
| 8,881,727 B2 | 11/2014 | Aloia et al. |
| 8,881,728 B2 | 11/2014 | Sher et al. |
| 8,887,716 B2 | 11/2014 | Dubach |
| 8,893,716 B2 | 11/2014 | Ratner |
| 8,893,717 B2 | 11/2014 | Montgomery et al. |
| 8,893,718 B2 | 11/2014 | Heinonen |
| 8,893,719 B2 | 11/2014 | Lavi et al. |
| 8,895,083 B2 | 11/2014 | Solomon et al. |
| 8,899,232 B2 | 12/2014 | Farrugia et al. |
| 8,900,353 B2 | 12/2014 | Thompson et al. |
| 8,905,025 B2 | 12/2014 | Borrello |
| 8,905,026 B2 | 12/2014 | Grychowski et al. |
| 8,905,979 B2 | 12/2014 | Herting et al. |
| 8,910,627 B2 | 12/2014 | Iwatschenko et al. |
| 8,910,631 B2 | 12/2014 | Colla et al. |
| 8,910,632 B2 | 12/2014 | Tiedje |
| 8,910,633 B2 | 12/2014 | Younes |
| 8,915,247 B2 | 12/2014 | Chalvignac et al. |
| 8,915,248 B2 | 12/2014 | Wilkinson et al. |
| 8,919,343 B2 | 12/2014 | Radomski et al. |
| 8,919,344 B2 | 12/2014 | Bowditch et al. |
| 8,925,550 B2 | 1/2015 | Warren |
| 8,931,478 B2 | 1/2015 | Dunsmore et al. |
| 8,938,288 B2 | 1/2015 | Wood et al. |
| 9,114,224 B2 | 8/2015 | Avni |
| 9,168,347 B2 | 10/2015 | Stevens et al. |
| 9,174,015 B2 | 11/2015 | Stevens et al. |
| 9,227,032 B2 | 1/2016 | Kwok et al. |
| 9,238,115 B2 | 1/2016 | Homuth et al. |
| 9,259,546 B2 | 2/2016 | Garde et al. |
| 9,956,317 B2 | 5/2018 | Rahimian |
| 2002/0096173 A1 | 7/2002 | Berthon-Jones et al. |
| 2003/0051731 A1 | 3/2003 | Be'eri et al. |
| 2003/0062045 A1 | 4/2003 | Woodring et al. |
| 2003/0208465 A1 | 11/2003 | Yurko et al. |
| 2003/0225339 A1 | 12/2003 | Orr et al. |
| 2004/0100477 A1 | 5/2004 | Morita et al. |
| 2004/0216743 A1* | 11/2004 | Orr ............... A61M 16/0045 128/205.12 |
| 2004/0226562 A1 | 11/2004 | Bordewick |
| 2005/0005935 A1 | 1/2005 | Gradon |
| 2005/0016536 A1 | 1/2005 | Rapoport et al. |
| 2005/0039749 A1* | 2/2005 | Emerson ........... A61M 16/0006 128/204.23 |
| 2005/0051174 A1 | 3/2005 | Emerson |
| 2005/0098179 A1 | 5/2005 | Burton et al. |
| 2005/0139212 A1 | 6/2005 | Bourdon |
| 2005/0211249 A1 | 9/2005 | Wagner et al. |
| 2005/0235993 A1 | 10/2005 | Baecke et al. |
| 2006/0011195 A1 | 1/2006 | Zarychta |
| 2006/0137681 A1 | 6/2006 | Von Hollen et al. |
| 2006/0178245 A1 | 8/2006 | Schiller et al. |
| 2006/0260358 A1 | 11/2006 | Kun |
| 2006/0272642 A1 | 12/2006 | Chalvignac |
| 2007/0017522 A1 | 1/2007 | Be-Eri et al. |
| 2007/0017523 A1 | 1/2007 | Be-Eri et al. |
| 2007/0044796 A1 | 3/2007 | Zdrojkowski et al. |
| 2007/0089740 A1 | 4/2007 | Baumert et al. |
| 2007/0101999 A1 | 5/2007 | Duquette et al. |
| 2007/0186928 A1 | 8/2007 | Be'Eri |
| 2007/0189919 A1 | 8/2007 | Prince et al. |
| 2007/0193581 A1 | 8/2007 | Laurila et al. |
| 2007/0199566 A1* | 8/2007 | Be'eri ............. A61M 16/0069 128/204.23 |
| 2007/0283958 A1 | 12/2007 | Naghavi |
| 2008/0000475 A1 | 1/2008 | Hill |

(56) References Cited

U.S. PATENT DOCUMENTS

| | | |
|---|---|---|
| 2008/0000477 A1 | 1/2008 | Huster et al. |
| 2008/0000479 A1 | 1/2008 | Elaz et al. |
| 2008/0011301 A1 | 1/2008 | Qian |
| 2008/0029096 A1 | 2/2008 | Kollmeyer et al. |
| 2008/0053443 A1 | 3/2008 | Estes et al. |
| 2008/0053444 A1 | 3/2008 | Estes et al. |
| 2008/0086065 A1 | 4/2008 | Holm et al. |
| 2008/0092894 A1 | 4/2008 | Nicolazzi et al. |
| 2008/0142004 A1 | 6/2008 | Wasnick |
| 2008/0142011 A1 | 6/2008 | Aylsworth et al. |
| 2008/0142019 A1* | 6/2008 | Lewis ................ A61M 16/024 128/207.18 |
| 2008/0190428 A1 | 8/2008 | Yu |
| 2008/0196723 A1* | 8/2008 | Tilley ...................... A62B 7/10 128/204.23 |
| 2008/0223361 A1 | 9/2008 | Nieuwstad |
| 2008/0257349 A1 | 10/2008 | Hedner et al. |
| 2008/0283062 A1 | 11/2008 | Esposito, Jr. |
| 2008/0295839 A1 | 12/2008 | Habashi |
| 2009/0007915 A1 | 1/2009 | Brunner et al. |
| 2009/0171256 A1 | 7/2009 | Fiorina |
| 2010/0059055 A1 | 3/2010 | Brungart et al. |
| 2010/0108064 A1 | 5/2010 | Blackwell et al. |
| 2010/0113957 A1 | 5/2010 | Williams et al. |
| 2010/0116270 A1 | 5/2010 | Edwards et al. |
| 2010/0116272 A1 | 5/2010 | Row et al. |
| 2010/0122698 A1 | 5/2010 | Shaffer et al. |
| 2010/0126509 A1 | 5/2010 | Chang |
| 2010/0163043 A1 | 7/2010 | Hart et al. |
| 2010/0163046 A1 | 7/2010 | Fisher et al. |
| 2010/0168511 A1 | 7/2010 | Muni et al. |
| 2010/0174210 A1 | 7/2010 | Han et al. |
| 2010/0199991 A1 | 8/2010 | Koledin |
| 2010/0218764 A1 | 9/2010 | Kwok et al. |
| 2010/0224194 A1 | 9/2010 | Walker et al. |
| 2010/0224195 A1 | 9/2010 | Henry |
| 2010/0229865 A1 | 9/2010 | Boussignac |
| 2010/0229867 A1 | 9/2010 | Bertinetti et al. |
| 2010/0236551 A1 | 9/2010 | Enk |
| 2010/0258122 A1 | 10/2010 | Boussignac |
| 2010/0326441 A1 | 12/2010 | Zucker et al. |
| 2011/0029910 A1 | 2/2011 | Thiessen |
| 2011/0030685 A1 | 2/2011 | Wilkinson et al. |
| 2011/0061654 A1 | 3/2011 | Kuo |
| 2011/0094511 A1 | 4/2011 | Zachariah et al. |
| 2011/0100364 A1 | 5/2011 | Faram |
| 2011/0120471 A1 | 5/2011 | Freeman |
| 2011/0146680 A1 | 6/2011 | Conway |
| 2011/0168179 A1 | 7/2011 | Boone et al. |
| 2011/0174307 A1 | 7/2011 | Lessi et al. |
| 2011/0180070 A1 | 7/2011 | Ho et al. |
| 2011/0197881 A1 | 8/2011 | Abulrassoul et al. |
| 2011/0197882 A1 | 8/2011 | Truschel et al. |
| 2011/0203587 A1 | 8/2011 | Bertinetti et al. |
| 2011/0209704 A1 | 9/2011 | Jafari et al. |
| 2011/0232642 A1 | 9/2011 | Bliss et al. |
| 2011/0247619 A1 | 10/2011 | Formica et al. |
| 2011/0259330 A1 | 10/2011 | Jafari et al. |
| 2011/0259331 A1 | 10/2011 | Witt et al. |
| 2011/0265792 A1 | 11/2011 | Crawford et al. |
| 2011/0271960 A1 | 11/2011 | Milne et al. |
| 2011/0284000 A1 | 11/2011 | Schnaars et al. |
| 2011/0288428 A1 | 11/2011 | Valentine |
| 2011/0290240 A1 | 12/2011 | Meyer et al. |
| 2011/0297153 A1 | 12/2011 | Grimsey |
| 2011/0297155 A1 | 12/2011 | Shelly et al. |
| 2012/0003620 A1 | 1/2012 | Pittman et al. |
| 2012/0006325 A1 | 1/2012 | Kelly |
| 2012/0037160 A1 | 2/2012 | Sung |
| 2012/0040301 A1 | 2/2012 | Ngiam |
| 2012/0060836 A1 | 3/2012 | El-Shammaa et al. |
| 2012/0060838 A1 | 3/2012 | Laura Lapoint et al. |
| 2012/0060839 A1 | 3/2012 | Pittman et al. |
| 2012/0067348 A1 | 3/2012 | Steck et al. |
| 2012/0097164 A1 | 4/2012 | Rozario et al. |
| 2012/0103335 A1 | 5/2012 | Zeevi |
| 2012/0118289 A1 | 5/2012 | Han |
| 2012/0118290 A1 | 5/2012 | Sinderby et al. |
| 2012/0125333 A1 | 5/2012 | Bedford et al. |
| 2012/0145154 A1 | 6/2012 | Baloa Welzien et al. |
| 2012/0152248 A1 | 6/2012 | Richey, II et al. |
| 2012/0160242 A1 | 6/2012 | Gutirrez Fonseca et al. |
| 2012/0180791 A1 | 7/2012 | Ciccone |
| 2012/0190998 A1 | 7/2012 | Armitstead et al. |
| 2012/0192870 A1 | 8/2012 | Dugan et al. |
| 2012/0199129 A1 | 8/2012 | Kenyon et al. |
| 2012/0204868 A1 | 8/2012 | Allan et al. |
| 2012/0204875 A1 | 8/2012 | Brazy et al. |
| 2012/0216809 A1 | 8/2012 | Milne et al. |
| 2012/0234323 A1 | 9/2012 | Connor |
| 2012/0238801 A1 | 9/2012 | McQueen |
| 2012/0240931 A1 | 9/2012 | Shelford |
| 2012/0255460 A1 | 10/2012 | Kawakami et al. |
| 2012/0255551 A1 | 10/2012 | Boussignac |
| 2012/0272955 A1 | 11/2012 | Cool et al. |
| 2012/0279500 A1 | 11/2012 | Singvogel et al. |
| 2012/0283592 A1 | 11/2012 | Schuessler et al. |
| 2012/0285454 A1 | 11/2012 | Nibu et al. |
| 2012/0285460 A1* | 11/2012 | Smith ............... A61M 16/0006 128/205.24 |
| 2012/0304993 A1 | 12/2012 | Nitta et al. |
| 2012/0325220 A1 | 12/2012 | Heinonen et al. |
| 2013/0000644 A1 | 1/2013 | Thiessen |
| 2013/0019864 A1 | 1/2013 | Wondka |
| 2013/0025598 A1 | 1/2013 | Eiseman |
| 2013/0032147 A1 | 2/2013 | Robinson et al. |
| 2013/0032148 A1 | 2/2013 | Neely |
| 2013/0032150 A1 | 2/2013 | Zaiser et al. |
| 2013/0037026 A1 | 2/2013 | Miller |
| 2013/0042867 A1 | 2/2013 | Kwok et al. |
| 2013/0056007 A1 | 3/2013 | Pacey |
| 2013/0068227 A1 | 3/2013 | Adams |
| 2013/0092163 A1 | 4/2013 | Puccini, Sr. |
| 2013/0104883 A1 | 5/2013 | Lalonde |
| 2013/0104889 A1 | 5/2013 | Steinhauer et al. |
| 2013/0104890 A1 | 5/2013 | Steinhauer et al. |
| 2013/0104891 A1 | 5/2013 | Steinhauer et al. |
| 2013/0104892 A1 | 5/2013 | Steinhauer et al. |
| 2013/0104893 A1 | 5/2013 | Steinhauer et al. |
| 2013/0118493 A1 | 5/2013 | Umlauft et al. |
| 2013/0146055 A1 | 6/2013 | Jafari et al. |
| 2013/0167842 A1 | 7/2013 | Jafari et al. |
| 2013/0174838 A1 | 7/2013 | Youngblood |
| 2013/0174844 A1 | 7/2013 | Doll et al. |
| 2013/0184568 A1 | 7/2013 | Muni et al. |
| 2013/0186399 A1 | 7/2013 | Gutmark et al. |
| 2013/0192598 A1 | 8/2013 | Tomlin et al. |
| 2013/0192600 A1 | 8/2013 | Eklund et al. |
| 2013/0199530 A1 | 8/2013 | Burger |
| 2013/0199531 A1 | 8/2013 | Ramanathan et al. |
| 2013/0204082 A1 | 8/2013 | Fischer, Jr. |
| 2013/0206140 A1 | 8/2013 | Kepler et al. |
| 2013/0220324 A1 | 8/2013 | Jafari et al. |
| 2013/0220325 A1 | 8/2013 | Davis et al. |
| 2013/0228174 A1 | 9/2013 | Guo et al. |
| 2013/0228179 A1 | 9/2013 | Fischer, Jr. |
| 2013/0239970 A1 | 9/2013 | Pizzini |
| 2013/0239971 A1 | 9/2013 | Dantanarayana et al. |
| 2013/0247912 A1 | 9/2013 | Löser et al. |
| 2013/0263854 A1 | 10/2013 | Taylor et al. |
| 2013/0269699 A1* | 10/2013 | Gaussa ............. A61M 16/0875 128/205.23 |
| 2013/0284170 A1 | 10/2013 | Mansour et al. |
| 2013/0284171 A1 | 10/2013 | Adam et al. |
| 2013/0284176 A1 | 10/2013 | Dickerson et al. |
| 2013/0291863 A1 | 11/2013 | Ledwith |
| 2013/0291868 A1 | 11/2013 | Boussignac |
| 2013/0306072 A1 | 11/2013 | Moir et al. |
| 2013/0312743 A1 | 11/2013 | Kshirsagar et al. |
| 2013/0319413 A1 | 12/2013 | Porteous et al. |
| 2013/0340752 A1 | 12/2013 | Landis et al. |
| 2013/0340757 A1 | 12/2013 | Smith et al. |
| 2014/0000604 A1 | 1/2014 | Steinhauer et al. |
| 2014/0000616 A1 | 1/2014 | Haibach |

(56) References Cited

U.S. PATENT DOCUMENTS

| | | |
|---|---|---|
| 2014/0014108 A1 | 1/2014 | Dillard |
| 2014/0014109 A1 | 1/2014 | Grasmuck |
| 2014/0018605 A1 | 1/2014 | Soltesz et al. |
| 2014/0020684 A1 | 1/2014 | Klasek et al. |
| 2014/0032241 A1* | 1/2014 | Coffeng ............ A61B 5/743 705/3 |
| 2014/0041663 A1 | 2/2014 | Daly et al. |
| 2014/0060537 A1 | 3/2014 | Hansmann et al. |
| 2014/0069427 A1 | 3/2014 | Farnaby et al. |
| 2014/0069432 A1 | 3/2014 | Mebasser et al. |
| 2014/0090645 A1 | 4/2014 | Sears et al. |
| 2014/0090647 A1 | 4/2014 | Fuhrman et al. |
| 2014/0102449 A1 | 4/2014 | Lalonde |
| 2014/0102452 A1 | 4/2014 | Forrester |
| 2014/0116437 A1 | 5/2014 | Cook |
| 2014/0116441 A1 | 5/2014 | McDaniel |
| 2014/0144447 A1 | 5/2014 | Kuypers et al. |
| 2014/0150790 A1 | 6/2014 | Meyer et al. |
| 2014/0154134 A1 | 6/2014 | Leyva |
| 2014/0158131 A1 | 6/2014 | Kenyon et al. |
| 2014/0166013 A1 | 6/2014 | Stenzler et al. |
| 2014/0190481 A1 | 7/2014 | Jam |
| 2014/0202462 A1 | 7/2014 | Stoks et al. |
| 2014/0216460 A1 | 8/2014 | Bothma et al. |
| 2014/0216461 A1 | 8/2014 | Koeppel |
| 2014/0236041 A1 | 8/2014 | Gulliver et al. |
| 2014/0238412 A1 | 8/2014 | Fan |
| 2014/0261427 A1 | 9/2014 | Foote |
| 2014/0283836 A1 | 9/2014 | Kwok et al. |
| 2014/0299130 A1 | 10/2014 | Librett et al. |
| 2014/0299131 A1 | 10/2014 | Chodkowshi et al. |
| 2014/0299132 A1 | 10/2014 | Librett et al. |
| 2014/0305431 A1 | 10/2014 | Holley et al. |
| 2014/0311483 A1 | 10/2014 | Engelbreth et al. |
| 2014/0318540 A1 | 10/2014 | Brandt et al. |
| 2014/0338669 A1 | 11/2014 | Zhao et al. |
| 2014/0348955 A1 | 11/2014 | Baldassarre |
| 2014/0352695 A1 | 12/2014 | Friberg et al. |
| 2014/0352696 A1 | 12/2014 | Heidmann et al. |
| 2014/0373843 A1 | 12/2014 | Gray |
| 2014/0377377 A1 | 12/2014 | Potenziano et al. |
| 2015/0136134 A1 | 5/2015 | Kissel et al. |
| 2015/0231350 A1 | 8/2015 | Baloa Welzien et al. |
| 2018/0085541 A1 | 3/2018 | Ye et al. |

FOREIGN PATENT DOCUMENTS

| | | |
|---|---|---|
| EP | 1017352 B1 | 12/2004 |
| JP | H6-312158 A | 11/1994 |
| JP | 2009-509610 A | 3/2009 |
| JP | 2009-509610 A | 8/2009 |
| JP | 2007-502180 A | 1/2020 |
| WO | 1998049993 A1 | 11/1998 |
| WO | 2006004439 A2 | 1/2006 |
| WO | 2011116428 A1 | 9/2011 |
| WO | 2013/182944 A1 | 12/2013 |

OTHER PUBLICATIONS

Extended European Search Report for European Patent Application No. 16773588.5 dated Mar. 5, 2018; 7 pages.

Nippy® Clearway Cough Assistor Instructions for Use Manual; Doc 2007 Version 5; Feb. 2015; 42 pages.

Extended European Search Report for European Patent Application No. 19173636.2 dated Jul. 5, 2019; 7 pages.

Notification of Reasons for Rejection for Japanese Patent Application No. 2019-019296 dated Jan. 21, 2020 and its English translation (9 pages).

Examination report No. 1 for standard patent application for Australian Patent Application No. 2016243801 dated Dec. 4, 2019; 5 pages.

* cited by examiner

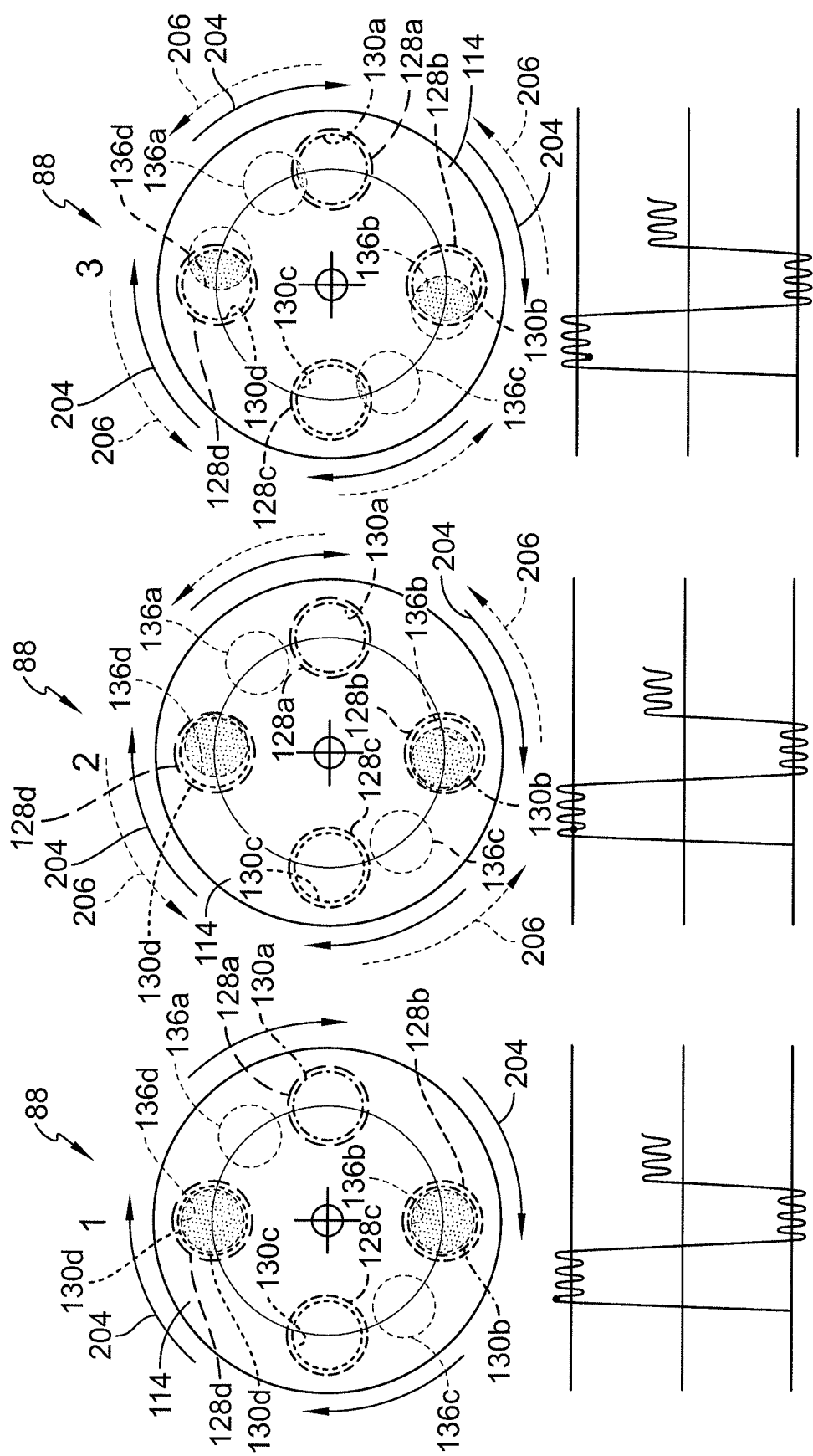

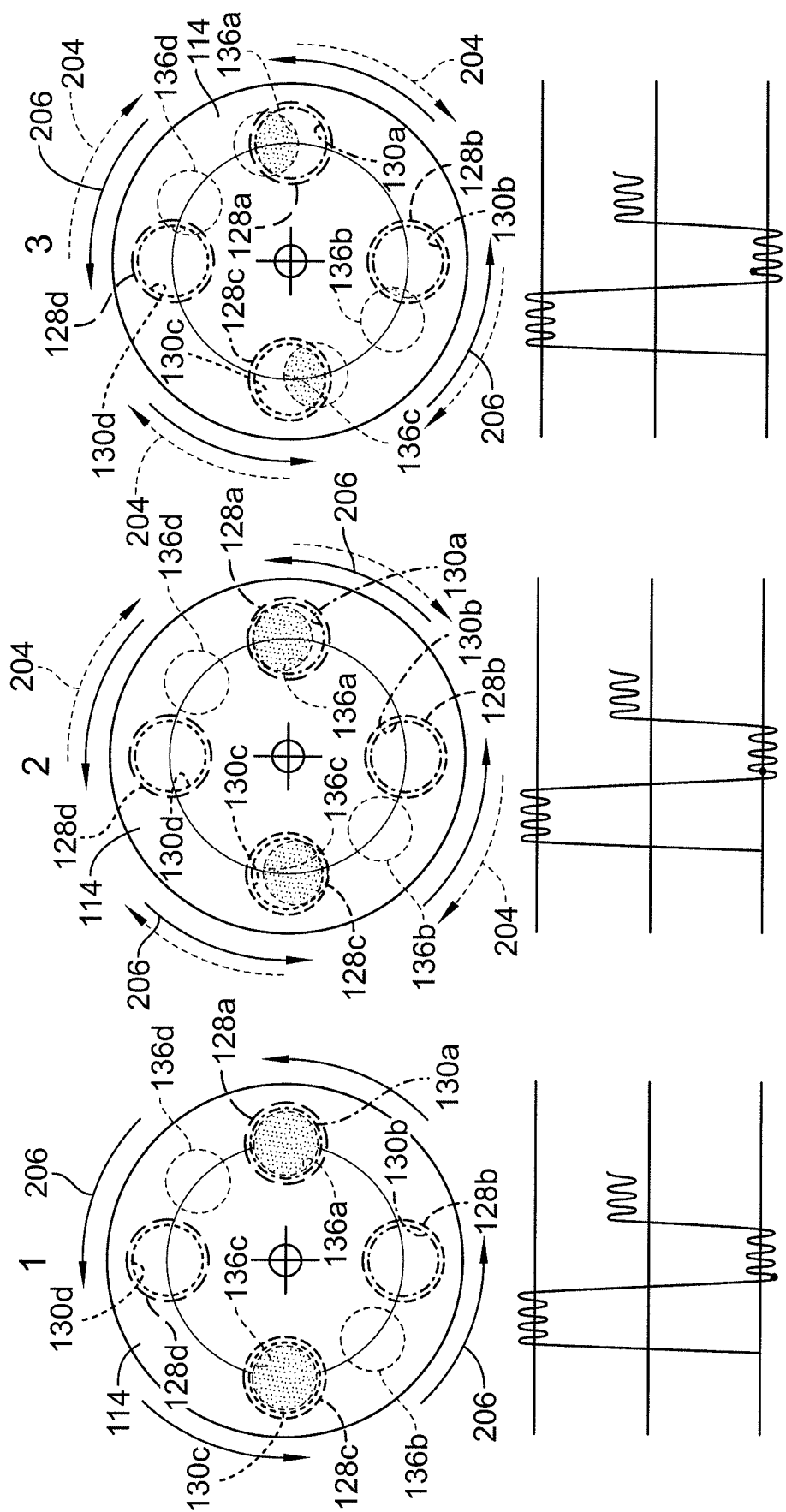

RESPIRATORY THERAPY CYCLE CONTROL AND FEEDBACK

The present application is a continuation of U.S. application Ser. No. 15/563,201, filed Sep. 29, 2017, which is a U.S. national phase of PCT/SG2016/050166, filed on Apr. 1, 2016, which claimed priority, under 35 U.S.C. § 119(a), of Malaysian Patent Application No. PI 2015000844 which was filed Apr. 2, 2015 and which also claimed the benefit, under 35 U.S.C. § 119(e), of U.S. Provisional Patent Application No. 62/170,335 which was filed Jun. 3, 2015, and each of which is hereby incorporated by reference herein.

BACKGROUND

The present disclosure relates to respiratory devices and particularly, to manifolds for respiratory therapy devices. More particularly, the present disclosure relates to respiratory devices that are operable to apply varying levels of oscillating pressure to an airway of a patient.

Respiratory devices that provide positive pressure to a person's airway are known. For example, there are Continuous Positive Airway Pressure (CPAP) devices that apply positive pressure to a person's airway at a substantially constant level during the person's inhalation and exhalation. There are also Bi-Level CPAP devices that apply varying levels of positive pressure to a person, such as applying a first amount of positive pressure during inhalation and a second amount of positive pressure during exhalation.

Respiratory devices that provide negative pressure or suction to a person's airway are also known. One category of such devices is mechanical insufflation/exsufflation (MIE) devices. These devices are sometimes referred to as cough assist devices. This is because application of positive pressure followed by application of negative pressure to a person's airway simulates a cough and assists the person in expelling mucus from their airway. One such known cough assist device is the VITALCOUGH™ System available from Hill-Rom Company, Inc. In this regard, see U.S. Pat. No. 8,539,952 which is hereby incorporated by reference herein.

Respiratory devices that are capable of applying both positive and negative pressure to a person's airway sometimes have a pressure source, such as a blower, and at least one valve that changes position to selectively connect either the outlet of the blower or the inlet of the blower to a patient interface, such as a mask or mouthpiece and related tubing, to apply the positive pressure or the negative pressure, respectively to the person's airway. Other respiratory devices have separate positive pressure and negative pressure sources.

Some respiratory devices include additional structural elements, such as one or more valves, diaphragm pumps, acoustic devices, or piezoelectric devices that operate to provide oscillations in the baseline pressure levels being applied to the person's airway. These additional structural elements to produce the oscillations add cost, size and weight to the respiratory device. Patients and caregivers, therefore, may appreciate respiratory devices capable of producing oscillatory pressures, such as positive pressures or negative pressures or both, but that are smaller, less expensive, and lighter in weight than known respiratory devices.

SUMMARY

An apparatus, system, or method may comprise one or more of the features recited in the appended claims and/or the following features which, alone or in any combination, may comprise patentable subject matter:

A respiratory device may include a blower that may have an inlet and an outlet, a patient interface, and a valve that may include a valve member that is rotatable through a first angular displacement in a first direction from a first position to a second position. The outlet of the blower may be coupled to the patient interface so that positive pressure may be provided to a patient's airway via the patient interface when the valve member is in the first position. The inlet of the blower may be coupled to the patient interface so that negative pressure may be provided to the patient's airway via the patient interface when the valve member is in the second position. The valve member may be rotatably oscillated back and forth through a second angular displacement that may be smaller than the first angular displacement in the first direction and a second direction opposite to the first direction when the valve member is in the first position and when the valve member is in the second position so that oscillations in the positive pressure and negative pressure, respectively, may be provided to the patient's airway.

In some embodiments, the first angular displacement may be less than 90°, such as optionally being about 22.5°. The second angular displacement may be about 10°, for example. A frequency of oscillation of the valve member may be adjustable between about 1 Hertz and about 20 Hertz. The respiratory device may have a motor that may be operable to rotate and oscillate the valve member. The motor may include a stepper motor, for example.

In some embodiments, the valve member may include a rotatable plate and the valve may include a pair of stationary plates between which the rotatable plate may be sandwiched. The rotatable plate may have a circular outer periphery, for example. The valve may further include an annular shim that may be situated between the pair of stationary plates and that may surround the outer periphery of the rotatable plate.

If desired, the stationary plates may have four holes. A center of each hole of the four holes of the stationary plates may be spaced from another center of the four holes by about 90° around an axis about which the rotatable plate may rotate. The rotatable plate may have four holes grouped into pairs of holes. A center of each hole of the pair of holes of the rotatable plate may be spaced from a center of the other hole of the pair by about 45° around the axis. A first plate of the pair of stationary plates may have a first hole and a second hole of its four holes pneumatically coupled to the inlet of the blower and may have a third hole and fourth hole of its four holes pneumatically coupled to the outlet of the blower.

In some embodiments, when the rotatable plate is in the first position, a first hole of the four holes of the rotatable plate may be aligned with the first hole of the first stationary plate and a solid portion of the rotatable plate may block the second hole of the first stationary plate. When the rotatable plate is in the second position, the first hole of the first stationary plate may be blocked by another solid portion of the rotatable plate and a second hole of the rotatable plate may be aligned with the second hole of the first stationary plate.

According to this disclosure, when the rotatable plate is in the first position, a third hole of the rotatable plate may be aligned with the third hole of the first stationary plate and another solid portion of the rotatable plate may block the fourth hole of the first stationary plate. When the rotatable plate is in the second position, the third hole of the first stationary plate may be blocked by yet another solid portion of the rotatable plate and a fourth hole of the rotatable plate may be aligned with the fourth hole of the first stationary plate.

In some embodiments, a second plate of the pair of stationary plates may have a first hole and a second hole of its four holes pneumatically coupled to the patient interface and may have a third hole and fourth hole of its four holes pneumatically coupled to atmosphere. When the rotatable plate is in the first position, a first hole of the four holes of the rotatable plate may be aligned with the first hole of the second stationary plate and a solid portion of the rotatable plate may block the second hole of the second stationary plate. When the rotatable plate is in the second position, the first hole of the second stationary plate may be blocked by another solid portion of the rotatable plate and a second hole of the rotatable plate may be aligned with the second hole of the second stationary plate.

According to this disclosure, when the rotatable plate is in the first position, a third hole of the rotatable plate may be aligned with the third hole of the second stationary plate and another solid portion of the rotatable plate may block the fourth hole of the second stationary plate. When the rotatable plate is in the second position, the third hole of the second stationary plate may be blocked by yet another solid portion of the rotatable plate and a fourth hole of the rotatable plate may be aligned with the fourth hole of the second stationary plate.

In some embodiments, the valve member may include a rotatable spool that may be located within a stationary cylinder. The rotatable spool may have a first set of holes and the stationary cylinder may have a second set of holes. A first subset of the first set of holes of the rotatable spool may align with a first subset of the second set of holes of the stationary cylinder when the rotatable spool is in the first position and a second subset of holes of the second holes may be blocked by solid portions of the rotatable spool. A second subset of the first set of holes of the rotatable spool may align with the second subset of the second set of holes of the stationary cylinder when the rotatable spool is in the second position and the first subset of holes of the second holes may be blocked by other solid portions of the rotatable spool.

In some embodiments, a speed of the blower may be controlled so that the positive pressure provided to the airway of the patient may substantially match a positive target pressure that may be selected by a user and so that the negative pressure provided to the airway of the patient may substantially match a negative target pressure that may be selected by the user. The blower speed may be controlled so that a positive rest pressure, less than the positive target pressure, may be provided to the airway of the patient after the negative target pressure is applied to the airway of the patient and before the next positive target pressure is applied to the airway of the patient. The blower speed may be controlled so that a sigh pressure is applied to the airway of the patient at the end of a therapy session, the sigh pressure being greater than the positive rest pressure but less than the positive target pressure.

The respiratory device may further include a sensor that may sense a beginning of an inspiration of the patient and control circuitry coupled to the sensor and to the valve. The control circuitry may signal the valve to move to the first position in response to the sensor sensing the beginning of the inspiration of the patient. The control circuitry may signal the blower to operate to provide the positive pressure to the airway of the patient at a positive target pressure. The sensor may comprise a pressure sensor or a flow sensor or both, for example.

In some embodiments, the control circuitry may be programmable with a pause time during which sensing of the beginning of an inspiration of the patient may be ignored by the control circuitry and the control circuitry may signal the blower to operate to provide a rest pressure to the airway of the patient. The rest pressure may be a positive pressure that is less than the positive target pressure, for example.

In some embodiments, the valve member may be bow-tie shaped. Alternatively or additionally, the respiratory device may further include a third stationary plate that may be situated between the second stationary plate and the rotatable plate. In such embodiments, at least one spring may be situated between the second stationary plate and the third stationary plate to bias the third stationary plate against the rotatable plate. In some embodiments, each of the stationary plates may have four holes and the third stationary plate may be formed to include four tubular portions. Each tubular portion may be in registry with a respective hole of the four holes of the second stationary plate. Optionally, the at least one spring may include four springs. Each spring of the four springs may be mounted on a respective tubular portion of the four tubular portions.

In some contemplated embodiments, the second stationary plate may include an annular rim that may surround a first outer periphery of the third stationary plate and a second outer periphery of the rotatable plate. In some such embodiments, the second stationary plate may include an annular flange that may project radially from the annular rim. The annular flange may be fastened to the first stationary plate.

The respiratory device may further include control circuitry coupled to the blower and to the valve and may further include a graphical user interface (GUI) coupled to the control circuitry. Optionally, one or more of the following may be coupled to the control circuitry: a port for connection to a wireless communication module, a universal serial bus (USB) port, and a port for connection to a pulse oximetry device. In some embodiments, the GUI may be operable to display one or more of the following: peak flow information, pressure information, flow information, volume information, a pressure graph, a volume graph, a flow graph, a flow vs. volume graph, and a pressure vs. time graph.

According to this disclosure, the respiratory device may further include a wireless communication module that may be operable to transmit data wirelessly from the respiratory device. The wireless communication module may operate according to the Bluetooth protocol, if desired. The wireless communication module may receive information wirelessly and provide the information to the control circuitry of the respiratory device.

The respiratory device may further include a housing in which the blower and valve are housed and a hose connector that may be coupled to the housing. The hose connector may be configured to retain a hose of the patient interface adjacent the housing when the patient interface is not in use. In some embodiments, the housing may include a handle and the hose connector may include a hook extending from a back of the handle. In some embodiments, the housing may include a top wall and the hose connector may comprise a hose clip coupled to the top wall. The respiratory device may include a power cord extending from the housing and the hose clip may be configured as a cord wrap around which the power cord may be wrapped when not in use.

According to this disclosure, the respiratory device may further include a port pneumatically coupled to the valve and an adapter that may interconnect the port with a hose of the patient interface. The respiratory device may include a housing in which the blower and valve are housed and a carrying case in which the housing may fit. The carrying case may have a section with a door that may be openable to provide access to user controls on the housing without the need to remove the housing from the case. In some embodiments, the door may pivot upwardly from a closed position to an open position to expose the user controls for use. In some embodiments, the door may pivot downwardly from a closed position to an open position to expose the user controls for use. Optionally, the carrying case may be configured for attachment to a wheel chair.

According to an aspect of this disclosure, a respiratory device may include a blower that may have an inlet and an outlet, a patient interface, and a valve that may include a valve member that may be operable to oscillate by cyclically rotating through an angular displacement in a first direction and in a second direction opposite to the first direction. The blower may be operable to produce an inhalation pressure, an exhalation pressure that may be less than the inhalation pressure, and a rest pressure that may be less than the inhalation pressure and more than the exhalation pressure. The valve member may be operable to oscillate during the application of the inhalation pressure, the exhalation pressure and the rest pressure so that oscillations in the inhalation pressure, the exhalation pressure, and the rest pressure respectively, may be provided to the patient's airway.

In some embodiments, the angular displacement may be less than 90°, such as possibly being less than 22.5°, for example. It is contemplated that the angular displacement may be about 10°, if desired. A frequency of oscillation of the valve member may be adjustable between about 1 Hertz and about 20 Hertz in some embodiments. The respiratory device may further have a motor that may be operable to rotate and oscillate the valve member. The motor may comprise a stepper motor, for example.

According to another aspect of this disclosure, a respiratory device may include a blower that may have an inlet and an outlet, a patient interface, a valve that may be coupled to the blower and that may be operable to control a pressure applied to the patient interface, a sensor that may sense at least one of pressure and flow applied to the patient interface, and control circuitry that may be coupled to the blower, the valve, and the sensor. The control circuitry operating the blower and the valve to apply a first threshold pressure to the patient interface for a first preset amount of time in response to an inspiratory trigger being sensed by the sensor, the control circuitry operating the blower and the valve to apply a second threshold pressure to the patient interface during a rest phase that occurs after the first preset amount of time, the control circuitry operating to ignore one or more inspiratory triggers that are sensed by the sensor and that occur during the rest phase.

In some embodiments, the control circuitry may operate the blower and the valve to apply a third threshold pressure for a second preset amount of time after the first preset amount of time and before the rest phase but this need not be the case. It is contemplated that the first threshold pressure may comprise a first positive pressure and the second threshold pressure may comprise a negative pressure. It is also contemplated that the second threshold pressure may comprise a second positive pressure that may be less than the first positive pressure.

According to this disclosure, the valve may be selectively coupleable to the blower inlet and the blower outlet so that positive pressure and negative pressure may be selectively applied to the patient interface. If desired, the valve may be operable to oscillate the positive pressure and the negative pressure applied to the patient interface. The valve may include a rotatable plate that may be rotated through a first angular displacement to change between application of the positive pressure to the patient interface and application of the negative pressure to the patient interface. The rotatable plate may be moved back and forth through a second angular displacement to oscillate the positive pressure and the negative pressure. The second angular displacement may be less than the first angular displacement.

In some embodiments, the valve may include a rotatable spool that may be rotated through a first angular displacement to change between application of the positive pressure to the patient interface and application of the negative pressure to the patient interface. The rotatable spool may be moved back and forth through a second angular displacement to oscillate the positive pressure and the negative pressure. The second angular displacement may be less than the first angular displacement.

In some embodiments, the control circuitry may ignore a preset number of inspiratory triggers sensed by the sensor during the rest phase and then may operate the blower and the valve to reapply the first threshold pressure in response to the next inspiratory trigger sensed by the sensor after the preset number of inspiratory triggers were ignored. Alternatively or additionally, the rest phase may last for at least a preset rest duration and the control circuitry may operate the blower and the valve to reapply the first threshold pressure in response to the next inspiratory trigger sensed by the sensor after the preset duration.

In some embodiments, the control circuitry may operate the blower and the valve so that a sigh pressure may be applied to the patient interface at the end of a therapy session. The sigh pressure may be different than the first threshold pressure and may be different than the second threshold pressure. For example, the sigh pressure may be less than the first threshold pressure and greater than the second threshold pressure.

According to an aspect of this disclosure, a respiratory device may include a pressure source to produce pressure to be applied to a patient's airway, a housing that may contain the pressure source, an outlet port that may be accessible on the housing, and at least one patient interface that may be configured to be coupled to the outlet port. The patient interface may include a filter unit that may include an air filter carrier and at least one prong that may extend from the air filter carrier. The respiratory device may have at least one switch that may be situated in the housing. The housing may have at least one prong-receiving aperture adjacent the outlet port. The at least one prong may extend through the aperture and may activate the switch when the respective patient interface is coupled to the outlet port. The pressure source may be disabled from operation unless the at least one switch is activated.

In some embodiments, the at least one patient interface may include a first patient interface and a second patient interface. The at least one prong of the first patient interface may have only one prong and the at least one prong of the second patient interface may have two prongs. The at least one switch may include first and second switches and the at least one prong-receiving aperture may include first and second apertures. The respiratory device may have a controller that may distinguish whether the first patient interface or the second patient interface is coupled to the outlet port based on how many of the first and second switches are activated. Thus, in some embodiments, it is contemplated that therapy mode options that may be delivered through the outlet port may be different depending upon which of the first and second patient interfaces are coupled to the outlet port.

In some embodiments having a first patient interface and a second patient interface, the at least one prong of the first patient interface may include only two prongs and the at least one prong of the second patient interface may include three prongs. In such embodiments, the at least one switch may include first, second, and third switches and the at least one prong-receiving aperture may include first, second and third apertures. Further in such embodiments, the respiratory device may include a controller that may distinguish whether the first patient interface or the second patient interface is coupled to the outlet port based on how many of the first and second switches are activated. Thus, in these embodiments, therapy mode options delivered through the outlet port may be different depending upon which of the first and second patient interfaces are coupled to the outlet port.

In some embodiments, the respiratory device may further include a controller and a user input that may be operable to signal the controller to override the disabling of the pressure source when the switch is not activated thereby to permit the pressure source to operate even if the at least one switch is not activated. For example, the user input may be an input on a graphical display screen such as one or more icons or buttons.

According to a further aspect of the present disclosure, a handset for a respiratory device may include a generally banana-shaped tube that may have an upper surface that may be generally convex from end-to-end of the generally banana-shaped tube and a bottom surface that may be generally concave from end-to-end of the generally banana-shaped tube. The generally banana-shaped tube may have opposite first and second open ends and may have a nebulizer port that may be provided at an apex of the upper surface such that, in use, a nebulizer may extend upwardly from a top of the handset.

In some embodiments, the handset may further include a plug that may close the nebulizer port when the nebulizer is absent. The nebulizer port may include a cylindrical wall that may project into an interior region of the generally banana-shaped tube. Alternatively or additionally, the nebulizer port may include an annular ridge that may extend upwardly from the apex of the upper surface.

In some embodiments, the handset may further have an aperture that may extend through the generally banana-shaped tube adjacent the first open end of the generally banana-shaped tube. In such embodiments, the handset may also have a ring that may be rotatable between a first position in which the aperture may be open to atmosphere and a second position in which the aperture may be closed.

In some embodiments, the ring may include a sleeve that may wrap around a majority of a circumference of the generally banana-shaped tube in abutting rotative bearing engagement therewith and the ring may have an offset portion that may be coupled to the sleeve and that may define a channel that aligns with the aperture when the ring is in the first position so that the aperture may communicate with atmosphere through the channel and that may be out of alignment with the aperture when the ring is in the second position.

The generally banana-shaped tube may have first and second depressions and the ring may include a flexible finger with a detent that may be received in the first depression when the ring is in the first position and that may be received in the second depression when the ring is in the second position. The generally banana-shaped tube may have a circumferential groove formed therearound and the sleeve of the ring may include at least one tab that may project into the groove to retain the ring on the generally banana-shaped tube.

In some embodiments, the ring may include a finger tab that may extend outwardly from the offset portion of the ring. The finger tab may be usable to rotate the ring relative to the generally banana-shaped tube between the first and second positions. The aperture may include an open slot located at the upper surface. The slot may be oriented in a longitudinal dimension of the generally banana-shaped tube.

According to still a further aspect of this disclosure, a respiratory device may include a pressure source to produce pressure to be applied to a patient's airway, a housing that may contain the pressure source, an outlet port that may be accessible on the housing, a valve that may be situated pneumatically between the pressure source and the outlet port, and at least one pressure sensor and at least one flow sensor to measure pressure and flow, respectively, in a flow path that may be between the valve and the outlet port. The respiratory device may include a patient interface that may have a tube having a first end that may be coupled to the outlet port and a mask that may be coupled to a second end of the tube. The respiratory device may also include a controller that may receive signals from the pressure sensor and the flow sensor to determine an inspiratory trigger indicative that the patient may have started to inhale. The pressure source or the valve or both may be operationally adjusted in response to detection of the inspiratory trigger. Based on a flow sensor signal from the flow sensor the controller may be configured to determine mask removal or mask leakage and to stop operation of the pressure source.

In some embodiments, the controller may determine mask removal by comparing the flow sensor signal to an open flow threshold on an iterative basis. For example, at least fifty iterations of flow sensor signal data point comparisons to the open flow threshold may be required before the operation of the pressure source may be stopped. Each iteration may take about 5 milliseconds in some embodiments.

In some embodiments, the controller may determine mask leakage by comparing the flow sensor signal to a leakage threshold on an iterative basis. For example, at least fifty iterations of flow sensor signal data point comparisons to the leakage threshold may be required before the operation of the pressure source may be stopped. Each iteration may take about 5 milliseconds in some embodiments. It is contemplated that, in some embodiments, mask leakage less than the leakage threshold and greater than no leakage may result in continued operation of the pressure source.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which:

FIG. 10 is a diagrammatic view showing, in an upper portion of the view, the rotatable plate being in a maximum open position relative to the stationary plates during application of a maximum amount of positive pressure from the blower to the patient and showing, in a lower portion of the view, a graph showing oscillatory positive pressure, negative pressure and rest pressure profiles with a dot on the oscillatory positive pressure profile corresponding to the position of the rotatable plate in the upper portion of the view;

FIG. 11 is a diagrammatic view, similar to FIG. 10, showing, in an upper portion of the view, the rotatable plate being in an intermediate position relative to the stationary plates during application of an intermediate or baseline amount of positive pressure from the blower to the patient and showing, in a lower portion of the view, a graph similar to that of FIG. 10 but with a dot on the oscillatory positive pressure profile corresponding to the intermediate position of the rotatable plate in the upper portion of the view;

FIG. 12 is a diagrammatic view, similar to FIGS. 10 and 11, showing, in an upper portion of the view, the rotatable plate being in a minimally open position relative to the stationary plates during application of a minimum amount of positive pressure from the blower to the patient and showing, in a lower portion of the view, a graph similar to that of FIGS. 10 and 11 but with a dot on the oscillatory positive pressure profile corresponding to the minimally open position of the rotatable plate in the upper portion of the view;

FIG. 13 is a diagrammatic view showing, in an upper portion of the view, the rotatable plate being in a maximum open position relative to the stationary plates during application of a maximum amount of negative pressure from the blower to the patient and showing, in a lower portion of the view, a graph similar to that of FIGS. 10-12 but with a dot on the oscillatory negative pressure profile corresponding to the position of the rotatable plate in the upper portion of the view;

FIG. 14 is a diagrammatic view, similar to FIG. 13, showing, in an upper portion of the view, the rotatable plate being in an intermediate position relative to the stationary plates during application of an intermediate or baseline amount of negative pressure from the blower to the patient and showing, in a lower portion of the view, a graph similar to that of FIG. 13 but with a dot on the oscillatory negative pressure profile corresponding to the intermediate position of the rotatable plate in the upper portion of the view;

FIG. 15 is a diagrammatic view, similar to FIGS. 13 and 14, showing, in an upper portion of the view, the rotatable plate being in a minimally open position relative to the stationary plates during application of a minimum amount of negative pressure from the blower to the patient and showing, in a lower portion of the view, a graph similar to that of FIGS. 13 and 14 but with a dot on the oscillatory negative pressure profile corresponding to the minimally open position of the rotatable plate in the upper portion of the view;

DETAILED DESCRIPTION

Figure 1:
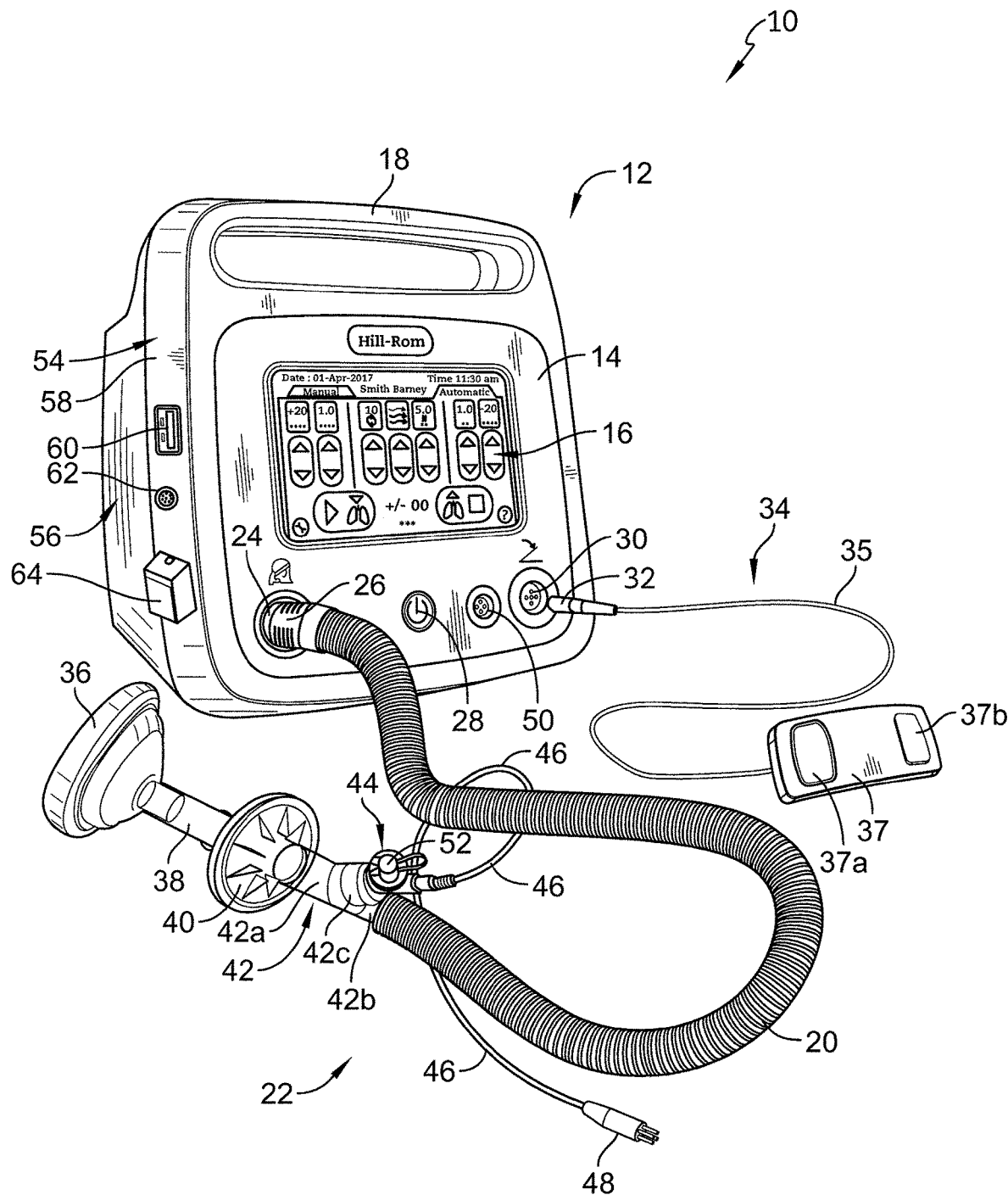
FIG. 1 is a perspective view of a respiratory device having a housing, a patient interface including a hose coupled to the housing at a hose port and a mask at an end of the hose, a foot switch having a connector arranged for connection to an electrical connector of the housing, a graphical user interface (GUI) accessible on a front wall of the housing to control operation of the respiratory device, and a wireless communication module coupled to a sidewall of the housing.
Figure 2:
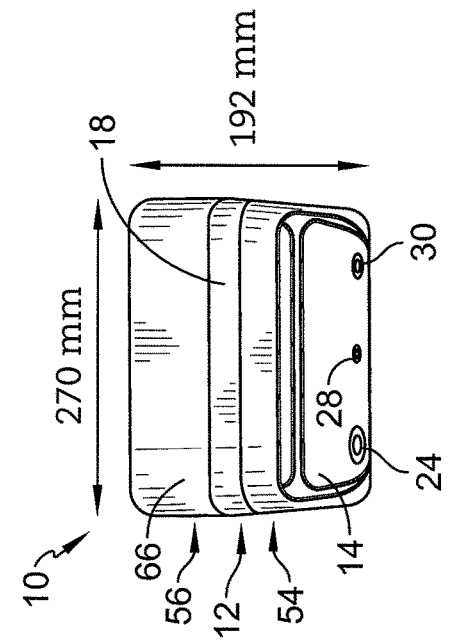
FIG. 2 is a front elevation view of the respiratory device of FIG. 1.

A respiratory device 10 includes a housing 12 having a front wall 14 on which a graphical user interface 16 is accessible to enter user inputs into device 10 and to see displayed information regarding the operation of device 10 as shown in FIG. 1. Housing 12 is configured with a handle 18 at its top which is gripped by a person to carry device 10. At a bottom region of front wall 14 of housing 12, a hose 20 of a patient interface 22 is attached to a hose port 24 by a hose adapter 26 as will be discussed in further detail below in connection with FIGS. 34-37. To the right of hose port 24 on front wall 14 of housing 12 is an on/off button 28 that is pressed sequentially to turn device 10 on and off. Device 10 also has a switch port 30 to which a coupler 32 of a foot switch controller 34 couples, if desired. Foot switch controller 34 includes an electrical cable 35 that extends from coupler 32 to a foot switch housing 37 that includes a first switch 37a and a second switch 37b.

As will be discussed in further detail below, device 10 is operable as an insufflation/exsufflation device or, as such devices are sometimes called, a cough assist device. Thus, device 10 is capable of applying positive pressure and negative pressure to a patient's airway, the positive pressure being applied during insufflation and the negative pressure being applied during exsufflation. In a manual mode of device 10 when foot switch controller 34 is being used, one of switches 37a, 37b is pressed to signal device 10 to apply the positive insufflation pressure to the patient through the patient interface 22 and the other of switches 37a, 37b is pressed to signal device 10 to apply the negative insufflation pressure to the patient through the patient interface 22. If neither of switches 37a, 37b is pressed, then a rest or pause pressure is applied to the patient's airway. If foot switch controller 34 is not being used, then user inputs on GUI 16 are selected during the manual mode of device 10 to switch between insufflation, exsufflation, and pause pressures. In some embodiments, device 10 is operable to provide other modes of respiratory therapy such as continuous positive expiratory pressure (CPEP) and continuous high frequency oscillation (CHFO), just to name a couple. CPEP and CHFO are sometimes referred to herein, collectively, as Intrapulmonary Percussive Ventilation (IPV).

In the illustrative example, patient interface 22 includes a mask 36 which is configured to engage a patient's face and generally seal the area around the patient's nose and mouth. In other embodiments, patient interface 22 includes a mouthpiece (not shown, but well-known in the art) rather than the illustrative mask 36 and the mouthpiece has an end portion that a patient places inside his or her mouth. Patient interface 22 includes a first tubular segment 38 extending from mask 36, a filter unit 40 coupled to tubular segment 38, and a tubular Y-connector 42 that interconnects filter unit 40 and hose 20. Filter unit 40 includes a filter (not shown) to filter the air and/or breathing gas being inspired and expired while the patient is wearing mask 36 during the operation of device 10.

Tubular Y-connector 42 has a first portion 42a that connects to filter unit 40, a second portion 42b that connects to an end of hose 20, and a third portion 42c that connects to a nebulizer 44. Use of nebulizer 44 with device 10 is optional and so, in those embodiments in which nebulizer 44 is omitted, tubular Y-connector 42 is not needed and is replaced by a tubular segment (not shown) that is similar to tubular segment 38. However, in the illustrative example, nebulizer 44 is a vibrating screen or vibrating plate nebulizer and so an electrical cable 46 extends from nebulizer 44 and terminates at an electrical connector 48 which is configured for coupling to an electrical nebulizer port 50 located at the lower region of front face 14 of housing 12 of device 10 between button 28 and port 30.

Nebulizer 44 includes a cap 52 which is opened from its illustrative closed position so that a nebulizer container (not shown) that contains a liquid substance or medicament is able to be attached to the nebulizer 44. When connector 48 is coupled to port 50 of device 10, an electrical signal is applied to nebulizer 44 to vibrate the screen or plate, thereby to nebulize the liquid substance contained in the nebulizer container. The nebulized substance flows from the nebulizer 44 and becomes entrained in the pressurized gas being provided to the patient by device 10 through the patient interface 22.

Still referring to FIG. 1, housing 12 includes a molded front housing shell 54 and a molded rear housing shell 56 that couple together to form the overall structure of housing 12. Front housing shell 54 includes front wall 14 and a sidewall 58 that is integrally formed with front wall 14. In the illustrative example, sidewall 58 of device 10 has a Universal Serial Bus (USB) port 60 to which other devices (e.g., tablet computers, laptop computers, memory sticks, printers, personal computers, etc.) with mating USB couplers can couple, as desired as indicated diagrammatically in FIG. 40. Sidewall 58 also has a pulse oximeter port 62 for coupling to a pulse oximeter (not shown) and a port (not shown in FIG. 1) to which a wireless communication module 64 couples. In some embodiments, module 64 communicates wirelessly according to the Bluetooth protocol, but all types of wireless communication are intended to be within the scope of the present disclosure.

Figure 3:
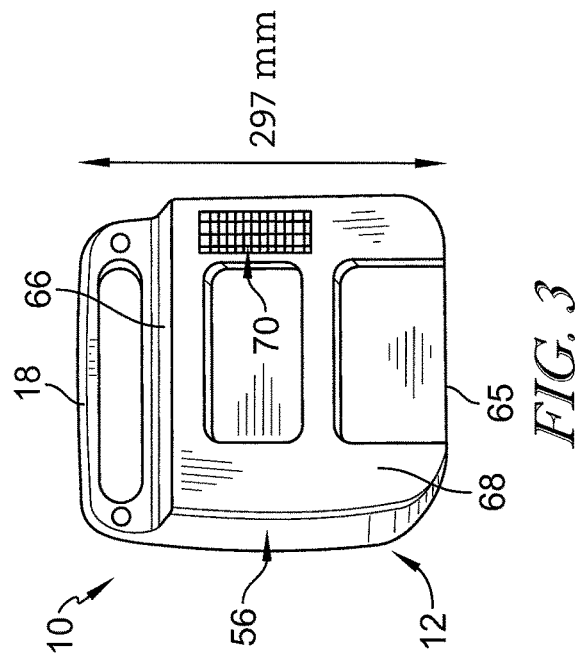
FIG. 3 is a rear elevation view of the respiratory device of FIG. 1.
Figure 4:
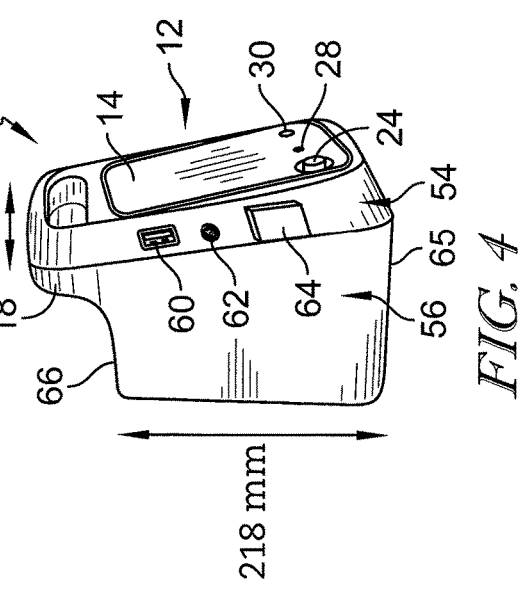
FIG. 4 is a side perspective view of the respiratory device of FIG. 1.
Figure 5:
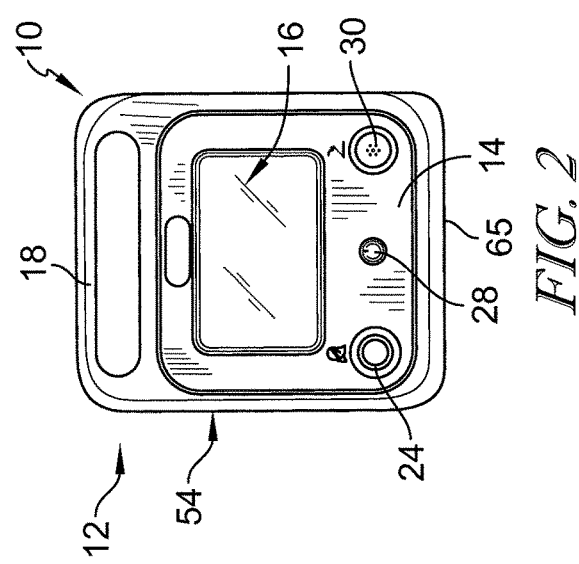
FIG. 5 is a top plan view of the respiratory device of FIG. 1.

Referring to FIGS. 2-5, front, rear, side and top views, respectively, of device 10 are shown. However, the device 10 of FIGS. 2-5 does not include port 50 and so the device 10 of FIGS. 2-5 is an example in which nebulizer 44 is not used. Otherwise, device 10 of FIGS. 2-5 is just like device 10 of FIG. 1 and so like reference numerals are used to denote like components. Dimensional information is included in FIGS. 3-5 for the illustrative device 10. Thus, the height of device 10 from its bottom 65 to a top of handle 18 is 297 millimeters (mm) as indicated in FIG. 3. The thickness from a front of handle to a back of handle 18 is 42 mm and a height of device 10 from its bottom to a top wall 66 of a rear portion of rear housing shell 56 is 218 mm as indicated in FIG. 4. A depth of device 10 from front to back is 192 mm and a width of device 10 from side to side is 270 mm as indicated in FIG. 5. Rear housing shell 56 of device 10 has a back wall 68 that includes a grill 70 with a plurality of openings to permit ambient air or atmosphere to flow into an interior region of housing 12 and to permit air in the interior region to flow out of housing 12 to atmosphere during the operation of device 10.

Figure 40:
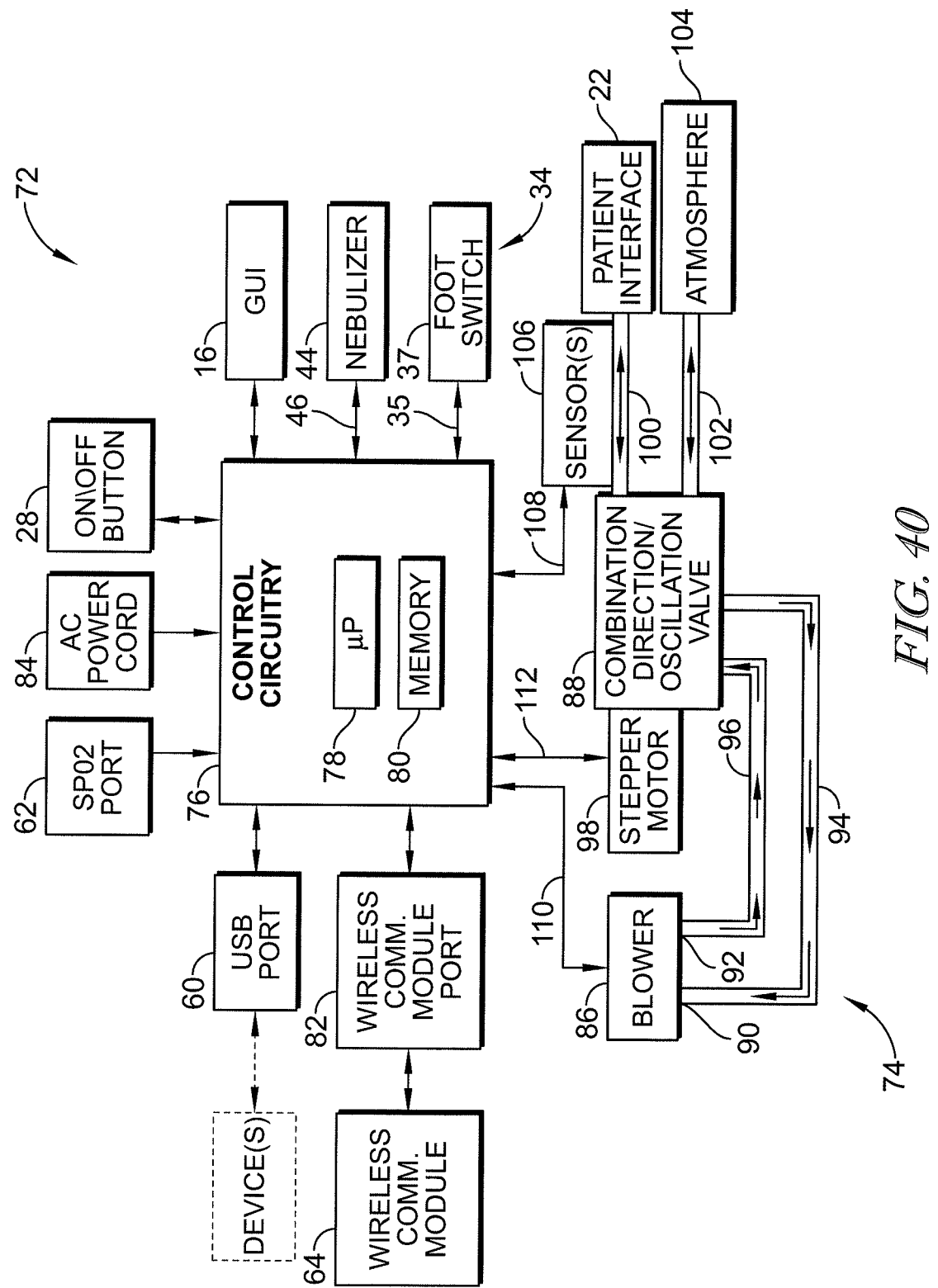
FIG. 40 is a diagrammatic view of the electrical system and pneumatic system of the respiratory devices of FIGS. 1-21.

Referring to FIG. 40, a diagrammatic view of the electrical system 72 and the pneumatic system 74 of device 10 is provided. Electrical system 72 includes control circuitry 76 which, in turn, includes a microprocessor 78 and memory 80. In some embodiments, microprocessor 78 and memory 80 are part of a single microcontroller integrated circuit chip. As shown in FIG. 40, GUI 16, on/off button 28, foot switch unit 34, nebulizer 44, SpO2 port 62, USB port 60, and wireless communication module 64 are coupled electrically to control circuitry 76. A wireless communication module port 82 is shown diagrammatically and provides the communication link between module 64 and circuitry 76.

An alternating current (AC) power cord 84 is also coupled to circuitry 76. Circuitry 76, therefore, includes components to convert the incoming AC power to the proper voltage levels, e.g., 5 Volts (V), 12 V, 24 V, etc., required by various components of systems 72, 74. In some embodiments, device 10 includes a lithium ion battery pack which is charged while power cord 84 is plugged into a power outlet. In some such embodiments, the components of device 10 are powered from the lithium ion battery pack regardless of whether cord 84 is plugged into a power outlet. Battery packs or batteries that operate according to technologies other than lithium ion technology are also within the scope of this disclosure for use in device 10.

It should be appreciated that although circuitry 76 is shown diagrammatically as a single block in FIG. 40, it is within the scope of this disclosure for circuitry 76 to include electrical components that are provided on multiple, separate circuit boards which are interconnected via suitable conductors. It is also within the scope of this disclosure for circuitry 76 to comprise a single circuit board with the associated electrical components mounted thereon. Of course, some components of electrical system 72 may not be attached to any circuit board at all. For example, button 28 and ports 60, 62, 82 may be physically mounted to housing 12 rather than to a circuit board. Ultimately, however, suitable conductors connect these components to control circuitry 76.

In FIG. 40, the double headed arrows leading between circuitry 76 and the various other components are intended to imply that bidirectional or two-way communication occurs between circuitry 76 and the associated components. However, this is not to exclude the possibility that other embodiments of device 10 may have one-way communication between circuitry 76 and one or more of the other elements. Similarly, the one-way arrows from port 62 and power cord 84 is not intended to exclude the possibility of two-way communication between circuitry 76 and these components in other embodiments. For example, data over power line communication technology may be employed, if desired, to transmit signals from circuitry 76 over AC power cord 84 away from device 10.

Still referring to FIG. 40, pneumatic system 74 includes a blower 86 and a combination direction/oscillation valve 88 pneumatically coupled to an inlet 90 and an outlet 92 of blower 86 via respective conduits 94, 96. System 74 includes a stepper motor 98 which controls movement of a valve member of valve 88 as will be discussed below in connection with a rotary plate valve embodiment shown in FIGS. 6-16 and in connection with a rotary spool valve embodiment shown in FIGS. 17-21. System 74 includes a conduit 100 that couples valve 88 to patient interface 22 and a conduit 102 that couples valve 88 to atmosphere 104.

One or more sensors 106 are placed in pneumatic communication with conduit 100 and are in electrical communication with control circuitry 76 via conductors 108. Thus, one could allocate sensor(s) 106 as being a component of either electrical system 72 or pneumatic system 74 or both. Sensor(s) 106 include a pressure sensor or a flow sensor or both. Suitable electrical conductors 110, 112 also interconnect blower 86 and stepper motor 98, respectively, to circuitry 76. In general, conductors 110, 112 communicate control signals from circuitry 76 to blower 86 and stepper motor 98 and communicate feedback signals from blower 86 and stepper motor 98 to circuitry 76. Examples of feedback signals from blower 86 include rotational speed of an impeller of the blower 86 and temperature of the blower 86. The control signal to the blower 86 may include, for example, a voltage signal such as a pulse width modulated (PWM) signal. Examples of feedback signals from stepper motor 98 include a step count number indicative of a position of an output shaft of the motor 98 and a temperature of the motor 98. The control signal to the stepper motor 98 may include, for example, a voltage pulse to move the motor output shaft by one step or a series of pulses to move the motor output shaft by a corresponding number of steps.

When positive pressure produced at outlet 92 of blower 86 is to be supplied to the patient via patient interface 22, valve 88 is operated so that pressurized air from blower 86 is communicated from conduit 96 through valve 88 to conduit 100 and so that ambient air from atmosphere 104 is communicated from conduit 102 through valve 88 to inlet 90 of blower 86. When negative pressure produced at inlet 90 of blower 86 is to be supplied to the patient interface 22, valve 88 is operated so that suction from blower 86 is communicated from conduit 94 through valve 88 to conduit 100 and so that pressurized air from blower 86 is communicated from conduit 96 through valve 88 to atmosphere 104 via conduit 102.

FIG. 40 has one-way arrows in conduits 94, 96 to indicate a direction of flow of air to or from inlet 90 and outlet 92 of blower 86, respectively, whereas bidirectional arrows are shown in conduits 100, 102 to indicate that air is sometimes flowing from valve 88 toward patient interface 22 or atmosphere 104 and that air is sometimes flowing from valve away from patient interface 22 or atmosphere 104. When air is flowing from valve 88 toward patient interface 22 to provide positive pressure to a person's airway, air is flowing toward valve 88 from atmosphere 104. Conversely, when air is flowing toward valve 88 from patient interface 22 to provide negative pressure to a person's airway, air is flowing away from valve 88 toward atmosphere 104. To state it another way, valve 88 is operable to switch between a positive pressure position in which air is drawn from atmosphere 104 to be pressurized by blower 86 for delivery to the patient via patient interface 22 and a negative pressure position in which air is drawn from the patient via patient interface 22 and is blown to atmosphere 104 by blower 86.

According to this disclosure, valve 88 is also operable while in the positive pressure position and/or the negative pressure position to produce oscillations in the pressure being delivered to patient interface 22. It is contemplated by this disclosure that, in some embodiments, only one stepper motor 98 is used in device 10 to control whether valve 88 is in the positive pressure position or the negative pressure position and to control whether the valve 88 produces oscillations while in either of these positions. Using only one stepper motor 98 in device 10 is an improvement from a cost, size and weight standpoint over known prior art devices that use multiple stepper motors or components in addition to a direction valve to produce oscillatory pressure.

Figure 6:
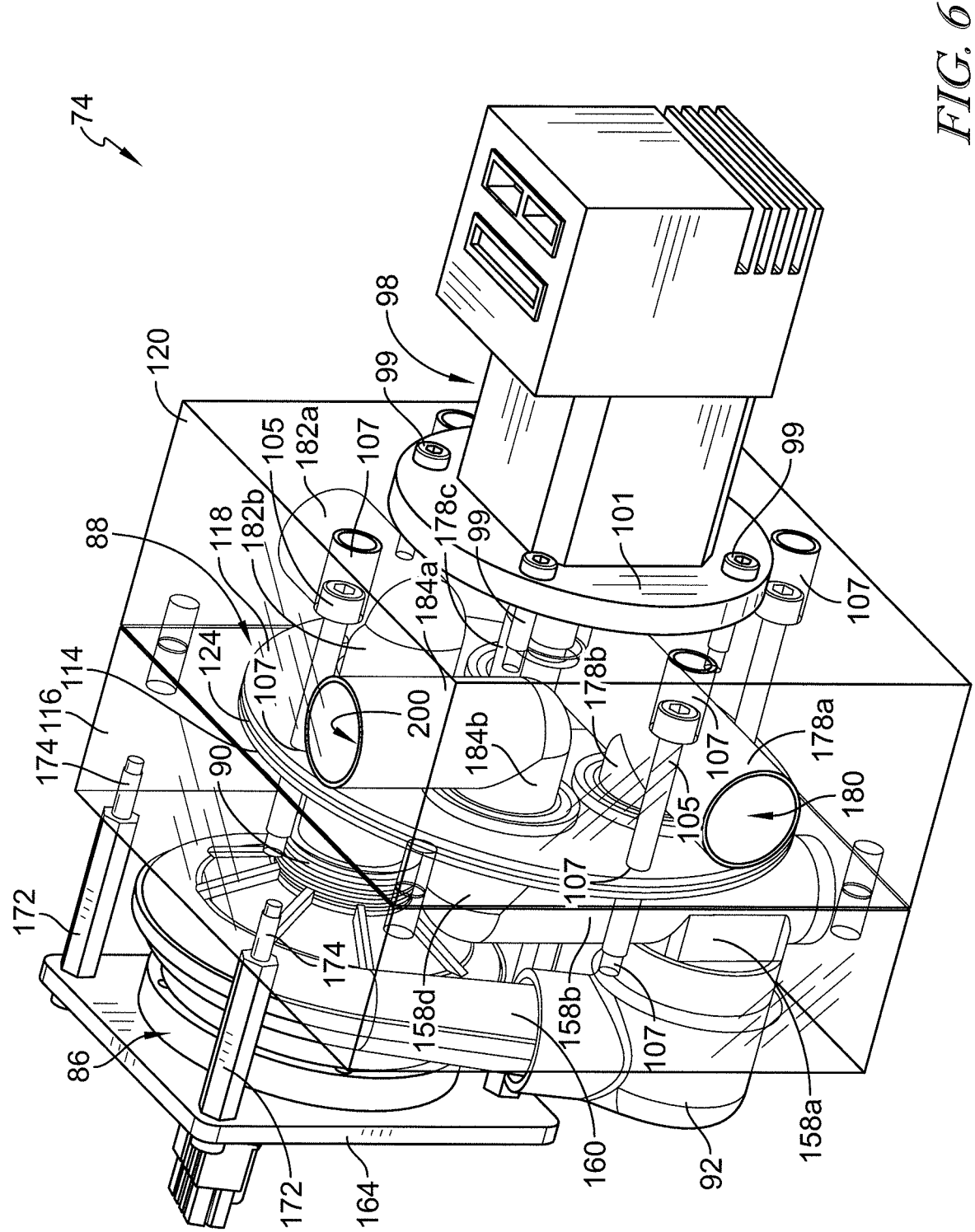
FIG. 6 is a perspective view of internal components of the respiratory device of FIG. 1 showing a blower, a rotary plate valve and manifold assembly to the right of the blower, and a stepper motor to the right of the rotary plate valve and manifold assembly.
Figure 7:
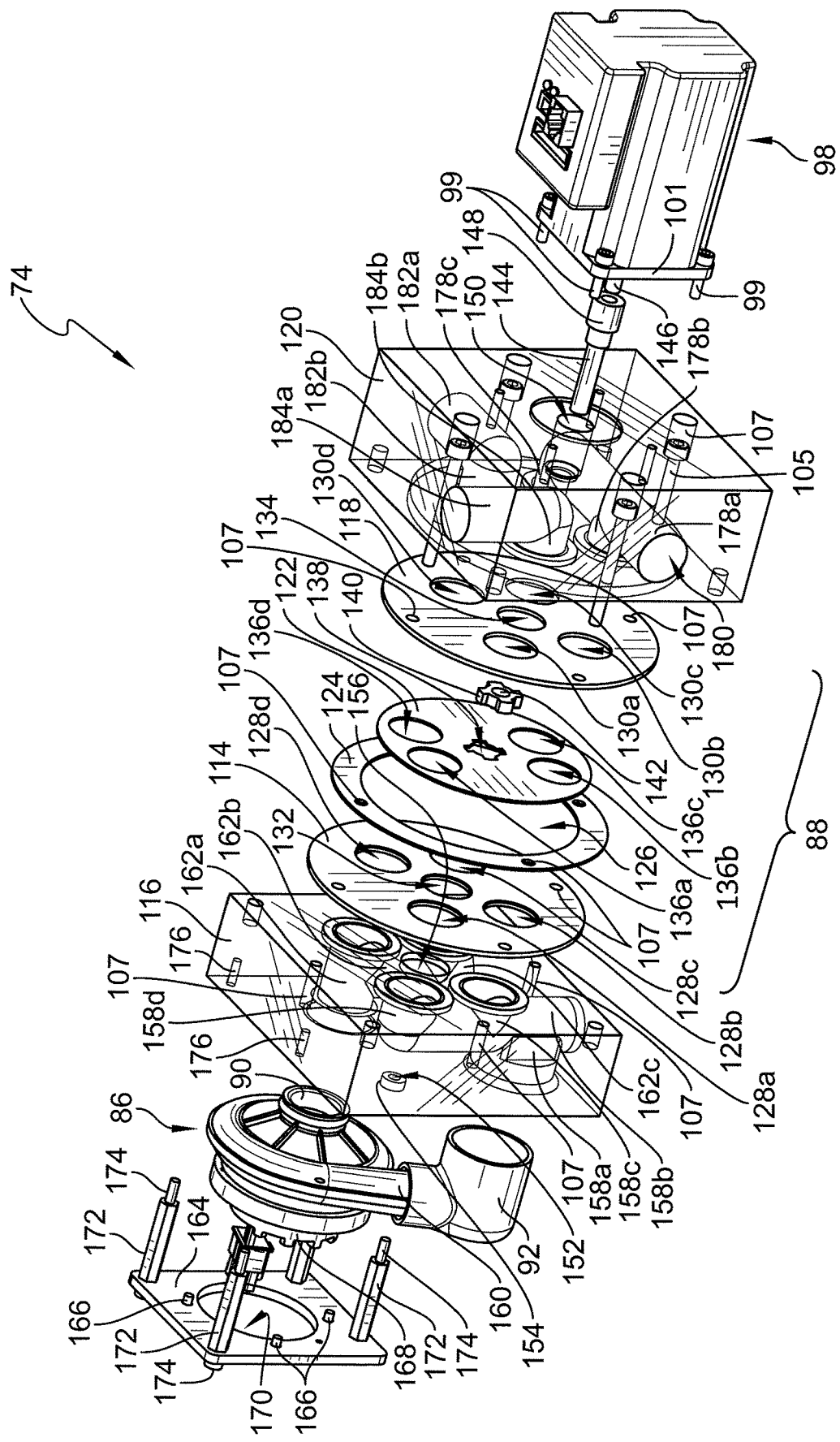
FIG. 7 is an exploded perspective view of the components of FIG. 6 showing a blower on the left hand side of the figure, a stepper motor on a right hand side of the figure, first and second manifold blocks adjacent the blower and stepper motor, respectively, first and second circular stationary plates adjacent the first and second manifold blocks respectively, a circular rotatable plate situated between the first and second circular stationary plates, an annular shim adjacent the circular rotatable plate, and the annular shim having a central circular opening that receives the rotatable plate therein.
Figure 8:
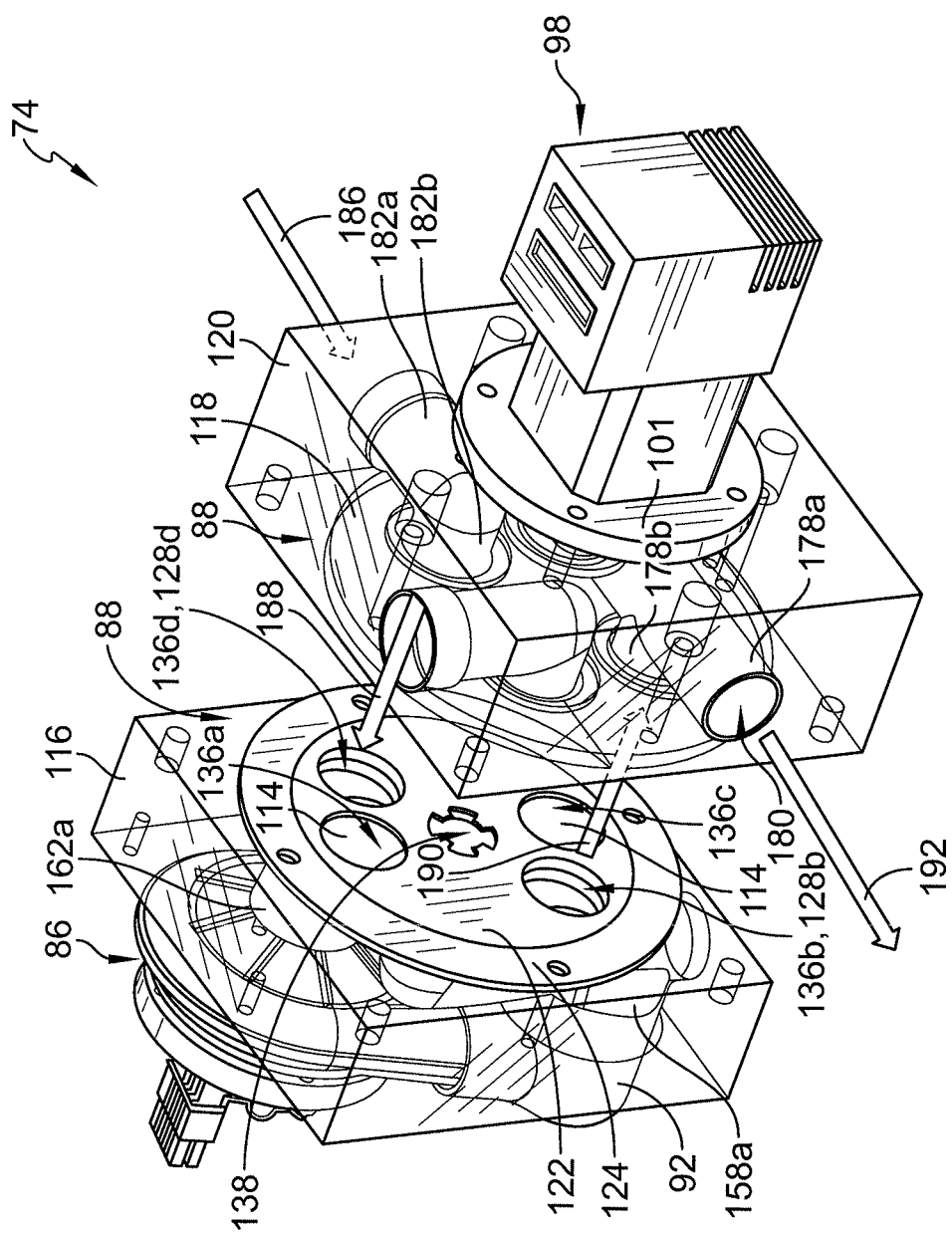
FIG. 8 is a partial exploded perspective view showing the rotatable plate and annular shim locate against the first manifold block, the rotatable plate being in a first position, and showing a series of arrows that indicate a flow of air from the atmosphere through the manifold blocks, blower and rotary plate valve toward a patient interface during application of positive pressure during insufflation of a patient.
Figure 9:
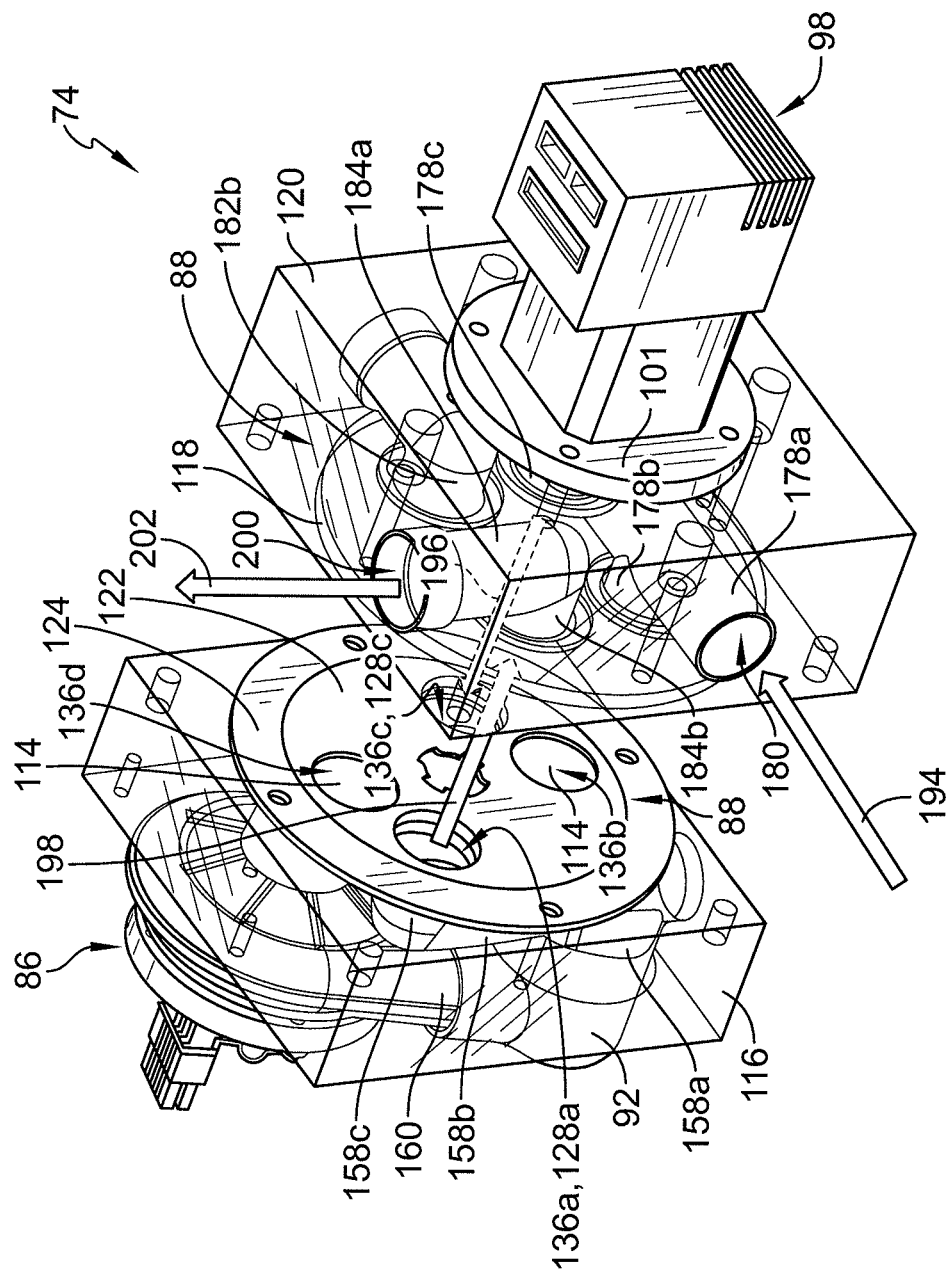
FIG. 9 is a partial exploded perspective view, similar to FIG. 8, showing the rotatable plate and annular shim locate against the first manifold block, the rotatable plate being in a second position after moving through a first angular displacement from the first position, and showing a series of arrows that indicate a flow of air from the patient interface through the manifold blocks, blower and rotary plate valve to exhaust to atmosphere during application of negative pressure during exsufflation of a patient.

Referring now to FIGS. 6-9, the rotary plate valve embodiment of valve 88 includes a first stationary plate 114 attached to a first manifold block 116, a second stationary plate 118 attached to a second manifold block 120, and a rotatable plate 122 that is sandwiched between the first and second stationary plates 114, 118. Plates 114, 118, 122 are circular or round in shape with plates 114, 118 having substantially equivalent diameters and plate 122 having a diameter less than that of plates 114, 118. Valve 88 further includes an annular shim 124 that surrounds the outer periphery of plate 122 and serves as a spacer between plates 114, 118 to provide a space that accommodates rotatable plate 122. In this regard, shim 124 is round or circular having an outer periphery that is substantially equivalent to the outer peripheries of plates 114, 118 and having a large central bore 126, shown in FIG. 7, that is sized to receive plate 122 therein within only a minimal amount of clearance therebetween as shown in FIGS. 8 and 9.

Plate 114 has four holes 128a, 128b, 128c, 128d and plate 118 has four holes 130a, 130b, 130c, 130d as shown best in FIG. 7. Plate 114 has a central hole 132 and plate 118 has a central hole 134. Holes 128a, 128b, 128c, 128d of plate 114 align with respective holes 130a, 130b, 130c, 130d of plate 118. In the illustrative example, holes 128a-d, 130a-d, 132, 134 are each round. Furthermore, each hole 128a-d and each hole 130a-d is spaced circumferentially by 90° from each of the next two adjacent holes 128a-d, 130a-d of respective plates 114, 118 when measured from center-to-center of each hole 128a-d, 130a-d. The diameter of each hole 128a-d, 130a-d is substantially equivalent to each of the other holes 128a-d, 130a-d and is about 25% or less of the diameter of the respective plate 114, 118.

Plate 122 has four holes 136a, 136b, 136c, 136d as shown best in FIG. 7. Holes 136a-d are the same size and shape as holes 128a-d, 130d but are grouped into two pairs that are closer together circumferentially than 90°. In particular, holes 136a, 136d are a first pair and holes 136b, 136c are a second pair. Holes 136a, 136 are spaced apart from each other circumferentially by about 45° and holes 136b, 136c are spaced apart from each other circumferentially by about 45° when measured center-to-center. Plate 122 has a cross-shaped central hole 138 that receives a cross-shaped hub 140 shown in FIG. 7. Hub 140 has a central hole 142 therethrough which receives a valve shaft 144. Shaft 144 mounts to an output shaft 146 of stepper motor 98 with a coupler 148. A set of fasteners 99 such as bolts, screws, or dowel pins, extend through apertures in a flange 101 of stepper motor 98 and are received in holes 103 of manifold block 120 to mount stepper motor 98 to block 120. With reference to FIGS. 6 and 7, a set of fasteners 105 extend through holes 107 provided in blocks 116, 118, plates 114, 118, and shim 124 to couple these elements together.

Coupler 148 includes, or serves as, a bushing or bearing for shafts 144, 146 and is received in a bore 150 formed in a central region of manifold block 120. An end of shaft 144 opposite from coupler 148 is received in a bore 152 of a bushing or bearing 154 which, in turn, is received in bore 156 formed in manifold block 116. Thus, shaft 144 extends through bore 150 of manifold block 120, hole 134 of plate 118, hole 142 of hub 140 (as well as hole 138 of plate 122), hole 132 of plate 114 and bore 156 of manifold block 116. Hub 140 is press fit onto shaft 144, or is otherwise keyed to shaft 144, so that rotational motion imparted to shaft 144 by output shaft 146 of stepper motor 98 is transferred to rotatable plate 122.

Manifold block 116 includes a series of passageways that cooperate to form the conduits 94, 96 discussed above in connection with FIG. 40. Manifold block 120 includes a series of passageways that cooperate to form the conduits 100, 102 discussed above in connection with FIG. 40. In particular, manifold block 116 includes passageways 158a, 158b, 158c, 158d, shown in FIG. 7, that correspond to passageway 96 of FIG. 40 which receives pressurized air from blower outlet 92. In the illustrative example, outlet 92 is formed as an elbow fitting attached to an end of an outlet conduit 160 of blower 86. Outlet 92 pneumatically couples to passageway 158a so that pressurized air is communicated from blower 86 through passageways 158a, 158b to passageways 158c, 158d. An outlet of passageway 158c is pneumatically coupled to hole 128b of plate 114 and is aligned with hole 130b of plate 118. An outlet of passageway 158d is pneumatically coupled to hole 128a of plate 114 and is aligned with hole 130a of plate 118.

Manifold block 116 also includes passageways 162a, 162b, 162c shown in FIG. 7, that correspond to passageway 94 of FIG. 40 which receives suction from blower inlet 90. In the illustrative example, inlet 90 of blower 86 is formed as a small tubular segment that pneumatically couples to an outlet of passageway 162a. Suction produced at outlet 90 of blower pneumatically couples to passageway 162a so that suction (i.e., negative pressure) is communicated from blower 86 through passageway 162a to passageways 162b, 162c. An inlet of passageway 162a is pneumatically coupled to hole 128d of plate 114 and is aligned with hole 130d of plate 118. An inlet of passageway 162c is pneumatically coupled to hole 128c of plate 114 and is aligned with hole 130c of plate 118.

Blower 86 is attached to a plate 164 with suitable fasteners 166 such as bolts, screws, or dowel pins. A motor 168 of blower 86 extends through a hole 170 in plate 164. A set of standoffs 172 keep plate 164 at a proper distance from manifold block 116 to accommodate blower 86. As shown in FIG. 7, a set of fasteners 174 extend from standoffs 172 and are received by holes 176 formed in manifold block 116 (only two holes 176 can be seen in FIG. 7). Thus, blower 86 is sandwiched between plate 164 and manifold block 116, although motor 168 of blower 86 projects through hole 170 of plate 164 as mentioned above.

Manifold block 120 includes a series of passageways 178a, 178b, 178c, shown in FIG. 7, that correspond to conduit 100 of FIG. 40 which receives either positive pressure or negative pressure from blower 86. An opening 180 of passageway 178a is coupled to the patient interface 22. An inlet of passageway 178b is pneumatically coupled to hole 130b of plate 118 and is aligned with hole 128b of plate 114 and with the outlet of passageway 158c of manifold block 116. An outlet of passageway 178c is pneumatically coupled to hole 130c of plate 118 and is aligned with hole 128c of plate 114 and with the inlet of passageway 162c of manifold block 116.

Manifold 120 also includes a first passageway 182a, 182b and a second passageway 184a, 184b that, together, correspond to conduit 102 of FIG. 40. First passageway 182a, 182b serves an air intake from atmosphere and second passageway 184a, 184b serves as an exhaust to atmosphere. An outlet of passageway 182b is pneumatically coupled to hole 130d of plate 118 and is aligned with hole 128d of plate 114 and with an inlet of passageway 162a of manifold block 116. An inlet of passageway 184b is pneumatically coupled to hole 130a of plate 118 and is aligned with hole 128a of plate 114 and with an outlet of passageway 158d of manifold block 116.

Depending upon the position of plate 122 relative to plates 114, 118 some of holes 128a-d, holes 130a-d, and 136a-d are aligned to provide pneumatic communication between corresponding passageways 158c, 158d, 162a, 162c of block 116 and passageways 178b, 178c, 182b, 184b of block 120 and others of holes 128a-d, holes 130a-d, and 136a-d are blocked to prevent pneumatic communication between corresponding passageways 158c, 158d, 162a, 162c of block 116 and passageways 178b, 178c, 182b, 184b of block 120. For example, in FIG. 8, rotatable plate 122 is in a first position during application of positive pressure to patient interface 22 through opening 180 of manifold block 120 and, in FIG. 9, rotatable plate 122 is in a second position during application of suction or negative pressure to patient interface 22 through opening 180 of manifold block 120. When moving between the first and second positions, plate 122 rotates through a first angular displacement of less than 45°, such as about 22.5°.

With reference to FIG. 8, when plate 122 is in the first position and blower 86 is operated, atmospheric air is drawn into passageway 182a of block 120 as indicated by arrow 186 and then is drawn through passageway 182b, hole 130d of plate 118, hole 136d of plate 122, hole 128d of plate 114 and into passageway 162a of block 116 as indicated by arrow 188. The air in passageway 162a is drawn into blower 86 through inlet 90 and is pressurized by an impeller (not shown) of blower 86. The pressurized air is forced by blower 86 through outlet 92 and, in turn, is forced through passageways 158a, 158c, hole 128b of plate 114, hole 136b of plate 122, hole 130b of plate 118 and into passageway 178b as indicated by arrow 190. The air in passageway 178b is then forced through passageway 178a and out of opening 180 to the patient interface 22 (not shown in FIG. 8) as indicated by arrow 192. While plate 122 is in the first position, passageways 178c, 184b of block 120, holes 130a, 130c of plate 118, holes 128a, 128c of plate 114, and passageways 158d, 162c of block 116 are closed off or blocked by respective solid portions of plate 122 (e.g., the portions of plate 122 between holes 136a, 136b and between holes 136c, 136d).

With reference to FIG. 9, when plate 122 is in the second position and blower 86 is operated, air from the patient interface 22 is drawn into passageway 178a of block 120 through opening 180 as indicated by arrow 194 and then is drawn through passageway 178c, hole 130c of plate 118, hole 136c of plate 122, hole 128c of plate 114 and into passageway 162c of block 116 as indicated by arrow 196. The air in passageway 162c is drawn through passageways 162a, 162b and into blower 86 through inlet 90 and is pressurized by the impeller of blower 86. The pressurized air is forced by blower 86 through outlet 92 and, in turn, is forced through passageways 158a-c, hole 128a of plate 114, hole 136a of plate 122, hole 130a of plate 118 and into passageway 184b as indicated by arrow 198. The air in passageway 184b is then forced through passageway 184a and out of an opening 200 to the atmosphere as indicated by arrow 202. While plate 122 is in the second position, passageways 178b, 182b of block 120, holes 130b, 130d of plate 118, holes 128b, 128d of plate 114, and passageways 158c, 162a of block 116 are closed off or blocked by respective solid portions of plate 122 (e.g., the portions of plate 122 between holes 136a, 136b and between holes 136c, 136d).

An example of a suitable blower 86 for use in device 10 is the model no. U85MX-024KX-4 blower available from Micronel AG of Tagelswangen, Switzerland. Examples of a suitable stepper motor 98 for use in device 10 include the model no. STM17Q-3AE stepper motor available from Applied Motion Products, Inc. of Watsonville, Calif., U.S.A. and the model no. 42095-07PD-01RO stepper motor available from LIN Engineering of Morgan Hill, Calif., U.S.A.

As shown in FIGS. 10-12, when plate 122 is in the first position, plate 122 can be oscillated back and forth in the directions of first and second arrows 204, 206 through a second angular displacement that is less than the first angular displacement mentioned above. The second angular displacement corresponds to the amount of movement of plate 122 in direction 204 from the maximum pressure position of FIG. 10, though an intermediate position of FIG. 11, to a minimum pressure position of FIG. 12. The second angular displacement also corresponds to the amount of movement of plate 122 in direction 206 from the minimum pressure position of FIG. 12 back to the maximum pressure position of FIG. 10.

In the illustrative example, the second angular displacement is about 10°. Stepper motor 98 is operable so that the frequency of oscillation of plate 122 is within the range of about 1 Hertz (Hz) to about 20 Hz, as selected by a user on GUI 16. As viewed in FIGS. 10-12, plate 122 rotates in a clockwise direction 204 from the maximum pressure position of FIG. 10 to the intermediate position of FIG. 11 and then to the minimum pressure position of FIG. 12. From the minimum pressure position of FIG. 12, plate 122 rotates in counterclockwise direction 206 to the intermediate position of FIG. 11 and then back to the maximum pressure position of FIG. 10.

In FIGS. 10-12, the dashed circles are labeled with the reference numbers corresponding to the holes of plates 114, 118, 122 and the holes of each plate 114, 118, 122 are depicted diagrammatically as having different sizes or diameters. However, it should be appreciated that the holes of each respective plate 114, 118, 122 are substantially equal in size or diameter in the illustrative embodiment. Furthermore, the stippling in FIGS. 10-12 indicates the amount of space available for pressurized air to pass through the rotary plate valve 88. Finally, a dot is superimposed on the pressure graphs that are located in FIGS. 10-12 beneath the respective diagrammatic valve 88 depictions.

The dot in FIG. 10 is at a top of a positive pressure sinusoidal trace because plate 122 is at the maximum pressure position having holes 128d, 130d, 136d aligned with each other and having holes 128b, 130b, 136b aligned with each other. The dot in FIG. 11 is at a hypothetical positive baseline pressure corresponding to the intermediate position of plate 122 having hole 136d misaligned by a relatively small amount relative to holes 128d, 130d and having hole 136b misaligned by a relatively small amount relative to holes 128b, 130b. The dot in FIG. 12 is at the bottom of the positive pressure sinusoidal trace because plate 122 is at the minimum pressure position having hole 136d misaligned by a relatively large amount relative to holes 128d, 130d and having hole 136b misaligned by a relatively large amount relative to holes 128b, 130b.

When plate 122 is in the minimum pressure position of FIG. 12, a pair of small passages is created by holes 136a, 136c with respective holes 128a, 130a and 128c, 130c. At the patient interface 22, the air flow through these small passages contributes to the reduction in airflow through the larger passages formed by holes 128b, 130b, 136b and holes 128d, 130d, 136d. Thus, the pair of small passages of holes 128a, 130a, 136a and holes 128c, 130c, 136c has an effect to contribute to the reduction in positive pressure output to the patient interface 22.

As shown in FIGS. 13-15, when plate 122 is in the second position, plate 122 can also be oscillated back and forth in the directions of first and second arrows 204, 206 through the second angular displacement mentioned above. In FIGS. 13-15, the second angular displacement corresponds to the amount of movement of plate 122 in direction 206 from the maximum pressure position of FIG. 13, though an intermediate position of FIG. 14, to a minimum pressure position of FIG. 15. The second angular displacement of FIGS. 13-15 also corresponds to the amount of movement of plate 122 in direction 204 from the minimum pressure position of FIG. 15 back to the maximum pressure position of FIG. 13.

In the illustrative example, the second angular displacement is about 10° regardless of whether plate 122 is in the first or second position. Furthermore, stepper motor 98 is operable so that the frequency of oscillation of plate 122 is within the range of about 1 Hertz (Hz) to about 20 Hz, as selected by a user on GUI 16, regardless of whether plate 122 is in the first or second position. As viewed in FIGS. 13-15, plate 122 rotates in counterclockwise direction 206 from the maximum pressure position of FIG. 13 to the intermediate position of FIG. 14 and then to the minimum pressure position of FIG. 15. From the minimum pressure position of FIG. 15, plate 122 rotates in clockwise direction 204 to the intermediate position of FIG. 14 and then back to the maximum pressure position of FIG. 13.

As was the case with FIGS. 10-12, in FIGS. 13-15, the dashed circles are labeled with the reference numbers corresponding to the holes of plates 114, 118, 122 and the holes of each plate 114, 118, 122 are depicted diagrammatically as having different sizes or diameters. As was also the case with FIGS. 10-12, the stippling in FIGS. 13-15 indicates the amount of space available for pressurized air to pass through the rotary plate valve 88. Finally, a dot is superimposed on the pressure graphs that are located in FIGS. 13-15 beneath the respective diagrammatic valve 88 depictions.

The dot in FIG. 13 is at a bottom of a negative pressure sinusoidal trace because plate 122 is at the maximum pressure position having holes 128a, 130a, 136a aligned with each other and having holes 128c, 130c, 136c aligned with each other. The dot in FIG. 14 is at a hypothetical negative baseline pressure corresponding to the intermediate position of plate 122 having hole 136a misaligned by a relatively small amount relative to holes 128a, 130a and having hole 136c misaligned by a relatively small amount relative to holes 128c, 130c. The dot in FIG. 15 is at the top of the negative pressure sinusoidal trace because plate 122 is at the minimum pressure position having hole 136a misaligned by a relatively large amount relative to holes 128a, 130a and having hole 136c misaligned by a relatively large amount relative to holes 128c, 130c.

When plate 122 is in the minimum pressure position of FIG. 15, a pair of small passages is created by holes 136b, 136d with respective holes 128b, 130b and 128d, 130d. At the patient interface 22, the air flow through these small passages slightly counteracts the airflow through the larger passages formed by holes 128a, 130a, 136a and holes 128c, 130c, 136c. However, the pair of small passages of holes 128b, 130b, 136b and holes 128d, 130d, 136d has only a negligible effect on the negative pressure applied to the patient interface 22.

According to this disclosure, valve 88 is controllable to generate a pause or rest pressure at the patient interface 22. While the pause pressure is programmable by a user to be set at any pressure, positive or negative, that respiratory device 10 is capable of generating, the pause pressure is typically a positive pressure that is less than the insufflation pressure. The graphs in FIGS. 10-15 each show a positive pause pressure to the right of the negative exsufflation pressure in accordance with a typical scenario.

Figure 16:
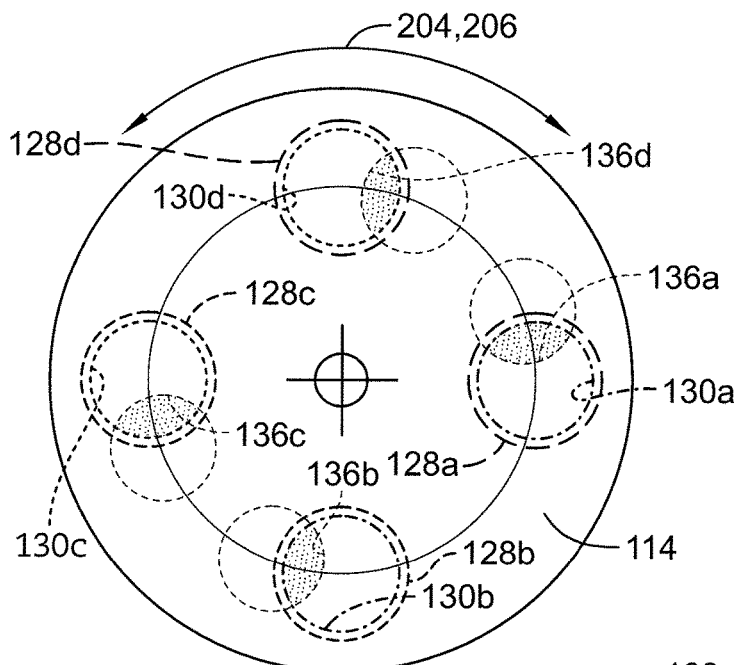
FIG. 16 is a diagrammatic view similar to the upper portions of FIGS. 10-15, showing the rotatable plate in a rest position in which both positive and negative pressure from the blower is applied to the patient interface in roughly equal amounts to establish a zero baseline rest pressure and a double headed arrow indicating that the rotatable plate is able to oscillate in back and forth in first and second directions to create oscillations above and below the zero baseline rest pressure.

Referring now to FIG. 16, if the rest pressure is set to zero pressure (i.e., neither above nor below atmospheric pressure), then rotatable plate 122 is moved to a position in which a substantially equivalent amount of positive pressure and negative pressure is applied to patient interface 22. Thus, when plate 122 is in the position shown in FIG. 16 relative to plates 114, 118, the air flow passages through valve 88 formed by hole 136a with holes 128a, 130a, formed by hole 136b with holes 128b, 130b, formed by hole 136c with holes 128c, 130c, and formed by hole 136d with holes 128d, 130d are substantially equivalent in size. As indicated by double headed arrow 204, 206 in FIG. 16, plate 122 is also able to be cyclically oscillated back and forth in opposite directions to create oscillations in the rest or pause pressure. Such oscillations in the rest pressure are shown in the graphs of FIGS. 10-15. It is also possible for plate 122 to be positioned to create a rest pressure that has a positive baseline pressure or a negative baseline pressure, as desired, based on user inputs on GUI 16.

Referring now to FIGS. 17-21, a rotary spool valve embodiment of valve 88 includes a stationary cylinder 208 that is retained between a first manifold block 210 and a second manifold block 212. The rotary spool valve 88 includes a rotatable cylinder or spool 214, shown best in FIG. 18, which is received in the bore of stationary cylinder 208. Rotary motion of output shaft 146 of stepper motor 98 is transferred to spool 214 through a rotatable hub 216, a cross-shaped member 218 having a bore 219 that receives a complimentary shaped lug 220 of hub 216, and a plug 222 having a cross-shaped hole (not shown) that receives the cross-shaped member 218. Plug 222 threads into the bore of spool 214 at the end of spool 214 nearest stepper motor 98.

Figure 17:
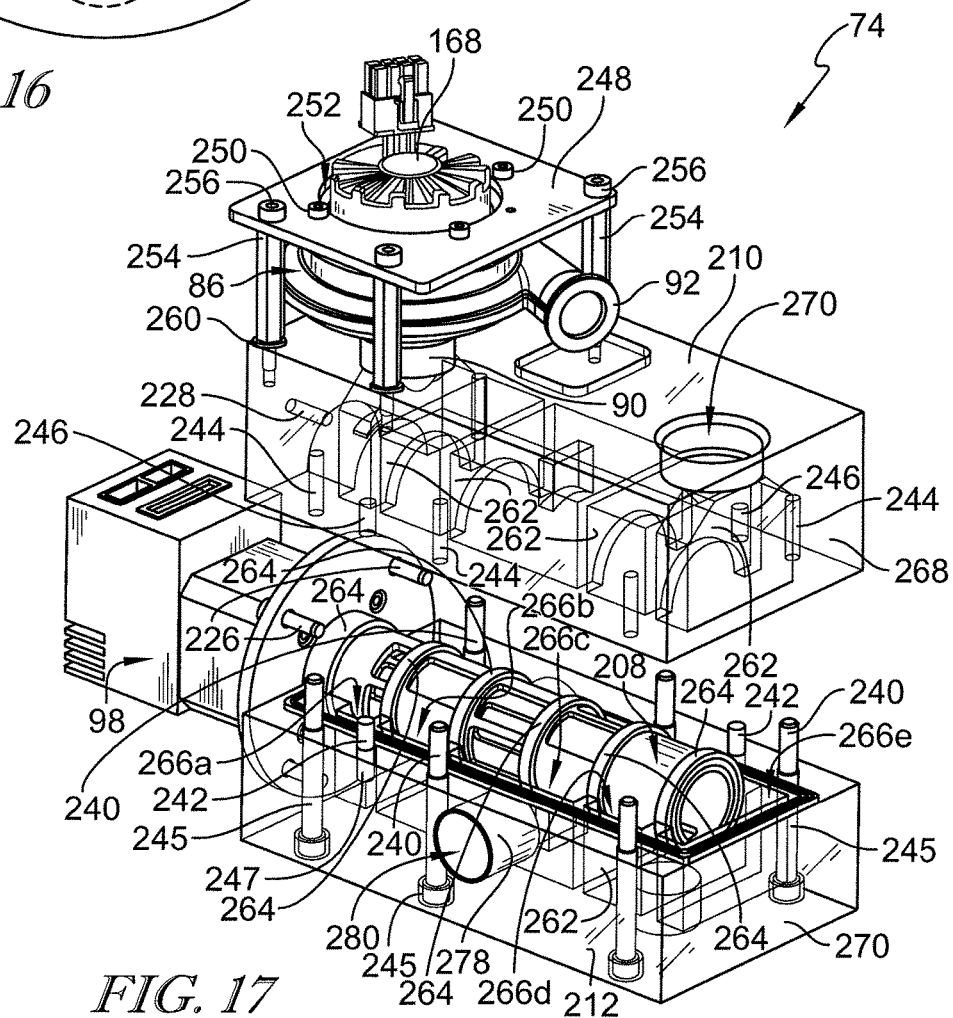
FIG. 17 is a partial exploded perspective view of components of an alternative embodiment of a portion of a respiratory device showing a first manifold block carrying a blower, the first manifold block being spaced above a second manifold block that supports a rotary spool valve having a stationary cylinder and rotatable cylinder or spool located within an interior region of the stationary cylinder, and the rotatable cylinder being coupled to a stepper motor located to the left of the first and second manifold blocks.
Figure 18:
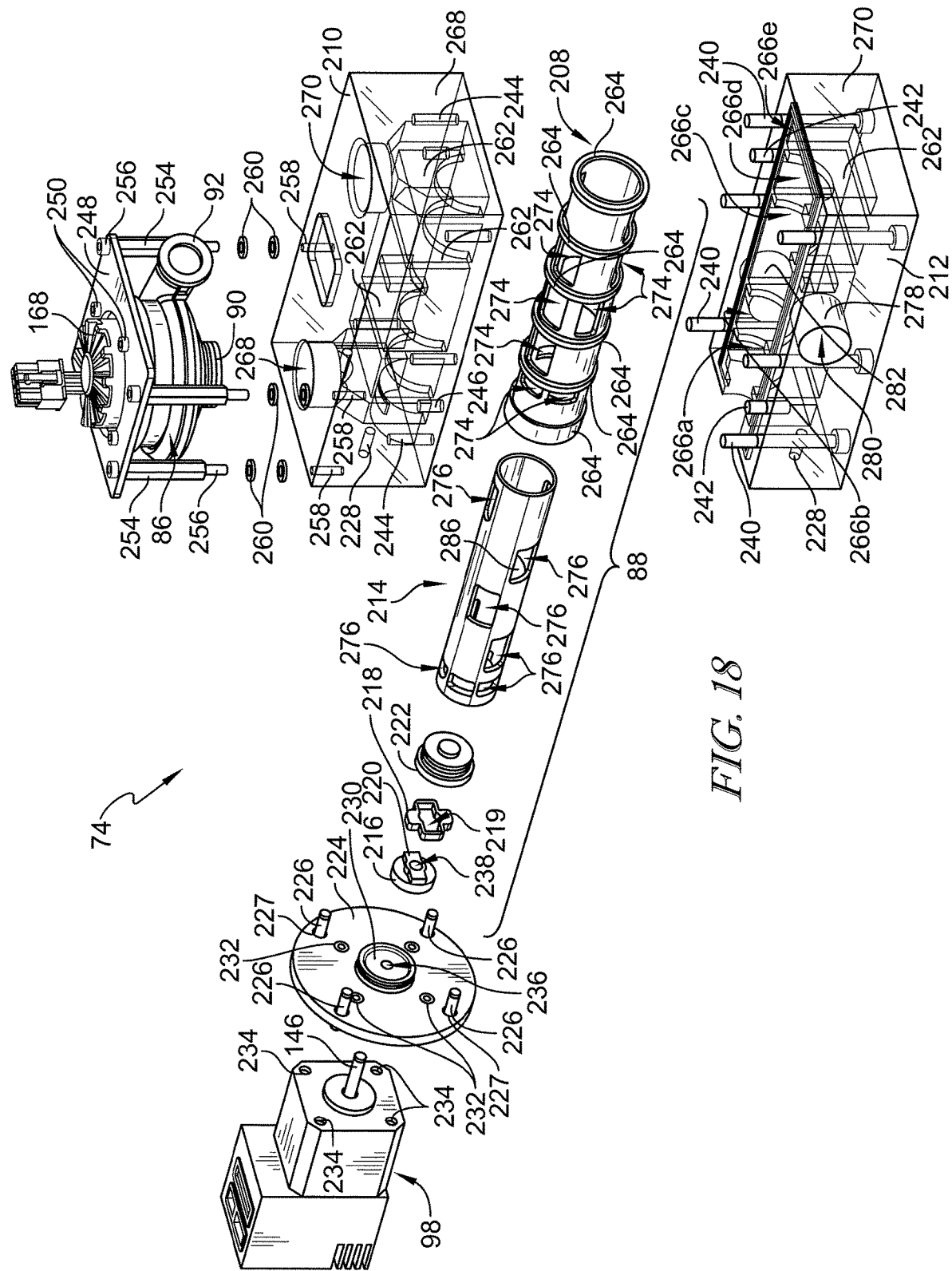
FIG. 18 is an exploded view of the components of FIG. 17 showing the stepper motor on the left hand side of the view, a circular coupling plate spaced to the right of stepper motor, a set of rotary couplers spaced to the right of the circular coupling plate, the rotatable cylinder spaced to the right of the rotary couplers, the stationary cylinder spaced to the right of the rotatable cylinder, the first manifold block spaced above the stationary cylinder, the second manifold block spaced beneath the stationary cylinder, and the blower spaced above the first manifold block.

A circular plate 224 attaches to manifold blocks 210, 212 by use of four fasteners 226, such as bolts, screws, or dowel pins, that extend through apertures 227 provided near the periphery of plate 224 and are received in holes 228 provided in manifold blocks 210, 212 as shown in FIGS. 17 and 18. Plate 224 has a circular hub 230 at its center that is situated adjacent rotatable hub 216. Plate 224 also has an additional set of apertures 232 that receive fasteners (not shown) which thread or press fit into apertures 234 of stepper motor 98 to mount stepper motor 98 to plate 224. A small hole 236 extends through the center of plate 224 and hub 230. Output shaft 146 of stepper motor extends through hole 236 and is received in a hole 238 provided in rotatable hub 216. Hub 216 is press fit onto shaft 146 or is otherwise keyed to shaft 146 to rotate therewith.

In addition to fasteners 226 that interconnect plate 224 with manifold blocks 210, 212, fasteners 240 such as bolts or screws, and dowel pins 242 are provided to connect manifold blocks 210, 212 together. As shown in FIGS. 17 and 18, fasteners 240 and dowel pins 242 are oriented vertically whereas fasteners 226 are oriented horizontally. Manifold blocks 210, 212 have holes 244, 245, respectively, that receive fasteners 240 and holes 246, 247 that receive dowel pins 242.

Blower 86 is attached to a plate 248 with suitable fasteners 250 such as bolts, screws, or dowel pins. Motor 168 of blower 86 extends through a hole 252 in plate 248. A set of standoffs 254 keep plate 248 elevated at a proper distance from at top of manifold block 210 to accommodate blower 86. As shown in FIGS. 17 and 18, a set of fasteners 256 extend through standoffs 254 and are received by holes 258 formed in manifold block 210 (only three holes 258 can be seen in FIG. 18). Thus, blower 86 is sandwiched between plate 248 and manifold block 210, although motor 168 of blower 86 projects through hole 252 of plate 248 as shown in FIGS. 17 and 18. One or more washers 260 may be used, as desired, to fine tune the spacing between the top surface of manifold block 210 and plate 248. Washers 260 are positioned on the lower ends of fasteners 256 beneath standoffs 254 and atop manifold block 210.

Figure 19:
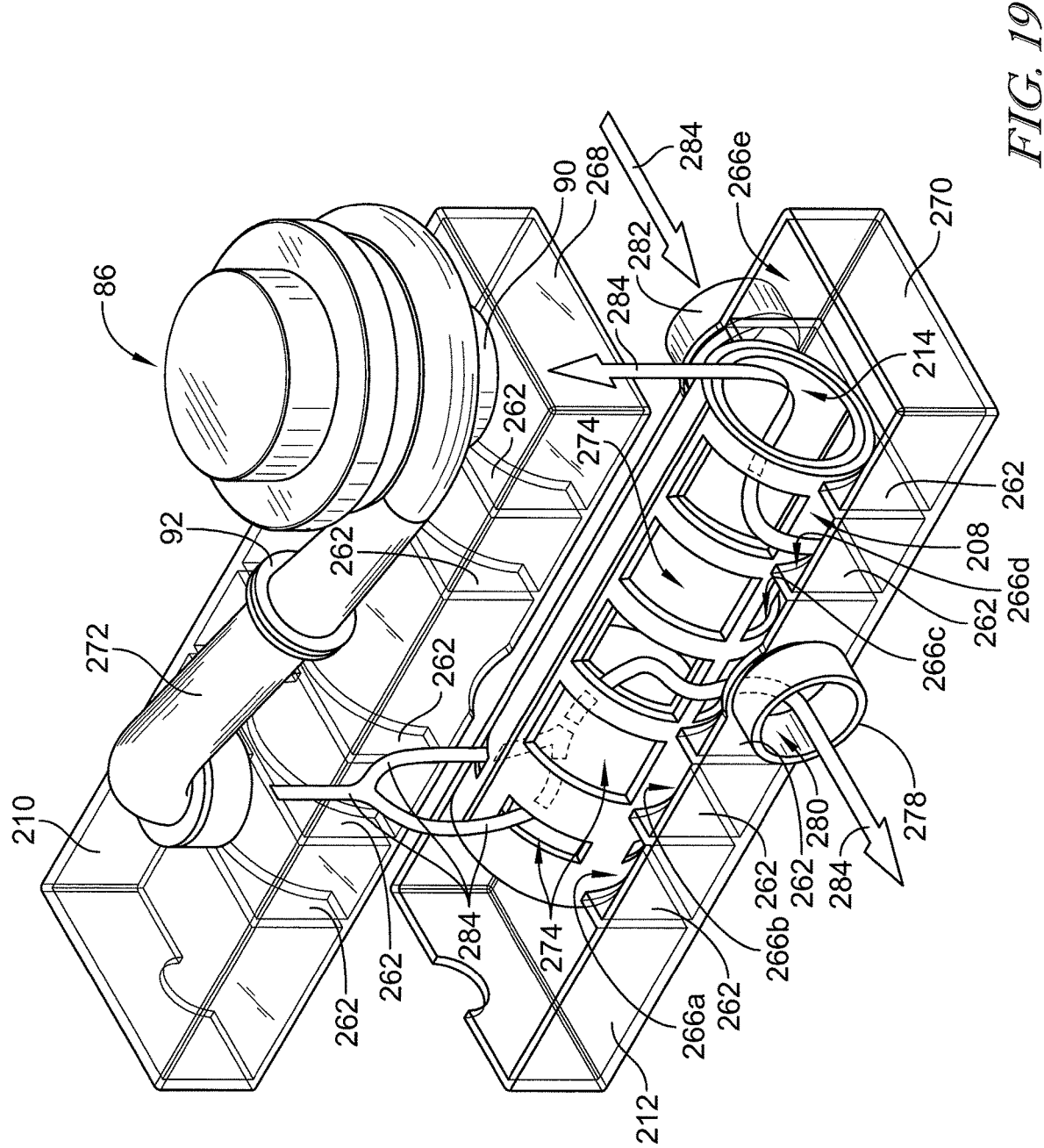
FIG. 19 is a partial exploded perspective view of the manifold blocks, blower, and rotary spool valve of FIGS. 17 and 18 showing the rotatable spool being in a first position relative to the stationary cylinder, and showing a series of arrows that indicate a flow of air from the atmosphere through the manifold blocks to the blower and from the blower through the rotary spool valve for exit toward the patient interface during application of positive pressure during insufflation of the patient.
Figure 20:
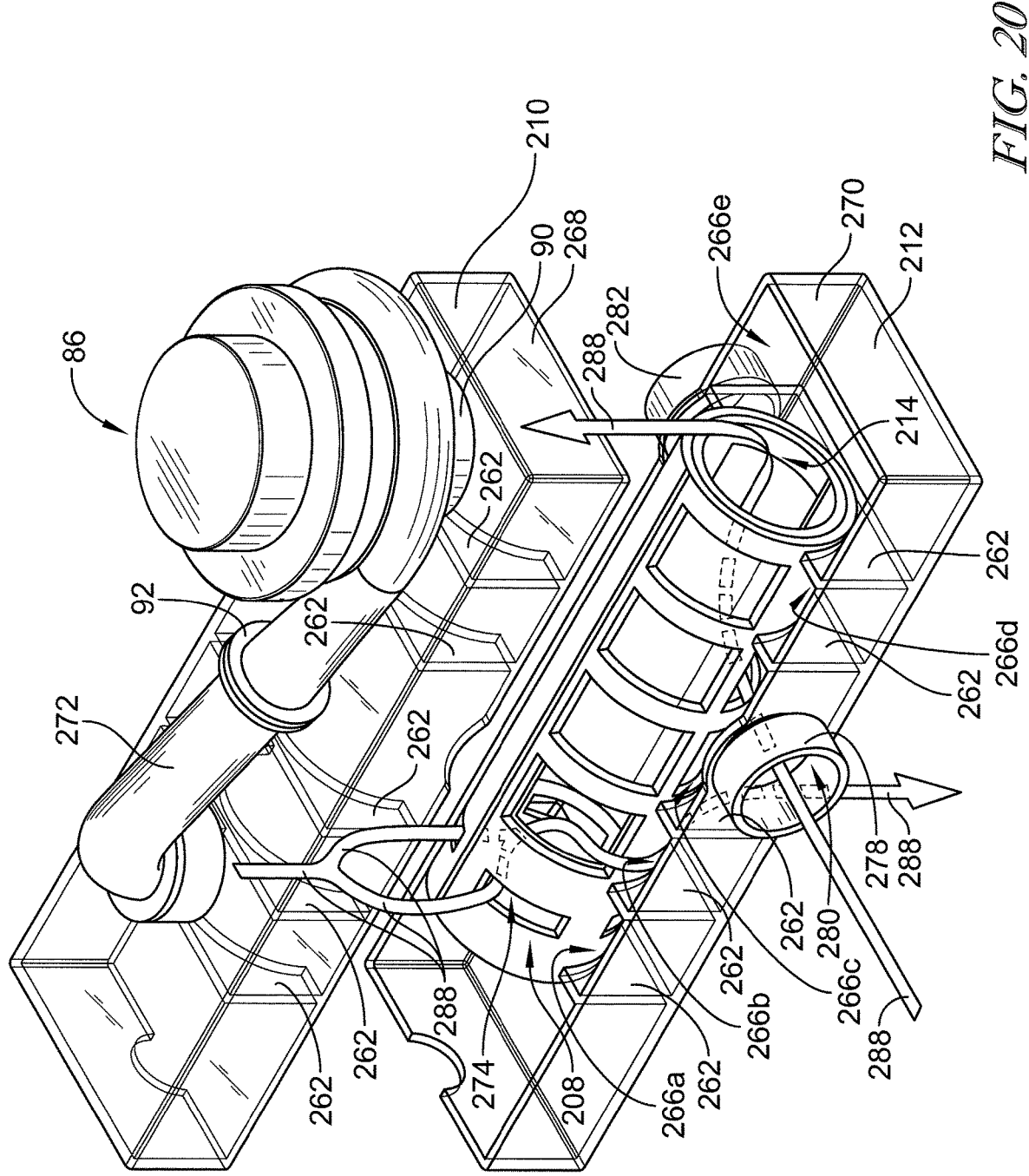
FIG. 20 is a partial exploded perspective view similar to FIG. 19 showing the rotatable spool being in a second position relative to the stationary cylinder, and showing a series of arrows that indicate a flow of air from the patient interface through the rotary spool valve to the blower and from the blower through the rotary spool valve for exit to the atmosphere during application of negative pressure during exsufflation of the patient.
Figure 21:
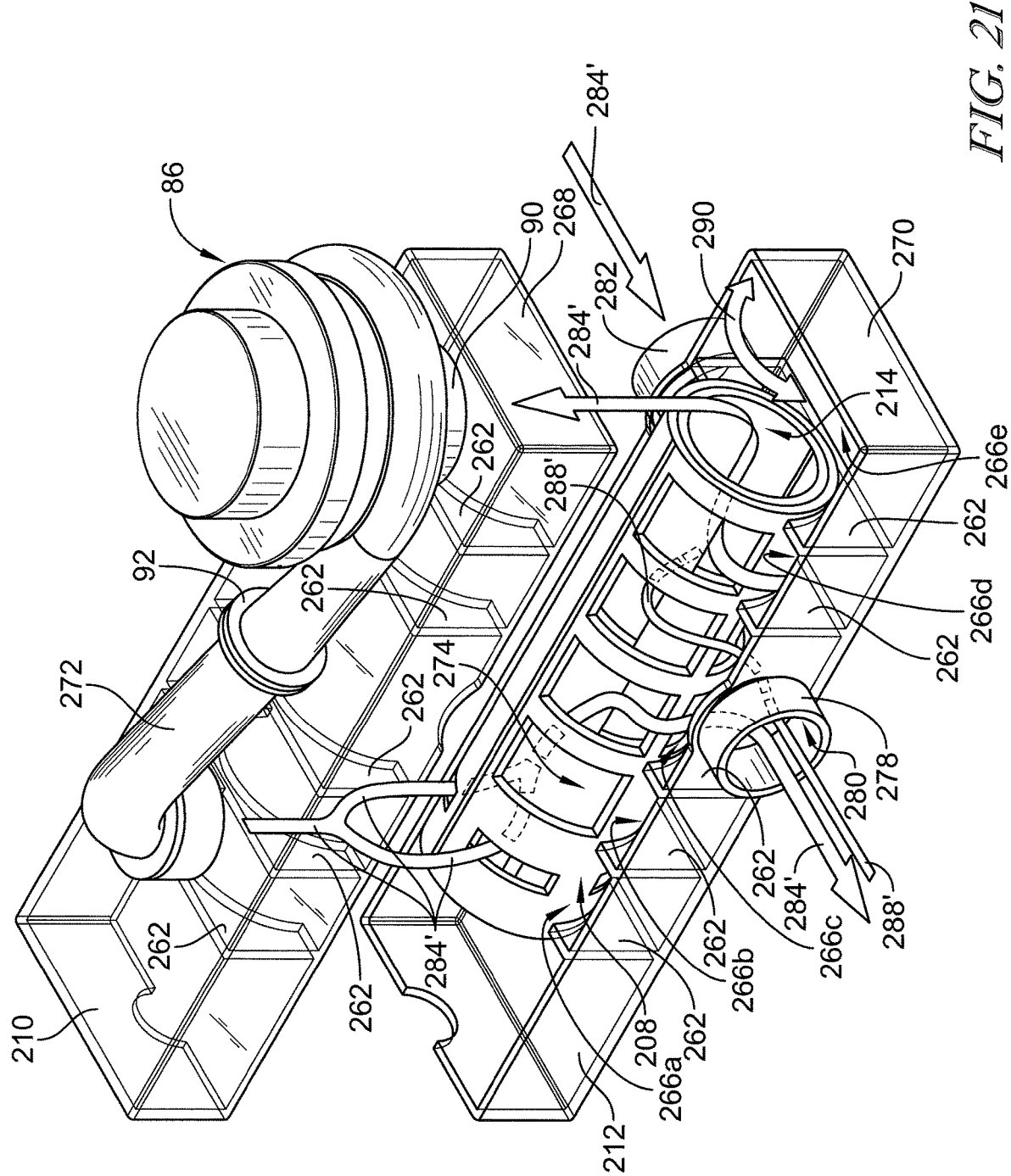
FIG. 21 is a partial exploded perspective view similar to FIGS. 19 and 20 showing the rotatable spool being in an intermediate position between the first and second positions, and showing a series of arrows that indicate that both positive and negative pressure components are applied to the patient interface during application of a rest pressure to the patient and showing a double headed arcuate arrow to indicate that the rotatable spool is able to oscillate back and forth in first and second directions to produce oscillations in the pressure applied to the patient interface.

Manifold blocks 210, 212 each have a set of arch-shaped partition walls 262 as shown best in FIGS. 19-21. Stationary cylinder 208 is captured between partition walls 262 with each partition wall 262 of manifold block 210 being substantially vertically aligned with a respective partition wall 262 of manifold block 212. In some embodiments, annular rings or gaskets 264 are provided around stationary cylinder 208 at spaced locations corresponding to the locations of respective partition walls 262 as shown, for example, in FIGS. 17 and 18. Thus, the arch-shaped edges of partition walls 262 clamp against the rings 264 to enhance the pneumatic sealing between walls 262 and cylinder 208. The walls 262 cooperate to form a set of pockets 266a, 266b, 266c, 266d, 266e, although end walls 268, 270 of manifold blocks 210, 212, respectively, provide one of the boundaries for pocket 266e. Also, open ends of cylinder 208 and spool 214 are situated in pocket 266e. The opposite end of cylinder 208 and spool 214 are closed off by plug 222.

In the embodiment of FIGS. 17 and 18, blower 86 is located on manifold block 210 so that inlet 90 of blower 86 is in pneumatic communication with pocket 266a through a hole 268 formed in the top of manifold block 210 above pocket 266a. Outlet 92 of blower is in pneumatic communication with pocket 266e through a hole 270 formed in the top of manifold block 210 above pocket 266e. A conduit (not shown) extends from outlet 92 of blower 86 to hole 270. In the embodiment of FIGS. 19-21, the situation is reversed in that the inlet 90 of blower 86 is in pneumatic communication with pocket 266e and outlet 92 of blower 86 is in pneumatic communication with pocket 266a via a conduit 272. Thus, the rotary spool valve 88 according to the present disclosure is able to operate in an acceptable manner regardless of whether the inlet 90 or outlet 92 of blower 86 is coupled to pocket 266a with the other of inlet 90 or outlet 92 coupled to pocket 266e.

Stationary cylinder 208 has a set of generally rectangular apertures or holes 274 and spool 214 has a set of generally rectangular apertures or holes 276 as shown best in FIG. 18. A tube 278 of manifold block 212 has an opening 280 in pneumatic communication with pocket 266c. Opening 280 is also in communication with patient interface 22. Another tube 282 of manifold block 212 has an opening (not shown but similar to opening 280) in pneumatic communication with atmosphere. In the embodiment of FIGS. 17 and 18, tube 282 communicates pneumatically with pocket 266b and in the embodiment of FIGS. 19-21, tube 282 communicates pneumatically with pocket 266d.

Spool 214 is movable by stepper motor 98 between first and second positions relative to cylinder 208. In the first position of spool 214, positive pressure is output from opening 280 to patient interface 22 and in the second position of spool 214, negative pressure is applied to patient interface 22 from opening 280. When spool 214 is in the first position, a first subset of holes 276 of spool 214 is aligned with a first subset of holes 274 of cylinder 208. When spool 214 is in the second position, a second subset of holes 276 is aligned with a second subset of holes 274 of cylinder 208. Some, but not all, of the holes 274, 276 of the first subset are also included in the second subset.

With regard to FIG. 19 in which spool 214 is in the first position, a first set of arrows 284 is provided to show the flow of air through tube 282 into pocket 266d, then through one of holes 274 and one of holes 276 associated with pocket 266d into the interior region of spool 214 where it flows out of the open end of spool 214 into pocket 266e. From pocket 266e, the air is drawn upwardly into the inlet 90 of blower 86 to be pressurized by the blower impeller and forced out of the outlet of blower and tube 272 into pocket 266a. From pocket 266a, the air is forced back into the interior region of spool 214 through holes 274, 276 associated with pocket 266a and then the air enters pocket 266c through holes 274, 276 associated with pocket 266c. The air in pocket 266c is then forced through opening 280 of tube 278 to apply positive pressure to the patient interface 22.

Spool 214 includes an internal wall 286 which can be seen, for example, in FIG. 18 through one of holes 274. The internal wall 286 is approximately at the midpoint of the length of spool 214. The internal wall 286 blocks pneumatic communication within the interior region of spool 214 between the blower inlet side and blower outlet side of spool 214. So, in FIG. 19 for example, the internal wall 286 prevents the pressurized air entering pocket 266c from simply flowing all the way back through spool 214 to pocket 266e. It can be seen by the routing of arrows 284 in FIG. 19 that pocket 266b is bypassed by the air flow. Thus, solid portions of spool 214 block or close off the holes 274 of cylinder 208 that are associated with pocket 266b.

With regard to FIG. 20 in which spool 214 is in the second position, a second set of arrows 288 is provided to show the flow of air from the patient interface 22 through tube 278 into pocket 266c, then through one of holes 274 and one of holes 276 associated with pocket 266c into the interior region of spool 214 where it flows out of the open end of spool 214 into pocket 266e. From pocket 266e, the air is drawn upwardly into the inlet 90 of blower 86 to be pressurized by the blower impeller and forced out of the outlet of blower and tube 272 into pocket 266a. From pocket 266a, the air is forced back into the interior region of spool 214 through holes 274, 276 associated with pocket 266a and then the air enters pocket 266b through holes 274, 276 associated with pocket 266b. The air in pocket 266c is then forced to atmosphere through an exhaust opening (not shown) associated with pocket 266b in a bottom of manifold block 212. It can be seen by the routing of arrows 288 in FIG. 20 that pocket 266d is bypassed by the air flow. Thus, solid portions of spool 214 block or close off the holes 274 of cylinder 208 that are associated with pocket 266d.

Referring now to FIG. 21, spool 214 is in an intermediate position between the first and second positions so that a pause or rest pressure is applied to the patient interface 22 via opening 280 of tube 278. In the intermediate position, holes 274, 276 associated with pocket 266c on both sides of the internal partition wall 286 of spool 214 are partially opened. As a result, two air flow arrows 284', 288' are shown in FIG. 21 to indicate the air flow. Arrow 288' represents air being drawn into pocket 266c due to holes 274, 276 on the blower inlet side of pocket 266c being opened partially. Air flow 288' merges with airflow 284' entering the interior region of spool 214 through tube 282, pocket 266d, and the holes 274, 276 associated with pocket 266d. From that point onward, the air flow indicated by arrows 284' is the same as that discussed above in connection with arrows 284 and so that portion of the discussion need not be repeated. The fact that arrows 284' are illustrated as being thicker than arrows 288' is intended to imply that the rest pressure is a positive pressure. However, it is within the scope of this disclosure for spool 214 to be positioned relative to cylinder 208 so as to produce a negative rest pressure or a zero rest pressure.

A double headed arrow 290 is shown in FIG. 21 to indicate that spool 214 is able to be cyclically oscillated back and forth by stepper motor 98 through an angular displacement that is less than the angular displacement that spool 214 undergoes when moving between the first and second positions. This rotary oscillation of spool 214 in the first and second directions indicated by arrow 290 produces oscillations in the pressure applied to the patient interface 22 via opening 280 of tube 278. Such oscillatory movement of spool 214 can be programmed to occur when spool 214 is in the first position, the second position, or any position therebetween. That is, oscillations in the pressure can be supplied to the patient interface during insufflation, exsufflation and pauses times.

While any materials of suitable strength may be used to construct the various components of the rotary spool valve 88, in some embodiments, plates 224, 248 are made of aluminum; spool 214, hub 216, and plug 222 are made of acetyl plastic material; element 218 and cylinder 208 are made of acrylonitrile butadiene styrene (ABS) plastic material; manifold blocks 210, 212 are made of acrylic plastic material; rings 264 are made of a silicone sponge material; and conduit 272 is made of rubber.

Figure 22:
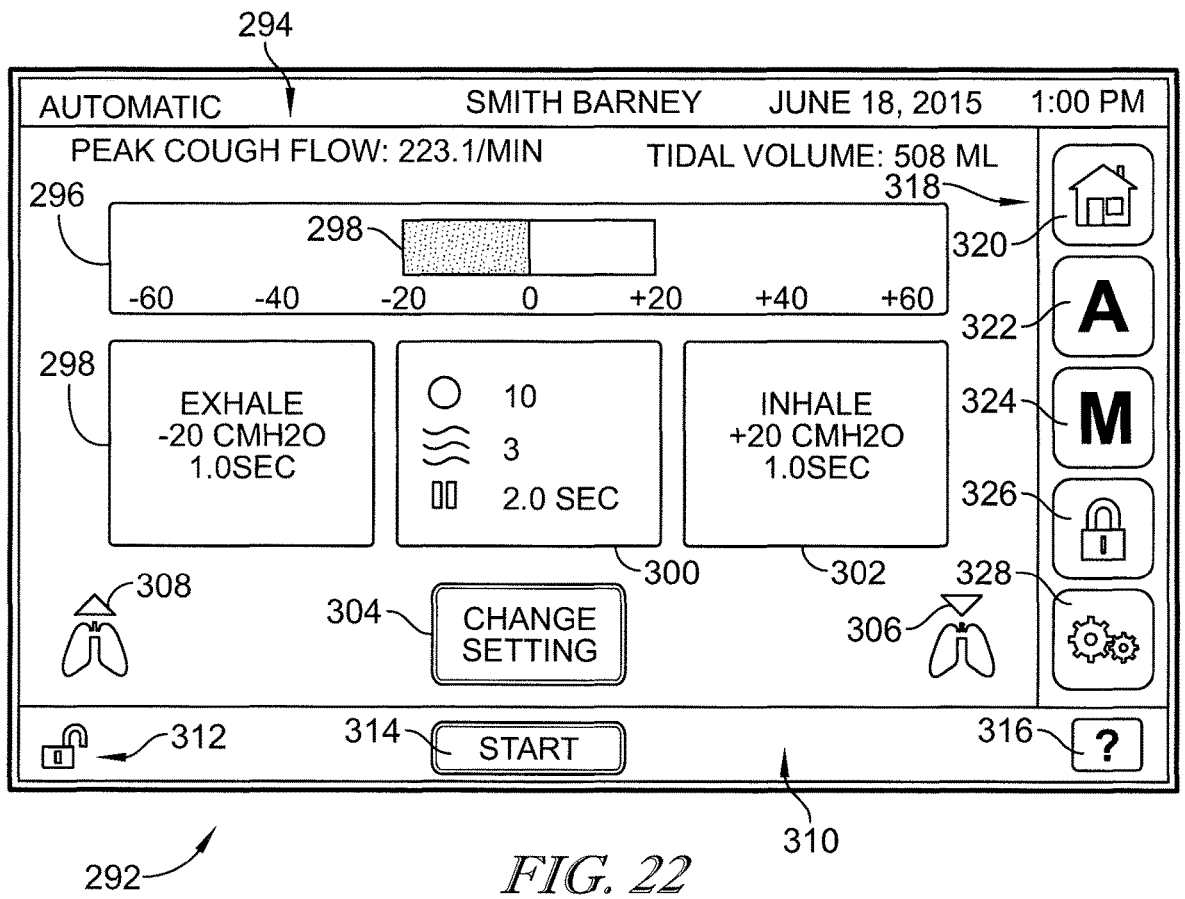
FIG. 22 is an example of a screen shot of the GUI of FIG. 1 when the respiratory device is operating in an automatic mode.

Referring now to FIG. 22, an example of a screen shot 292 of the GUI 16 is shown when the respiratory device 10 is operating in an automatic mode. Screen 292 includes a header 294 that has text indicating that device 10 is operating in the automatic mode and including a patient's name, the date and the time. Beneath the header 294 on screen 292 are numerical values for Peak Cough Flow and Tidal Volume. The values shown are determined based on signals received by control circuitry 76 from one or more of sensors 106 which are shown diagrammatically in FIG. 40.

Screen 292 of FIG. 22 also has a window 296 with a bar graph 298 that indicates a programmed range of the positive insufflation pressure and the negative insufflation pressure to be applied to the patient during treatment. In the illustrative example the positive insufflation pressure is programmed at 20 cmH$_2$O and the negative exsufflation pressure is programmed at −20 cmH$_2$O. As indicated in window 296, device is capable of being programmed to have a maximum insufflation pressure of 60 cmH$_2$O and a maximum (i.e., most negative) exsufflation pressure of −60 cmH$_2$O.

Beneath window 296 on screen 292 are three windows 298, 300, 302 which have information concerning the programmed settings for exsufflation, pause, and insufflation, respectively. In the illustrative example, the programmed 20 cmH$_2$O insufflation pressure is set to be applied to the patient for 1.0 second as indicated in window 302, the −20 cmH$_2$O exsufflation pressure is set to be applied to the patient for 1.0 second as indicated in window 298, and then a pause pressure of 10 cmH$_2$O at a flow setting of 3 is to be applied to the patient for 2.0 seconds as indicated in window 300.

Beneath window 300 on screen 296 is a change setting button 304 that is selected by a user to re-program the operating parameters of device 10, such as those shown in windows 298, 300, 302. To the right and left of button 304, respectively, is an inhale column indicator 306 that is illuminated to indicate when the insufflation pressure is being applied to patient interface 22 by device 10 and an exhale column indicator 308 that is illuminated to indicate when the exsufflation pressure is being applied to patient interface 22 by device 10. A footer 310 at the bottom of screen 292 includes a lock status icon 312 to indicate whether device 10 is locked from use or unlocked for use, a start button 314 that is touched by a user to start device 10 operating according to the programmed parameters, and a help icon 316 that is selected to obtain help regarding the operation of device 10.

A menu 318 of icons appears in a column at the right hand side of screen 292. Menu 318 includes a home icon 320 that is selected by a user to return to a home screen of device 10, an automatic icon 322 that is selected by a user to place device 10 in the automatic mode, a manual icon 324 that is selected by a user to place device 10 in a manual mode, a lock icon 326 that is selected by a user to lock device 10 from use (if device 10 is locked then an unlock icon appears in menu 318 in lieu of icon 326), and a general settings icon 328 that is selected by a user to adjust settings and perform various administration functions relating to device 10.

The automatic and manual modes of device 10 are very similar to those described in U.S. Pat. No. 8,539,952 which is already incorporated by reference herein. However, one of the primary differences between the device of U.S. Pat. No. 8,539,952 and device 10 is that after the pause period, the positive insufflation pressure is applied to patient interface 22 in response to an inspiratory trigger being sensed by one or more of sensor(s) 106. That is, the insufflation pressure is applied to patient interface 22 by device 10 when the patient begins to inhale. With regard to illustrative device 10, the change from insufflation mode to exsufflation mode and then the change from exsufflation mode to pause mode are dependent upon the programmed times. However, that is not to say that in other embodiments, device 10 could not sense an expiratory trigger to switch from insufflation mode to exsufflation mode and/or a subsequent inspiratory trigger to switch from exsufflation mode to pause mode.

Figure 23:
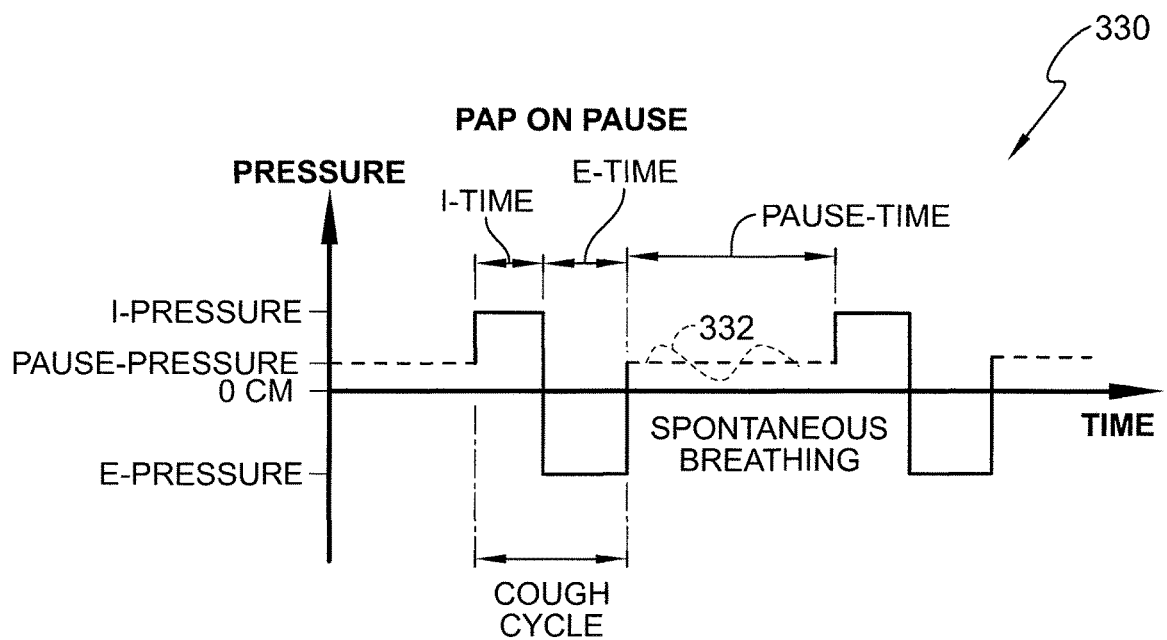
FIG. 23 is a graph showing a pressure v. time curve showing a positive insufflation pressure (I-pressure), a negative exsufflation pressure (E-pressure), and a pause pressure (aka rest pressure) that is a positive pressure less than the I-pressure during which the patient breaths spontaneously for multiple breaths.

Referring now to FIG. 23, a graph 330 shows a pressure v. time curve. Along a Pressure axis of graph 330 are shown the following: an I-pressure corresponding to the insufflation pressure discussed above, a Pause-pressure corresponding to the pause or rest pressure discussed above, and an E-pressure corresponding to the exsufflation pressure discussed above. Along a Time axis of graph 330 are shown the following: an I-time corresponding to the time during which insufflation pressure is applied by device 10, an E-time corresponding to the time during which exsufflation pressure is applied by device 10, and a Pause-time corresponding to the pause time of device 10. Graph 330 shows that the insufflation and exsufflation together are considered to be a cough cycle according to this disclosure. Graph 330 includes a generally sinusoidal dotted line 332 superimposed on the pause pressure line to indicate that the patient breaths spontaneously for multiple breaths during the pause time.

Figure 24:
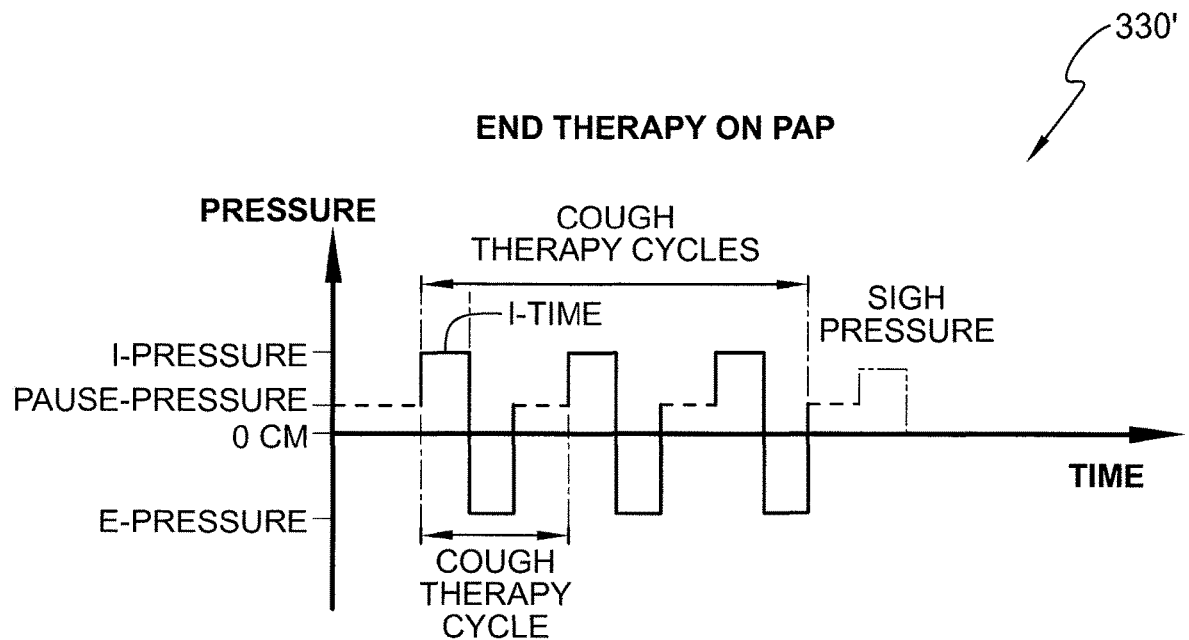
FIG. 24 is a graph, similar to FIG. 23, but showing a sigh pressure at the end of the treatment cycle, the sigh pressure being less than the I-pressure and greater than the pause pressure.

Referring now to FIG. 24, a graph 330', which is similar to graph 330 of FIG. 23, is shown. Graph 330' indicates that the insufflation, exsufflation, and pause together are considered to be a cough therapy cycle. In the illustrative example of graph 330', the therapy applied by device 10 includes three cough therapy cycles. Graph 330' also shows that device 10 is operated to apply a sigh pressure at the end of the treatment cycle. The sigh pressure is among the parameters that a user programs into device 10 using GUI 16. In the illustrative example, the sigh pressure is less than the I-pressure (i.e., the insufflation pressure) and greater than the pause pressure.

Figure 25:
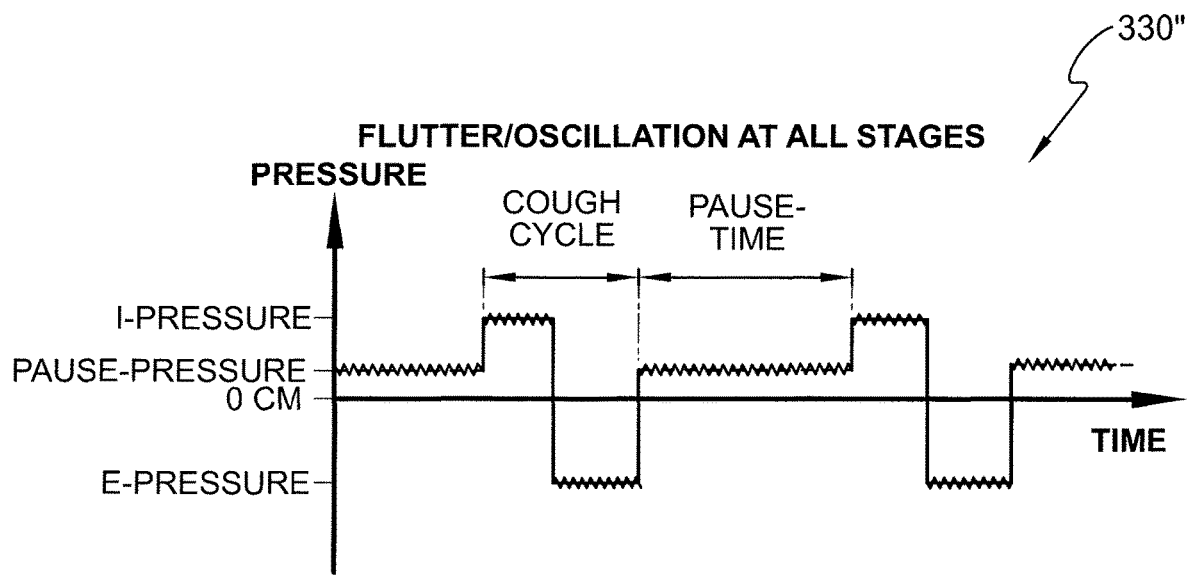
FIG. 25 is a graph, similar to FIG. 23, showing that the respiratory devices of FIGS. 1-21 are capable of producing oscillations in the pressure applied to the patient during insufflation, exsufflation and pause times.

Referring now to FIG. 25 a graph 330", similar graph 330 of FIG. 23, is shown. Graph 330" shows that device 10 is capable of producing oscillations in the pressure applied to the patient during insufflation, exsufflation and pause times. The oscillations are a result of the oscillatory movement of rotatable plate 122 in directions 204, 206 relative to stationary plates 114, 118 in one embodiment as discussed above or as a result of the oscillatory movement of rotatable spool 218 in the directions indicated by double headed arrow 290 relative to stationary cylinder 208 in another embodiment as discussed above.

Figure 26:
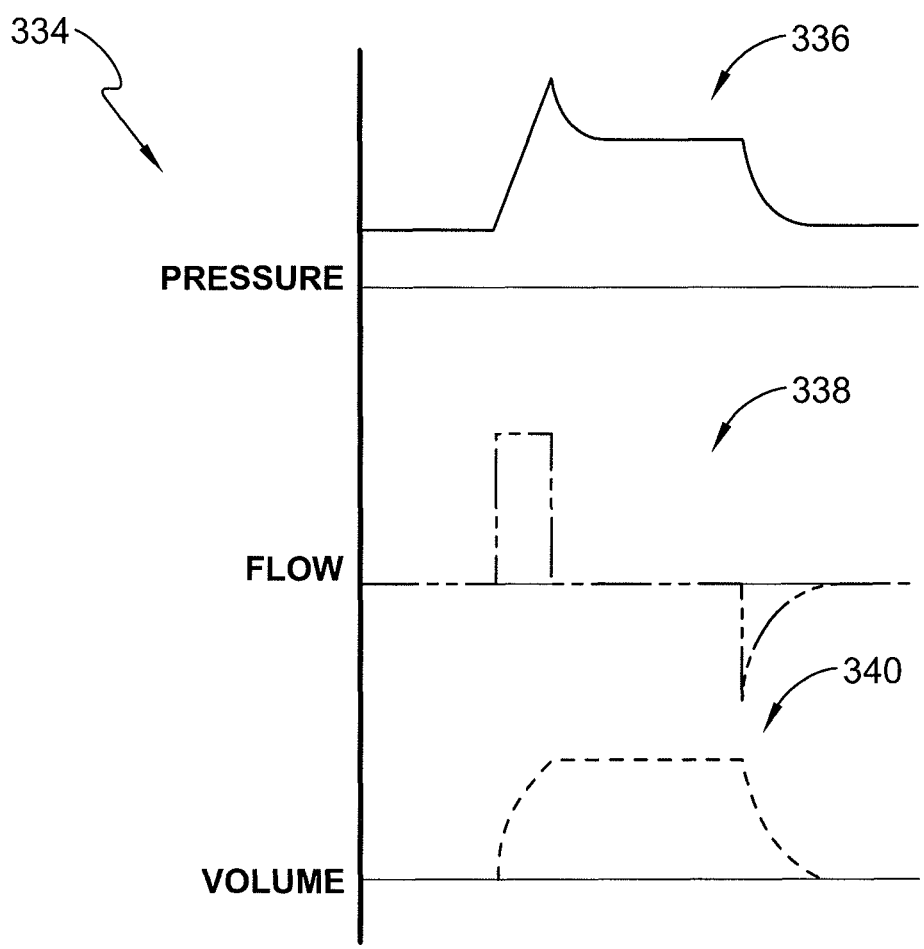
FIG. 26 is a graph showing examples of pressure, flow and volume graphs that are viewable on the GUI of the respiratory devices of FIGS. 1-21 based on measurements taken by one or more sensors of the device.
Figure 27:
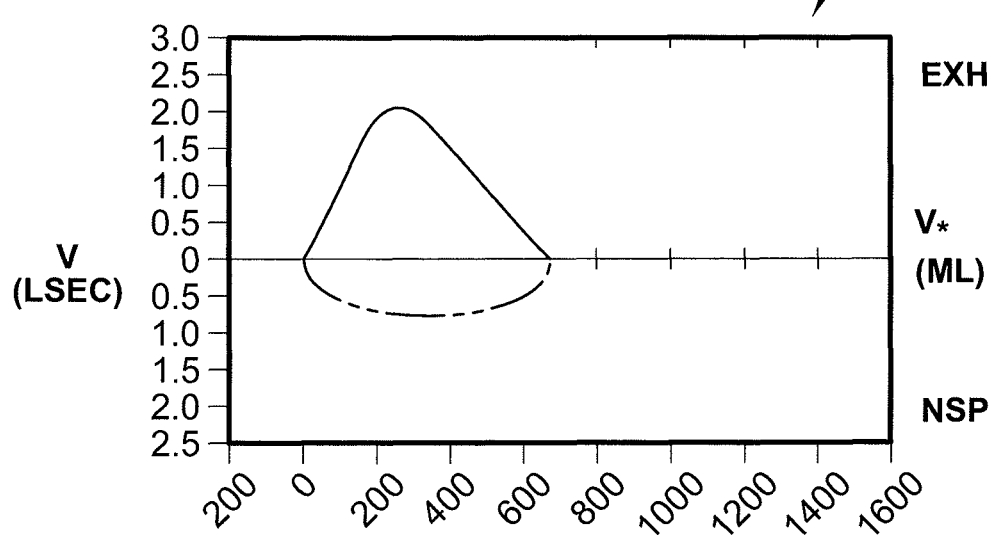
FIG. 27 is graph showing an example of a spirometry curve of volumetric flow rate v. volume that is viewable on the GUI of the respiratory devices of FIGS. 1-21.

In some embodiments, control circuitry 76 of device 10 is programmed to store and/or analyze data sensed by the one or more sensors 106. For example, FIG. 26 shows a multi-trace graph 334 including pressure, flow and volume graphs 336, 338, 340 that are viewable on the GUI 16 of device 10. As another example, FIG. 27 shows a graph 342 including a spirometry curve of volumetric flow rate v. volume that is viewable on the GUI 16 of device 10.

Figure 28:
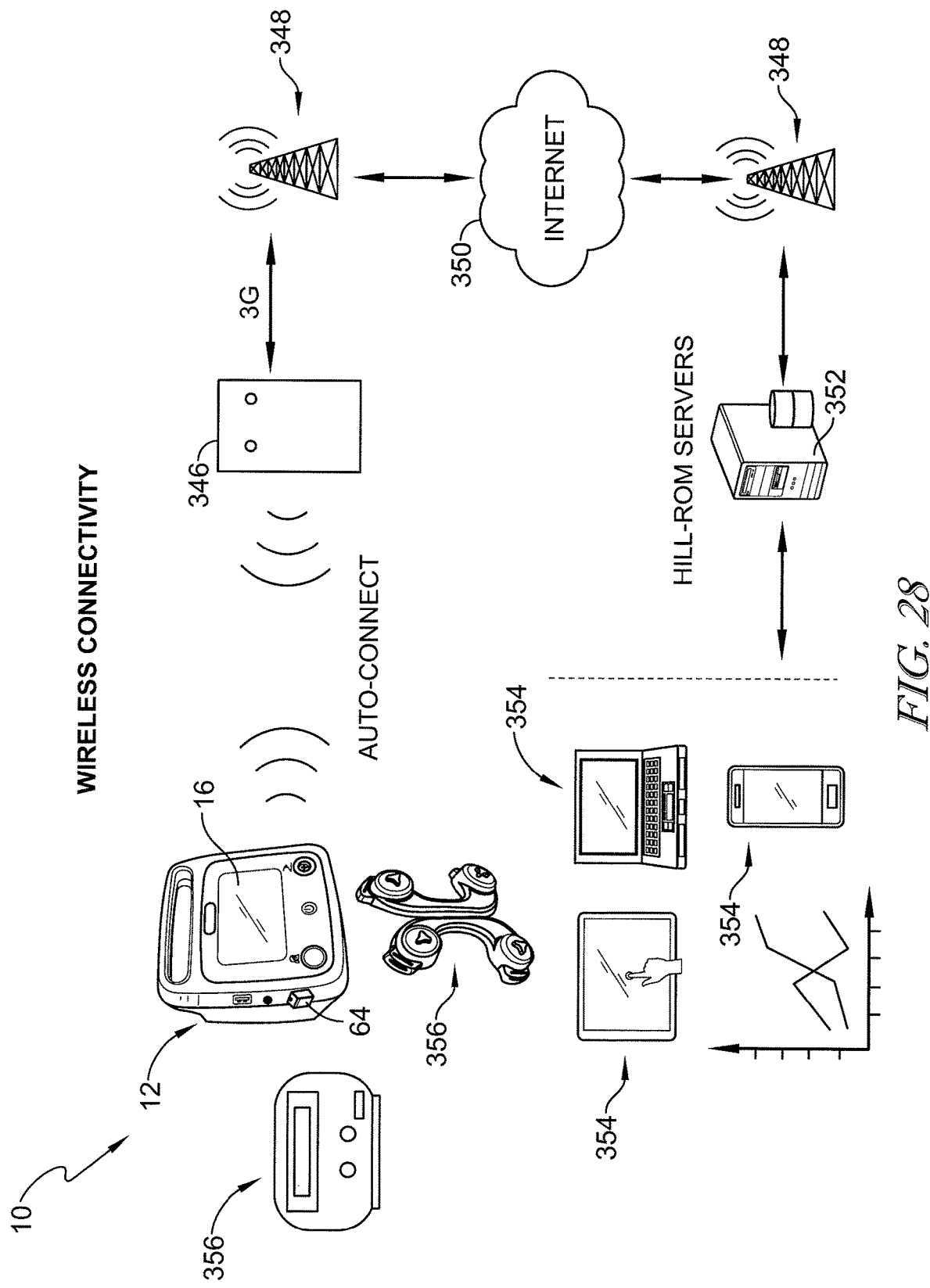
FIG. 28 is a diagrammatic view showing the wireless communication capability of the respiratory devices of FIGS. 1-21 showing the respiratory device sending and receiving data via communication infrastructure to and from one or more remote servers that are coupled to one or more remote computer devices that are configured to analyze or process data received from one or more remote respiratory devices'.

Referring now to FIG. 28, wireless communication module 64 of device 10 is operable to send and receive data to and from a wireless access point 346 which, in turn, is coupled via communication infrastructure 348 such as the Internet 350 to one or more remote servers 352. Infrastructure 348 and Internet are shown diagrammatically in FIG.

28. The double headed arrows between the various components in FIG. 28 are intended to represent the two-way communication capability between device 10 and server(s) 352. Server 352, therefore, is at a facility that is remote from the facility at which device 10 is located. Server 352 is communicatively coupled to one or more remote computer devices 354 such as the illustrative tablet computer, lap top computer, and smart phone. Devices 354 are configured with software to analyze or process data received from one or more remote respiratory devices 10. If desired, device 10 is configured to communicate wirelessly with other respiratory devices 356 so that device 10 is able to coordinate the delivery of multiple types of respiratory treatment to a patient using devices 10, 356.

Figure 29:
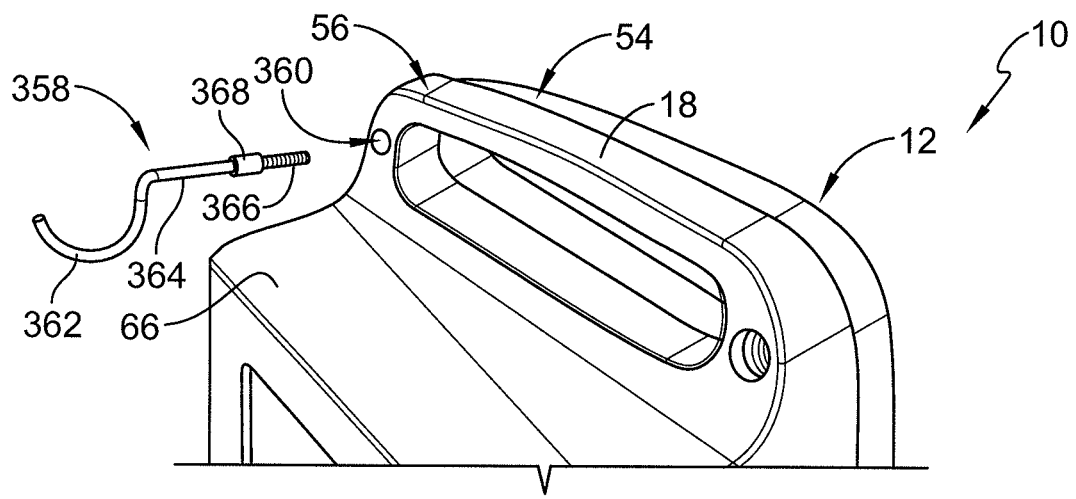
FIG. 29 is a partial exploded perspective view showing a combination fastener/hose retention hook arranged for insertion into a hole provided at a back of handle of the housing of the respiratory device of FIG. 1.
Figure 30:
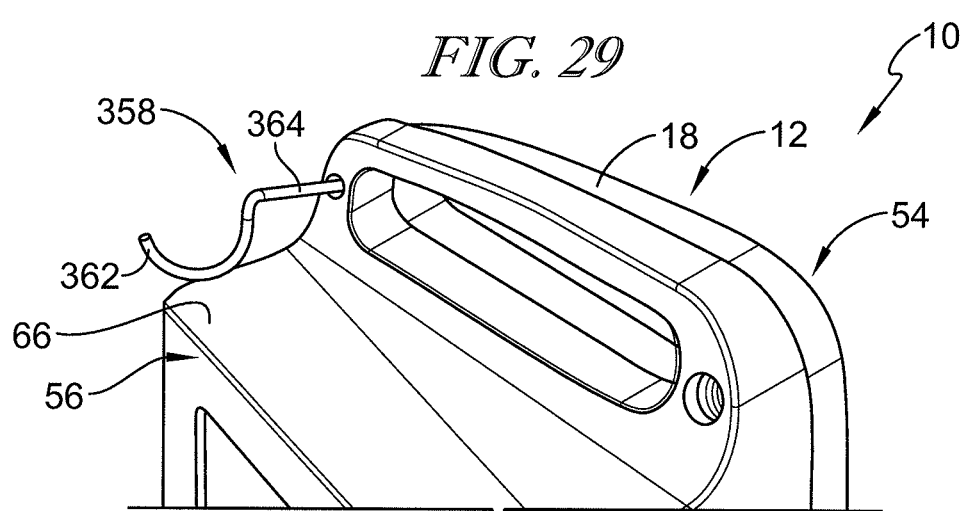
FIG. 30 is a partial perspective view, similar to FIG. 29, showing the combination fastener/hose retention hook attached to the handle of the housing.
Figure 31:
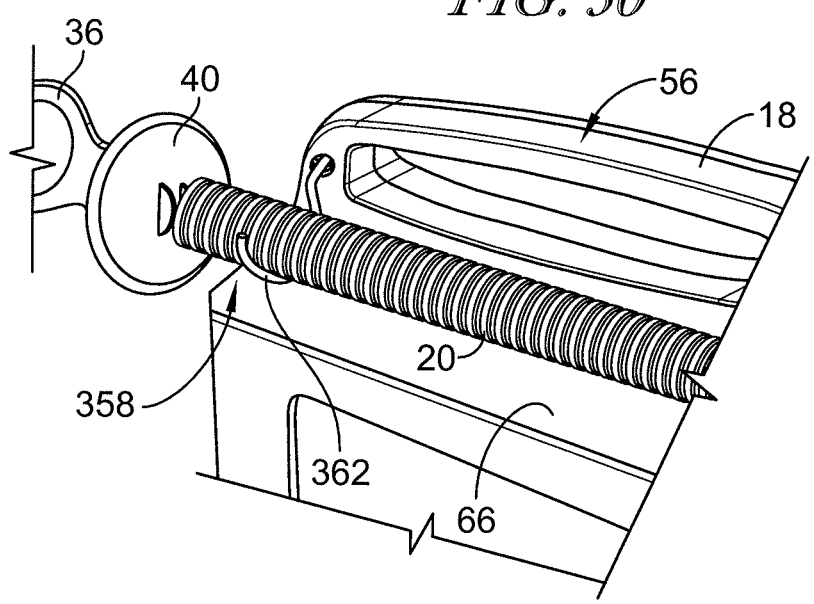
FIG. 31 is a partial perspective view, similar to FIG. 30, showing the hose of the patient interface retained on the combination fastener/hose retention hook in a storage position.

Referring now to FIG. 29, a combination fastener/hose retention hook 358 is arranged for insertion into a hole 360 provided in a portion of shell 56 that serves as a back of handle 18 of the housing 12 of device 10. Hook 358 includes a hook portion 362, a non-threaded straight portion 364, a threaded straight portion 366, and an enlarged shoulder portion 368 that interconnects portions 364, 366. Threaded portion 366 fastens shells 54, 56 together along with other threaded fasteners (not shown). Shoulder portion 358 abuts a portion of shell 56 inside of hole 360 when hook 358 is attached to shells 54, 56. As shown in FIG. 30, after hook 358 is attached to the handle 18 of the housing 12, straight portion 364 projects from hole 360 and positions hook portion 372 in elevated spaced relation with top wall 66 of shell 56. Hook portion 372 is configured to receive hose 20 as shown in FIG. 31, thereby to retain hose 20 in a storage position.

Figure 32:
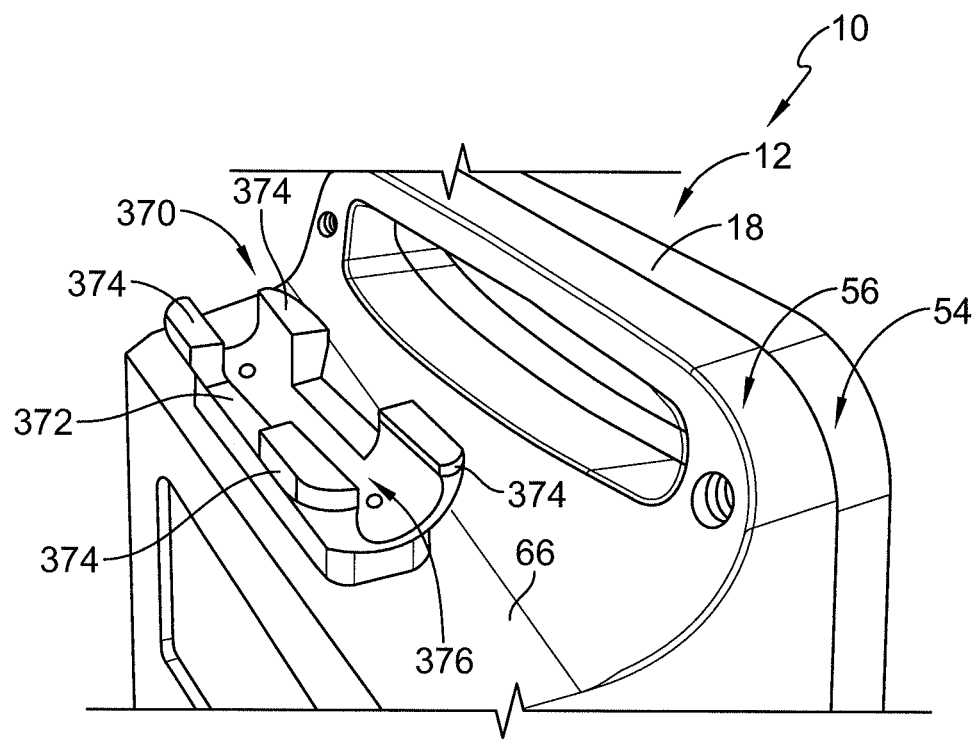
FIG. 32 is a partial perspective view showing an alternative hose retention device mounted to a top wall of the housing of the respiratory device of FIG. 1 behind the handle.
Figure 33:
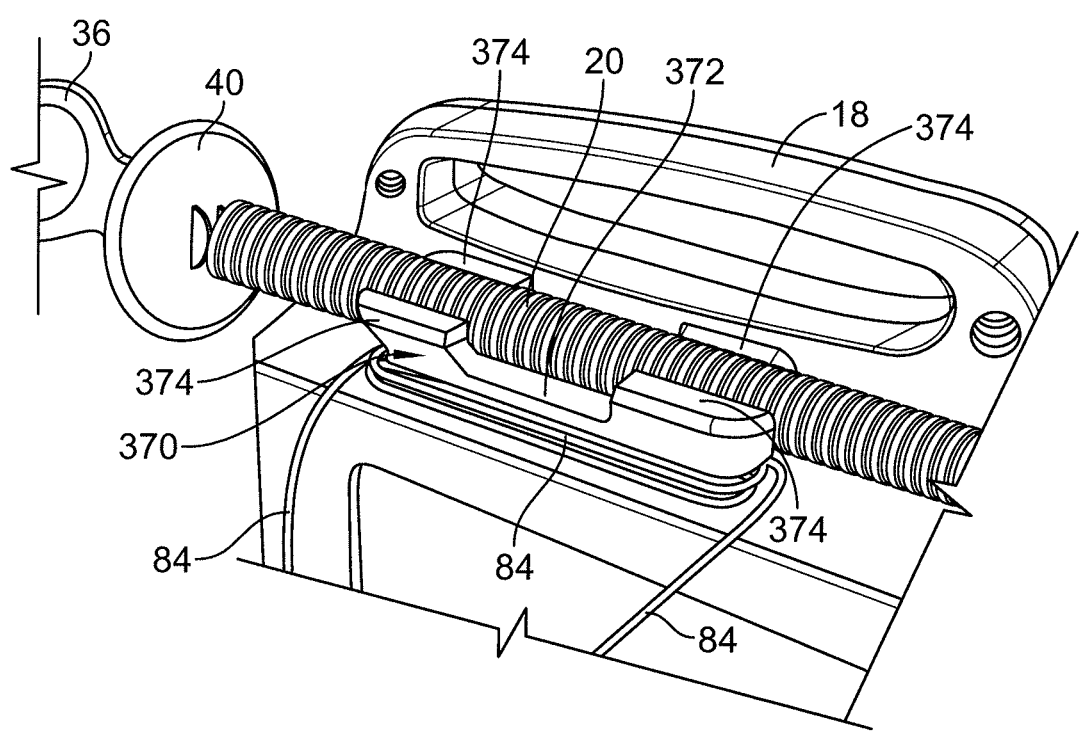
FIG. 33 is a partial perspective view showing the hose retained on the hose retention device of FIG. 32 in a storage position and showing the hose retention device also being configured to serve as a cord wrap around which a power cord of the respiratory device is able to be wrapped.
Figure 34:
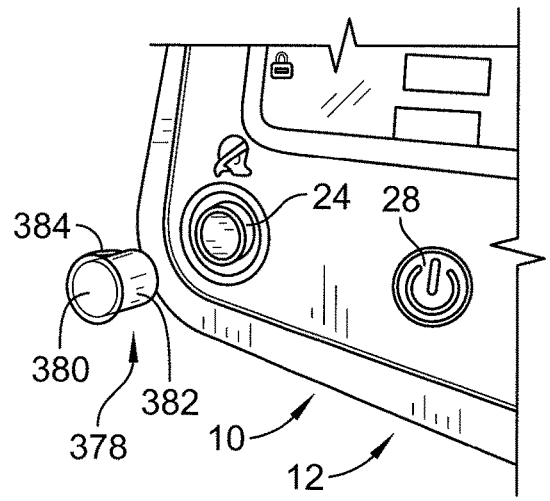
FIG. 34 is a partial exploded perspective view of a lower front corner of the housing of the respiratory devices of FIGS. 1-21 showing a hose adapter exploded away from a hose port of the respiratory device.

Referring now to FIGS. 32 and 33, an alternative hose retention device 370 is mounted to top wall 66 of housing 12 of device 10 behind the handle 18. Device 370 includes a lower portion 372 and a set of cleats 374 that are grouped in pairs that project upwardly at the opposite ends of lower portion 372. Cleats 374 and lower portion 372 are shaped to define a hose-receiving trough 376, shown in FIG. 32, that is configured to receive hose 20 therein to retain hose 20 in a storage position as shown in FIG. 33. Hose retention device 370 is also configured to serve as a cord wrap around which power cord 84 of device 10 is able to be wrapped as shown in FIG. 33. In particular, cord 84 wraps around lower portion 372 of device 370 beneath cleats 374.

Figure 35:
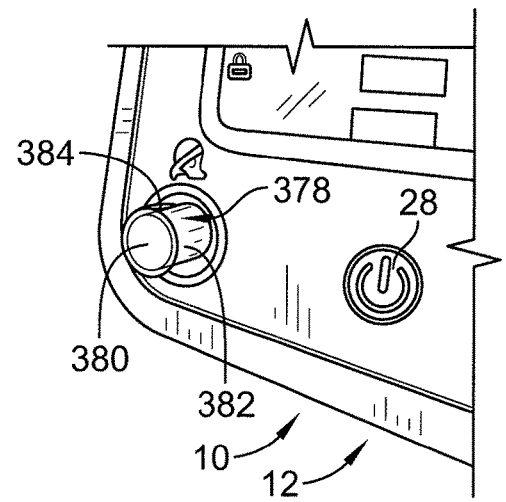
FIG. 35 is a perspective view, similar to FIG. 34, showing the hose adapter attached to the hose port.
Figure 36:
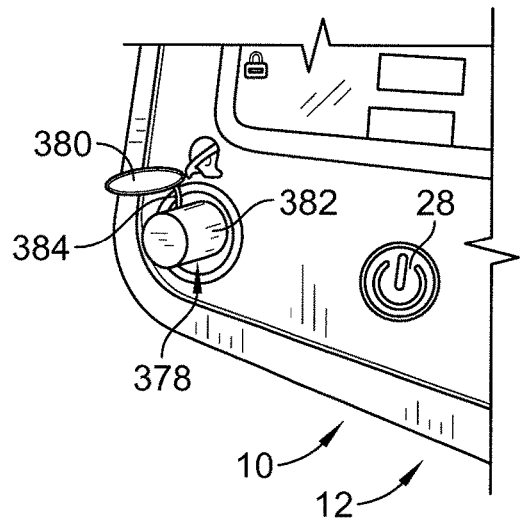
FIG. 36 is a perspective view, similar to FIG. 35, showing a cap of the hose adapter moved to an open position.
Figure 37:
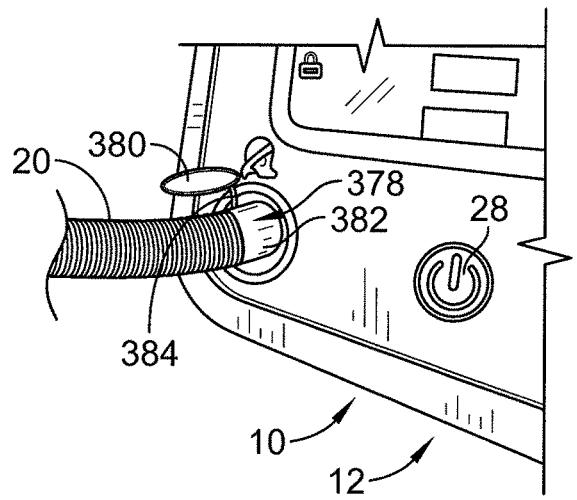
FIG. 37 is a perspective view, similar to FIG. 36, showing an end of the hose of the patient interface attached to the hose adapter.

Referring now to FIGS. 34-37, in some embodiments, a hose adapter 378 is used to connect hose 20 to port 24. Adapter is sized to slip over port 24 with a slight press fit therebetween. After adapter 378 is attached to port 24, as shown in FIG. 35, a cap 380 of adapter 378 is opened from a tubular portion 382 of adapter 378 as shown in FIG. 36. A tether 384 interconnects cap 380 and tubular portion 382 so that cap 380 does not get separated from tubular portion 382 and lost after opening. After cap 380 is opened, an open end of hose 20 opposite from mask 36 (or mouthpiece) is slipped over an end region of tubular portion 382 of adapter 378 with a slight press fit therebetween. After device 10 has been used for a respiratory therapy or treatment session, hose 20 is decoupled from adapter 378 and cap 380 is moved back to the closed position. Use of adapter 378 keeps port 24 from becoming contaminated as easily as otherwise may occur without the use of adapter 378. In some embodiments, adapter 378 is made from a medical grade plastic material that can be cleaned easily.

Figure 38:
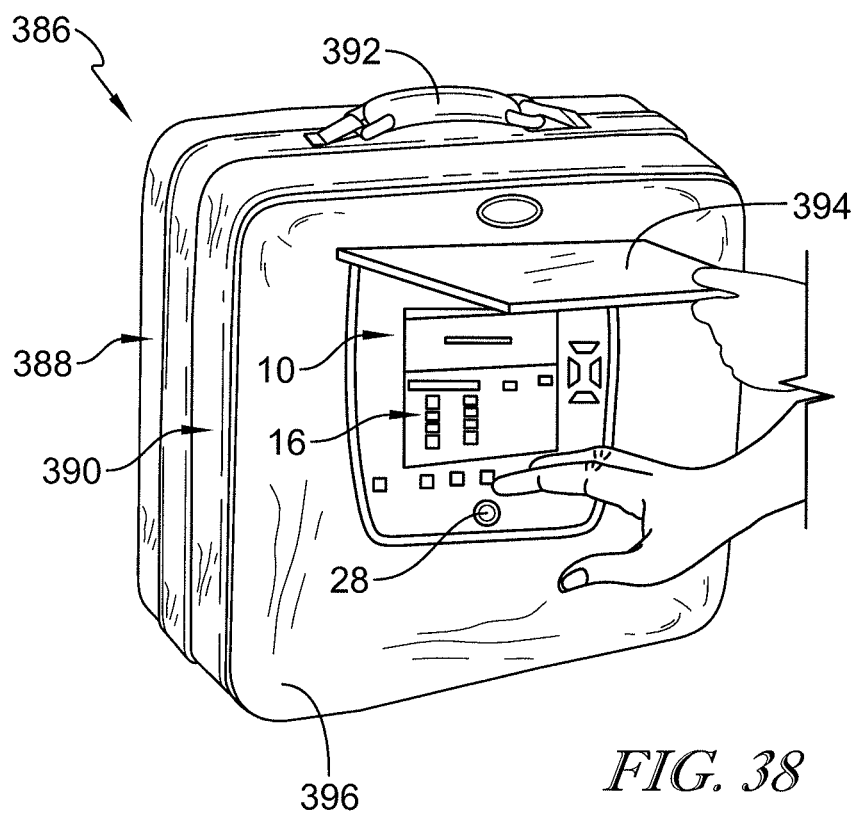
FIG. 38 is a perspective view showing a carrying case configured for carrying the respiratory devices of FIGS. 1-21, the carrying case having a door that is opened by pivoting upwardly to provide access to user controls on the housing of the respiratory device without the need to remove the respiratory device from the carrying case.

Referring now to FIG. 38, a carrying case 386 is configured for carrying device 10 therein. Case 386 has a base portion 388 and a lid portion 390 that is openable and closable relative to base portion 388 so that device 10 can be inserted into the interior region of case 386 and removed from case 386 as desired. A carrying handle 392 is provided at a top of case 386 for a user to grasp while carrying case 386. Lid portion 390 of case 386 has a door 394 that is opened relative to a main front panel 396 of lid portion 390 by pivoting upwardly to provide access to user controls shown on GUI 16 of device 10 and to provide access to on/off button 28. Thus, the user inputs of GUI 16 and button 28 can be used without the need to remove device 10 from carrying case 386.

Figure 39:
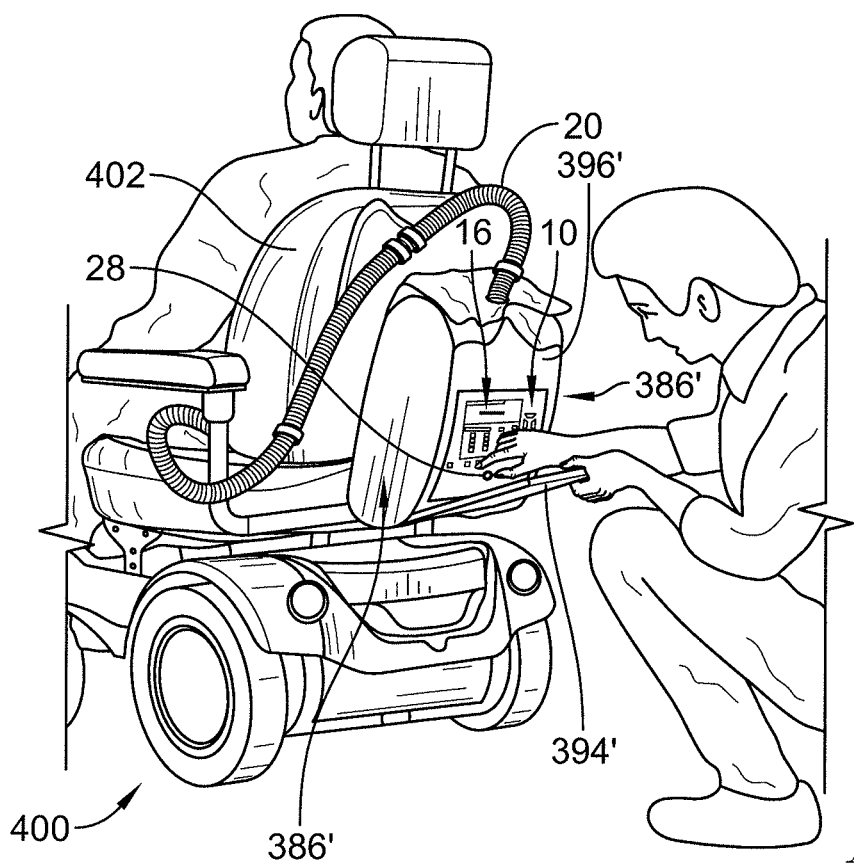
FIG. 39 is a perspective view showing a carrying case configured for carrying the respiratory devices of FIGS. 1-21, the carrying case being configured for attachment to a wheelchair, and the carrying case having a door that is opened by pivoting downwardly to provide access to user controls on the housing of the respiratory device without the need to remove the respiratory device from the carrying case.

Referring now to FIG. 39, an alternative embodiment of a carrying case 386' is also configured for carrying device 10 therein. However, carrying case 386' is configured for attachment to a wheelchair 400 and particularly, to a rear portion of a backrest 402 of the wheelchair 400. Case 386' has a door 394' that is opened by pivoting downwardly relative to a main front panel 396' of case 386' to provide access to user controls on GUI 16 of device 10 and to provide access to on/off button 28 of device 10 without the need to remove device 10 from carrying case 386'. In some embodiments, suitable fasteners such as snaps, zippers, straps, buckles, or hook-and-loop fasteners are provided to retain doors 394, 394' in the closed positions relative to the respective front panels 396, 396'.

Figure 41:
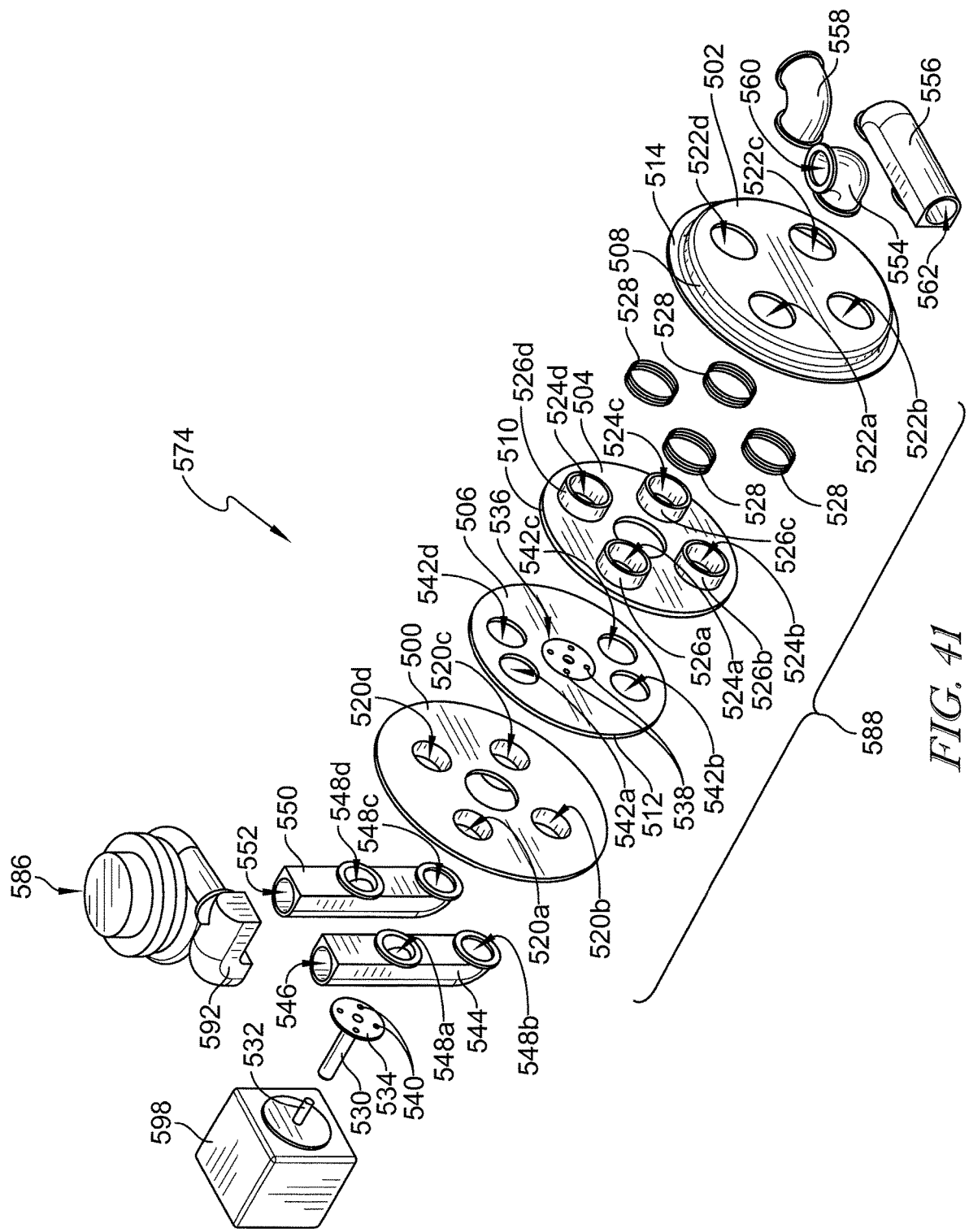
FIG. 41 is an exploded perspective view, similar to FIG. 7, showing components of an alternative embodiment of a respiratory device including a stepper motor and blower at the left hand side of the page and showing a rotary valve having a multi-piece manifold with first and second stationary plates, separate tubular elements that attach to the stationary plates, a rotary valve member that attaches to a shaft of the stepper motor to rotate and oscillate therewith, a stationary biasing plate that is biased against the rotary valve member by a set of springs that are situated between the second stationary plate and the biasing plate.

Referring now to FIG. 41, some components of an alternative embodiment pneumatic system 574 are shown. System 574 includes a stepper motor 598, a blower 586, and a rotary valve 588. Rotary valve 588 includes a first stationary plate 500, a second stationary plate 502, a third stationary plate 504, and a rotatable valve member or plate 506. Each of plates 500, 502, 504, 506 is circular or round in shape. Plates 504, 506 are sandwiched between plates 500, 502. Second stationary plate 502 has an annular rim 508 that surrounds an outer periphery 510 of third stationary plate 504 and an outer periphery 512 of rotatable plate 506. Second stationary plate 502 also includes an annular flange 514 that projects radially outwardly from annular rim 508. Annular flange 514 is fastened to first stationary plate 500 such as by gluing or welding, for example.

First stationary plate 500 has four holes 520a, 520b, 520c, 520d; second stationary plate 502 has four holes 522a, 522b, 522c, 522d; and third stationary plate 504 has four holes 524a, 524b, 524c, 524d. Holes 520a-d, 522a-d, and 524a-d are aligned with each other. That is the "a-series" holes of plates 500, 502, 504 are aligned; the "b-series" holes of plates 500, 502, 504 are aligned; the "c-series" holes of plates 500, 502, 504 are aligned; and the "d-series" holes of plates 500, 502, 504 are aligned.

Third stationary plate 504 is formed to include four tubular portions 526a, 526b, 526c, 526d. Tubular portions 526a-d define, in part, the holes 524a-d, respectively, that extend though plate 504. Each tubular portion 526a-d is in registry with, such as by being received within, a respective hole 522a-d of the four holes 522a-d of the second stationary plate 502. Valve 588 includes four springs 528. Each spring 528 of the four springs 528 is mounted on a respective tubular portion 526a-d of the four tubular portions 526a-d. Spring 528, therefore, are situated between second stationary plate 502 and third stationary plate 504 to bias the third stationary plate 504 against rotatable plate 506 which, in turn, biases rotatable plate 506 against first stationary plate 500. Thus, third stationary plate 504 is sometimes referred to herein as a biasing plate.

Still referring to FIG. 41, a valve shaft 530 mounts to an output shaft 532 of stepper motor 598. A hub 534 at a distal end of shaft 532 attaches to a central region of 536 of rotatable plate 506 by suitable fasteners such as bolts that are received in apertures 538 of plate 506 and apertures 540 of hub 534. Rotatable plate 506 has four holes 542a, 542b, 542c, 542d. Stepper motor 598 acts through shafts 530, 532 to rotate plate 506 so that various ones of holes 542a-d of rotatable plate 506 are aligned or misaligned with various ones of holes 520a-d, 522a-d, 524a-d of stationary plates 500, 502, 504. Thus, the discussion above regarding the operation of valve 88 of pneumatic system 74 to produce positive pressure, negative pressure, and oscillatory pressure at port 24 and therefore, within patient interface 22, is equally applicable to valve 588 of pneumatic system 574. That discussion is not repeated for the sake of brevity. Suffice it to say that rotatable plate 506 has a first position in which positive pressure from blower 586 is delivered to port 24 and a second position in which negative pressure from blower 586 is delivered to port 24. Plate 506 can be oscillated back and forth by stepper motor 598 with respect to the first position and with respective to the second position to produce oscillations in the pressure, be it positive or negative, provided at port 24.

Unlike pneumatic system 74 which has manifold blocks 116, 120, pneumatic system 574 has individual tubular manifold elements. In particular, a first manifold tube 544 has an inlet passage 546 coupled to an outlet 592 of blower 586 and a pair of outlet passages 548a, 548b coupled to holes 520a, 520b, respectively, of first stationary plate 500. Similarly, a second manifold tube 550 has an outlet passage 552 coupled to an inlet of blower 586 (not shown but similar to inlet 90 of blower 86) and a pair of inlet passages 548c, 548d coupled to holes 520c, 520d, respectively, of first stationary plate 500. At the opposite side of valve 588, a third manifold tube 554, a fourth manifold tube 556, and a fifth manifold tube 558 are provided. Tube 554 has a passage 560 that couples to hole 522a of plate 502; tube 556 has a passage 562 that couples to holes 522b, 522c of plate 502 through respective ports of tube 556; and tube 558 has a passage (not shown, but similar to passage 560 of tube 554) that couples to hole 522d of plate 502.

Tube 556 couples to the patient port 24 of respiratory device 10 for delivery of positive pressure or negative pressure to port 24 depending upon the position of rotatable plate 506. Tubes 554, 558 are each coupled to ambient atmosphere. Manifold tubes 544, 550, 554, 556, 558 are fixed to the respective stationary plates 400, 502 via suitable fastening mechanisms such as glue or welding, for example. In some embodiments, tubular portions 526a-d project through holes 522a-d to be received in the respective passages of manifold tubes 554, 556, 558.

Figure 42:
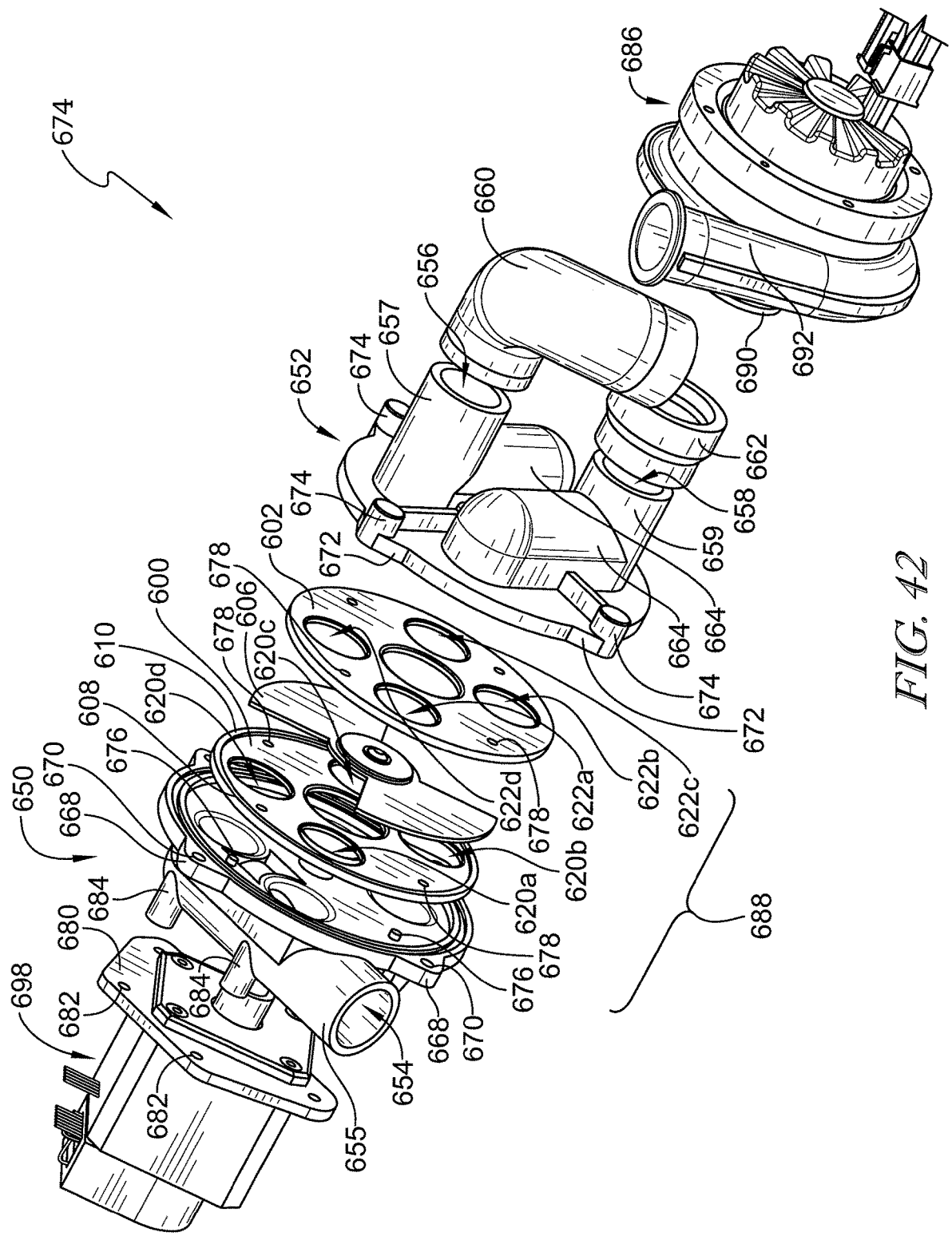
FIG. 42 is an exploded perspective view, similar to FIGS. 7 and 41, showing components of another alternative embodiment respiratory device including a stepper motor at the left hand side of the page, a blower at the right hand side of the page, and a valve and manifold assembly situated therebetween and having first and second molded manifold portions, first and second stationary plates and a bow-tie shaped rotary valve member which is sandwiched between the first and second stationary plates.
Figure 43:
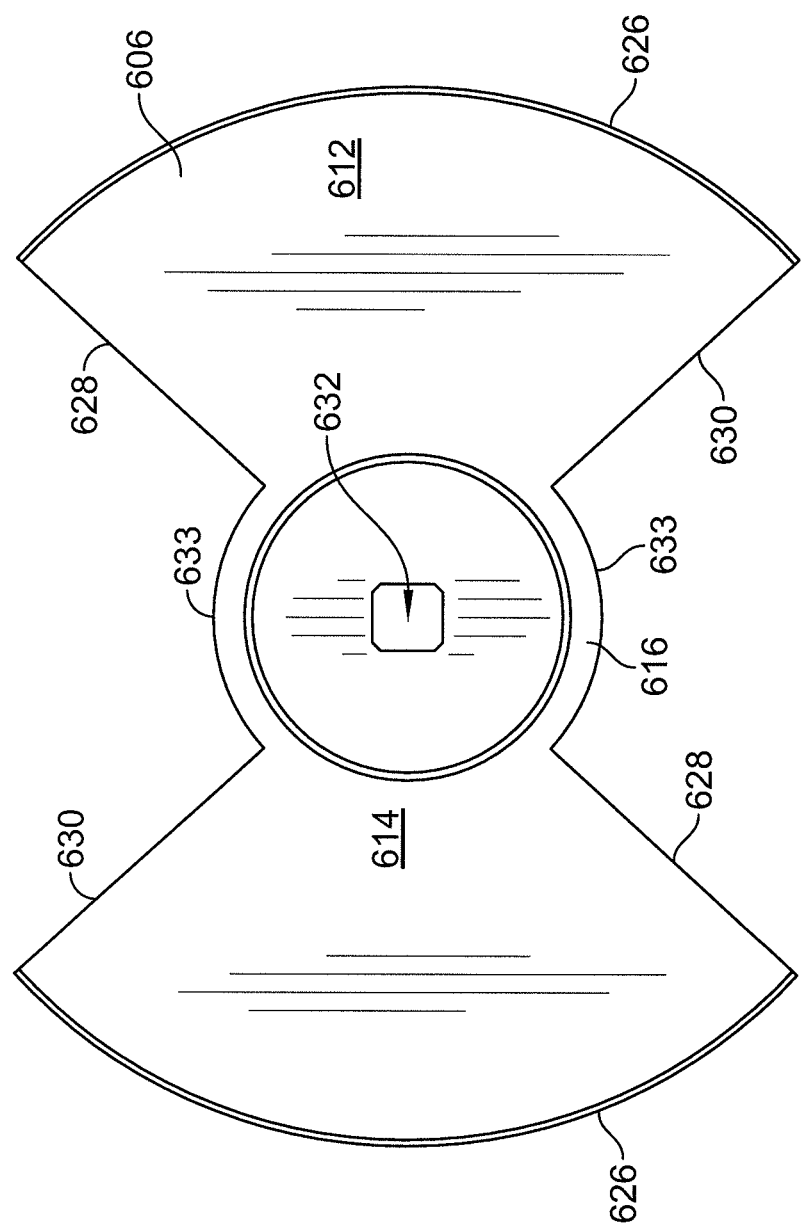
FIG. 43 is a front elevation view of the bow-tie shaped rotary valve member of FIG. 42.
Figure 44:
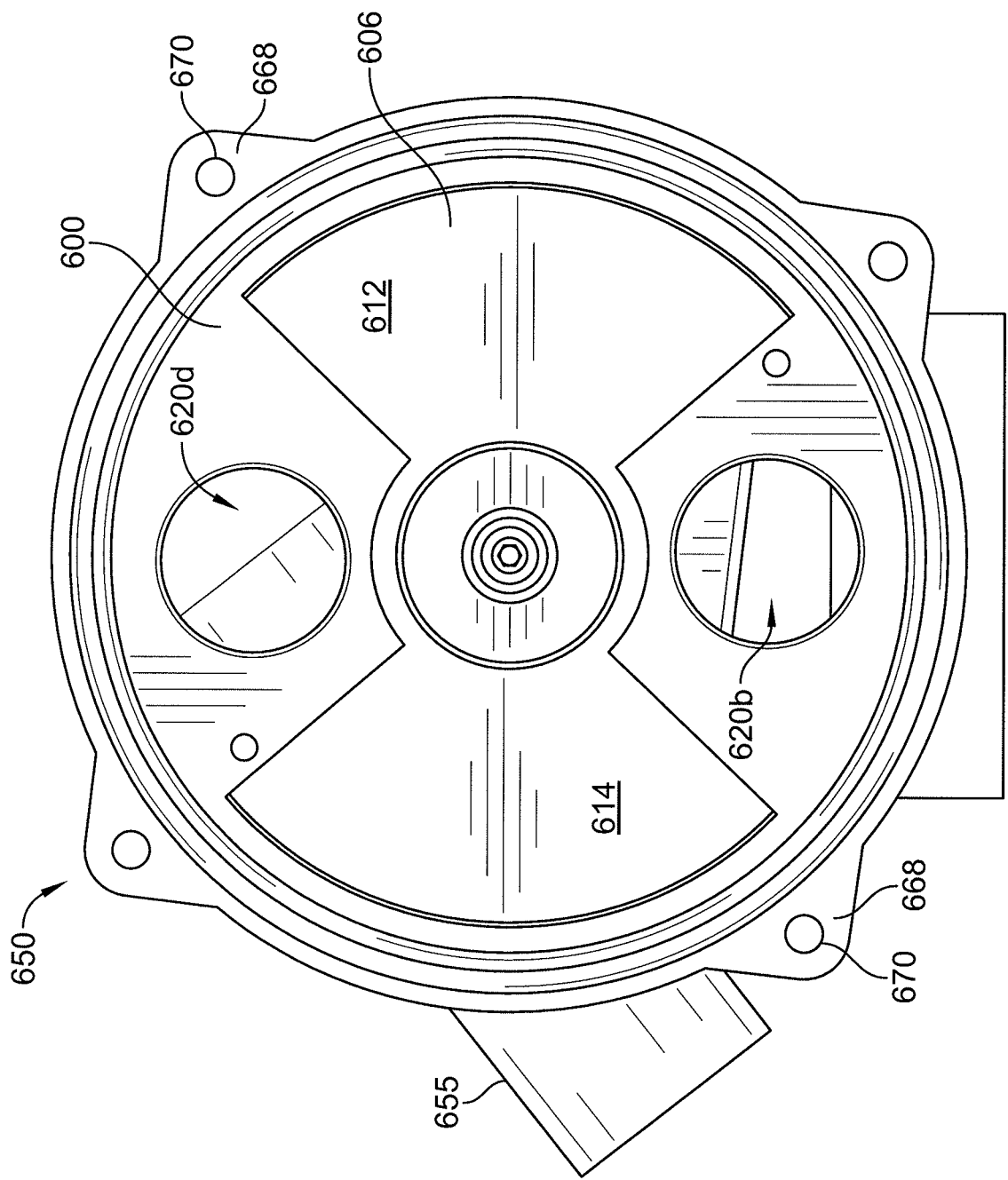
FIG. 44 is a front elevation view showing the bow-tie shaped rotary valve member of FIG. 43 located adjacent the first stationary plate which is installed into the first manifold portion, the bow-tie shaped rotary valve member being oriented in a first position in which first and second flow passages are not blocked by wing portions of the bow-tie shaped rotary valve member.
Figure 45:
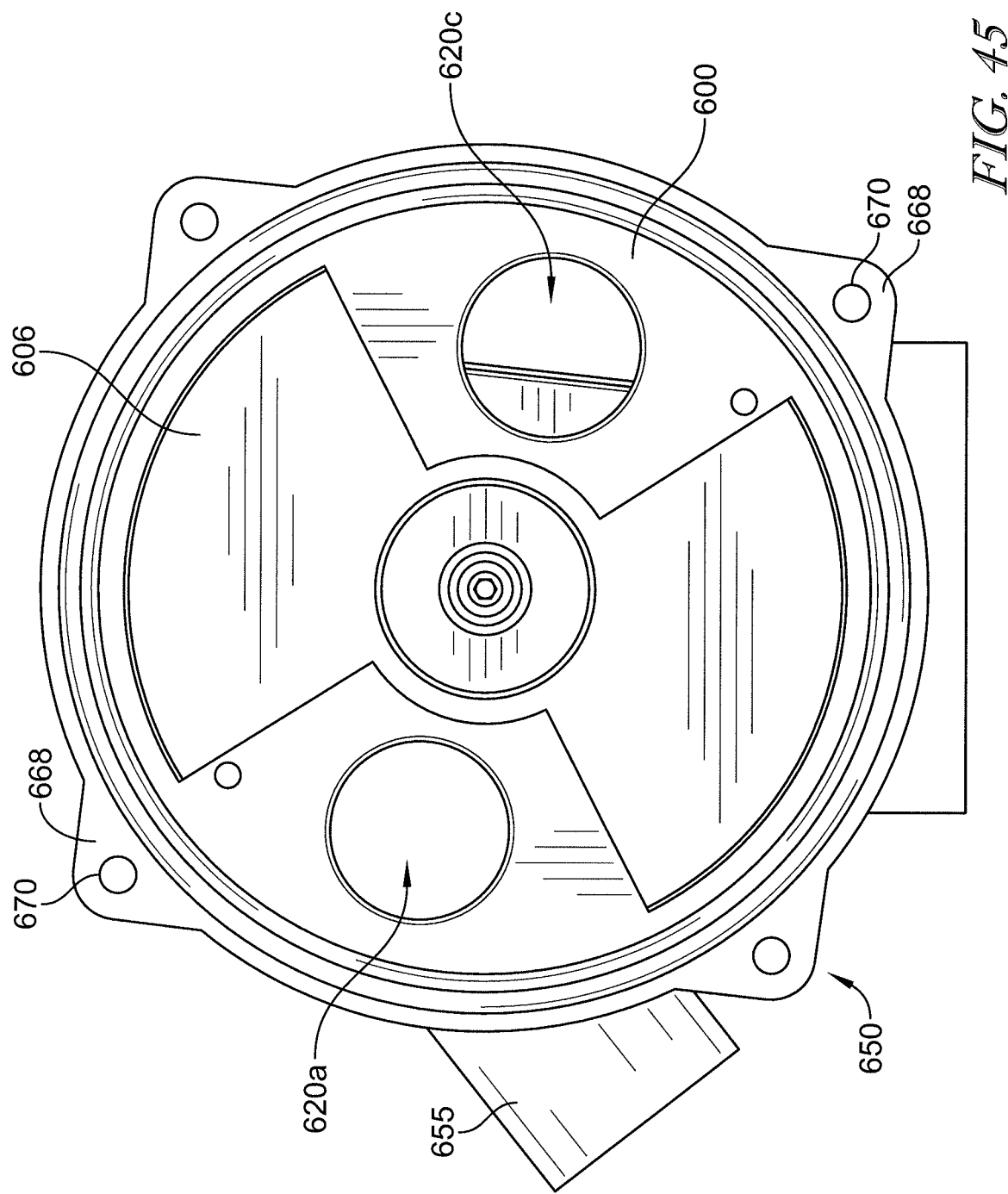
FIG. 45 is a view, similar to FIG. 44, showing the bow-tie shaped rotary valve member rotated to a second position having the wing portions blocking the first and second passages such that third and fourth flow passages are not blocked by the wing portions.
Figure 46:
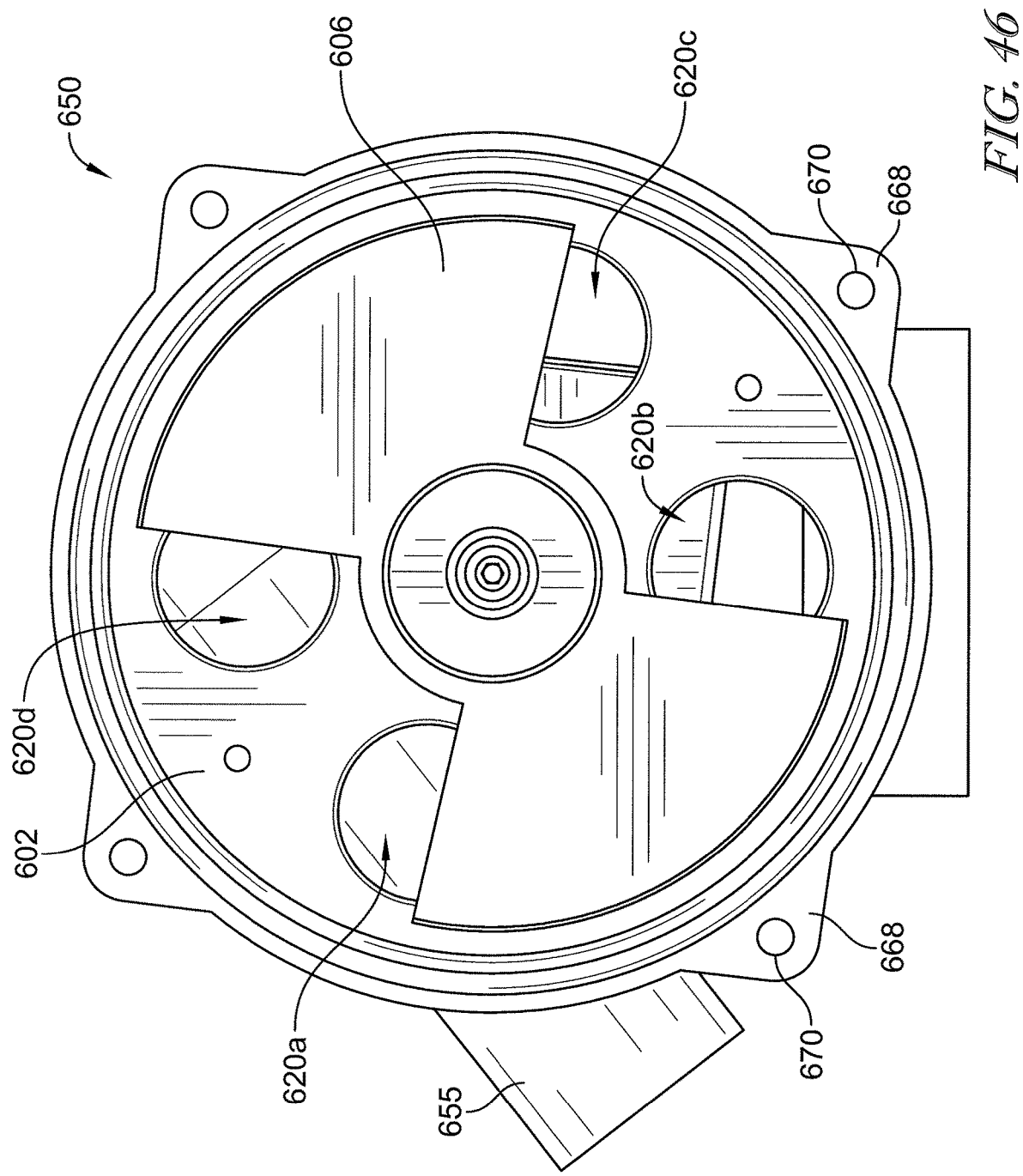
FIG. 46 is a view, similar to FIGS. 44 and 45, showing the bow-tie shaped rotary valve member rotated to a third position partially blocking the first, second, third, and forth passages.

Referring now to FIGS. 42-46, some components of an alternative embodiment pneumatic system 674 are shown. System 674 includes a stepper motor 698, a blower 686, and a rotary valve 688. Rotary valve 688 includes a first stationary plate 600, a second stationary plate 602, and a rotatable valve member or plate 606 as shown in FIG. 42. Both stationary plates 600, 602 are circular or round in shape. However, unlike valves 88, 588 which have circular rotatable valve plates 122, 506, respectively, the rotatable plate 606 of valve 688 is bow-tie shaped as best shown in FIG. 43. Plate 606 is sandwiched between plates 600, 602. First stationary plate 600 has an annular rim 608 with an edge 610 that abuts plate 602. Rim 608 surrounds rotatable plate 606.

First stationary plate 600 has four holes 620a, 620b, 620c, 620d and second stationary plate 602 has four holes 622a, 622b, 622c, 622d. Holes 620a-d, 622a-d are aligned with each other. That is the "a-series" holes of plates 600, 602 are aligned; the "b-series" holes of plates 600, 602 are aligned; the "c-series" holes of plates 600, 602 are aligned; and the "d-series" holes of plates 600, 602 are aligned. Plate 606 has first and second wing portions 612, 614 connected by a hub portion 616 as shown in FIG. 43. Wing portions 612, 614 are each bounded by an arcuate edge 626, a first straight edge 628, and a second straight edge 630. Edges 628, 630 extending radially with respect to a center of hub 616 which is bounded by generally arcuate edges 633. Hub 616 has a non-round aperture 632 which, in the illustrative embodiment, is generally square-shaped with chamfered corner regions. The radii of curvature of edges 626, 633 are centered at the center of hub 616. Wing portions 612, 614 are sized and shaped such that each edge 630 is angularly spaced from its corresponding edge 630 by about 90 degrees.

Hub 616 of plate 606 is keyed to an output shaft of stepper motor 698 or to an extension shaft that couples to the output shaft of stepper motor 698. For example, a portion of the shaft received within aperture 632 is complementary in shape to the shape of aperture 632. Thus, plate 606 rotates with the output shaft of stepper motor 698. Stepper motor 698 rotates plate 606 so that wing portions 612, 614 of rotatable plate 606 are aligned or misaligned with various ones of holes 620a-d, 622a-d of stationary plates 600, 602. Thus, the discussion above regarding the operation of valve 88 of pneumatic system 74 and of valve 588 of pneumatic system 574 to produce positive pressure, negative pressure, and oscillatory pressure at port 24 and therefore, within patient interface 22, is equally applicable to valve 688 of pneumatic system 674. That discussion is not repeated for the sake of brevity. Suffice it to say that rotatable plate 606 has a first position, shown in FIG. 44, for example, in which positive pressure from blower 686 is delivered to port 24 and a second position, shown in FIG. 45, for example, in which negative pressure from blower 686 is delivered to port 24. Plate 606 can be oscillated back and forth by stepper motor 698 with respect to the first position and with respective to the second position to produce oscillations in the pressure, be it positive or negative, provided at port 24. Plate 606 can also be moved to a neutral position, shown in FIG. 46, for example, in which substantially equal amounts of positive and negative pressure are applied to port 24 thereby to cancel each other out to have a net effect of substantially zero at port 24.

Unlike pneumatic system 74 which has manifold blocks 116, 120 and unlike pneumatic system 574 which has individual manifold tubes 544, 550, 554, 556, 558, system 674 has a first molded or cast manifold portion or shell 650 and a second molded or cast manifold portion or shell 652. Manifold shells 650, 652 are monolithic pieces that contain all of the passages that couple to holes 620a-d of stationary plate 600, in the case of shell 650, and to holes 622a-d of plate 602, in the case of shell 652. In FIG. 42, a passage 654 of shell 650 which couples to patient port 24 can be seen. Passage 654 is defined by a tubular portion 655 of shell 650. It should be understood that shell 650 has one or more other passages (not shown) that communicate with atmosphere. Also in FIG. 42, passages 656, 658 of shell 652 can be seen. Passages 656, 658 are defined by tubular portions 657, 659 of shell 652, respectively.

Tubular portion 657 and its associated passage 656 of shell 652 couple to a positive pressure outlet 692 of blower 686 via a first conduit 660. Similarly, tubular portion 659 and its associated passage 658 of shell 650 couple to the negative pressure inlet 690 of blower 686 via a second conduit 662. Passage 656 of manifold shell 652 is in pneumatic communication with holes 622c, 622d of stationary plate 602 and passage 658 of manifold shell 652 is in pneumatic communication with holes 622a, 622b of stationary plate 602. Manifold shell 652 has a pair of tubular connecting portions 664 in this regard.

Suitable fasteners (not shown) such as bolts or screws (these terms are used interchangeably herein) are provided to couple manifold shells 650, 652 together. In this regard, shell 650 has ears 668 with apertures 670 and shell 652 has ears 672 with screw-receiving bosses 674. When shells 650, 652 are fastened together, plates 600, 602, 606 are sandwiched therebetween. A set of dowel pins 676 extend from shell 650 and are received in apertures 678 provided in plate 600. A similar set of dowel pins (not shown) extending from shell 652 are received in apertures 678 provided in plate 602. Receipt of the dowel pins 676 in apertures 678 of plates 600, 602 prevents plates from rotating relative to respective shells 650, 652. The dowel pins 676 do not extend into the space between plates 600, 602 so as not to interfere with rotation and oscillation of bow-tie shaped plate 606 within the space between stationary plates 600, 602. Fasteners such as screws or bolts (not shown) are also provided to couple stepper motor 698 to manifold shell 650. In this regard, a plate 680 of stepper motor 698 has apertures 682 and manifold shell 650 has screw-receiving bosses 684 for receipt of such fasteners.

Figure 72:
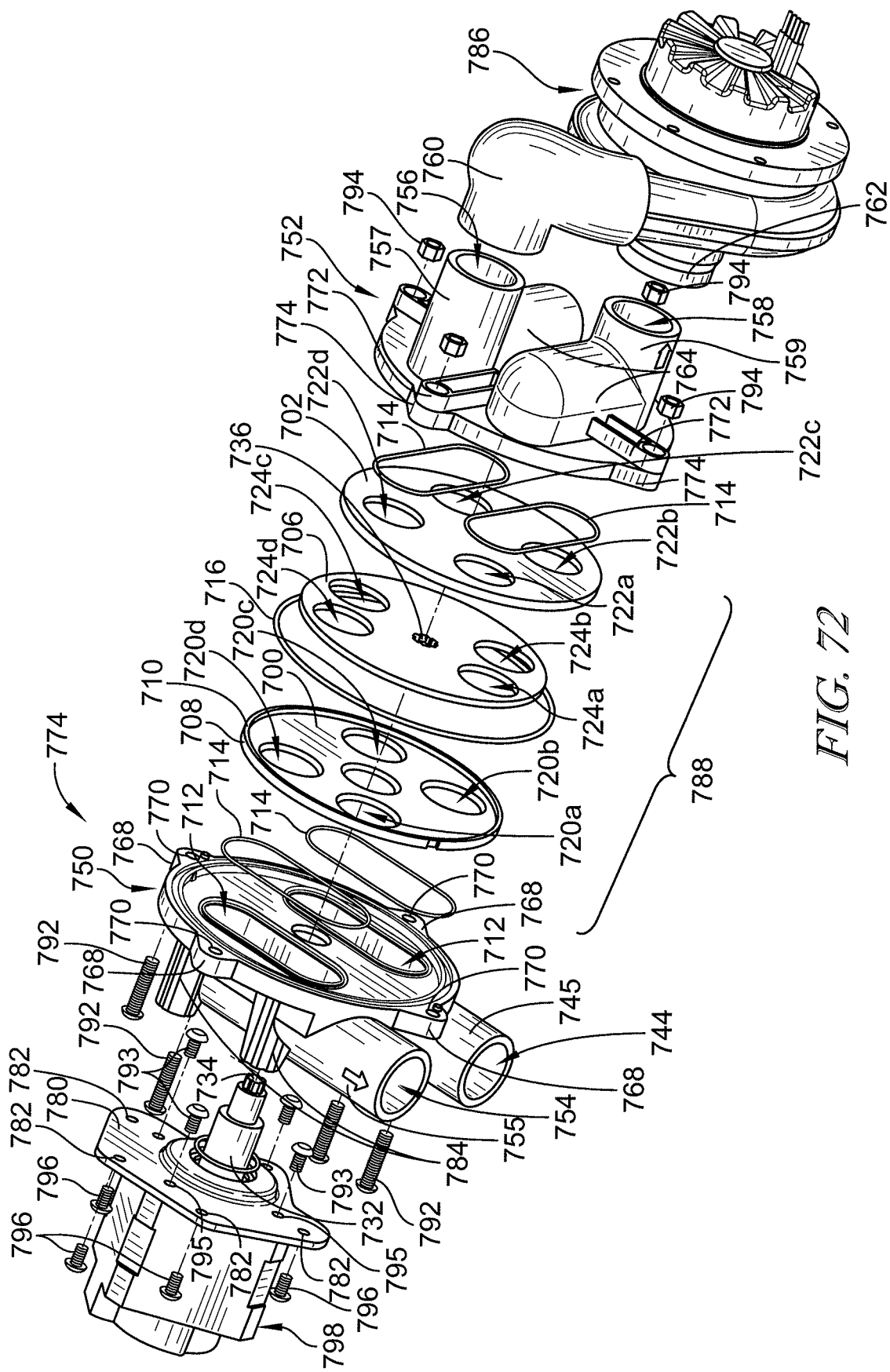
FIG. 72 is an exploded perspective view, similar to FIGS. 7, 41 and 42, showing components of another alternative embodiment respiratory device including a stepper motor at the left hand side of the page, a blower at the right hand side of the page, and a valve and manifold assembly situated therebetween and having first and second molded manifold portions, first and second stationary plates and a circular rotary valve member with surrounding O-ring which is sandwiched between the first and second stationary plates.

Referring now to FIG. 72, some components of an alternative embodiment pneumatic system 774 are shown. System 774 includes a stepper motor 798, a blower 786, and a rotary valve 788. Rotary valve 788 includes a first stationary plate 700, a second stationary plate 702, and a rotatable valve member or plate 706 as shown in FIG. 42. Plates 700, 702, 706 are each circular or round in shape. Plate 706 is sandwiched between plates 700, 702. First stationary plate 700 has an annular rim 708 with an edge 710 that abuts plate 702. Rim 708 surrounds rotatable plate 706.

First stationary plate 700 has four holes 720a, 720b, 720c, 720d; second stationary plate 702 has four holes 722a, 722b, 722c, 722d; and rotatable plate 706 has four holes 724a, 724b, 724c, 724d. Holes 720a-d, 722a-d are aligned with each other. That is the "a-series" holes of plates 700, 702 are aligned; the "b-series" holes of plates 700, 702 are aligned; the "c-series" holes of plates 700, 702 are aligned; and the "d-series" holes of plates 700, 702 are aligned. An output shaft extension 732 of stepper motor 798 has a non-round tip 734 which is received in a complementarily shaped non-round aperture 736 provided at the center of rotatable plate 706. Thus, plate 706 rotates with output shaft extension 732 of stepper motor 798. Extension 732 is mounted on an output shaft (not shown) of stepper motor 798.

Stepper motor 798 acts through shaft 732 to rotate plate 706 so that various ones of holes 724a-d of rotatable plate 706 are aligned or misaligned with various ones of holes 720a-d, 722a-d of stationary plates 700, 702. Thus, the discussion above regarding the operation of valve 88 of pneumatic system 74 and of valve 588 of pneumatic system 574 to produce positive pressure, negative pressure, and oscillatory pressure at port 24 and therefore, within patient interface 22, is equally applicable to valve 788 of pneumatic system 774. That discussion is not repeated for the sake of brevity. Suffice it to say that rotatable plate 706 has a first position in which positive pressure from blower 786 is delivered to port 24 and a second position in which negative pressure from blower 786 is delivered to port 24. Plate 706 can be oscillated back and forth by stepper motor 798 with respect to the first position and with respective to the second position to produce oscillations in the pressure, be it positive or negative, provided at port 24.

Similar to system 674, system 774 has a first molded or cast manifold portion or shell 750 and a second molded or cast manifold portion or shell 752. Manifold shells 750, 752 are monolithic pieces that contain all of the passages that couple to holes 720a-d of stationary plate 700, in the case of shell 750, and to holes 722a-d of plate 702, in the case of shell 752. Unlike shells 650, 652 described above, shells 750, 752 have oblong openings 712 that communicate with respective pairs of holes 720a-d, 722a-d. Gaskets 714 are provided around oblong openings 712 to seal against respective stationary plates 700, 702. A large O-ring type gasket 716 provides a seal between manifold shells 750, 752. Gasket 716 encompasses a periphery of rotatable 706.

In FIG. 72, a passage 754 of shell 750 which couples to patient port 24 can be seen. Passage 754 is defined by a tubular portion 755 of shell 750. Shell 750 also has a passage 744 defined by a tubular portion 745 that communicates with atmosphere. Passage 754 of tubular portion 755 of manifold shell 750 communicates with holes 720a, 720d of stationary plate 700 through an associated oblong opening 712 and passage 744 of tubular portion 745 of manifold shell 750 communicates with holes 720b, 720c of stationary plate 700 through an associated oblong opening 712. Also in FIG. 72, passages 756, 758 of shell 752 can be seen. Passages 756, 758 are defined by tubular portions 757, 759 of shell 752, respectively. Passage 756 of tubular portion 757 of manifold shell 752 communicates with holes 722c, 722d of stationary plate 702 through an associated oblong opening (not shown, but similar to passages 712 of shell 750) and passage 758 of tubular portion 759 of manifold shell 752 communicates with holes 722a, 722b of stationary plate 700 through an associated oblong opening (not shown, but similar to passages 712, of shell 750). Manifold shell 752 has a pair of tubular connecting portions 764 in this regard to communicate with the oblong openings. Tubular portion 757 and its associated passage 756 of shell 752 couples to a positive pressure outlet of blower 786 via a first conduit 760. Similarly, tubular portion 759 and its associated passage 758 of shell 752 couples to the negative pressure inlet of blower 786 via a second conduit 762.

Suitable fasteners such as bolts or screws 792 and nuts 794 are provided to couple manifold shells 750, 752 together. In this regard, shell 750 has ears 768 with apertures 770 and shell 752 has ears 774 with nut-receiving bosses 772. Bolts 792 extend through ears 768, 774 are threaded into nuts 794 which are received in bosses 772. When shells 750, 752 are fastened together, plates 700, 702, 706 are sandwiched therebetween. Fasteners such as screws or bolts 796 are also provided to couple stepper motor 798 to manifold shell 750. In this regard, a plate 780 of stepper motor 798 has apertures 782 and manifold shell 750 has screw-receiving bosses 784 for receipt of fasteners 796. Screws 793 extend through apertures 795 to couple plate 780 of stepper motor 798.

In some embodiments, blower 786 is a model no. U85MX-024KX-4 blower available from Micronel AG of Tagelswangen, Switzerland and stepper motor 798 is of the type available from Shinano Kenshi Corporation of Culver City, Calif. Plate 780 of stepper motor 798 is made of metal, such as stainless steel or aluminum, and motor shaft extension 732 is made of aluminum in some embodiments. Manifold shells 750, 752 are sometimes referred to as manifold "cases" and are made of a plastics material such as a polycarbonate (PC)/acrylonitrile butadiene styrene (ABS) compound which, in some embodiments, comprises General Electric (GE) CYCOLOY™ CX62244ME material. Stationary plates 700, 702 are made of stainless steel in some embodiments. Rotatable plate 706 is made of a plastics material such as polycarbonate with 15% polytetrafluoroethylene (PTFE) which, in some embodiments, comprises LNP™ LUBRICOMP™ DL003EXJ material. O-ring 716 is made of a silicone sponge material or silicon in some embodiments. Conduits 760, 762 are made of silicone rubber, such as a silicone rubber elastomer having a hardness of shore 50-57A, in some embodiments. Gaskets 714 are made of a soft silicone having a durometer of A50. Fasteners 792, 794, 795 are made of metal such as stainless steel or aluminum in some embodiments. The above-listed component part number and materials are examples of suitable parts and materials and is not intended to be limiting in any way.

Figure 73:
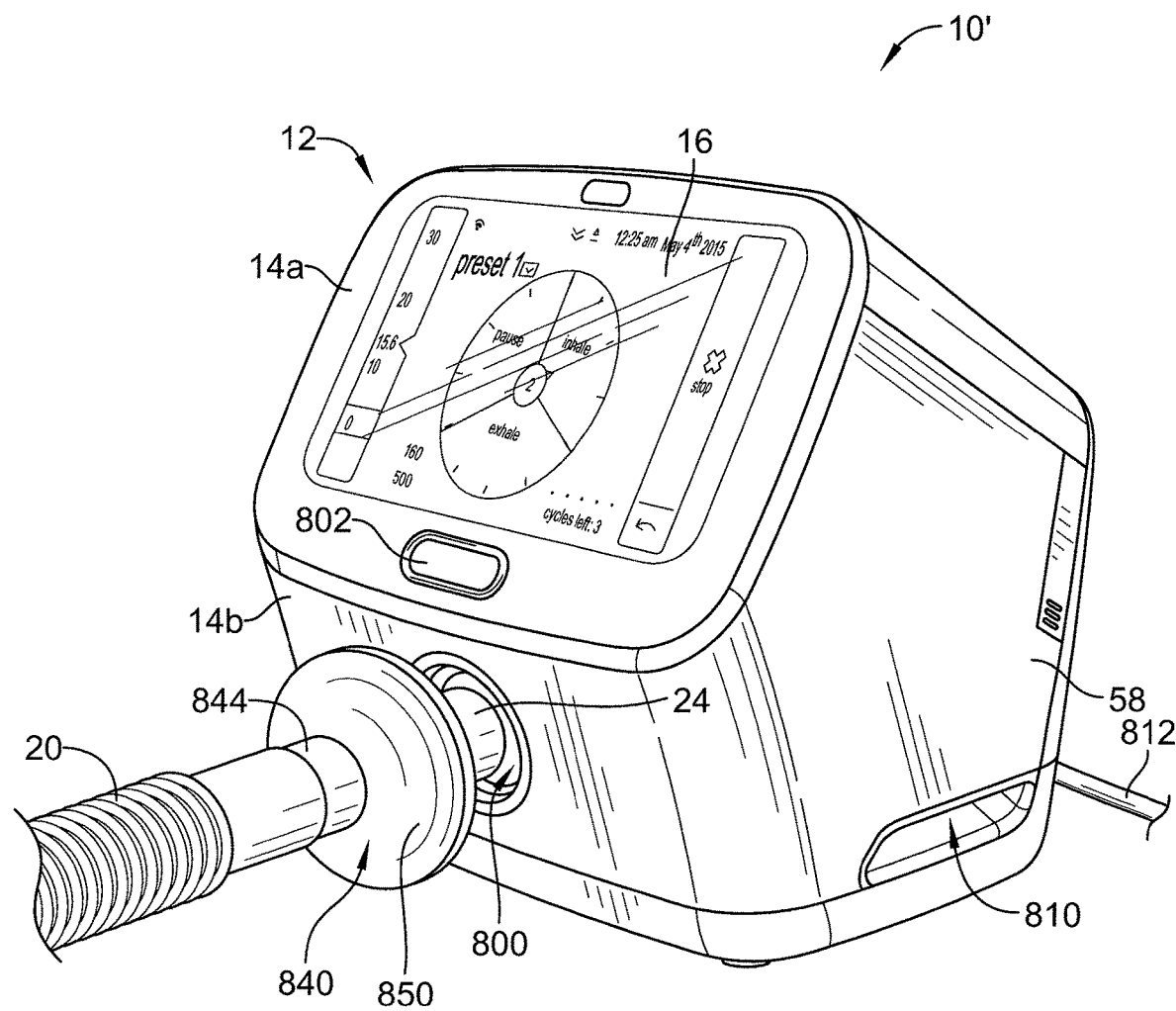
FIG. 73 is a front perspective view of another respiratory device having a housing, a patient interface including a hose coupled to the housing at a hose port via filter unit, a graphical user interface (GUI) accessible on a front wall of the housing to control operation of the respiratory device, and a wireless communication module coupled to a sidewall of the housing.

Referring now to FIGS. 73-76, a respiratory device 10' is provided and is very similar to device 10 described above. Thus, like reference numbers are used in describing device 10' as appropriate. Device 10' includes a housing 12 having a sloped upper front wall portion 14a on which a graphical user interface 16 is accessible to enter user inputs into device 10 and to see displayed information regarding the operation of device 10' as shown in FIG. 73. Housing 12 of device 10' also has a sloped bottom front wall portion 14b which slightly curves downwardly and rearwardly from the bottom of wall 14a.

A port 24 extends from an annular recess 800 provided in front wall portion 14b. Port 24 is referred to herein as a hose port or patient port, for example. Similar to device 10, device 10' is operable as an insufflation/exsufflation device (aka a cough assist device) and is also operable to deliver other respiratory therapies such as continuous positive expiratory pressure (CPEP) and continuous high frequency oscillation (CHFO), just to name a couple. A manual on/off button 802 is provided on front wall portion 14a beneath display 16 and above port 24 of wall portion 14b. Button 802 and port 24 are centered on their respective front wall portions between the opposite sidewalls 58 of device 10'. Unlike filter unit 40 of device 10, which is located adjacent mask 36, device 10' has a filter unit 840 which connects to port 24 and hose 20 connects to filter port 840 as shown in FIG. 73. Filter unit 840 is described in more detail below in connection with FIGS. 53-55.

Figure 74:
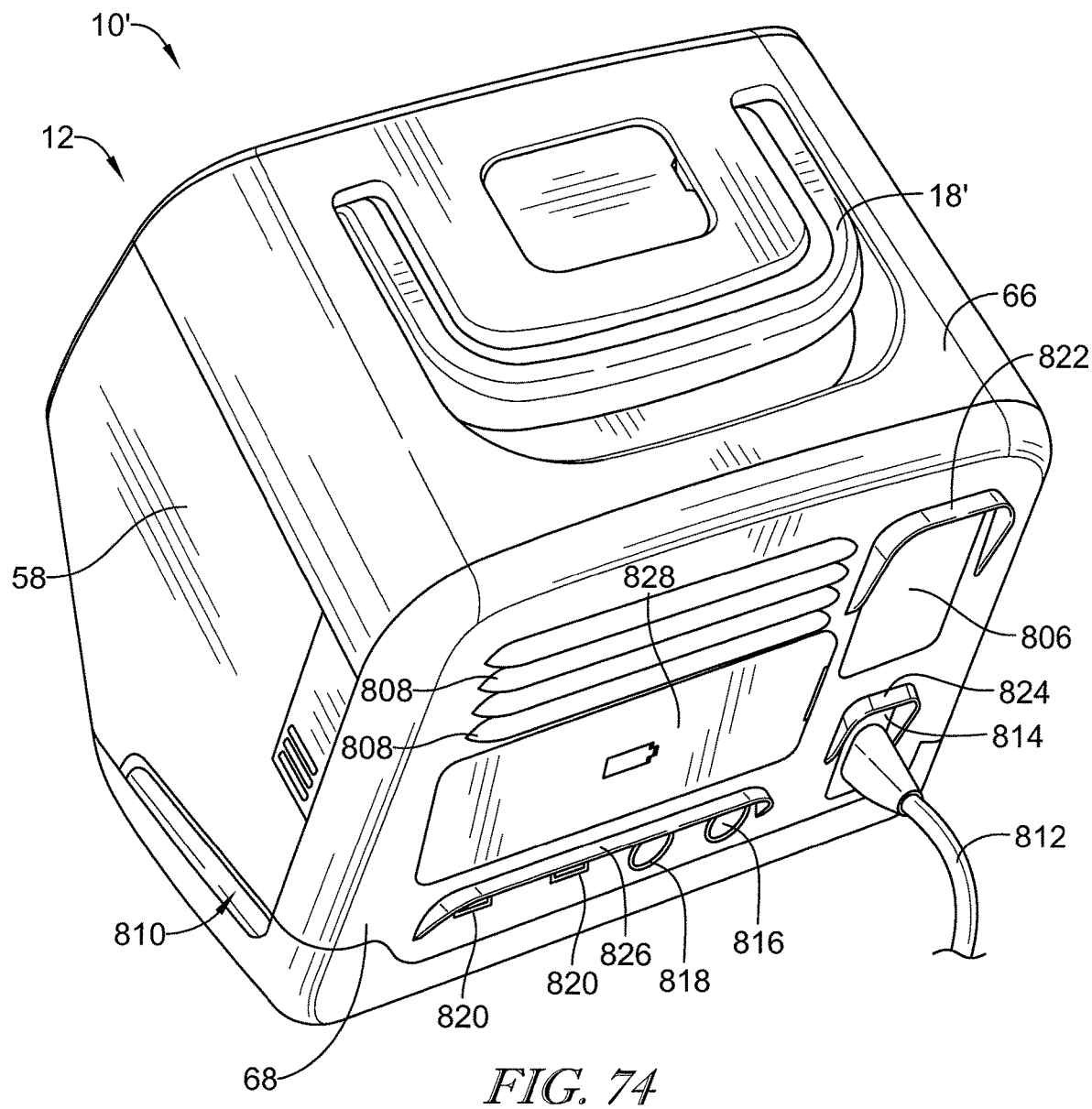
FIG. 74 is rear perspective view of the respiratory device of FIG. 73.

Referring now to FIG. 74, a top wall 66 of housing 12 of device 10' has a U-shaped handle recess 804 that receives a pivotable U-shaped handle 18' therein when handle 18' is in a storage position. Handle 18' pivots upwardly from its storage position toward front wall 14a of housing 12 so that a user is able to grasp a central region of handle 18' to carry device 10'. A back wall 68 of housing 12 if device 10' has a course air filter 806 through which air passes to reach the blower, such as blower 786, carried inside housing 12. Back wall 68 of device 10' includes horizontally oriented cooling vents 808 which cover elongated slots (not shown) through which ambient air enters and exits the interior region of housing 12 to cool the various electrical components, such as control circuitry 76 and stepper motor 798, contained in the interior region. Ventilation recesses 810 are provided in each of side walls 58 of device 10' to permit similar ambient air flow into and out of the interior region of housing 12 at the sides of device 10'.

A power cord 812 attaches to a power port 814 which is provided on back wall 68 of housing 12 of device 10' beneath course air filter 806. Cord 812 has a plug at its opposite end (not shown) which plugs into a standard AC power outlet (not shown) to provide power to device 10' in a known manner. Other connection ports are provided near a bottom of back wall 68 including a pulse oximeter (SpO2) port 816 to which a pulse oximeter couples, if desired; a foot on/off switch port 818 to which coupler 32 of foot switch controller 34 (see FIG. 1) couples, if desired; and a pair of Universal Serial Bus (USB) ports 820 for coupling of other peripheral devices, if desired. Ports 814, 816, 818, 820 are each electrically coupled to the control circuitry 76 contained in the interior region of housing 12 of device 10'. In some embodiments, a nebulizer port, similar to ports 814, 816 or similar to USB ports 920, is provided for coupling to an electrically operated nebulizer such as those described elsewhere herein.

Figure 75:
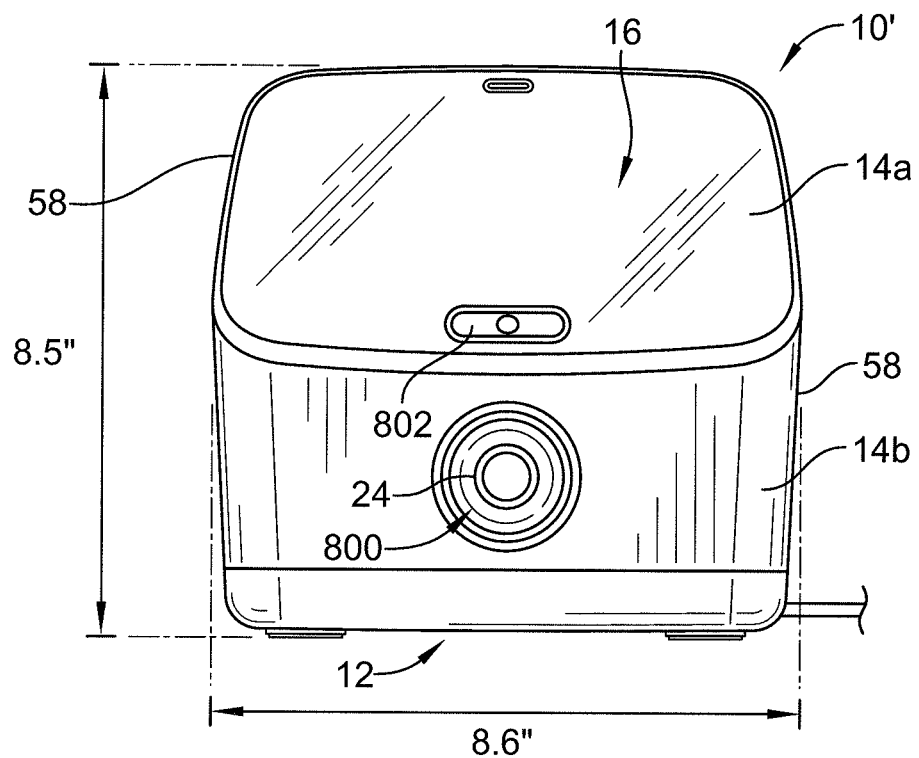
FIG. 75 is a front elevation view of the respiratory device of FIG. 73.
Figure 76:
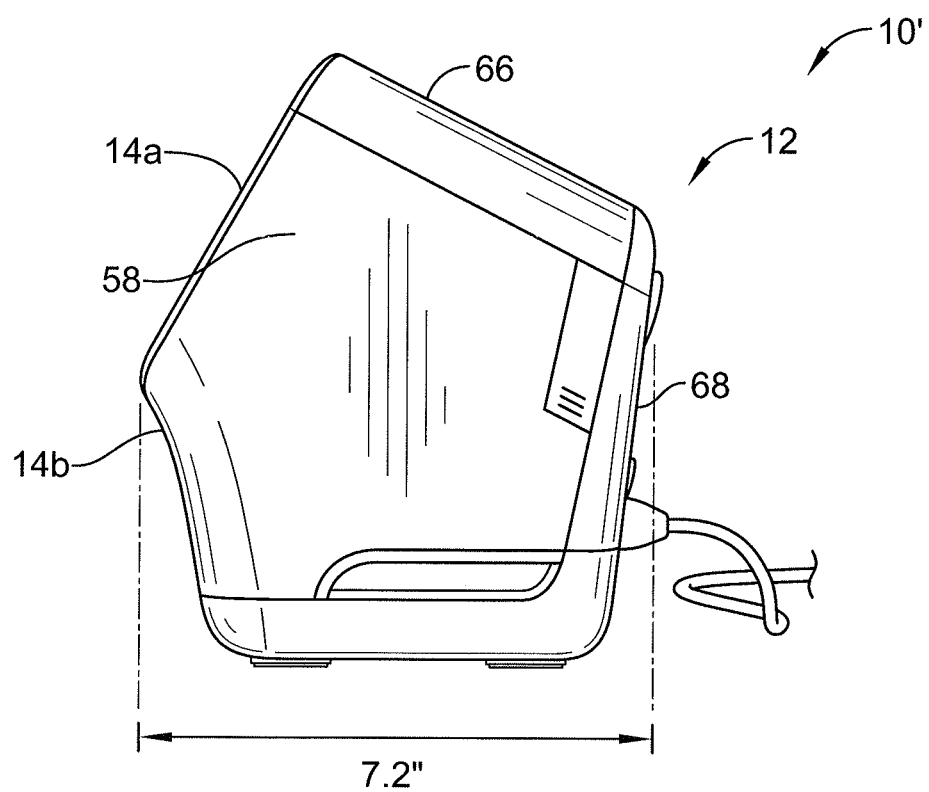
FIG. 76 is a side elevation view of the respiratory device of FIG. 73.

In the illustrative example of device 10', a first shroud 822 projects from back wall 68 above coarse air filter 806, a second shroud 824 projects from back wall 68 above power port 814, and a third shroud 826 projects from back wall 68 above ports 816, 818, 820. Shrouds 822, 824, 826 are each generally upside down U-shaped and provide a modicum of shielding and protection for filter 806 and ports 814, 816, 818, 820 such as to prevent falling objects or debris from inadvertently contacting filter 806 and ports 814, 816, 818, 820. Back wall 68 of device 10' also includes a battery cover 828 which is removable to expose a battery compartment (not shown) in which batteries (not shown) are situated for powering device 10' when power cord 812 is not plugged into an AC power outlet. FIGS. 75 and 76 show the overall dimension of device 10'. Thus, a width of device 10' is 8.6 inches (21.844 centimeters), the height of device 10' is 8.5 inches (21.59 centimeters), and the depth of device 10' is 7.2 inches (18.288 centimeters).

Figure 53:
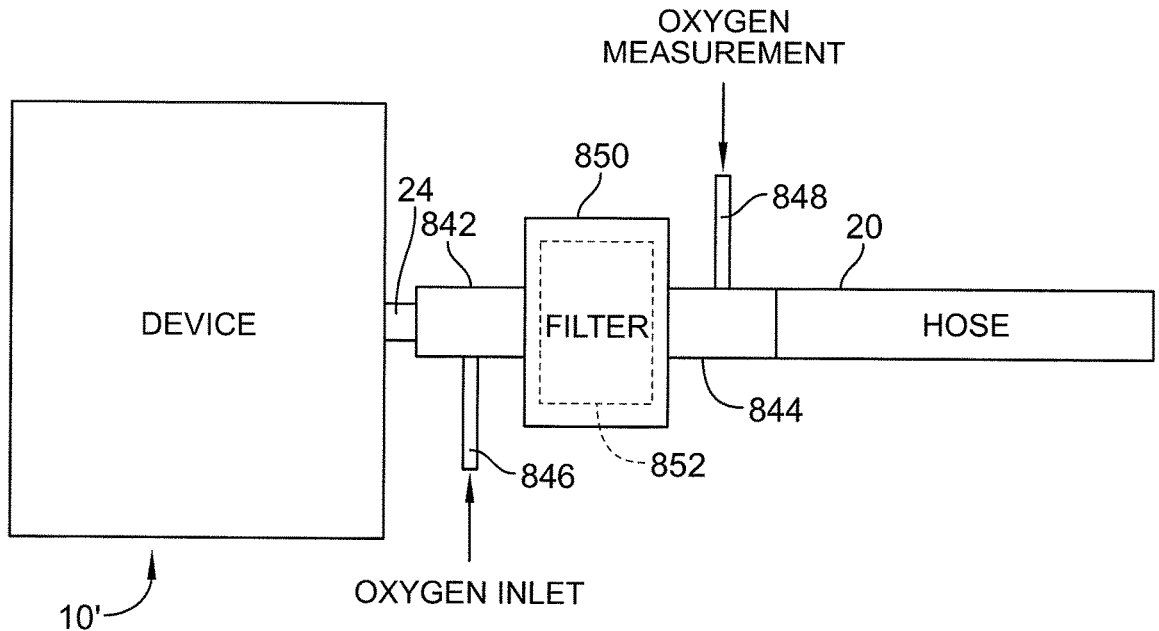
FIG. 53 is a diagrammatic view showing a filter unit coupled to a respiratory device and to a hose and having an oxygen inlet tube and an oxygen measurement tube coupled to respective inlet and outlet tubes of the filter unit on opposite sides of a filter.

Referring now to FIG. 53, in some embodiments of device 10', filter unit 840 has an inlet tube 842 which attaches to port 24, such as with a press fit, and an outlet tube 844 to which hose 20 couples, such as with a press fit. In the illustrative example, an oxygen inlet tube 846 is provided at tube 842 for coupling to a source of oxygen and an oxygen measurement tube 848 is provided at tube 844 for coupling to an oxygen measurement device which, for example, measures a concentration of oxygen within the stream of air flowing through filter unit 840 and entering hose 20 for ultimately delivery to the patient. Tubes 846, 848 tap into respective tubes 842, 844 at right angles in the illustrative example, but this need not be the case. Tubes 846, 848 are located on opposite sides of a filter housing 850 in which a filter 852 is carried. Filter 852 is an anti-bacterial filter in some embodiments. Caps, clamps, plugs, or other mechanisms for blocking air flow through tubes to close off tubes 846, 848 when an oxygen source is not coupled to tube 846 are contemplated by this disclosure.

Figure 47:
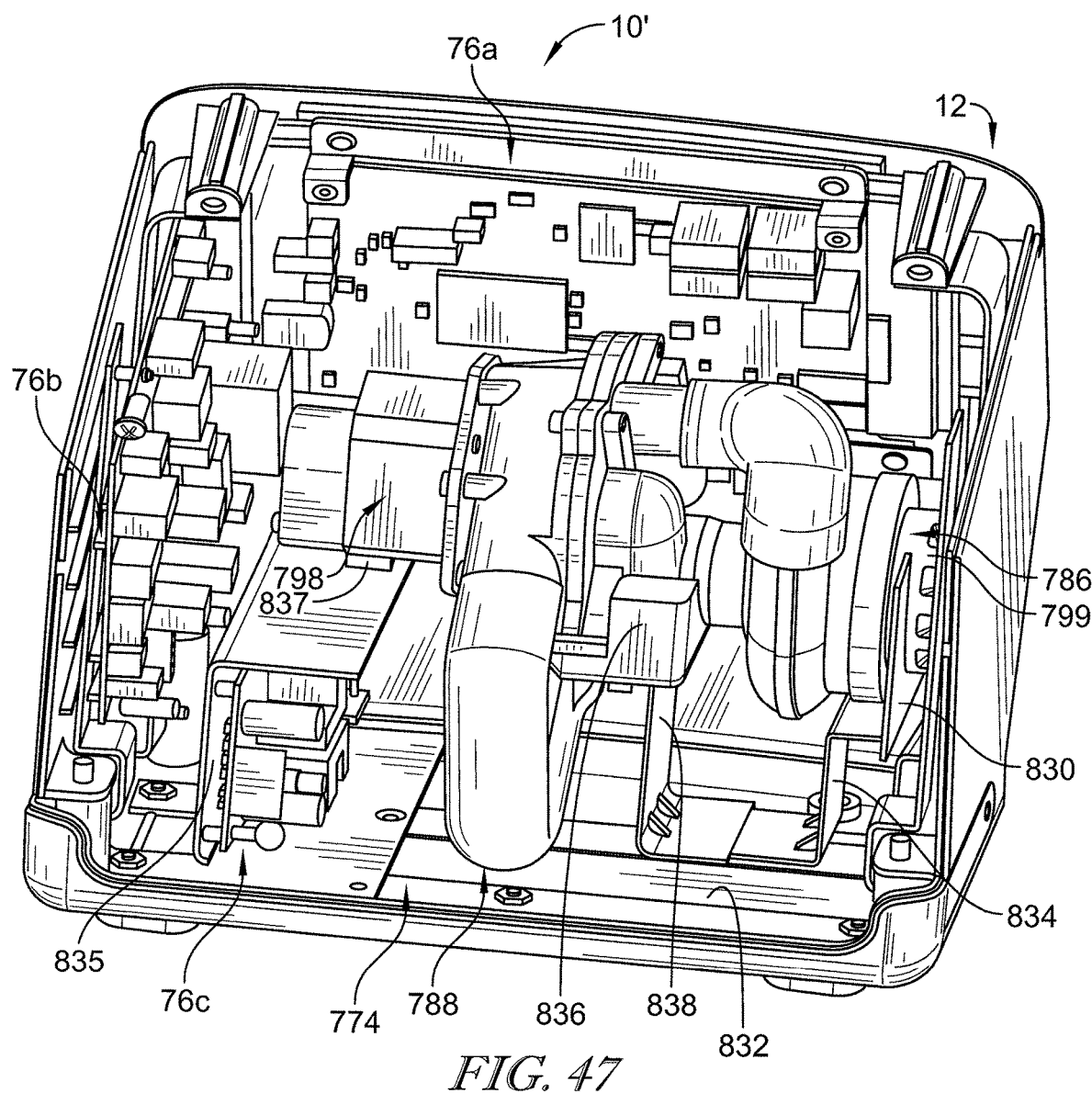
FIG. 47 is a perspective view showing the blower, stepper motor and manifold assembly of FIG. 72 installed within a housing of the associated respiratory device.
Figure 48:
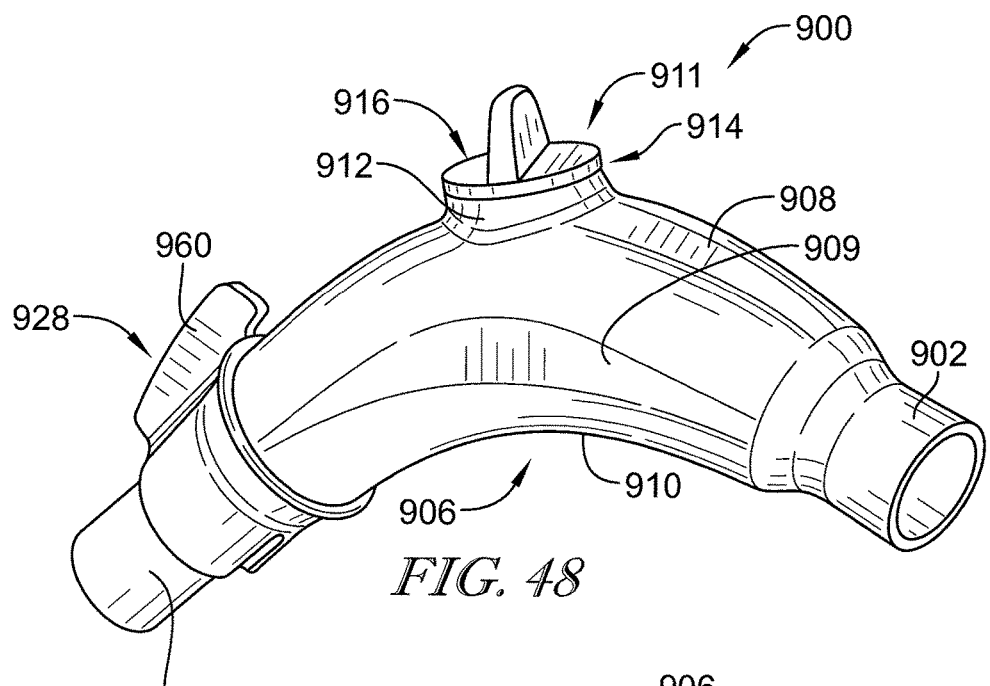
FIG. 48 is a perspective view of a handset that is coupleable to the tube of the patient interface of FIG. 1 in lieu of, or in addition to, the mask.

Referring now to FIG. 47, housing 12 of device 10' is shown with top wall 66 and back wall 68 omitted to expose the internal region of housing 12. Thus, circuit boards 76a, 76b, 76c of control circuitry 76 can be seen in FIG. 47. In the illustrative embodiment of device 10', pneumatic system 774 is situated in the interior region of housing 12. Thus, blower 786, rotary valve 788, and stepper 798 can also be seen in FIG. 47. A cylindrical motor housing portion 799 of blower 786 is cradled and supported by a vertically oriented U-shaped plate 830 which, in turn, is supported with respect to a bottom wall 832 of housing 12 by a Z-shaped bracket 834. Rotary valve 788 is cradled and supported by a block 836 which, in turn, is supported with respect to bottom wall 832 by an L-shaped bracket 838. Stepper motor 798 is supported by a block 837 that rests atop an upper horizontal wall of a C-shaped bracket 835. A bottom horizontal wall of C-shaped bracket 835 is supported with respect to bottom wall 832 of housing and circuit board 76c is attached to a vertical wall of C-shaped bracket 835.

Referring now to FIGS. 48-52, a handset 900 for use with respiratory devices 10, 10' is shown. Handset 900 may be used in lieu of mask 36 or in addition to mask. When used with mask 36, a cylindrical outlet end 902 of handset 900 is coupled to mask 36 and a cylindrical inlet end 904 is coupled to filter unit 40, in the case of device 10, or is coupled to hose 20, in the case of device 10'. When handset 900 is used without mask 36, a disposable mouthpiece is attached to end 902 and projects therefrom for receipt in the patient's mouth as is well known in the art. Thus, end 902 has a standard 22 millimeter diameter for interfacing with known mouthpieces used with respiratory devices.

Figure 50:
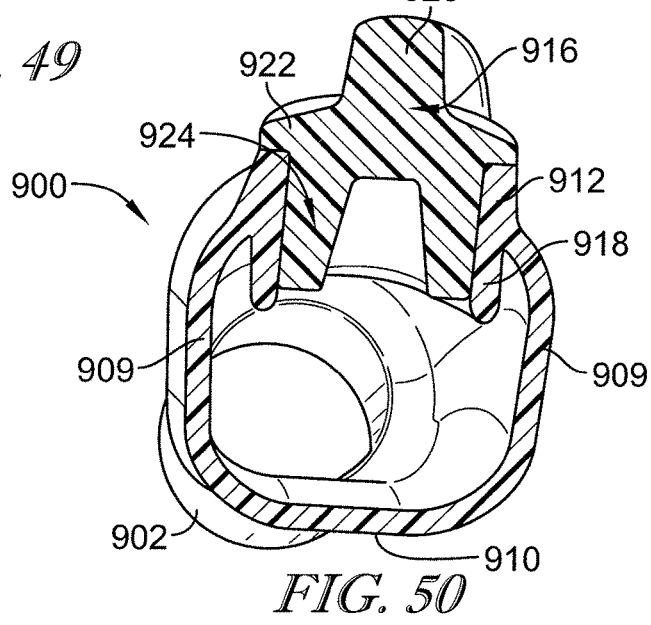
FIG. 50 is a cross sectional view of the handset of FIG. 48 taken along a lateral dimension of the handset through a threaded plug that is received in a nebulizer port of the handset in the absence of a nebulizer.

Handset 900 includes a generally banana-shaped tube 906 that has an upper surface 908 which is generally convex from end-to-end of the generally banana-shaped tube 906 and a bottom surface 910 which is generally concave from end-to-end of the generally banana-shaped tube 906. Side surfaces 909 interconnect top and bottom surfaces 908, 910 as shown in FIG. 50. Ends 902, 904 of generally banana-shaped tube 906 are open so that inhaled and exhaled gases are free to flow through tube 906 between ends 902, 904.

Handset 900 has a nebulizer port 911 provided at an apex 914 of upper surface 908 such that, in use, a nebulizer extends upwardly from a top of the handset 900. The apex 914 may generally be thought of as the uppermost region of surface 908 when tube 906 is placed on a horizontal surface with bottommost portions of ends 902, 904 engaging the horizontal surface. It is contemplated that an electrically operated vibrating plate or vibrating mesh nebulizer, such as nebulizer 44 of FIG. 1, for example, is used with handset 900 and is attached to port 911 so that nebulized medication is forced into the interior region of tube 906. In some embodiments, port has a 22 millimeter inside diameter such that a nebulizer available from Aerogen Ltd. of Galway, Ireland, for example, is coupleable to port 911. Because the nebulizer port 911 is at the apex 914 of tube 906, gravity assists in moving the nebulized medication downwardly into tube 906 and into the stream of gas moving through tube 906 from end 904 to end 902 and ultimately to the patient.

Figure 49:
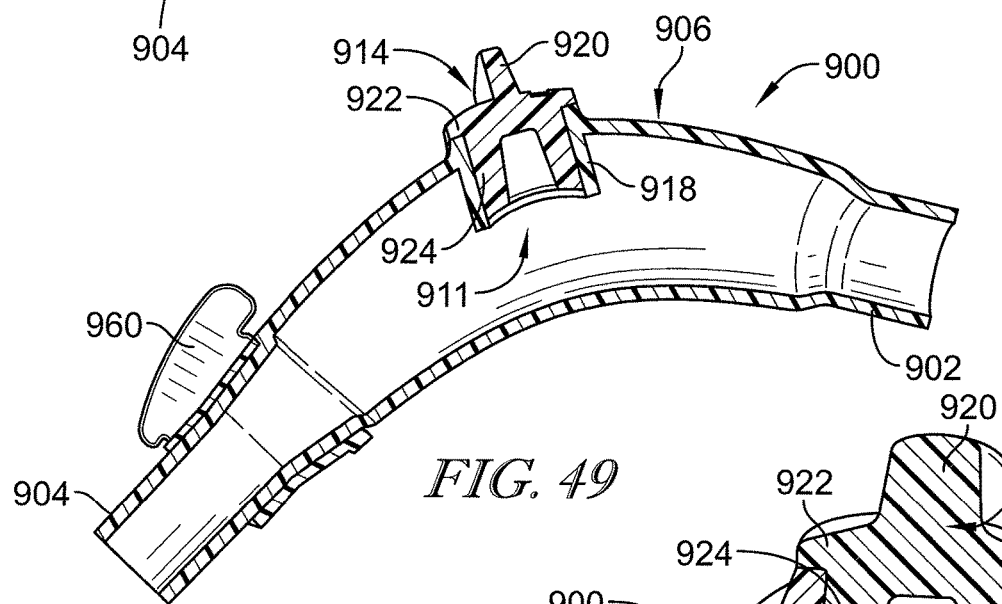
FIG. 49 is a cross sectional view of the handset of FIG. 48 taken along the long dimension of the handset.

In the illustrative embodiment, handset 900 includes a plug 916 that closes nebulizer port 911 when the nebulizer is absent. Nebulizer port 911 includes a cylindrical wall 918 that projects into an interior region of the generally banana-shaped tube 906 as shown in FIGS. 49 and 50. In the illustrative example, nebulizer port 911 includes an annular ridge 912 that extends upwardly from the apex of the upper surface 908 of tube 906. Plug 916 includes a grip tab 920 which is grabbed by a user to remove and install plug 916 with respect to port, an annular flange 922 which seats against a top edge of annular ridge 912 when plug 916 is installed in port 911, and a cylindrical wall 924 that extends downwardly from flange 922 to contact wall 918 and fill port 911. In some embodiments, handset 900 is made of a relatively hard plastics material and plug 916 is made of softer plastics material or an elastomeric material such as rubber.

Figure 51:
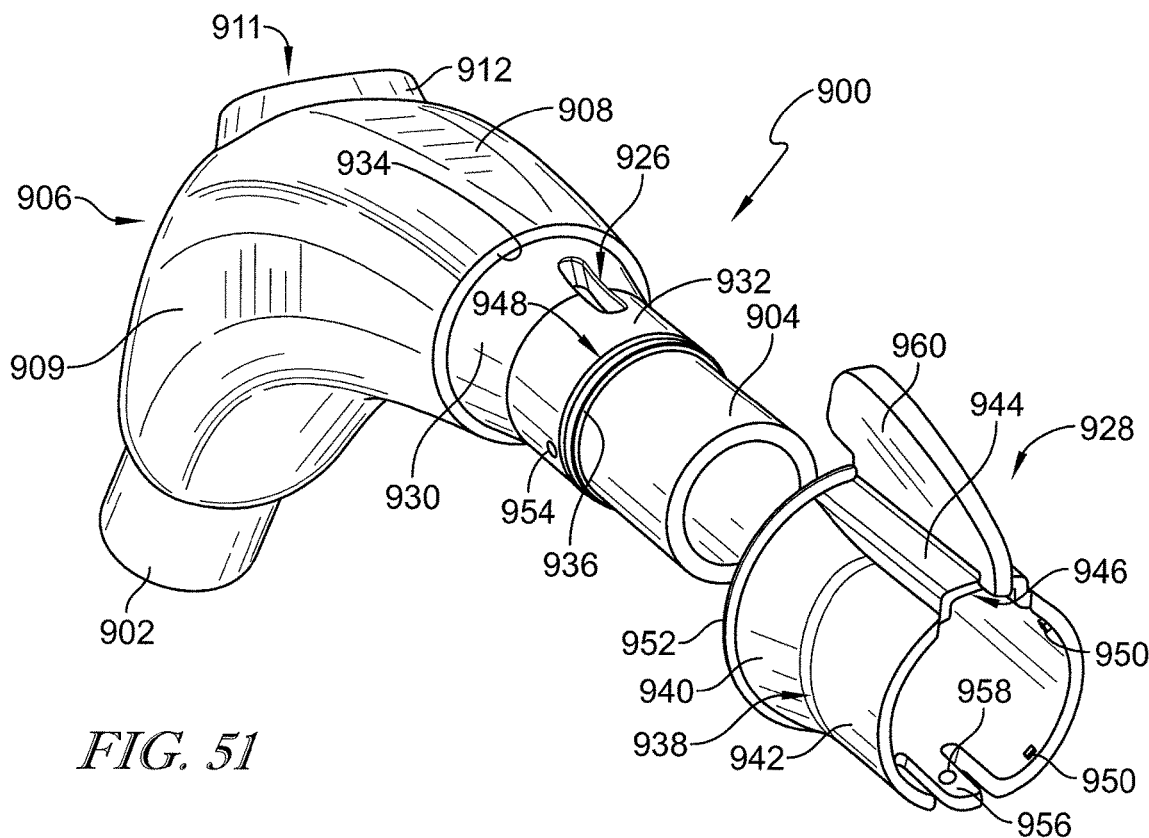
FIG. 51 is a perspective view of an end of the handset showing an adjustable ring exploded away from the end of the handset to expose an oblong aperture at a top of the handset adjacent the end, a detent-receiving depression at a side of the handset adjacent the end, and an annular retention groove adjacent the end, the adjustable ring having a large finger tab projecting from an offset channel portion of the ring, the ring being oriented in a first position with the channel portion aligned with the oblong aperture.
Figure 52:
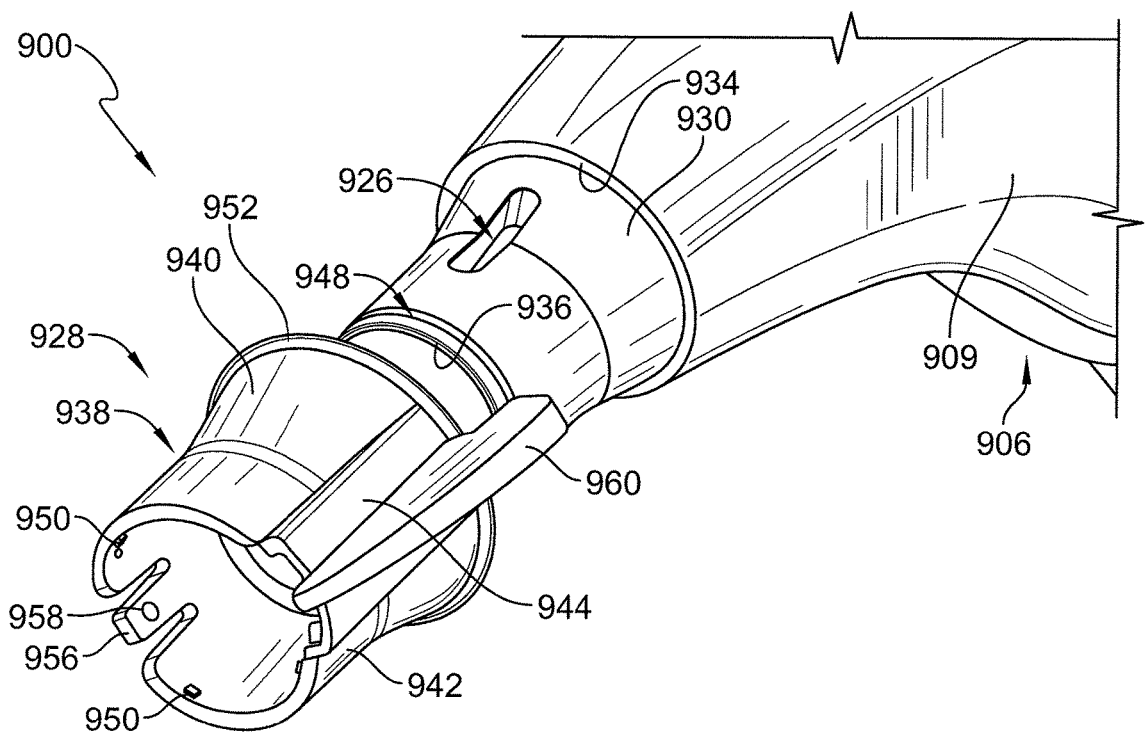
FIG. 52 is a perspective view, similar to FIG. 51 but at a different viewing angle, showing a flexible finger of the ring having a detent projecting radially inwardly therefrom and showing the ring oriented in a second position with the channel member misaligned with the aperture, the ring having projections that project radially inwardly from the ring and that are received in the retaining groove when the ring is assembled onto the end of the handset.

As shown in FIGS. 51 and 52, handset 900 has an aperture 926 that extends through the generally banana-shaped tube 906 adjacent the open end 904 of the generally banana-shaped tube 906. Handset 900 also has a ring 928 which is rotatable between a first position in which aperture 926 is open to atmosphere and a second position in which aperture 926 is closed. Tube 906 has a frustroconical region or wall 930 and a cylindrical region or wall 932 interconnecting region 930 and cylindrical end 904. Aperture 926 is fashioned as an open slot located at the upper surface 908 of tube 906 and bridging across the interface between frustroconical region 930 and cylindrical region 932. In the illustrative example, slot 926 is oriented in a longitudinal dimension of the generally banana-shaped tube 906. Tube 906 has a first annular shoulder 934 that provides a transition between the main body of tube 906 (i.e., the part of tube 906 having nebulizer port 911) and frustroconical region 930. Tube 906 also has a second annular shoulder 936 that provides a transition between cylindrical region 932 and cylindrical end 904.

In the illustrative embodiment, ring 928 includes a sleeve 938 that wraps around a majority of the circumference of regions 930, 932 of the generally banana-shaped tube 906 in abutting rotative bearing engagement therewith. Thus, sleeve 938 includes a frustroconical portion 940 and a cylindrical portion 942 which are complimentary in shape to regions 930, 932 of tube 906, respectively. Ring 928 also has an offset portion 944 that is coupled to the sleeve 938 and that defines a channel 946 which aligns with aperture 926 when ring 928 is in the first position so that aperture 926 and interior region of tube 906 may communicate with atmosphere through channel 946 and that is out of alignment with the aperture 926 when the ring is in the second position. Thus, aperture 926 is closed off by sleeve 938 when ring 928 is in the second position.

Tube 906 has a circumferential groove 948 formed around region 932 adjacent shoulder 936. Sleeve 938 of ring 928 has a set of tabs 950 that project into groove 948 when ring 928 is mounted to tube 906. Receipt of tabs 950 in groove 948 retains ring 928 on the generally banana-shaped tube 906. When ring 928 is mounted to tube 906, an annular ridge 952 at an end of region 940 lies adjacent to shoulder 934 with little, if any, clearance therebetween. Tube 906 has first and second depressions 954 (only one of which can be seen in FIG. 51) and ring 928 includes a flexible finger 956 having a detent 958 which is received in the first depression 954 when ring 928 is in the first position and which is received in the second depression 954 when ring 928 is in the second position. Thus, receipt of detent 958 in depressions 954 has a tendency to retain ring 928 in the respective first or second position depending which of the two depressions 954 receives detent 958. In the illustrative embodiment, ring 928 includes a finger tab 960 that extends outwardly from the offset portion 944. Finger tab 960 is used to rotate ring 928 relative to regions 930, 932 of the generally banana-shaped tube 906 between the first and second positions.

Figure 54:
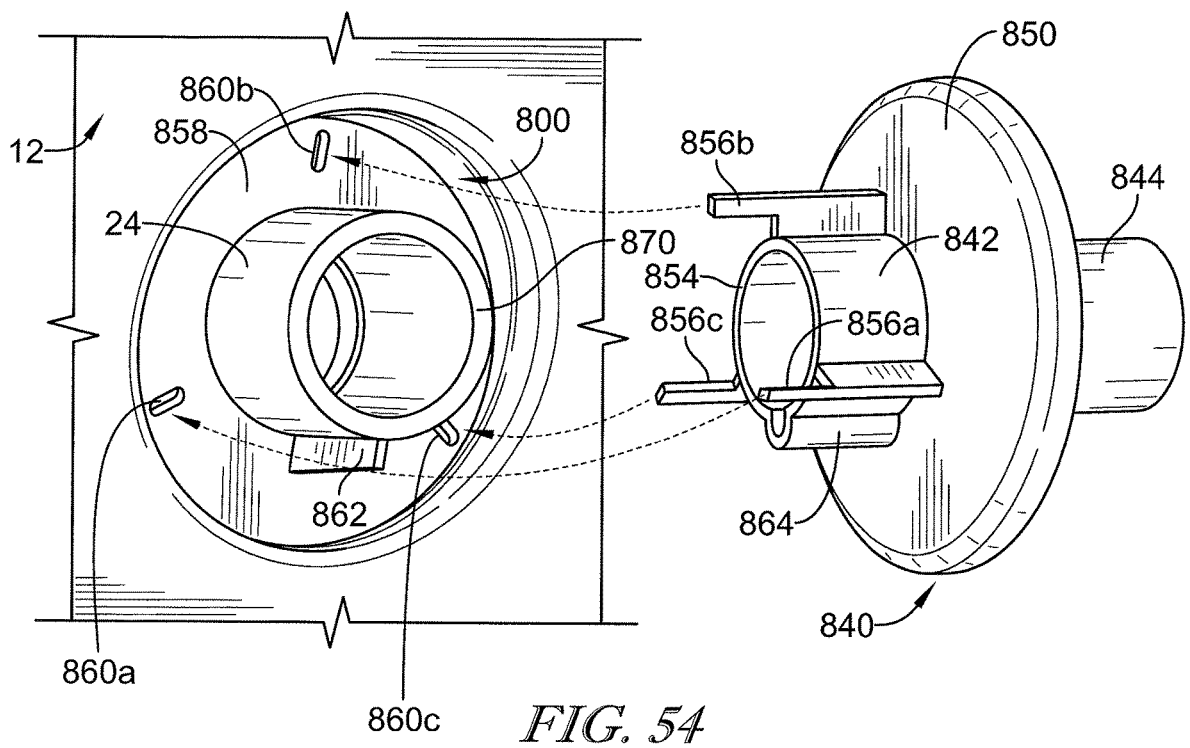
FIG. 54 is an exploded view showing a filter unit arranged for coupling to a patient port of a respiratory device, the filter unit having a set of prongs that enter into apertures spaced about a main tube of the port.
Figure 55:
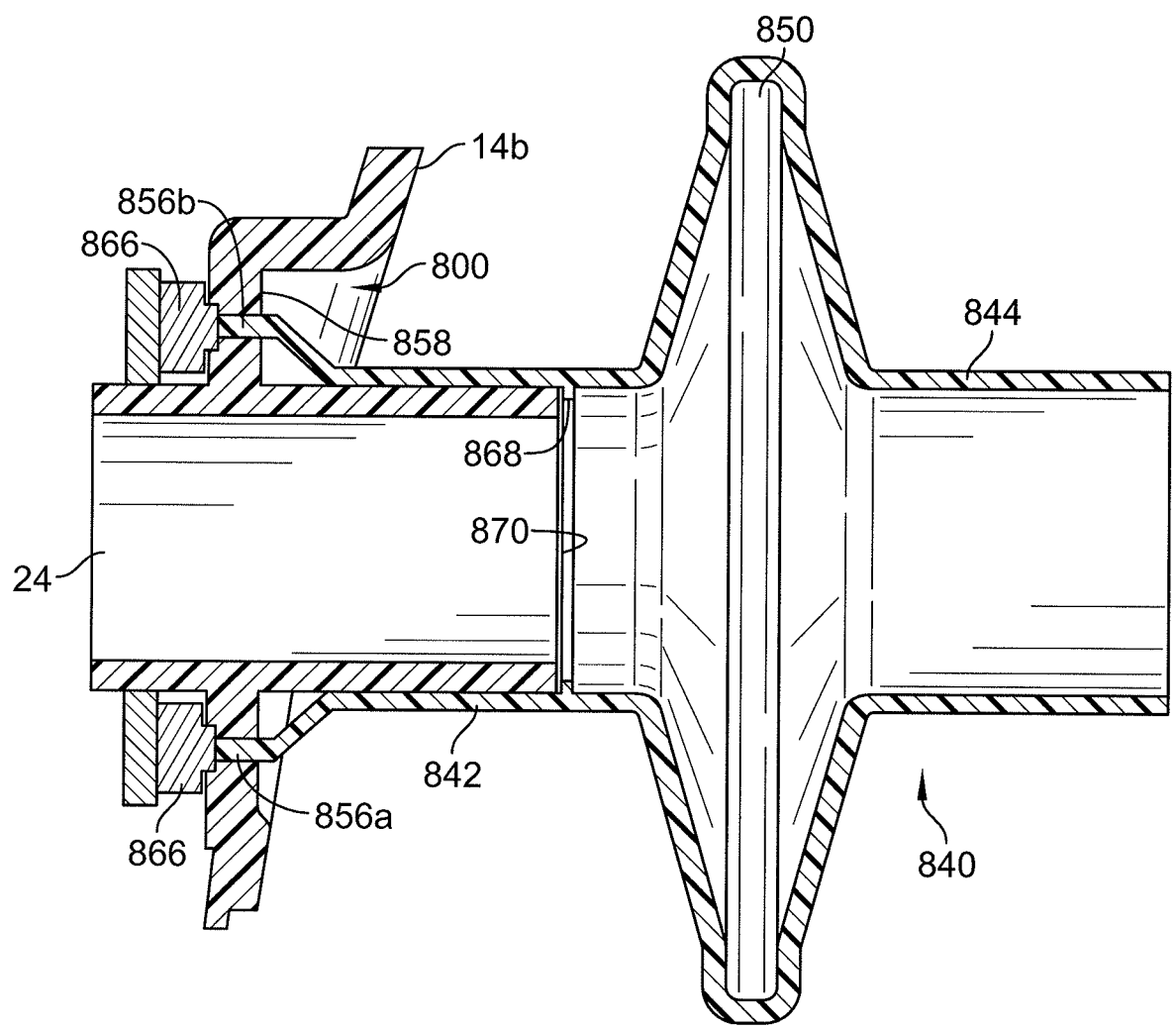
FIG. 55 is a cross sectional view of the filter unit and patient port showing the filter unit coupled to the port so that the prongs extend through the apertures to engage switches, various embodiments of the filter unit have a different number of prongs (e.g., one, two, three, etc.) which indicate the type of filter unit or patient interface being used with the respiratory device.

Referring now to FIGS. 54 and 55, in some embodiments, filter unit 840 has one or more prongs extending with respect to an end 854 of tube 842. In the illustrative example, three prongs 856a, 856b, 856c are included in filter unit 840 as shown in FIG. 54. Prongs 856a, 856b, 856c extend generally axially with respect to filter housing 850 which is sometimes referred to herein as a filter carrier 850. Housing 12 of device 10' has a port wall 858 defining a back of annular recess 800. Three prong-receiving apertures 860a, 860b, 860c are provided in wall 858 for receipt of prongs 856a, 856b, 856c, respectively.

In the illustrative example, prongs 856a, 856b, 856c are spaced by 120 degrees about the periphery of tube 854 and apertures 860a, 860b, 860c are spaced by 120 degrees about port 24. A tab or rib 862 extends radially outwardly from port 24 by a slight amount and tube 854 has a slot or channel 864 in which tab 862 is received to properly orient filter unit 840 with respect to port 24 so that prongs 856a, 856b, 856c are properly aligned with respective apertures 860a, 860b, 860c during attachment of filter unit 840 to port 24.

In the interior region of housing 12 of device 10' behind port wall 858, three switches 866 are provided with each switch 866 being accessible through a respective one of apertures 860a, 860b, 860c as shown in FIG. 55 with regard to two switches 866. Switches are electrically coupled, such as by hardwired connection, to control circuitry 76 of device 10'. Control circuitry 76, therefore, receives signals from switches 866 to indicate an on or off state of the switches 866 (aka a closed or open state). Switches 866 are normally in the open or off state in the absence of filter unit 840 being attached to port 24. When filter unit 840 is coupled to port 24 and prongs 856a, 856b, 856c extend through apertures 860a, 860b, 860c by a sufficient amount, switches 866 are moved to the on or closed state.

An annular rib 868 is provided in the bore of tube 842, as shown in FIG. 55. Rib 868 engages an annular end surface 870 of port 24 to stop the movement of tube 842 relative to port during installation of filter unit 840 onto port 24. When rib 842 engages surface 870, prongs 856a, 856b, 856c are properly positioned to close switches 866. Thus, rib 868 protects prongs 856a, 856b, 856c by preventing tube 842 from being pushed too far onto port 24. In some embodiments, port 24 and tube 842 are sized and configured according to the ISO 5356 standard for mating force and engagement.

In some embodiments, the pressure source of device 10', such as blower 786 is disabled from operation unless the at least one of switch 866 is activated (e.g., by being in the on or close state). Thus, control circuitry 76 of device 10' is configured to prevent operation of blower 786 unless at least one of switches 866 is in the on state. It is contemplated by this disclosure that filter units 840 of different types of patient interfaces 22 may have a different number of prongs 856a, 856b, 856c. It should be appreciated that seven permutations of patient interfaces 22 are possible with three switches 866 as follows:

(i) Interface 1 has only one prong 856a;
(ii) Interface 2 has only one prong 856b;
(iii) Interface 3 has only one prong 856c;
(iv) Interface 4 has only two prongs 856a, 856b;
(v) Interface 5 has only two prongs 856a, 856c
(vi) Interface 6 has only two prongs 856b, 856c; and
(vii) Interface 7 has all three of prongs 856a, 856b, 856c.

Depending upon which of switches 866 are closed and which are opened, control circuitry 76 is able to discern which type of patient interface is coupled to device 10'. However, by determining that at least one of switches 866 is closed, control system 76 of device 10' is generally assured that a filter unit 840 with corresponding filter 852 is present, such that operation of blower 786 is enabled. With filter 852 present, inadvertent foreign objects are unable to pass from device 10' to the patient through patient interface 22. This safety feature prevents device 10' from operating if hose 20 is coupled directly to port 24 without any filter unit 840 being present. In some embodiments, if none of switches 866 are closed, a message is displayed on screen 16 to remind the user to include filter unit 840 in the patient interface 22 being used with device 10'. In some embodiments, two of switches 866 are required to be closed by at least two prongs 856a, 856b, 856c before blower 786 is enabled for operation. In such embodiments, only four permutations of patient interface types is possible (e.g., choices (iv)-(vii) in the list above).

In some embodiments, it is contemplated that therapy mode options that may be delivered through outlet port 24 by device 10' may be different depending upon which type of patient interface 22 is coupled to the outlet port 24 as indicated by switch 866 closures. For example, patient interfaces 22 with a mask 36 may be required for device 10' to deliver MIE therapy to a patient by device 10' and handset 900 may be required for device 10' to deliver CPEP or CHFO therapy to a patient. A patient interface 22 with both a mask 36 and handset 900 may permit device 10' to deliver MIE, CPEP and CHFO therapies to a patient, just to give another example. In some embodiments, device 10' may include a user input operable to signal the controller 76 to override the disabling of the pressure source 786 when none of switches are activated, thereby to permit the pressure source 786 to operate even if no switches 866 are activated. For example, such a user input may be an input on graphical display screen 16 such as one or more icons or buttons. Alternatively or additionally, this sort of override user input may be provided as a manual switch or button on housing 12 of device 10'.

As mentioned above, device 10 senses an inspiratory trigger in connection with delivery of automatic MIE therapy to a patient. Device 10' also has this feature. According to this disclosure, sensors 106 of devices 10, 10' include at least one pressure sensor and at least on flow sensor. In some embodiments, two pressure sensors are provided so as to be compliant with the ISO 80601-2-12: 2011 standard relating to critical care ventilators. However, this need not be the case in other embodiments. In some embodiments, the following software algorithm is executed by control circuitry 76 of devices 10, 10' in connection with the inspiratory trigger:

```
1. //Read the Pressure and Flow Store it in Array
Flow[n] ; Pressure[n]
2. If Number_of_Samples > 10
// Calculate the last 10 sample average
Flow_Average[n] = Average (Flow[n]+Flow[n-1]+....+Flow[n-9])
Pressure_Average[n] = Average (Pressure[n]+Pressure[n-1]+....+Pressure[n-9])
3. // Calculate the First Order Difference of Flow and Pressure
Flow_Difference_Array[n] = Flow_Average[n] - Flow_Average[n-1]
Pressure_Difference_Array[n] = Pressure_Average[n] - Pressure_Average[n-1]
4. If(Flow_Difference_Array[n]) > 0.1    // possibly
trigger has begun here; Store this index as
"Trigger_Began_here"
temp_flow_sum = temp_flow_sum +
Flow_Difference_Array[n] // keep accumulating the
incremental difference in flow
if(temp_flow_sum) > FLOW_SENSITIVITY
    // Possibly could be a trigger, confirm if pressure is
dropped
temp_press_sum = Sum(Pressure_Difference_Array[n] +
Pressure_Difference_Array[n1]+
.....Pressure_difference_Array[Trigger_Began_here])
if(temp_press_sum < 0)    // patient's breathing pattern
always creates negative pressure
AND if(Flow[n] > FLOW_SENSITIVITY   // is current
flow value greater than sensitivity
Trigger_Found = True
else
temp_flow_sum = 0
Trigger_Began_here = 0
```

Figure 68:
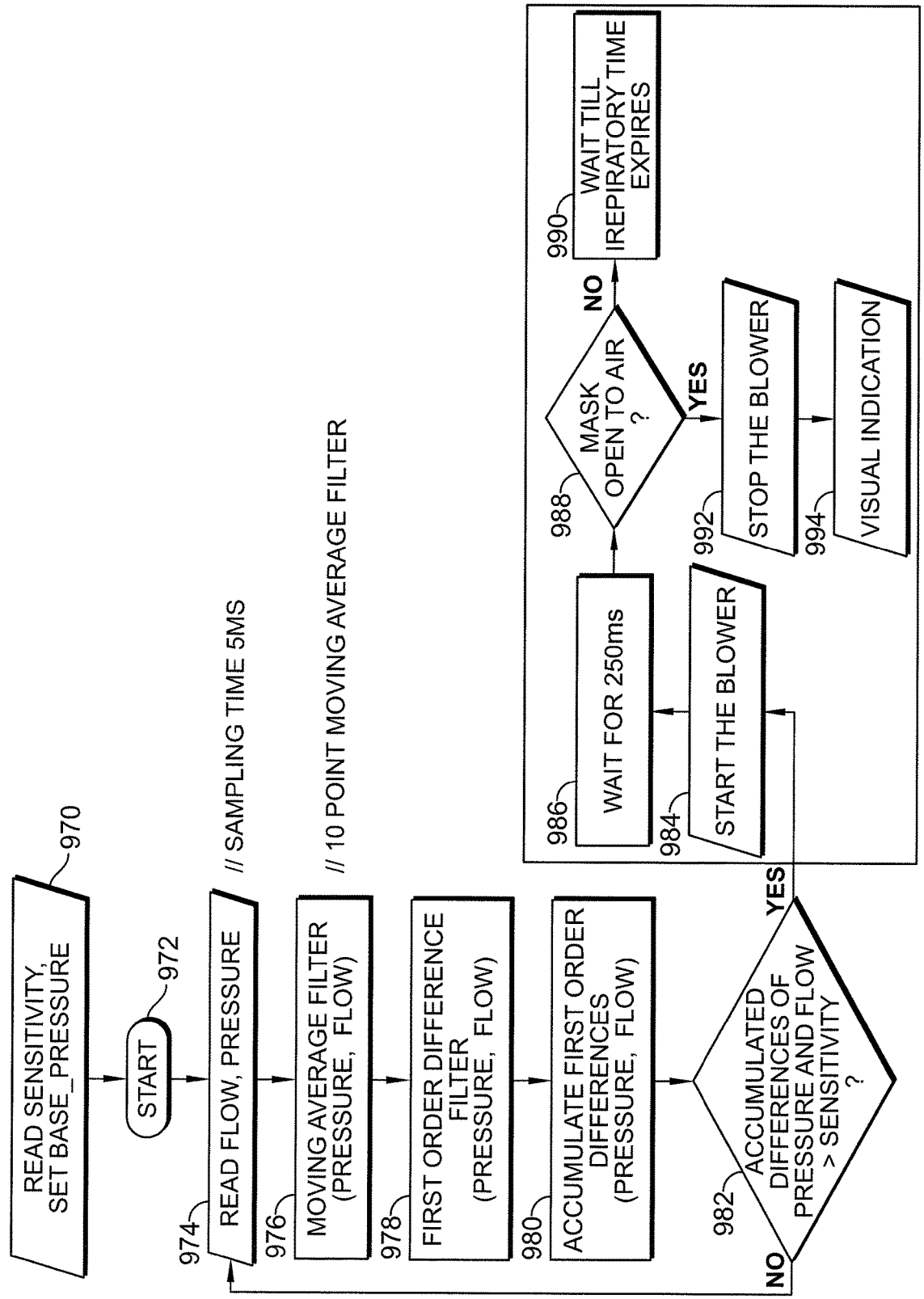
FIG. 68 is a flow chart of an inspiratory trigger and mask leakage/removal algorithm according to the present disclosure.

A flow chart illustrative of the preceding algorithm is shown in FIG. 68. At block 970 of FIG. 68, control circuitry 76 first reads sensitivity and sets a base pressure prior to starting the inspiratory trigger algorithm. After reading the sensitivity and setting the base pressure, the inspiratory trigger sensing algorithm starts as indicated at block 972. Once started, control circuitry 76 reads flow and pressure from sensors 106 at 5 millisecond sampling times as indicated at block 974. Control circuitry 76 implements a 10-point (i.e., 10 samples) moving average filter for pressure and flow data points as indicated at block 976. Control circuitry 76 then implements a first order difference filter for the pressure and flow samples as indicated at block 978. The first order differences of pressure and flow are accumulated by control circuitry 76 as indicated at block 980. Control circuitry 76 then compares the accumulated pressure and flow differences to the sensitivity to see if either of them are greater than the sensitivity as indicated at block 982.

If accumulated pressure and flow differences are not greater than the sensitivity at block 982, then the algorithm loops back to block 974 and proceeds from there. If accumulated pressure and flow differences are greater than the sensitivity at block 982, the control circuitry 76 starts the blower (e.g., operates the blower as necessary to achieve the programmed positive pressure inspiratory pressure for automatic MIE therapy) as indicated at block 984. The algorithm then waits for 250 milliseconds as indicated at block 986 and proceeds to check to determine if the mask 36 is removed from the patient (e.g., open to air) as indicated at block 988. If the mask 36 is not removed from the patient as determined at block 988, then the algorithm waits for the inspiratory time of the automatic MIE therapy to expire as indicated at block 990. If the mask 36 is removed from the patient as determined at block 988, then control circuitry 76 proceeds to stop the blower 786 from operating as indicated at block 992 and provides a visual indication of the mask removal on display 16 as indicated at block 994.

In connection with block 988 of the algorithm of FIG. 68, the following software algorithm is executed by control circuitry 76 of devices 10, 10' in connection with determining mask removal:

```
// Assumption Trigger_Found - true
1.      Read Flow : Flow[n]
2.      Calculate open_flow // based on drive voltage
3.      If(Flow[n] >= open_flow) // could be a false effort,
but could also be a HIGH breathing effort so don't make
decision immediately that mask is open
Confidence = confidence + 1
If(Confidence > 50) // for 5ms sampling time, translates to
about 250ms delay in turning off the blower
Turn_off_Blower( )
```

Figure 69:
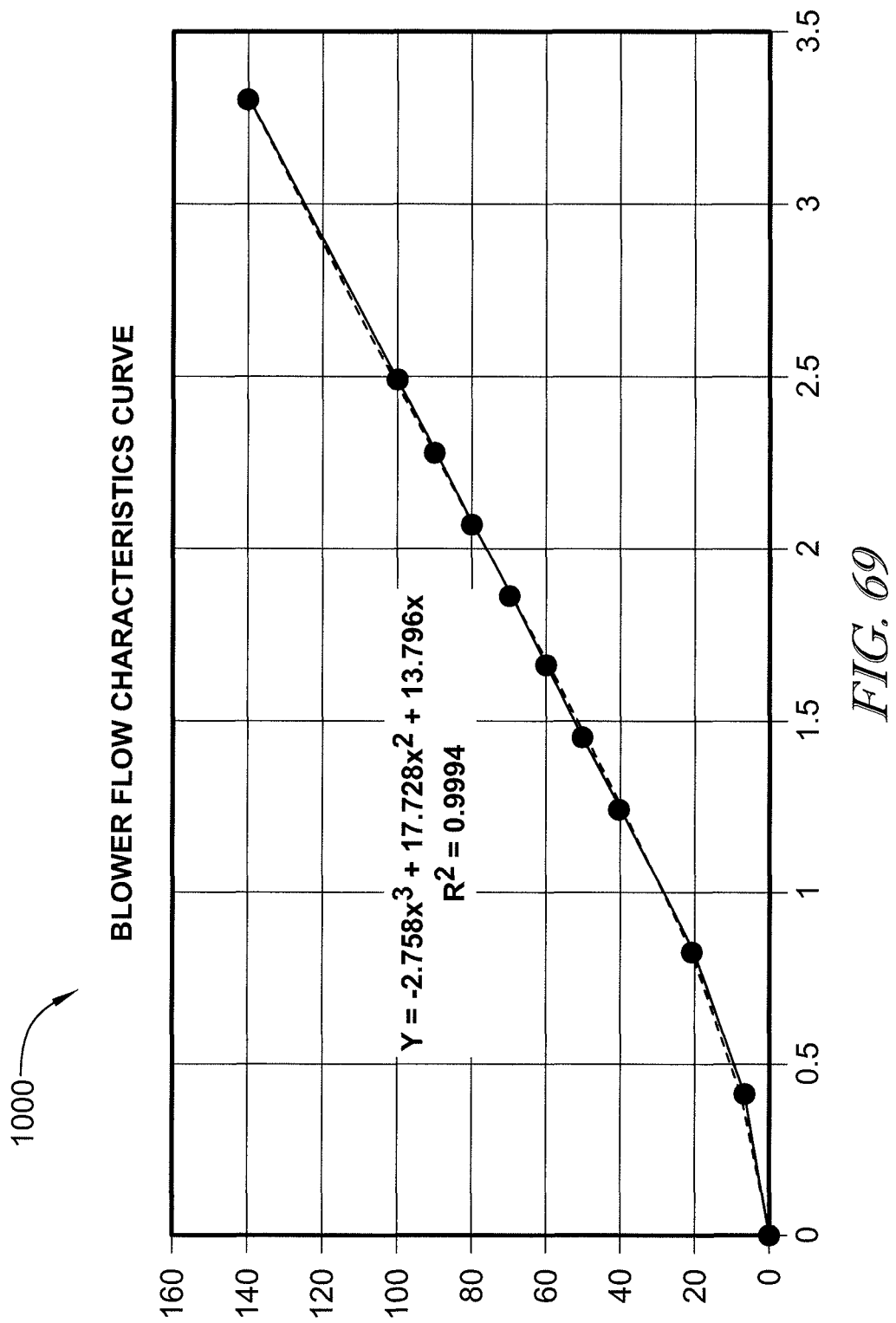
FIG. 69 is a graph showing an example of a blower flow characteristic curve.
Figure 70:
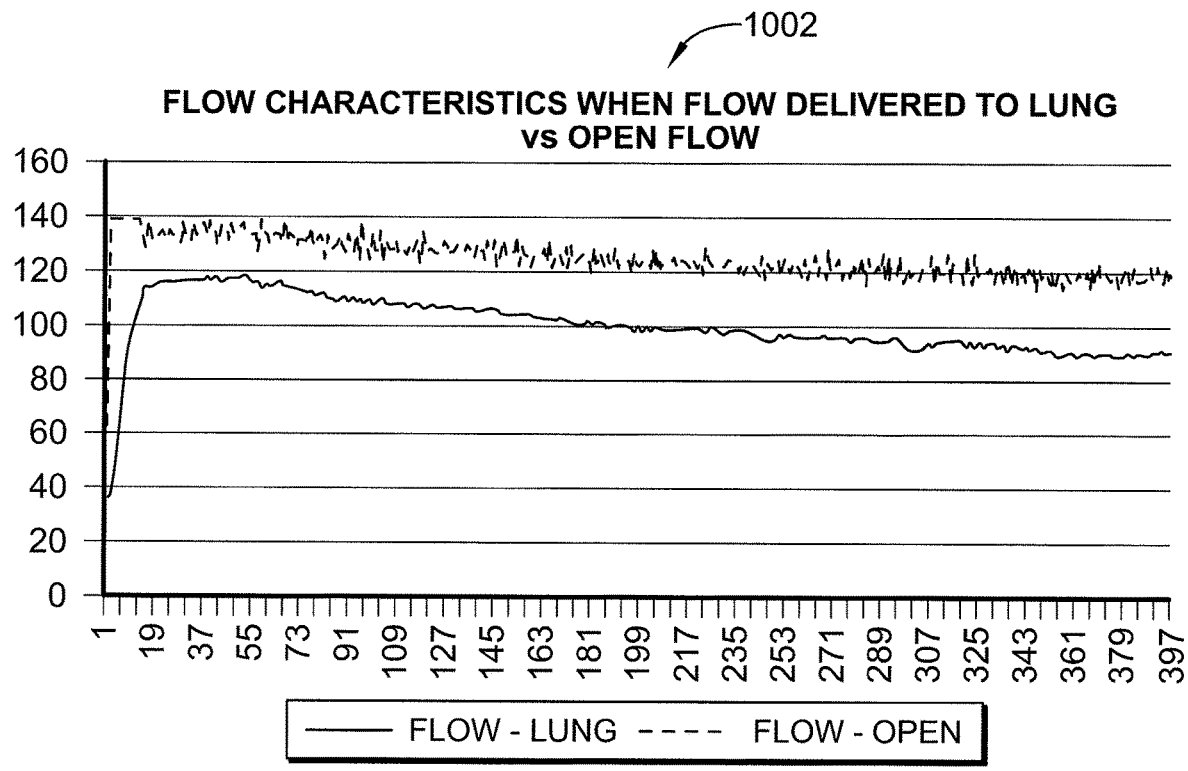
FIG. 70 is a graph showing an example of flow characteristics of a respiratory device comparing flow when being delivered to a patient's lungs vs. open flow.
Figure 71:
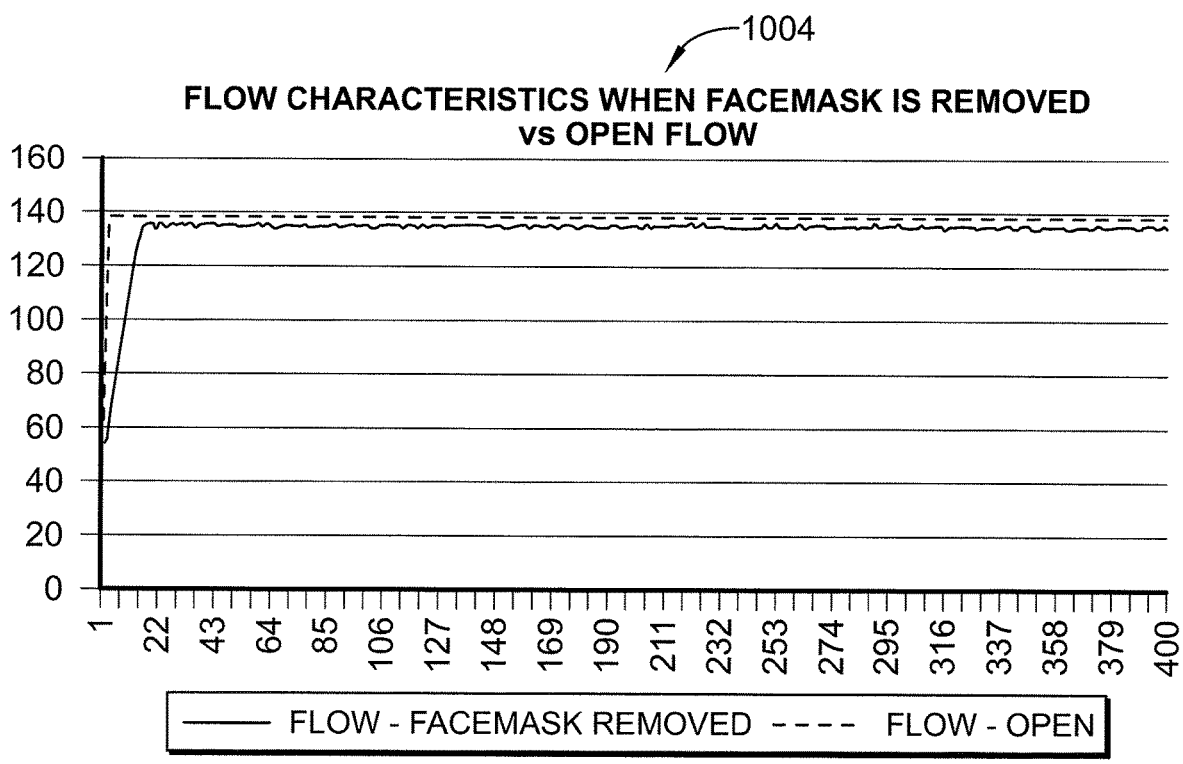
FIG. 71 is a graph showing an example of flow characteristics of a respiratory device comparing flow when the mask of the patient interface is removed from a patient vs. open flow.

If the mask 36 is disconnected or otherwise removed from the patient's face and open to atmospheric air, the flow is high and Pressure drops. As shown in graph 100 of FIG. 69, an illustrative blower 786 achieves 140 liters per minute of air flow within about 3 to 3.5 seconds of startup. A curve fit formula for blower start up is shown in graph 1000. FIG. 70 includes a graph 1002 which compares the flow characteristics when mask 36 is properly delivering air to a patient's lungs (e.g., illustrated by the lower curve of graph 1002) to the flow characteristics when mask 36 is open to atmosphere (i.e., illustrated in the upper curve of graph 1002) over a much longer period of time than is shown in graph 1000 of FIG. 69. Thus, when the mask 36 is properly connected to a patient, the flow rate as measured by a flow sensor in device 10 or device 10' is at least 10 liters per minute less than when the mask 36 is removed from the patient and open to atmosphere. FIG. 71 includes a graph 1004 which compares the flow characteristics when mask 36 is removed from a patient (e.g., illustrated by the lower curve of graph 1004) to the flow characteristics when mask 36 is open to atmosphere (i.e., illustrated in the upper curve of graph 1004) over a much longer period of time than is shown in graph 1000 of FIG. 69. Graph 1004 shows that the flow characteristics after mask removal are basically the same as those with open flow, as one would expect.

In connection with determining mask leakage, a similar algorithm is implemented, but instead of step 3 comparing flow[n] to open flow, flow[n] is compared to some lesser number that indicates that mask leakage is too high. That mask leakage threshold, like the open_flow value, is dependent upon drive voltage (i.e., the voltage being used to drive blower 786). In the graphs of FIGS. 70 and 71, the scenario in which blower 786 is operating at maximum capacity is illustrated. At maximum capacity, therefore, blower 786 delivers about 140 liters per minute of air. If the blower is operating at a lower capacity, then the open_flow and mask leakage threshold numbers of the above-described algorithm are adjusted accordingly. Such numbers may be determined through experimentation or trial-and-error, for example, and then may be implemented in software via an appropriate formula or via a look up table.

Based on the preceding discussion of inspiratory trigger detection and mask removal/leakage detection, it should be understood that, in some embodiments, the inspiratory trigger is detected by control circuitry 76 of devices 10, 10' based on information sensed by at least one pressure sensor and at least one flow sensor, whereas mask leakage or removal detection is detected by control circuitry 76 of devices 10, 10' based on information from the flow sensor only. In response to inspiratory trigger detection, the pressure source (e.g., blower 786) or the valve (e.g., rotary valve 788) or both are operationally adjusted to provide a desired positive pressure to the patient's airway. Based on a flow sensor signal from the flow sensor, the controller 76 is configured to determine mask removal or mask leakage and to stop operation of the pressure source. In some embodiments, the controller determines mask removal or leakage by comparing the flow sensor signal to an open flow threshold or a leakage threshold, respectively, on an iterative basis. For example, at least fifty iterations of flow sensor signal data point comparisons to the open flow threshold or the leakage threshold is required in the illustrative embodiment before the operation of the pressure source 786 is stopped. Each iteration takes about 5 milliseconds in some embodiments.

Figure 56:
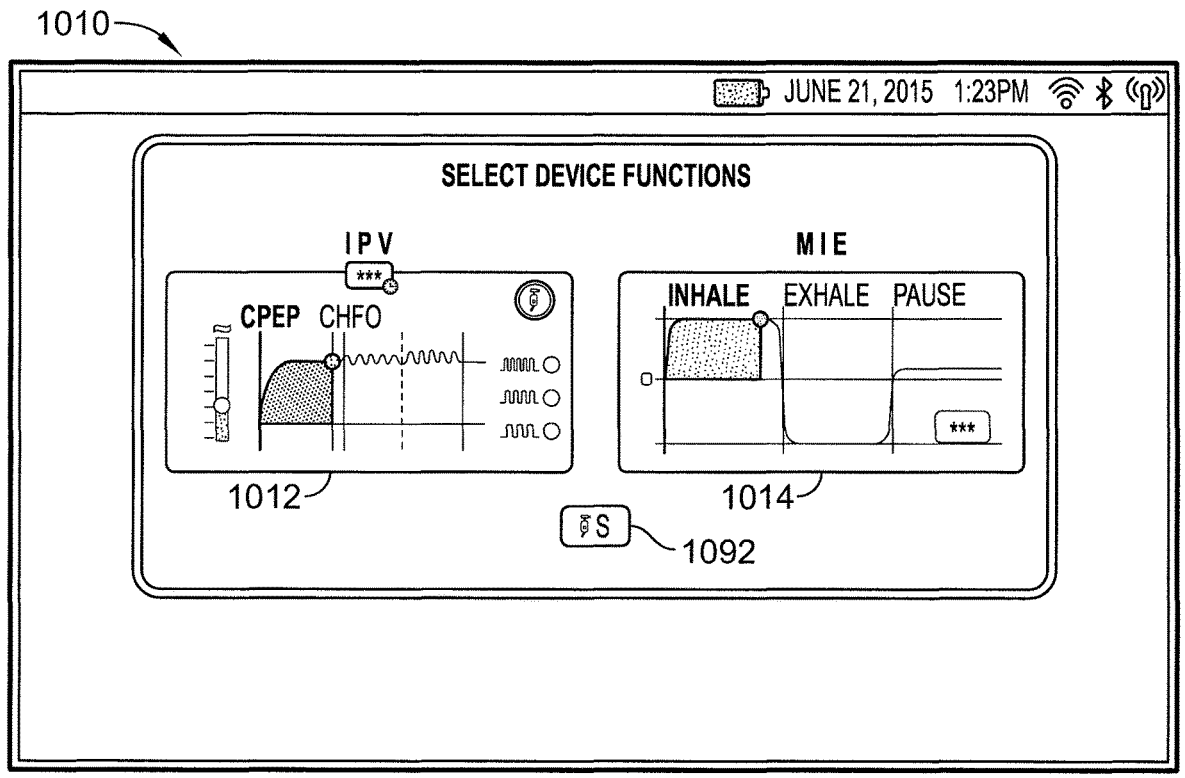
FIG. 56 is a screen shot of a home screen of a respiratory device, the home screen including icons or buttons that are selected to determine whether the respiratory device operates in a positive pressure therapy mode or in and insufflation/exsufflation therapy mode.
Figure 57:
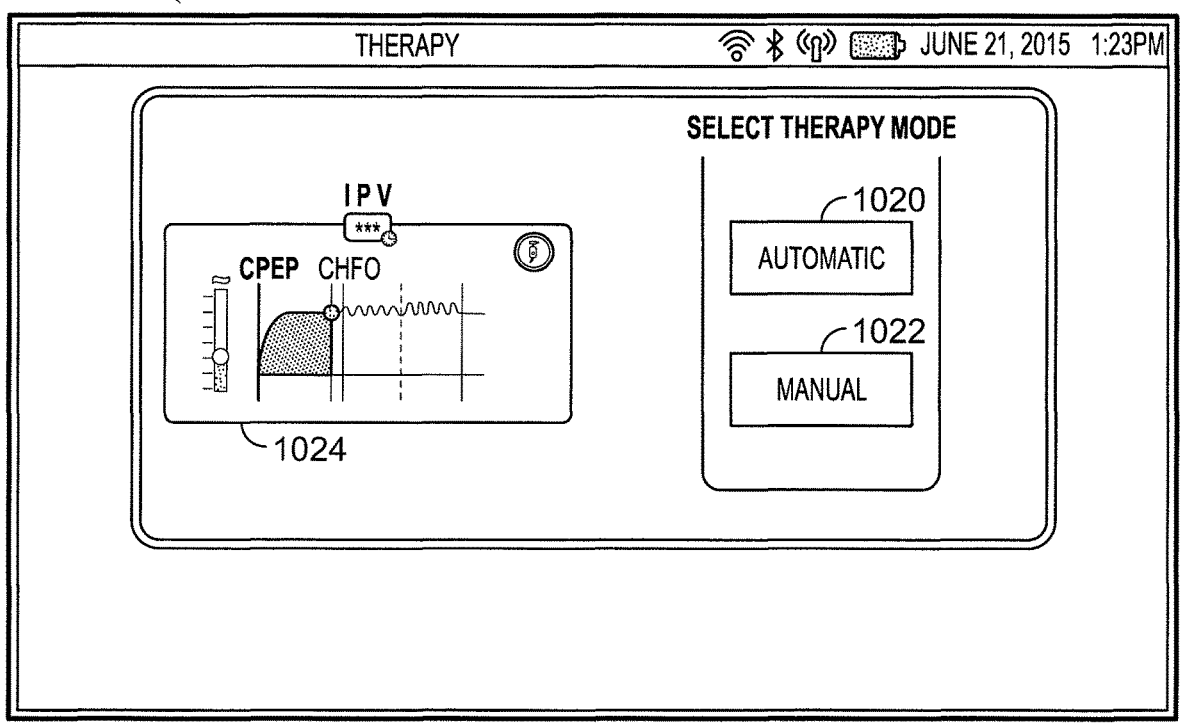
FIG. 57 is a screen shot of a positive pressure therapy screen that results if the positive pressure therapy mode button is selected on the home screen.
Figure 58:
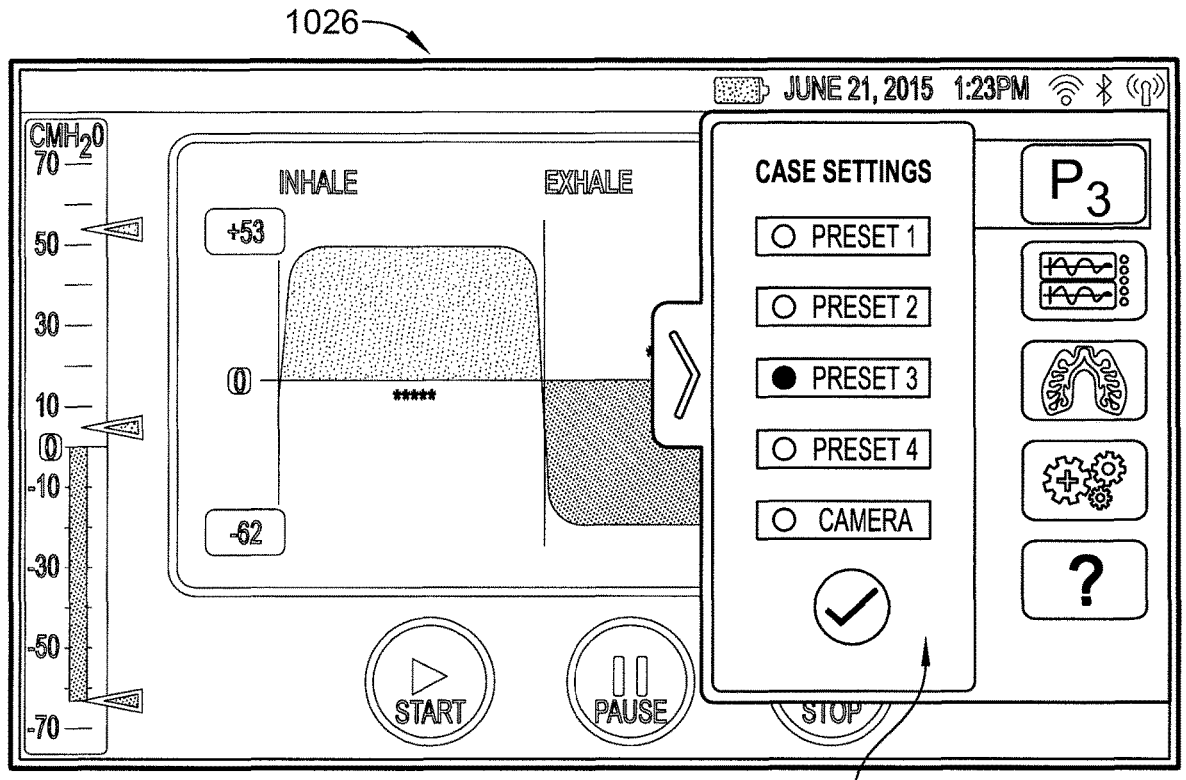
FIG. 58 is a presets screen that permits a user to select from a number of preset therapies that are stored in the respiratory device and that are listed on a selection menu.
Figure 59:
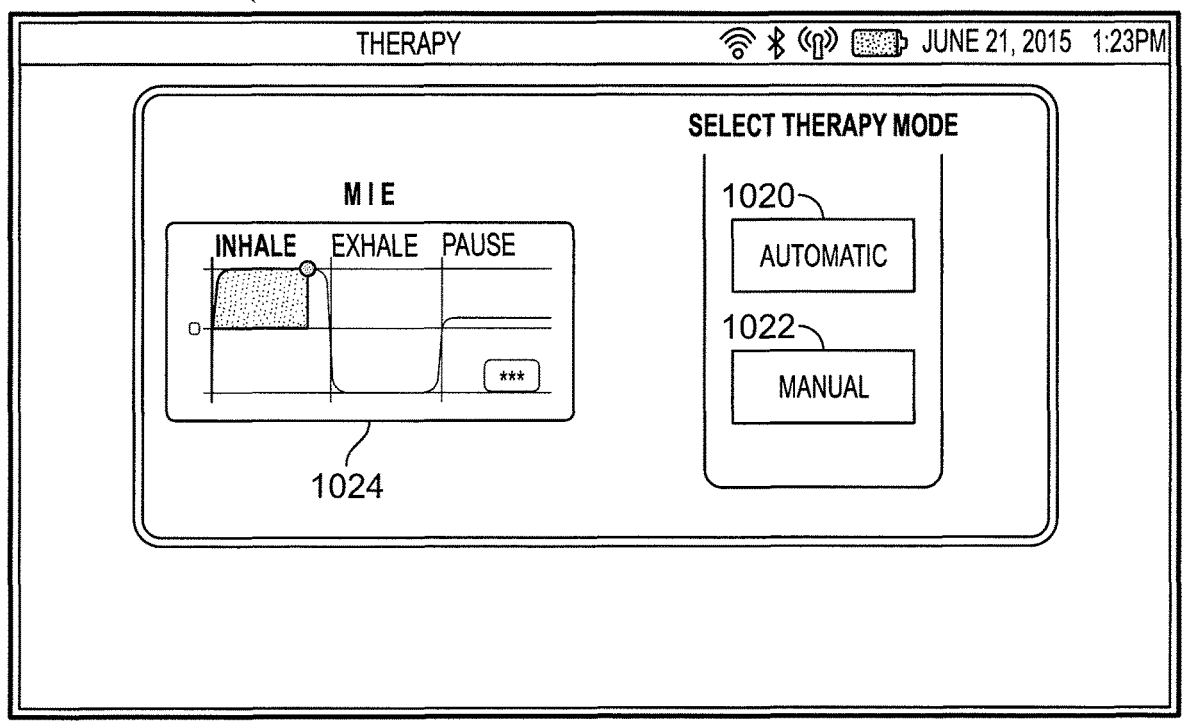
FIG. 59 is a screen shot of an insufflation/exsufflation therapy screen that results if the insufflation/exsufflation therapy mode button is selected on the home screen.

Referring now to FIGS. 56-67, various screens that appear on graphical user interface (GUI) 16 to control functions of each of devices 10, 10' are shown. As shown in FIG. 56, a home screen 1010 of a respiratory device includes an Intrapulmonary Percussive Ventilation (IPV) icon 1012 and a mechanical insufflation/exsufflation (MIE) 1014. If icon 1012 is selected on screen 1010, a positive pressure therapy screen 1016, shown in FIG. 57, results. If icon 1014 is selected on screen 1010, an insufflation/exsufflation therapy screen 1018, shown in FIG. 59, results. Each of screens 1016, 1018 includes an automatic icon 1020, a manual icon 1022 and a graph icon 1024 as shown in FIGS. 57 and 59.

If graph icon 1024 is selected on screen 1016 or 1018, then a preset screen 1026, shown in FIG. 58, results. Screen 1026 includes a menu 1028 from which preset therapies can be selected. If screen 1026 is reached from screen 1016, then the preset therapies in menu 1028 correspond to preset positive pressure therapies. On the other hand, if screen 1026 is reached from screen 1018, then the preset therapies in menu 1028 correspond to preset insufflation/exsufflation therapies. The parameters of the preset therapies selectable on menu 1028 are programmed by users of devices 10, 10'. Thus, target pressures (positive and/or negative), amplitude and frequency of pressure oscillations, time of therapy, inhalation time, exhalation time, pause time, and/or number of cycles of therapy are among the parameters that are programmable by the user, for example. During a preset therapy, these parameters may change from one numerical value to another numerical value based on the programming established by the user (e.g., patient or caregiver).

Figure 60:
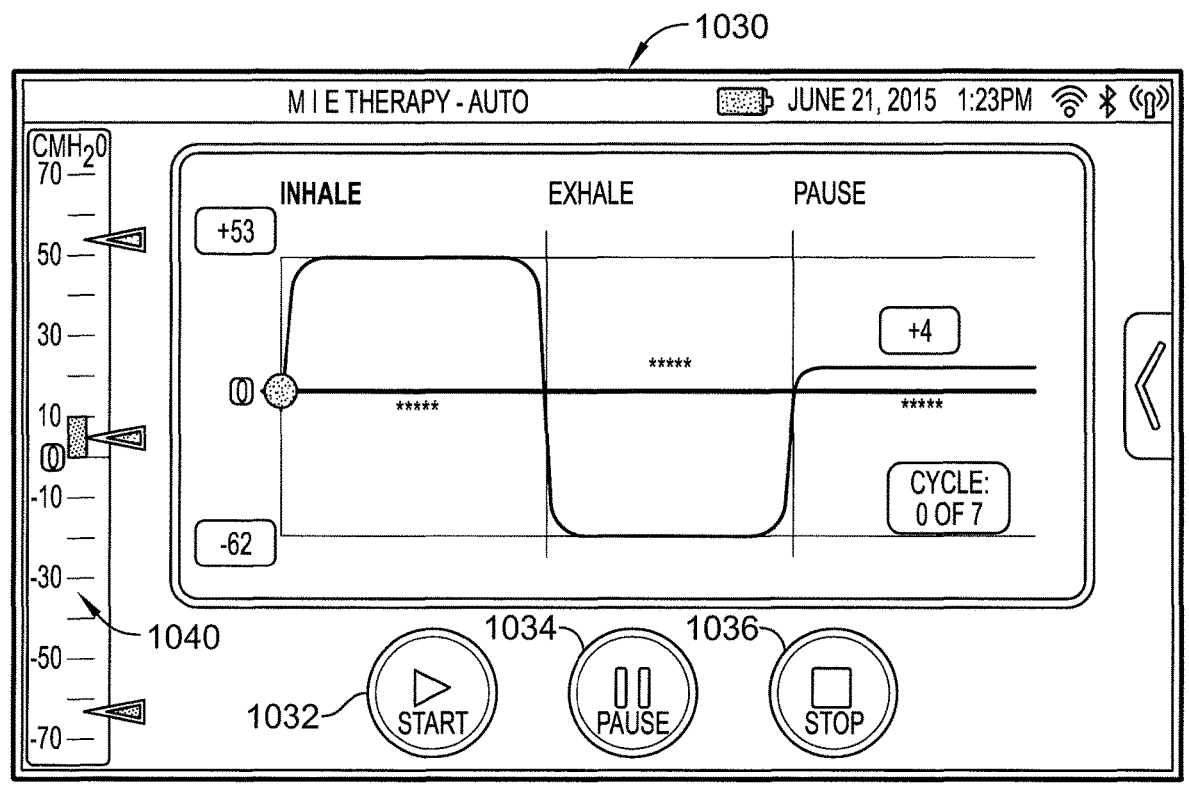
FIG. 60 an example of a first automatic insufflation/exsufflation mode therapy screen that results if an automatic mode button or icon of the screen of FIG. 59 is selected or if a preset therapy selected on the screen of FIG. 58 is a stored automatic insufflation/exsufflation therapy.
Figure 61:
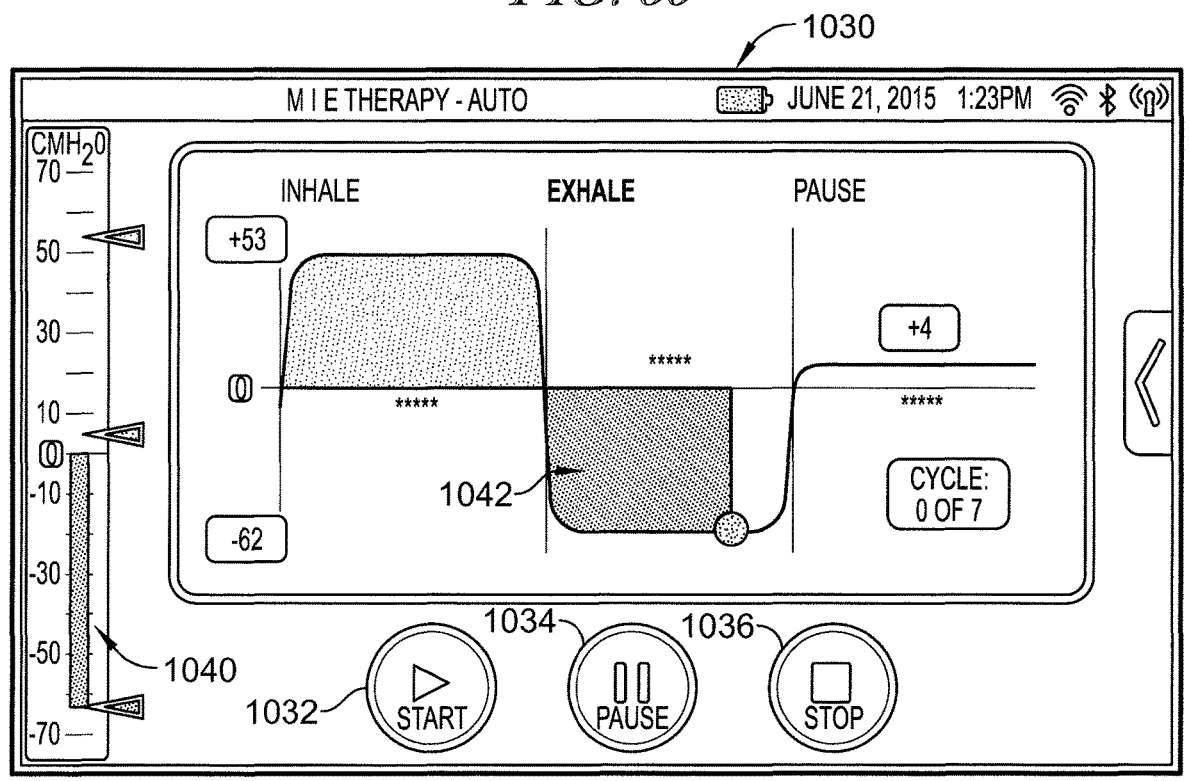
FIG. 61 is an example of a second automatic insufflation/exsufflation mode therapy screen showing various information about the status and progress of the automatic insufflation/exsufflation therapy as it occurs.

If automatic icon 1020 of screen 1018 of FIG. 59 is selected, then a first automatic insufflation/exsufflation mode therapy screen 1030 results as shown, for example, in FIG. 60. Screen 1030 is also exemplary of a screen that results if one of the insufflation/exsufflation presets is selected from menu 1028 of screen 1026. Screen 1030 includes a start button 1032 which is selected to start the associated MIE therapy, a pause button 1034 which is selected to pause the associated MIE therapy, and a stop button 1036 which is selected to stop the associated MIE therapy. Screen 1030 also has an information graph 1038 and an information bar 1040. Graph 1038 displays numerical parameters for the associated therapy including inhale pressure, exhale pressure, inhale time, exhale time, a therapy progress indicator which moves along the curve shown in graph 1038 during the associated therapy, pause pressure, pause time, and a running total of the number of cycles completed during the associated therapy. Bar 1040 includes an upper arrow serving as an inhale pressure marker, a middle arrow serving as a pause pressure marker, and a lower arrow serving as an exhale pressure marker. As shown in FIG. 61, if pause button 1034 is selected during delivery of MIE therapy, an area 1042 of graph 1038 becomes filled or colored in a manner to indicate that point of the therapy at which the pause button 1034 was selected.

Figure 62:
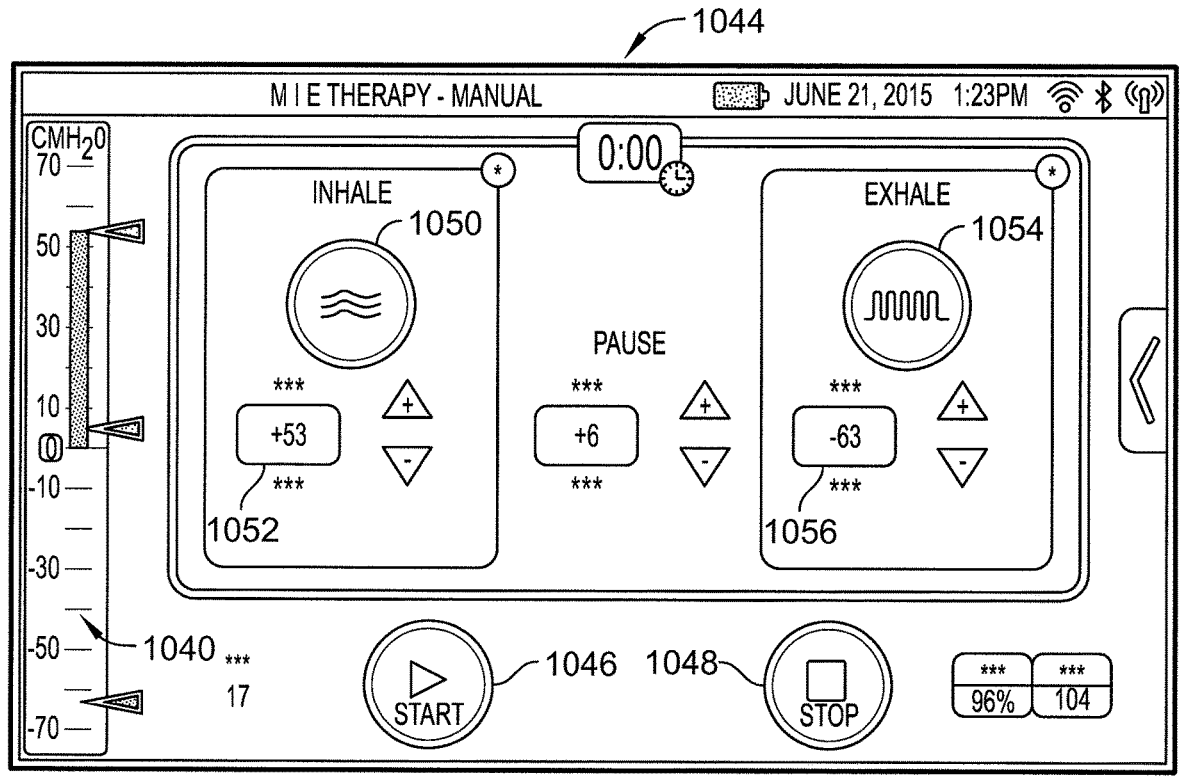
FIG. 62 an example of a first manual insufflation/exsufflation mode therapy screen that results if a manual mode button or icon of the screen of FIG. 59 is selected or if a preset therapy selected on the screen of FIG. 58 is a stored manual insufflation/exsufflation therapy.

If manual icon 1022 of screen 1018 of FIG. 59 is selected, then a first manual insufflation/exsufflation mode therapy screen 1044 results as shown, for example, in FIG. 62. Screen 1044 includes a start button 1046 which is selected to start the associated MIE therapy and a stop button 1048 which is selected to stop the associated MIE therapy. Screen 1044 includes information bar 1040 which was discussed above. Screen 1044 has an inhale button 1050 which is selected to cause positive pressure to be delivered to the patient's airway by device 10, 10' at a target positive pressure specified in a first window 1052. Screen 1044 also has an exhale button 1054 which is selected to cause negative pressure to be delivered to the patient's airway by device 10, 10' at a target negative pressure specified in a second window 1056.

Figure 63:
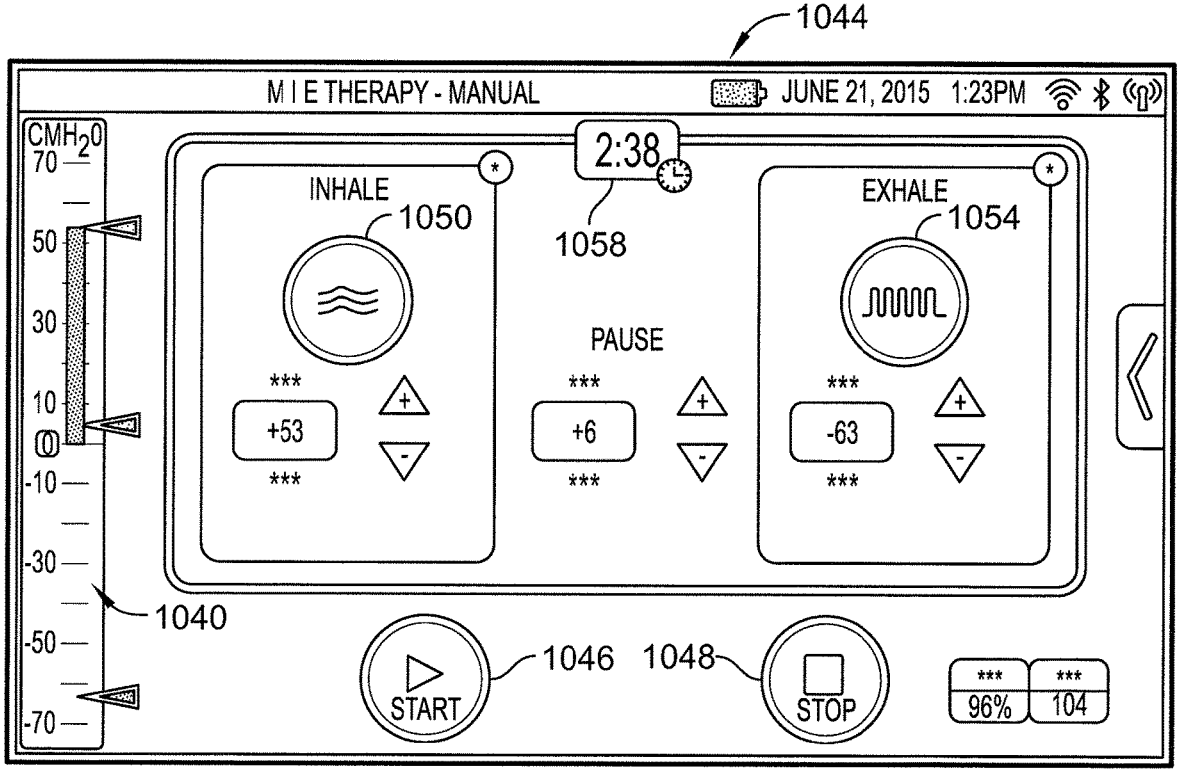
FIG. 63 is an example of a second manual insufflation/exsufflation mode therapy screen showing various information about the status and progress of the manual insufflation/exsufflation therapy as it occurs.

Thus, during manual MIE mode, the user cyclically presses buttons 1050, 1054, as desired, to deliver positive and negative pressure cyclically to the patient's airway. Buttons 1050, 1054 are lit up more brightly or become colored to indicate that they are active. The non-active one of buttons 1050, 1052 becomes grayed out until it is selected again by the user. To pause the manual MIE therapy, a user double clicks on either button 1050 or button 1054 depending upon which is one is active at the time. Up and down arrows are provided adjacent windows 1052, 1056 to permit the user to adjust the target pressures upwardly or downwardly. As shown in FIG. 63, a time of therapy window 1058 is provided to indicate the total amount of time that has transpired during the manual MIE therapy (e.g., 2 minutes, 38 seconds in the illustrative example). In some embodiments, one or more of screens 1030 of FIGS. 60 and 61 and screens 1044 of FIGS. 62 and 63 have a flutter button that is pressed to cause the pressure to oscillate during delivery of automatic or manual MIE therapy. In some embodiments, the frequency of oscillation is adjustable such as with up and down arrows or with a numeric key pad as described herein in connection with adjusting pressure settings of devices 10, 10'.

Figure 64:
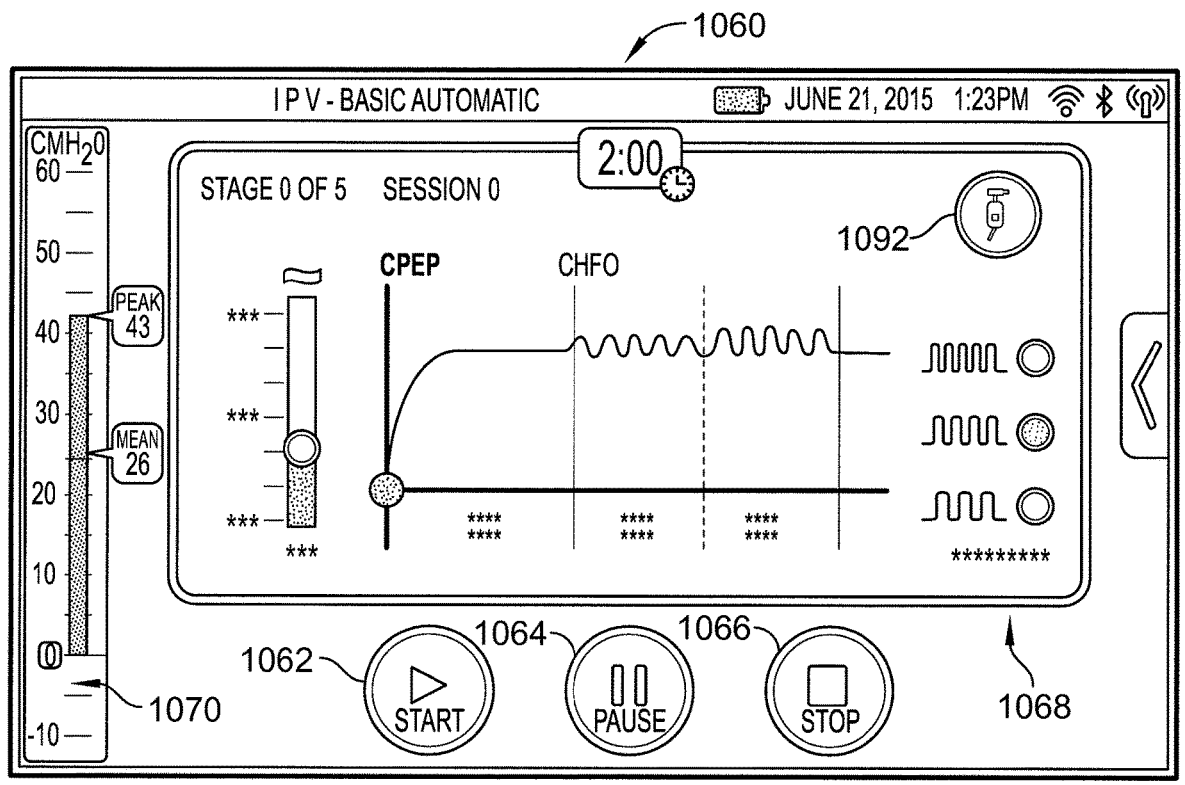
FIG. 64 an example of a first automatic positive pressure therapy mode screen that results if an automatic mode button or icon of the screen of FIG. 57 is selected or if a preset therapy selected on the screen of FIG. 58 is a stored automatic positive pressure therapy.

If automatic icon 1020 of screen 1016 of FIG. 57 is selected, then a first automatic IPV mode therapy screen 1060 results as shown, for example, in FIG. 64. Screen 1060 is also exemplary of a screen that results if one of the IPV presets is selected from menu 1028 of screen 1026. Screen 1060 includes a start button 1062 which is selected to start the associated IPV therapy, a pause button 1064 which is selected to pause the associated IPV therapy, and a stop button 1066 which is selected to stop the associated IPV therapy. Screen 1060 also has an information graph 1068 and an information bar 1070. Illustrative graph 1068 shows four stages of IPV therapy including a first stage of CPEP therapy, a second stage of CHFO therapy at a first oscillatory amplitude and/or frequency, a third stage of CHFO therapy at a second oscillatory amplitude and/or frequency, and a fourth stage of CPEP therapy.

Figure 65:
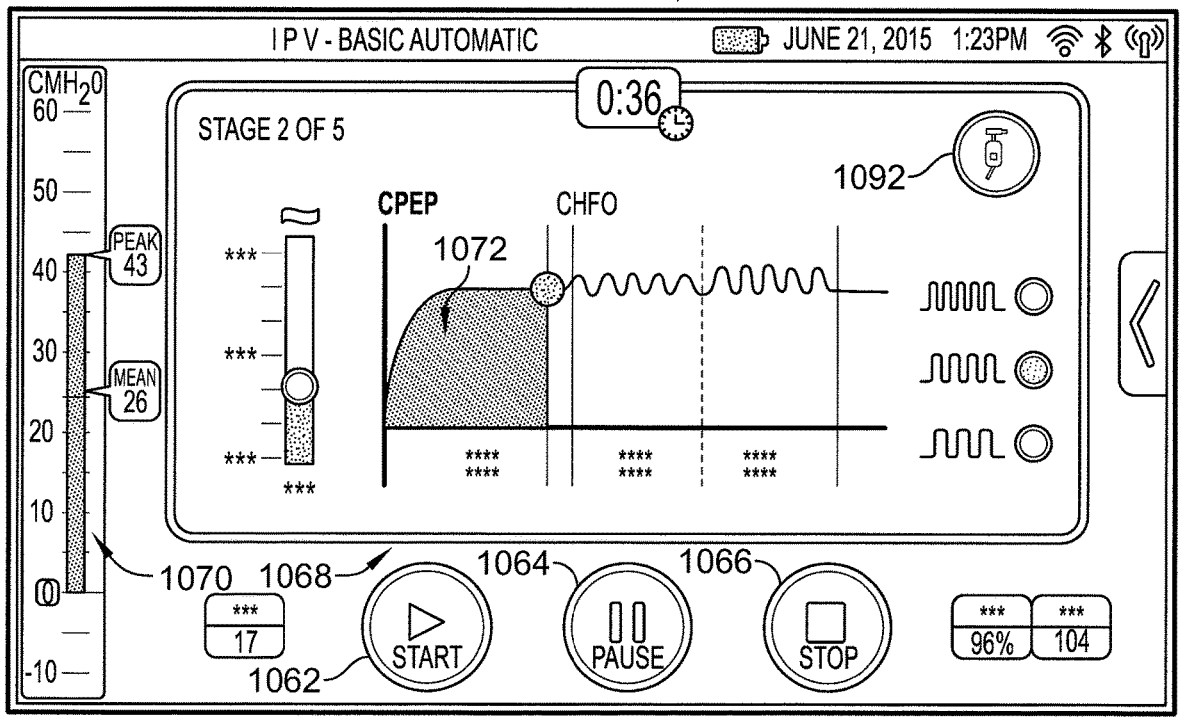
FIG. 65 is an example of a second automatic positive pressure therapy mode screen showing various information about the status and progress of the automatic positive pressure therapy as it occurs.

Graph 1068 displays numerical parameters for the associated therapy including CPEP pressure, CHFO pressure, time of CPEP stages, time of CHFO stages, a therapy progress indicator which moves along the curve shown in graph 1068 during the associated therapy, and a running total time for the associated therapy. Bar 1070 includes an upper arrow serving as an peak pressure marker and a lower arrow serving as a mean pressure marker. As shown in FIG. 65, if pause button 1064 is selected during delivery of IPV therapy, an area 1072 of graph 1068 becomes filled or colored in a manner to indicate that point of the therapy at which the pause button 1064 was selected.

Figure 66:
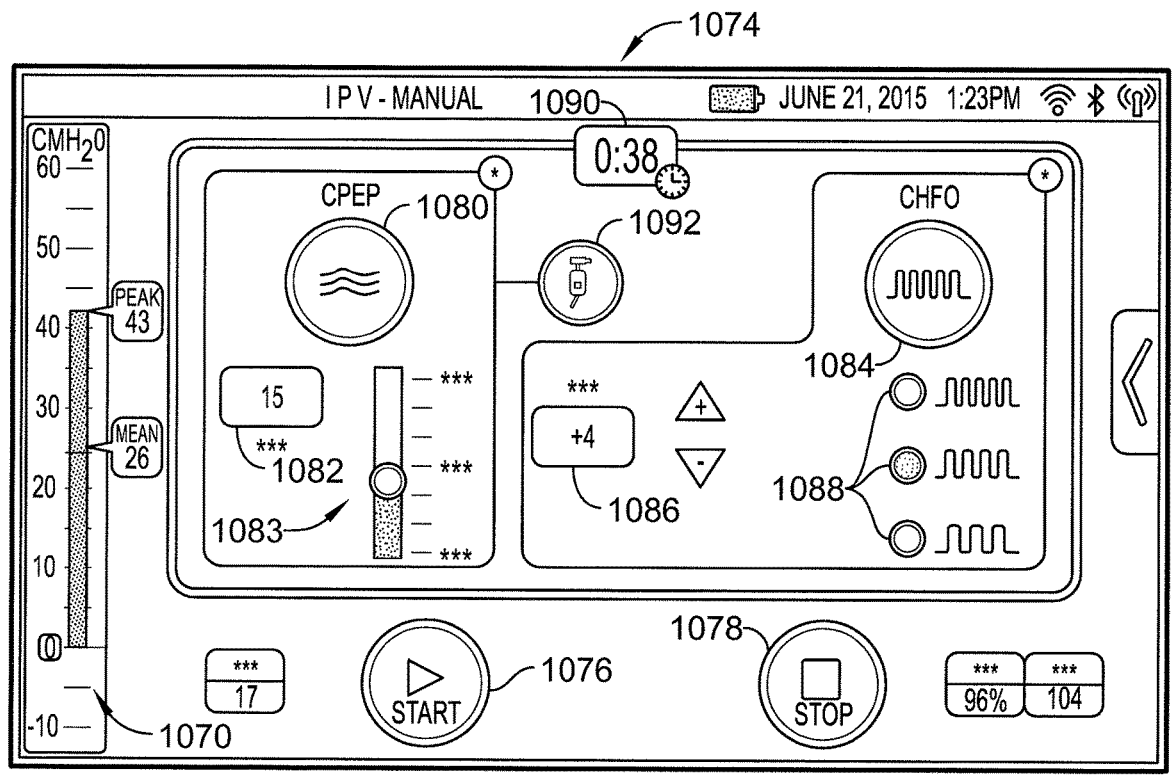
FIG. 66 an example of a first manual positive pressure therapy mode screen that results if a manual mode button or icon of the screen of FIG. 57 is selected or if a preset therapy selected on the screen of FIG. 58 is a stored manual positive pressure therapy.

If manual icon 1022 of screen 1016 of FIG. 57 is selected, then a first manual IPV mode therapy screen 1074 results as shown, for example, in FIG. 66. Screen 1074 includes a start button 1076 which is selected to start the associated IPV therapy and a stop button 1078 which is selected to stop the associated IPV therapy. Screen 1074 includes information bar 1070 which was discussed above. Screen 1074 has a CPEP button 1080 which is selected to cause CPEP therapy to be delivered to the patient's airway by device 10, 10' at a selected target positive pressure specified in a first window 1082. Thus, for manual CPEP therapy, the user first selects button 1080 to select CPEP and then selects the start button 1076 to start the CPEP therapy. The user is able to adjust the target positive pressure in window 1082 by moving an icon along bar 1083 or by selecting up or down arrows adjacent to bar 1083.

Figure 67:
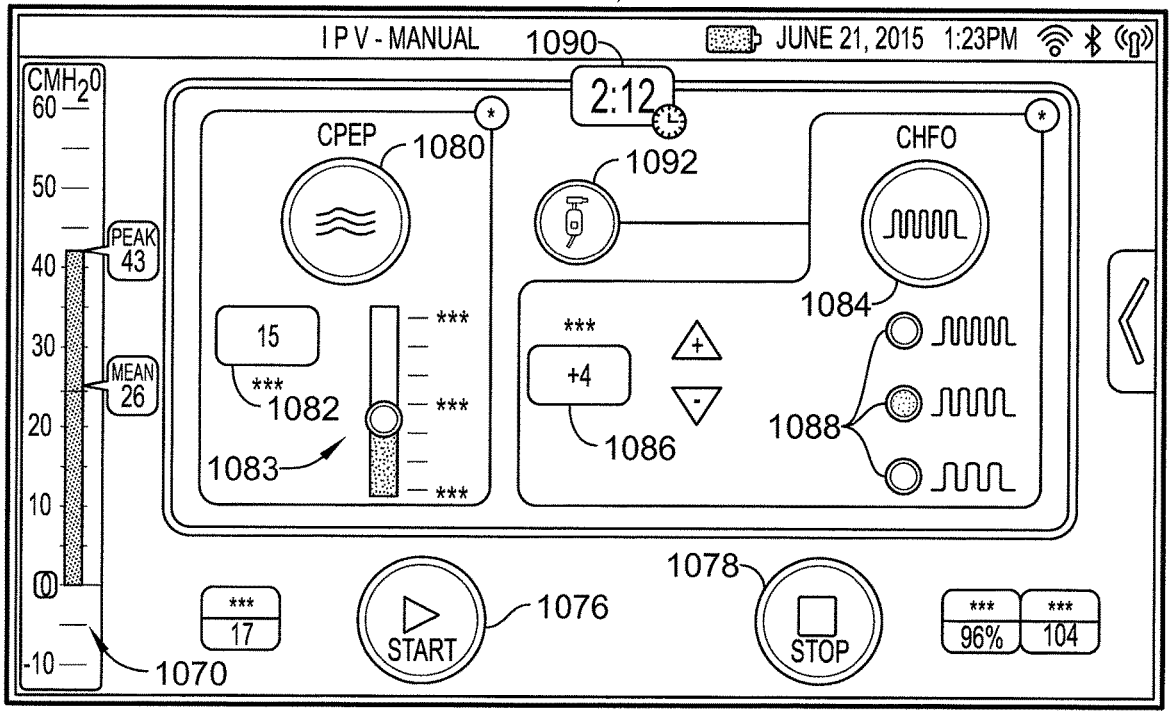
FIG. 67 is an example of a second manual positive pressure therapy mode screen showing various information about the status and progress of the manual positive pressure therapy as it occurs.

Screen 1074 also a CHFO button 1084 which is selected to cause CHFO therapy to be delivered to the patient's airway by device 10, 10' at a selected target positive pressure specified in a second window 1086 of screen 1074 and at a high, medium, or low frequency specified by selection of one of radio buttons 1088 as shown, for example, in FIG. 67. Up and down arrows are provided adjacent window 1086 to permit the user to adjust the CHFO target pressure upwardly or downwardly. As shown in FIGS. 64-67, a time of therapy window 1090 is provided to indicate the total amount of time that has transpired during the CPEP therapy or the CHFO therapy, as the case may be. As also shown in FIGS. 64-67, a nebulizer icon 1092 is provided and is selected by the user if nebulized medication is to be delivered to the patient from a nebulizer during the CPEP or CHFO therapy. Screen 1010 of FIG. 56 also has nebulizer icon 1092 which can be selected to start and stop delivery of nebulized medication by itself without MIE or IPV therapy also occurring.

CHFO therapy is a pneumatic form of chest physiotherapy that oscillates the airways with continuous pulses of positive pressure. CHFO therapy can be delivered from device 10, 10' to mechanically ventilated patients when connected in-line with the mechanical ventilator, if desired. In some embodiments, the frequencies associated with the high, medium, and low radio buttons 1088 include about 5 hertz (Hz)+/−1 Hz (300+/−60 beats per minute (bpm)) for the high frequency setting, about 4 Hz+/−1 Hz (240+/−60 bpm) for the medium frequency setting, and about 3 Hz+/−1 Hz (180+/−60 bpm) for the low frequency setting. Also, for CHFO therapy, device 10, 10' is configured to deliver gas peak flow rate in the range of about 80 to about 160 liters per minute (L/min) at the output port of handset 900 in some embodiments. Further, for CHFO therapy, the peak static pressure is configurable over a range of about 10 cmH2O to 50 cmH2O relative to ambient air pressure at the patient end of handset 900 with +/-3 cmH2O of tolerance, in some embodiments.

CPEP therapy provides continuous positive pressure to the patient's airway with the aim of holding open and expanding the patient's airway. During CPEP therapy, a static positive pressure is provided over a range of about 5 cmH2O to about 40 cmH2O relative to ambient air pressure at the output of handset 900 with +/−3 cmH2O of tolerance, in some embodiments. Also during CPEP therapy, at the 40 cmH2O setting, the peak air flow rate delivered by device 10, 10' is no less than 100 L/min in some embodiments. As indicated above, a nebulizer may be used with either CPEP therapy or CHFO therapy. In some embodiments, the flow rate of delivery of the aerosolized medication from the nebulizer is at least 0.2 milliliters per minute (mL/min).

In some embodiments, bar 1040 of FIGS. 60-63 and bar 1070 of FIGS. 64-67 has a coloring over a portion of the bar to indicate, in substantially real time, the pressure being delivered to port 24 of device 10, 10'. Thus, bars 1040, 1070 serve as dynamic or reactive digital monometers in some embodiments. In some embodiments, an information or "i" button is provided on one or more of the screens of FIGS. 56-67 and is selectable to bring up textual information adjacent to each of the graphical elements and buttons on the corresponding screen. The textual information explains the function or purpose of the adjacent graphical element or button. Screens 1030 of FIGS. 60 and 61 and screens 1060 of FIGS. 64 and 65 have a progress bubble or circle that moves along the associated pressure graph to indicate the point in the therapy regimen at which device 10, 10' is currently operating. In screens 60 and 61, the progress bubble returns to the beginning of the graph for each cycle of the associated therapy.

In some embodiments, pause buttons 1034, 1064 toggle with their associated start buttons 1032, 1062 rather than being showing on the screen simultaneously. That is, when start button 1032, 1062 is pressed, it becomes a pause button 1034, 1064 on the screen in the same location on the screen. If the pause button 1034, 1064 is pressed, it toggles back to being a start button 1032, 1062. In some embodiments, a summary screen is provided after each of the therapies (i.e., automatic MIE therapy, manual MIE therapy, automatic IPV therapy, and manual IPV therapy). The summary screen indicates various parameters, such as mean pressure, number of cycles, oscillation frequency, and so on. The summary screens, in some embodiments, have a button that is pressed to perform a spirometry session with the patient. In such sessions, a spirometer is attached to port 816 of device 10', for example, and the patient breathes into the spirometer to generate a spirometry curve of the type shown in FIG. 27.

In some embodiments, rather than using up and down arrows to adjust a numerical setting appearing in a window (e.g., windows 1052, 1056, 1082, 1086), the window itself can be selected and a numeric key pad will appear on display screen 16 so that a number can be entered directly into the window. In some embodiments, selection of an arrow tab at the right hand side of the screens of FIGS. 60-67 results in a menu of icons being displayed on the right hand side of the screen. The icons include, for example, a home icon which is selected to go to a home page, a device settings icon which is selected to adjust device settings, a preset icon which is selected to navigate to screens in which parameters for the various preset therapies can be adjusted or edited, and advanced graph icon which is selected to a more detailed graph of pressure occurring during a therapy, and a help icon which is selected to obtain help about the operation of device 10, 10'.

Although certain illustrative embodiments have been described in detail above, many embodiments, variations and modifications are possible that are still within the scope and spirit of this disclosure as described herein and as defined in the following claims.

The invention claimed is:

1. A respiratory therapy apparatus comprising
a housing,
a hose having a proximal end and a distal end,
a patient interface coupleable to the distal end of the hose and configured to deliver pressurized air to a patient's airway,
an outlet port carried by the housing and configured for pneumatic communication with the proximal end of the hose, wherein pressure produced within the housing at different target pressures during a therapy cycle is coupled to the patient's airway via the outlet port, the hose, and the patient interface, and
a graphical user interface (GUI) carried by the housing, the GUI displaying user inputs that are used to set the target pressures of the therapy cycle, the GUI displaying a graph of the therapy cycle, the graph being a continuous line depicting the target pressures of the therapy cycle as entered with the user inputs of the GUI and prior to the occurrence of the therapy cycle which is carried out by the pressure produced within the housing, and the GUI displaying a therapy progress indicator that moves along the graph during the therapy cycle corresponding to the pressure produced within the housing as the therapy cycle occurs with the therapy progress indicator moving from one of the target pressures to another of the target pressures as the therapy cycle occurs.

2. The respiratory therapy apparatus of claim 1, wherein the therapy progress indicator comprises a circular icon that moves along the graph during the therapy cycle.

3. The respiratory therapy apparatus of claim 1, wherein the graph displayed on the GUI depicts one complete cycle of the therapy cycle and when the therapy progress indicator reaches an end of the graph of the therapy cycle, the therapy progress indicator automatically returns back to a beginning of the graph of the therapy cycle.

4. The respiratory therapy apparatus of claim 1, wherein the therapy progress indicator moves from left to right along the graph during each therapy cycle.

5. The respiratory therapy apparatus of claim 1, wherein at least a portion of the graph of the therapy cycle is color coded.

6. The respiratory therapy apparatus of claim 1, wherein the GUI displays a pause button during the therapy cycle and selection of the pause button pauses the therapy cycle.

7. The respiratory therapy apparatus of claim 1, wherein the GUI is operable to display a pressure bar adjacent the graph, the pressure bar including at least one pressure icon indicative of a pressure occurring during the therapy cycle.

8. The respiratory therapy apparatus of claim 7, wherein the pressure icon comprises a triangular icon.

9. The respiratory therapy apparatus of claim 7, wherein the pressure bar comprises a vertically oriented bar having pressure gradations and numerical pressure values along a vertical length of the pressure bar.

10. The respiratory therapy apparatus of claim 9, wherein the numerical pressure values include positive pressures and negative pressures.

11. The respiratory therapy apparatus of claim 1, wherein the therapy cycle corresponds to a mechanical insufflation/exsufflation (MIE) therapy in which a first target pressure of the target pressures is a positive pressure corresponding to an insufflation phase of the MIE therapy and in which a second target pressure of the target pressures is a negative pressure corresponding to an exsufflation phase of the MIE therapy.

12. The respiratory therapy apparatus of claim 11, wherein the therapy cycle includes a pause phase having a third target pressure which is a positive pressure that is less than the first target pressure.

13. The respiratory therapy apparatus of claim 1, wherein the housing has a front wall and spaced apart first and second side walls and wherein the outlet is carried by the front wall of the housing and is generally centered between the first and second side walls of the housing.

14. The respiratory therapy apparatus of claim 13, wherein the GUI is also generally centered between the first and second side walls of the housing.

15. The respiratory therapy apparatus of claim 14, wherein the housing includes a GUI-carrying wall that is situated above the front wall and the GUI is carried by the GUI-carrying wall.

16. The respiratory therapy apparatus of claim 13, further comprising at least one communication port carried by the housing.

17. The respiratory therapy apparatus of claim 16, wherein the at least one communication port comprises at least one universal serial bus (USB) port.

18. The respiratory therapy apparatus of claim 16, wherein the at least one communication port comprises at least two universal serial bus (USB) ports.

19. The respiratory therapy apparatus of claim 1, further comprising
a pneumatic system carried by the housing, the pneumatic system being configured to deliver positive pressure and negative pressure to the outlet port,
control circuitry carried by the housing and coupled to the pneumatic system, and
the GUI being coupled to the control circuitry.

20. The respiratory therapy apparatus of claim 19, wherein the pneumatic system includes a blower having an inlet and an outlet, and a valve including a valve member that is rotatable through a first angular displacement in a first direction from a first position to a second position, wherein the outlet of the blower is coupled to the patient interface so that positive pressure is provided to a patient's airway via the patient interface when the valve member is in the first position, wherein the inlet of the blower is coupled to the patient interface so that negative pressure is provided to the patient's airway via the patient interface when the valve member is in the second position, wherein the valve member is rotatably oscillated back and forth through a second angular displacement that is smaller than the first angular displacement in the first direction and a second direction opposite to the first direction when the valve member is in the first position and when the valve member is in the second position so that oscillations in the positive pressure and negative pressure, respectively, are provided to the patient's airway.

21. The respiratory therapy apparatus of claim 19, wherein the pneumatic system includes a blower having an inlet and an outlet, a valve coupled to the blower and operable to control a pressure applied to the outlet port, and a sensor to sense at least one of pressure and flow applied to the outlet port, and wherein the control circuitry is coupled to the blower, the valve, and the sensor, the control circuitry operates the blower and the valve to apply a first threshold pressure to the outlet port for a first preset amount of time in response to an inspiratory trigger being sensed by the sensor, the control circuitry operates the blower and the valve to apply a second threshold pressure to the patient interface during a rest phase that occurs after the first preset amount of time, the control circuitry operates to ignore one or more inspiratory triggers that are sensed by the sensor and that occur during the rest phase.

22. The respiratory therapy apparatus of claim 19, further comprising at least one patient interface configured to be coupled to the outlet port, the patient interface including a filter housing that includes an air filter carrier and at least one prong extending from the air filter carrier, and at least one switch situated in the housing, the housing having at least one prong-receiving aperture adjacent the outlet port, the at least one prong extending through the aperture and activating the switch when the respective patient interface is coupled to the outlet port, the pneumatic system being disabled from operation unless the at least one switch is activated.

23. The respiratory therapy apparatus of claim 19, further comprising a handset pneumatically coupled to the outlet port, the handset comprising a generally banana-shaped tube having an upper surface that is generally convex from end-to-end of the generally banana-shaped tube and a bottom surface that is generally concave from end-to-end of the generally banana-shaped tube, the generally banana-shaped tube having opposite first and second open ends and having a nebulizer port that is provided at an apex of the upper surface such that, in use, a nebulizer extends upwardly from a top of the handset.

24. The respiratory therapy apparatus of claim 19, further comprising at least one pressure sensor and at least one flow sensor to measure pressure and flow, respectively, in a flow path between the pneumatic system and the outlet port, a patient interface comprising a tube having a first end coupled to the outlet port and a mask coupled to a second end of the tube, and the control circuitry receiving signals from the pressure sensor and the flow sensor to determine an inspiratory trigger indicative that the patient has started to inhale, the pneumatic system being operationally adjusted in response to detection of the inspiratory trigger, wherein based on a flow sensor signal from the flow sensor the control circuitry is configured to determine mask removal or mask leakage and to stop operation of the pneumatic system.

\* \* \* \* \*